(12) United States Patent
Khu et al.

(10) Patent No.: US 9,456,561 B2
(45) Date of Patent: Oct. 4, 2016

(54) METHODS AND COMPOSITIONS FOR PRODUCING ALUMINUM TOLERANT ALFALFA

(75) Inventors: Dong-Man Khu, Ardmore, OK (US); Joseph H. Bouton, Athens, GA (US); Maria J. Monteros, Ardmore, OK (US); Rafael Reyno, Tawarembo (UY); E. Charles Brummer, Ardmore, OK (US)

(73) Assignees: The Samuel Roberts Noble Foundation, Inc., Ardmore, OK (US); The University of Georgia Research Foundation, Inc., Athens, GA (US)

( * ) Notice: Subject to any disclaimer, the term of this patent is extended or adjusted under 35 U.S.C. 154(b) by 984 days.

(21) Appl. No.: 13/352,081

(22) Filed: Jan. 17, 2012

(65) Prior Publication Data
US 2012/0185961 A1  Jul. 19, 2012

Related U.S. Application Data

(60) Provisional application No. 61/433,205, filed on Jan. 15, 2011.

(51) Int. Cl.
| | |
|---|---|
| *C12Q 1/68* | (2006.01) |
| *A01H 1/04* | (2006.01) |
| *A01H 5/10* | (2006.01) |
| *A01H 5/12* | (2006.01) |

(52) U.S. Cl.
CPC ........ *A01H 1/04* (2013.01); *A01H 5/10* (2013.01); *A01H 5/12* (2013.01); *C12Q 1/6895* (2013.01); *C12Q 2600/156* (2013.01)

(58) Field of Classification Search
USPC .......................................................... 800/267
See application file for complete search history.

(56) References Cited

PUBLICATIONS

Narasimhamoorthy et al., 2007, Crop Sci. 47: 321-328.*
Sledge et al., 1997, Proc XVIII Int. Grassland Congr., Winnipeg, Canada, Jun. 8-19, pp. 4-9 through 4-10.*
Narasimhamoorthy et al., 2007, Theor. Appl. Genet. 114: 901-913.*
Batley and Edwards, 2007, In; Association Mapping in Plants, pp. 95-102.*
Brummer et al., 1993, Theor. Appl. Genet. 86: 329-332.*
Chandran et al., "Physiological and molecular characterization of aluminum resistance in *Medicago truncatula,*" *BMC Plant Biology,* 8: 89, 2008.
Ermolayev et al., "Comparison of Al-induced gene expression in sensitive and tolerant soybean cultivars," *J Exp Bot* 54:2745-2756, 2003.
Khu et al., "Identification and QTL mapping of aluminum tolerance in tetraploid alfalfa." ASA-CSSA-SSSA, 2009 International Annual Meeting: "Footprints in the Landscape: Sustainability through Plant and Soil Sciences," Nov. 1-5, 2009, Pittsburgh, PA, http://a-c-s.confex.com/crops/2009am/webprogram/Paper52681.html, accessed on Jun. 25, 2012.
Khu et al., "Identification of aluminum tolerance QTL in tetraploid alfalfa." Jul. 27, 2010, http://www.naaic.org/Meetings/National/2010meeting/DongManKhu.pdf, accessed on Jun. 25, 2012.
Khu et al., "Molecular mapping of aluminum tolerance QTL's in tetraploid alfalfa," Plant and Animal Genomes XIX Conference. Jan. 15-19, 2011, San Diego, CA, http://www.intl-pag.org/19/abstracts/P05f_PAGXIX_414.html, accessed on Jun. 25, 2012.
Khu et al., "QTL mapping of aluminum tolerance in tetraplod alfalfa," Joint Meeting of the 41$^{st}$ North American Alfalfa Improvement Conference and 20$^{th}$ Trifolium Conference, Jun. 1-4, 2008, Dallas, TX,http://www.naaic.org/Meetings/National/2008meeting/Khu.pdf, accessed on Jun. 25, 2012.
Khu et al., "Screening methods for aluminum tolerance in alfalfa," *Crop Sci* 52:161-167, 2012.
Maron et al., "Transcriptional profiling of aluminum toxicity and tolerance responses in maize roots," *New Phytologist* 179:116-128, 2008.
Narasimhamoorthy et al., "A comparison of hydroponics, soil, and root staining methods for evaluation of aluminum tolerance in *Medicago truncatula* (Barrel Medic) germplasm," *Crop. Sci* 47:321-328, 2007.
Reyno et al., "Mapping aluminum tolerance QTL in tetraploid alfalfa using a soil-based evaluation," Plant and Animal Genomes XIX Conference, Jan. 15-19, 2011, San Diego, CA, http://www.intl-pag.org/19/abstracts/P05f_PAGXIX_415.html, accessed on Jun. 25, 2012.
Sledge et al., "Identification and confirmation of aluminum tolerance QTL in diploid *Medicago sativa* subsp. coerulea," *Crop Sci* 42:1121-1128, 2002.
Tesfaye et al., "Overexpression of malate dehydrogenase in transgenic alfalfa enhances organic acid synthesis and confers tolerance to aluminum," *Plant Physiol.* 127:1836-1844, 2001.
Lehman et al., "Registration of CUF 101. 617 alfalfa". *Crop Sci.* 23: 398-399, 1983.
Li et al., "Prevalence of single nucleotide polymorphism among 27 diverse alfalfa genotypes as assessed by transcriptome sequencing," *BMC Genomics* 13:568, 2012.
Khu et al., "QTL mapping of aluminum tolerance in tetraploid alfalfa," In C. Huyghe (ed.) *Sustainable Use of Genetic Diversity in Forage and Turf Breeding,* Springer, Dordrecht, the Netherlands, p. 437-442, 2010.

* cited by examiner

*Primary Examiner* — David T Fox
*Assistant Examiner* — Bratislav Stankovic
(74) *Attorney, Agent, or Firm* — Dentons US LLP

(57) ABSTRACT

The invention relates to alfalfa plants and lines having aluminum tolerance. The invention also relates to parts of alfalfa plants from lines having aluminum tolerance, including seeds capable of growing aluminum tolerant alfalfa plants. Methods for the use and breeding of aluminum tolerant alfalfa plants are also provided.

13 Claims, 36 Drawing Sheets

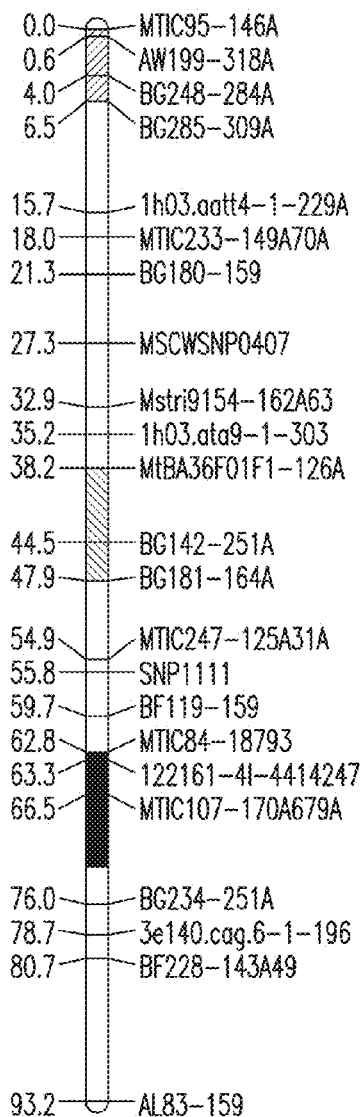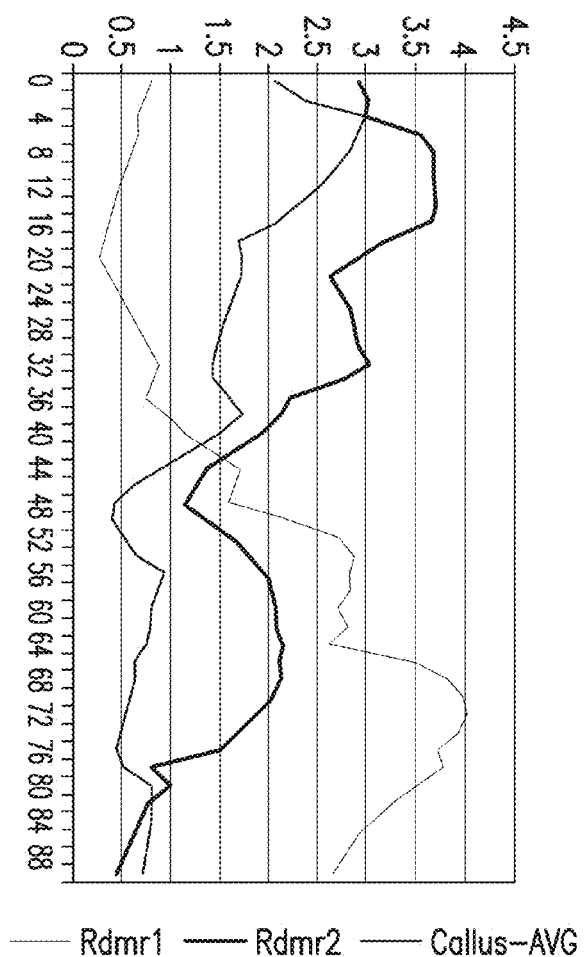
FIG. 5A

FIG. 5C
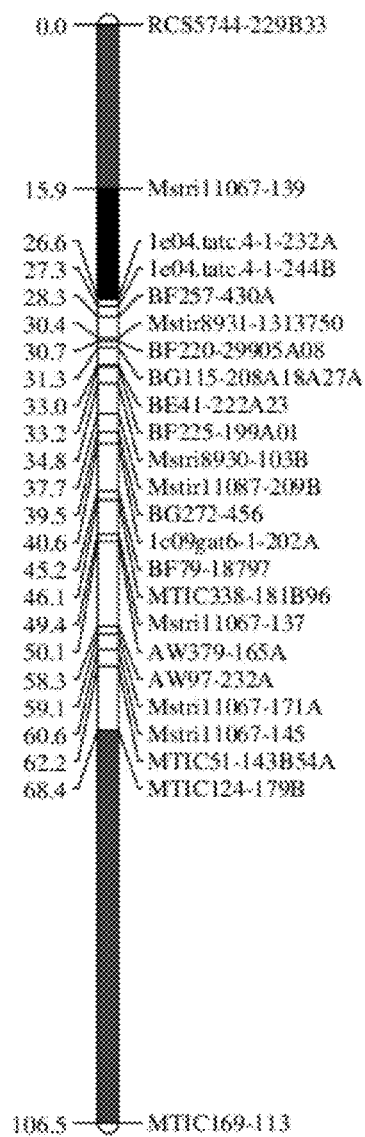
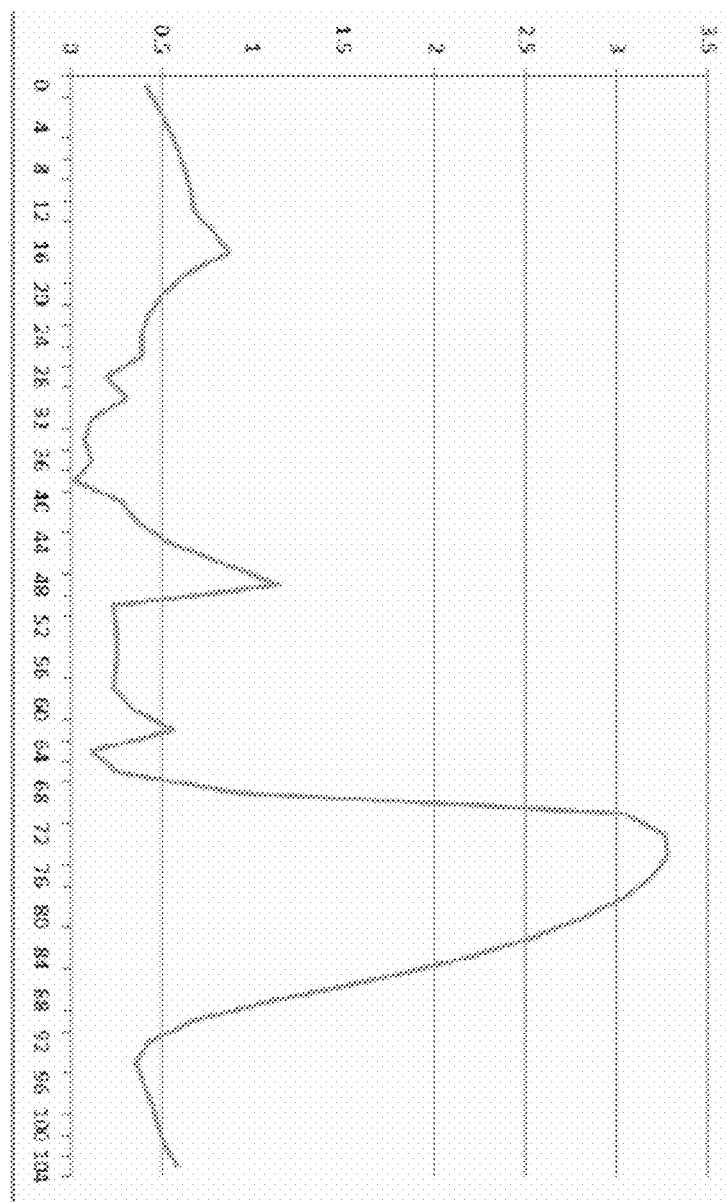

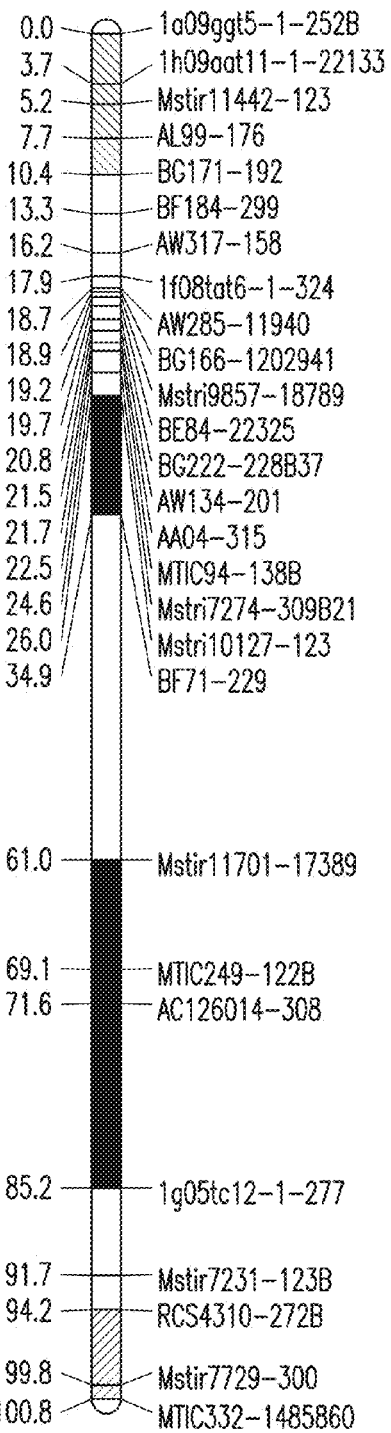
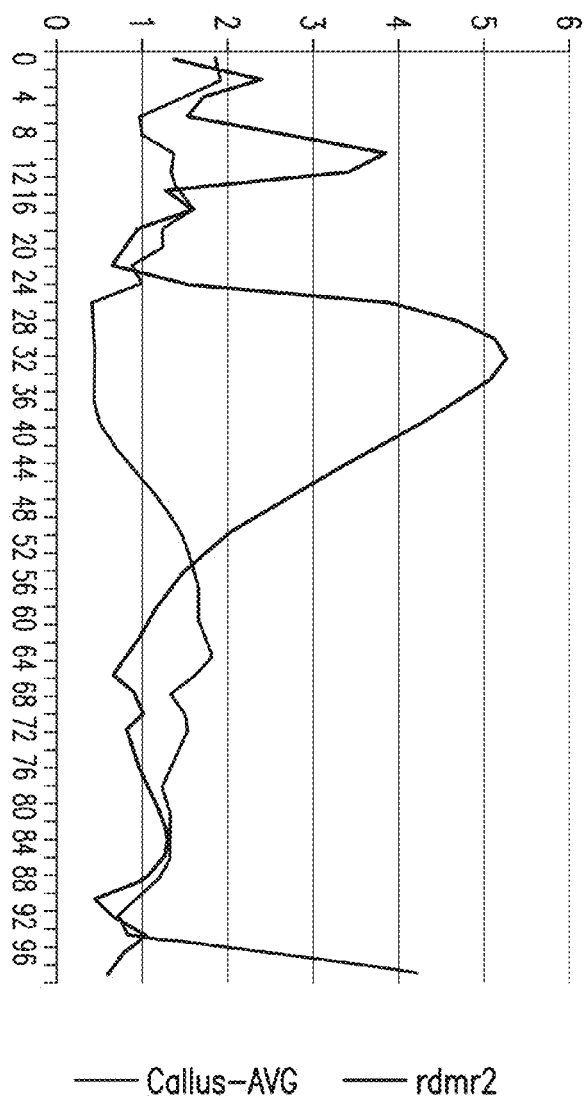
FIG. 5E

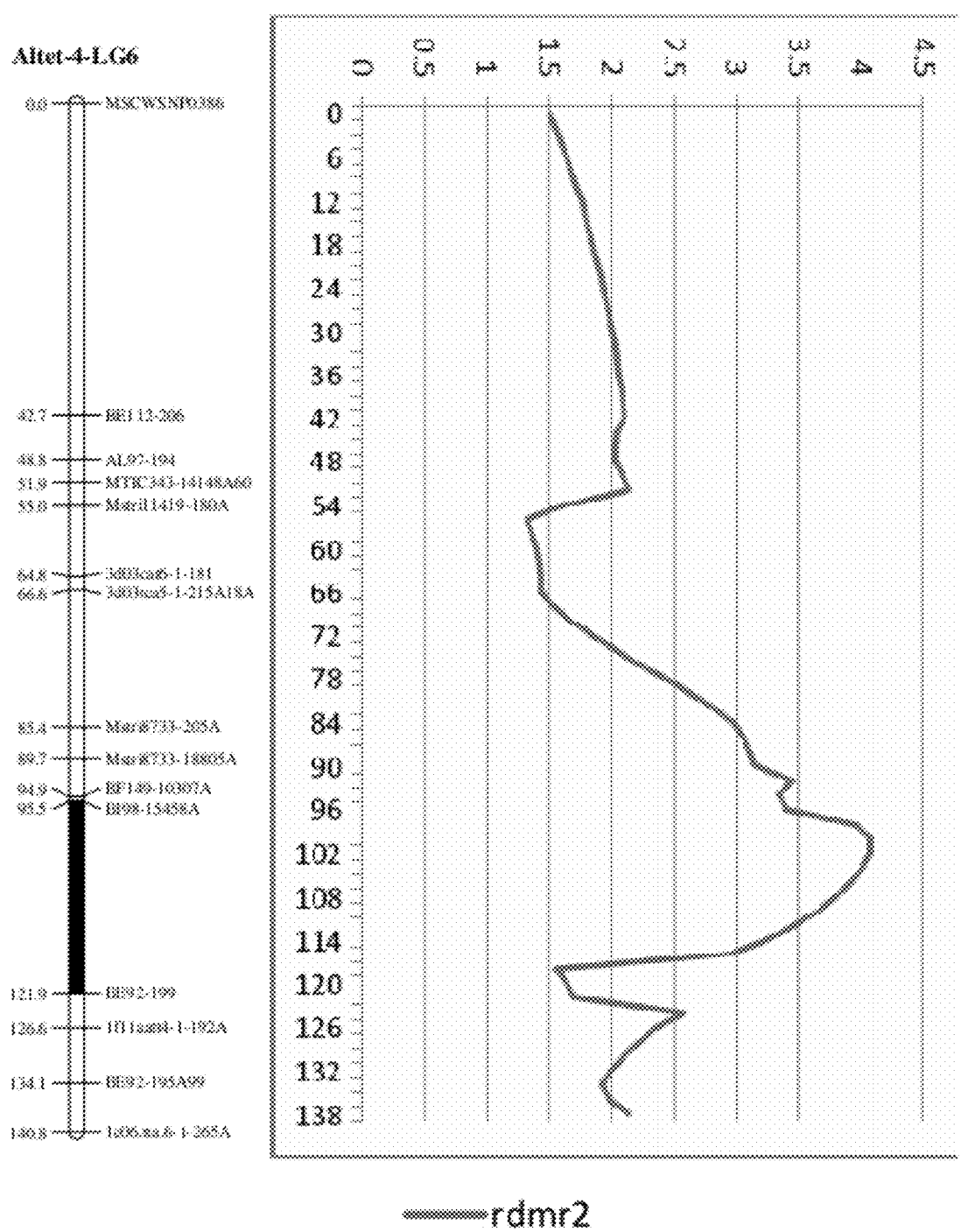

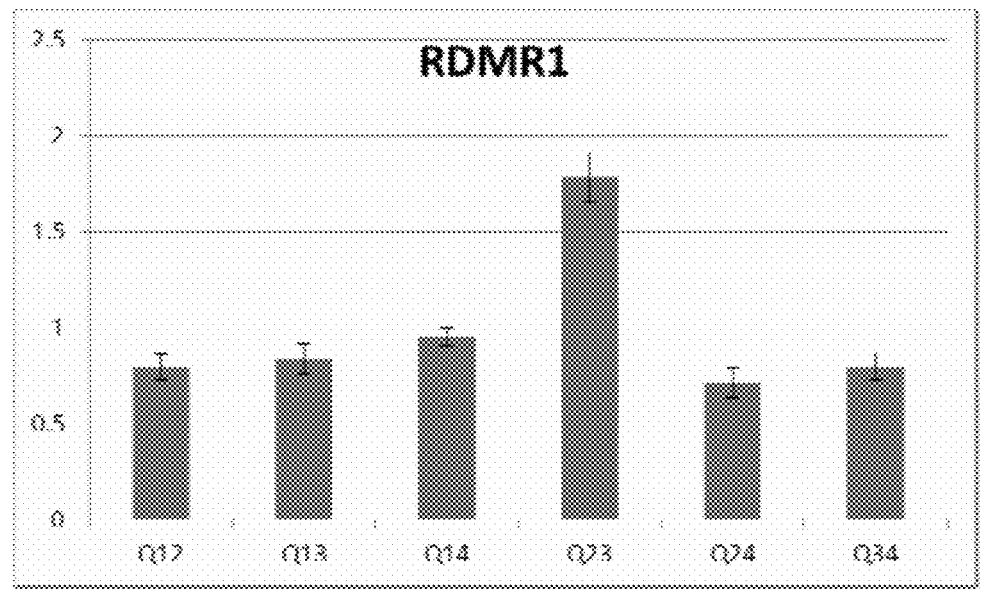
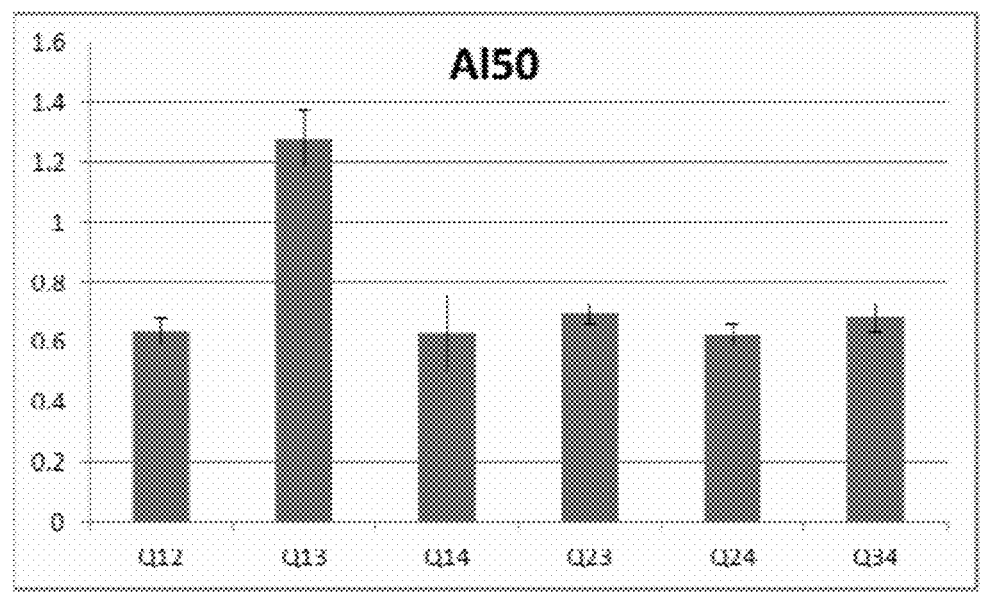

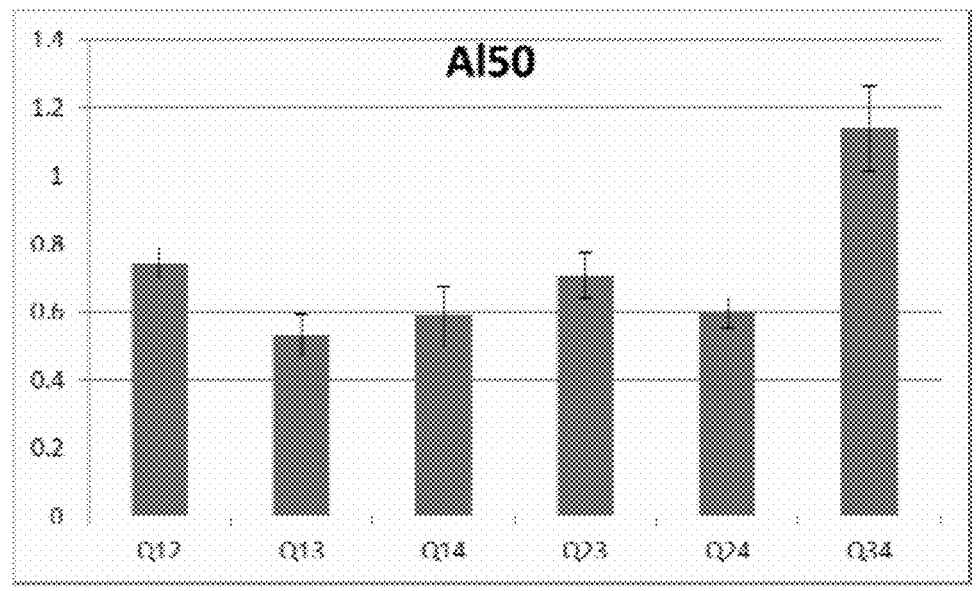
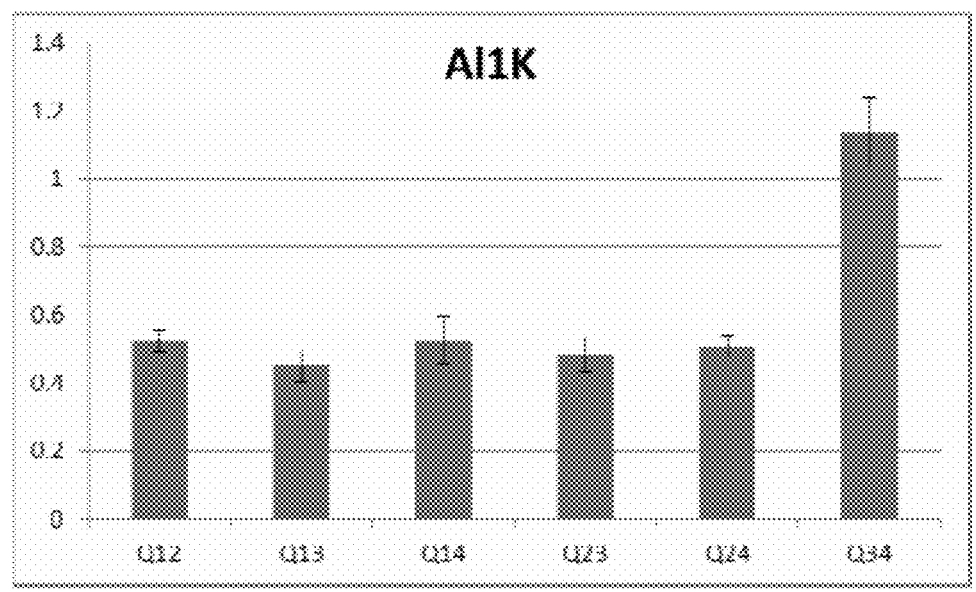

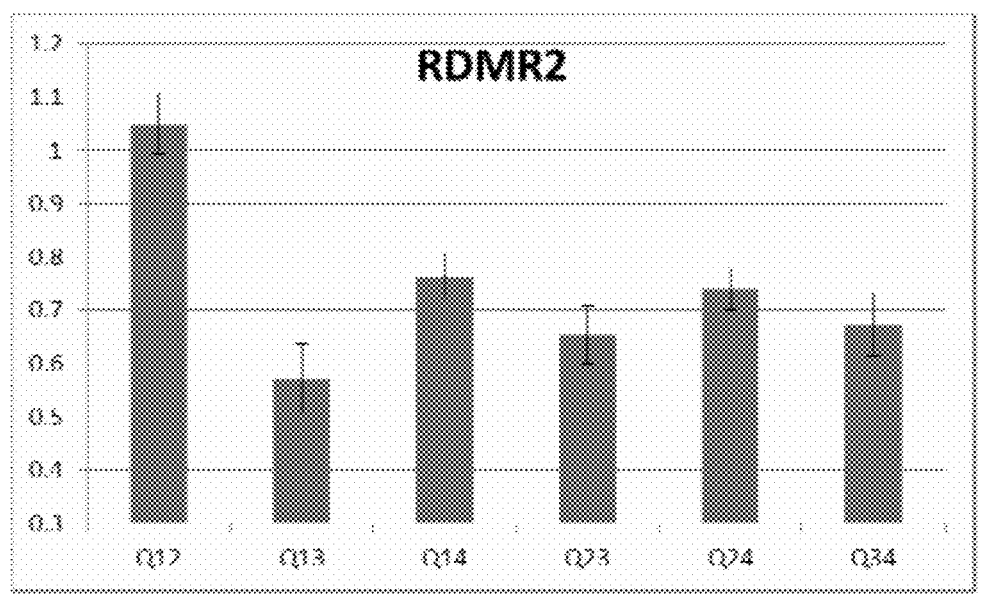

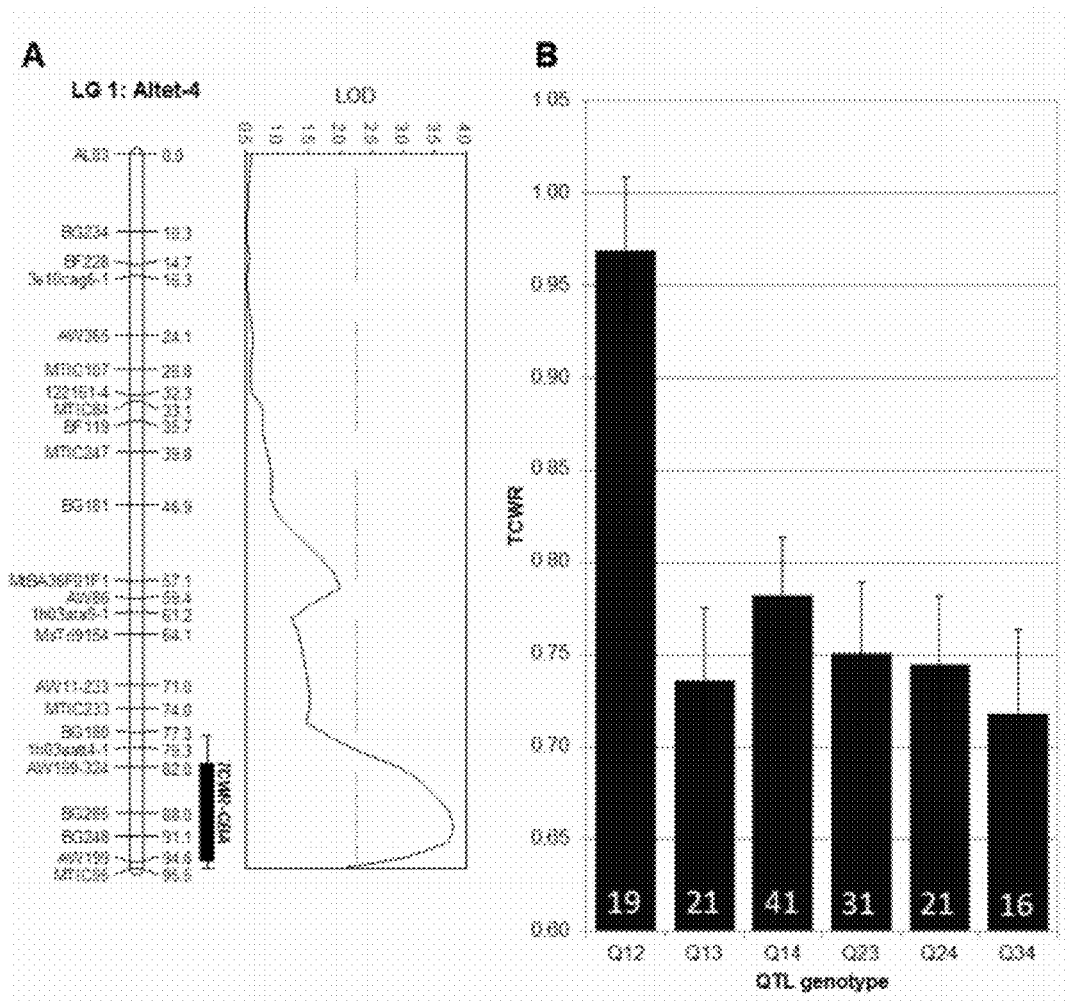
FIG 9A-B

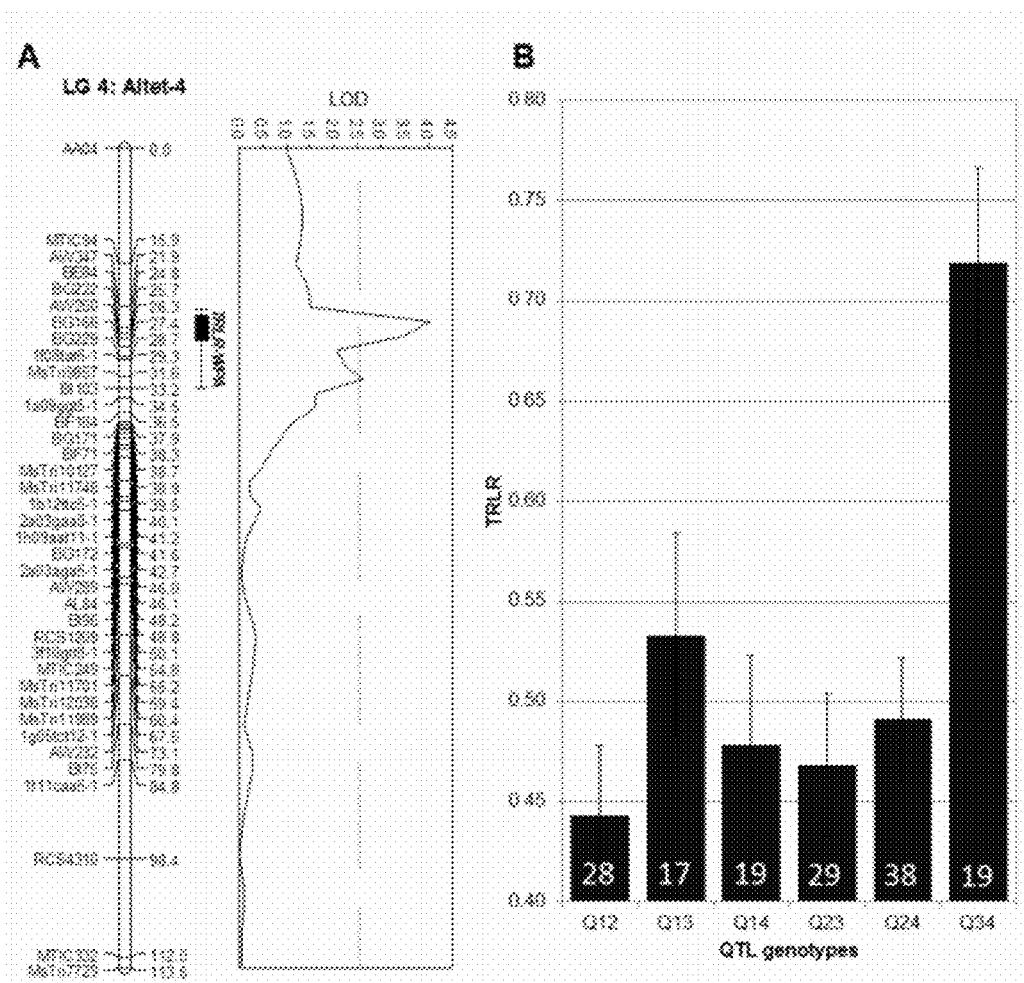
FIG. 10A-B

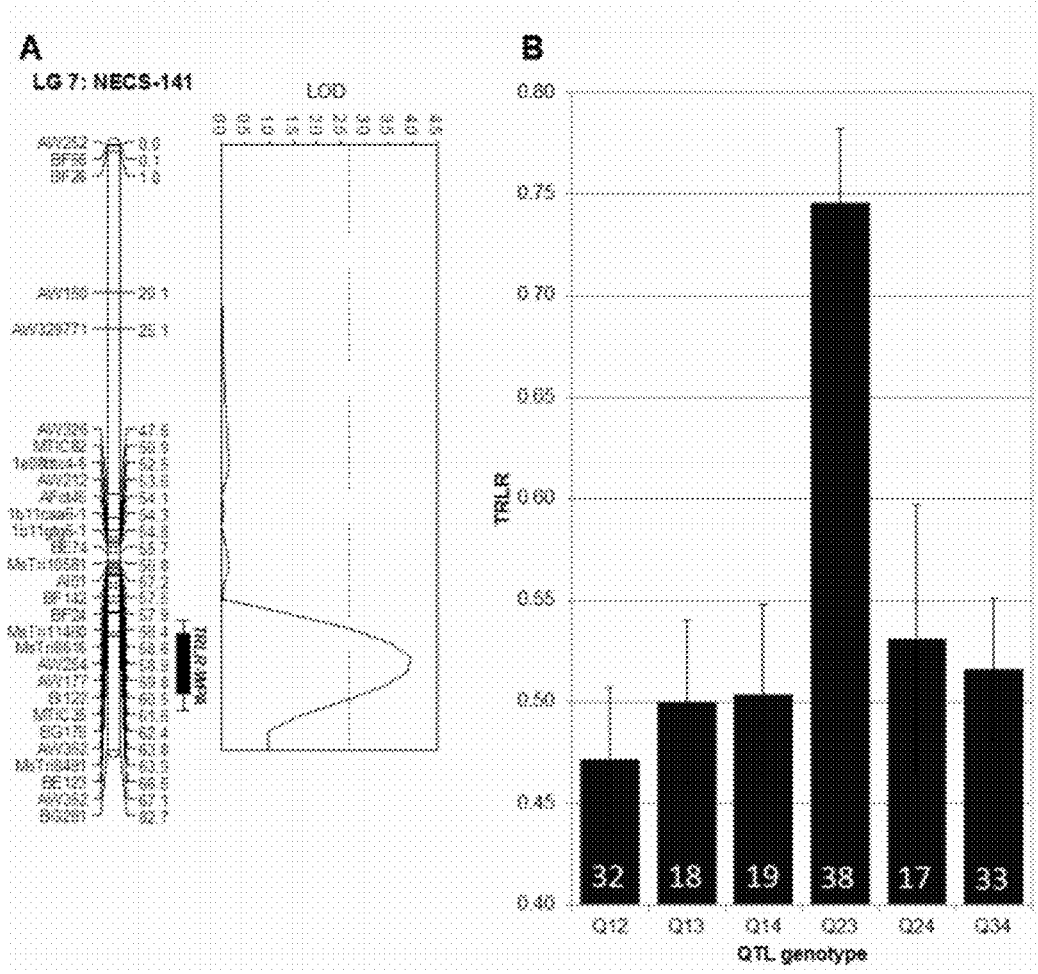
FIG. 11A-B

METHODS AND COMPOSITIONS FOR PRODUCING ALUMINUM TOLERANT ALFALFA

INCORPORATION OF SEQUENCE LISTING

A computer readable form of the sequence listing is contained in the file named "NBLE077_ST25.txt" which is 103 kb (measured in MS-Windows) and was created on Dec. 2, 2013, which is filed herewith and herein incorporated by reference.

CROSS-REFERENCE TO RELATED APPLICATIONS

This application claims the benefit of priority of U.S. Provisional Application Ser. No. 61/433,205, filed on Jan. 15, 2011, the disclosure of which is incorporated herein by reference in its entirety.

FIELD OF THE INVENTION

The invention relates to methods and compositions for producing alfalfa plants that tolerate the presence of aluminum in soil.

BACKGROUND OF THE INVENTION

Alfalfa (*Medicago sativa* subsp. *sativa*) is the most important forage legume in the United States. Alfalfa is tetraploid, having 4 homoeologous chromosomes for each of the 8 different chromosomes, for a total of 32 chromosomes. It is highly desirable for hay production and pasture for livestock because it produces more protein per hectare than grain or oilseed crops, and requires little or no nitrogen fertilizer because of its ability to carry out symbiotic nitrogen fixation. However, alfalfa is very sensitive to aluminum toxicity.

Aluminum ("Al") toxicity causes similar symptoms in many plant species. Micromolar concentrations of $Al^{+3}$ can damage the root system, sometimes within minutes of exposure. Damage to the root system then significantly reduces yields due to an insufficient intake of water and other nutrients. Heavy applications of limestone and P fertilizer are commonly used to prevent yield loss, but these amendments are often not economical or practical.

SUMMARY OF THE INVENTION

In a first aspect, there is provided a method for producing an aluminum tolerant alfalfa line or increasing the aluminum tolerance of an alfalfa line comprising introgres sing at least one chromosomal locus contributing to aluminum tolerance from a parent alfalfa plant into an alfalfa line. For example, the parent alfalfa plant may be an aluminum tolerant alfalfa plant, such as a plant that displays a reduction in one or more symptoms of aluminum toxicity relative to a control plant when the plant is in contact with aluminum (e.g., a 10%, 25%, 50%, 75%, or 90% reduction). Symptoms of aluminum toxicity that may be reduced in resistant plants include, but are not limited to, reduction or inhibition of root growth, increase in susceptibility to drought, nutrient deficiency, decreased yield, and leaf chlorosis and/or necrosis. In certain embodiments, the chromosomal locus maps between loci MTIC95-146A and BG285-309A, MtBA36F01F1-126A and BG181-164A, BF228-153 and AL81-228, or MTIC84-18793 and BG234-251A on linkage group 1; between loci RCS5744-229B33 and 1e04.tatc.4-1-232A or MTIC124-179B and MTIC169-113 on linkage group 3; between loci MTIC94-13538B and Mstir12038-216, AW347-324A and BF184-28404, 1a09ggt5-1-252B and BG171-192, Mstri10127-123 and BF71-229, Mstri11701-17389 and 1g05tct12-1-277, RCS4310-272B and MTIC332-1485860, or AL84-156A64A and Mstir11989-111 on linkage group 4; between loci TC105099-111 and 2c12.gga.5-1-165A, TC106861 and Mstri10743-120, Mstri10801-446A and Mstri10743-120, or AW389-482 and BG157-154 on linkage group 5; between loci BI98-15458A and 8E92-199 or MTIC250-133 and 3d03.atc.5-1-239B244 on linkage group 6; or between loci BG119-270 and MTIC183-170B or AW212-245A65 and BF26-289A96A04A on linkage group 7 (see e.g., marker maps provided in FIG. 5A-I). For example, the chromosomal locus may be linked to any of the markers in the regions between MTIC95-146A and BG285-309A, MtBA36F01F1-126A and BG181-164A, BF228-153 and AL81-228, or MTIC84-18793 and BG234-251A on chromosome 1; between RCS5744-229B33 and 1e04.tatc.4-1-232A or MTIC124-179B and MTIC169-113 on chromosome 3; between MTIC94-13538B and Mstir12038-216, AW347-324A and BF184-28404, 1a09ggt5-1-252B and BG171-192, Mstri10127-123 and BF71-229, Mstri11701-17389 and 1g05tct12-1-277, RCS4310-272B and MTIC332-1485860, or AL84-156A64A and Mstir11989-111 on chromosome 4; between TC105099-111 and 2c12.gga.5-1-165A, TC106861 and Mstri10743-120, Mstri10801-446A and Mstri10743-120, or AW389-482 and BG157-154 on chromosome 5; between BI98-15458A and 8E92-199 or MTIC250-133 and 3d03.atc.5-1-239B244 on chromosome 6; or between loci BG119-270 and MTIC183-170B or AW212-245A65 and BF26-289A96A04A on chromosome 7 as provided in the maps of FIG. 5A-I.

In some aspects, a method according to the invention comprises: (a) crossing a plant within the *Medicago* genus having aluminum tolerance with a *Medicago sativa* plant lacking substantial aluminum tolerance to form a first population; (b) selecting one or more members of said population having aluminum tolerance; and (c) backcrossing progeny obtained to plants of a *Medicago sativa* variety otherwise lacking the aluminum tolerance to obtain an introgressed variety comprising aluminum tolerance. In certain embodiments, steps (b) and (c) may be repeated until an aluminum tolerance trait has been introgressed into the genetic background of a plant line that initially lacked aluminum tolerance such that the introgressed plant comprises less than about 50%, 25%, 10%, 5%, or 1% genomic material from the initial aluminum tolerant plant. In some embodiments, the initial cross of step (a) further comprises using embryo rescue to form said first population. In certain embodiments, the steps are repeated about 1, 2, 3, 4, 5, 6, or more times.

In certain aspects, a less-aluminum-tolerant alfalfa line is an agronomically elite line. For example, the less-aluminum-tolerant alfalfa line may be a commercial *Medicago sativa* line, such as a line that is used to produce alfalfa hay or silage. The less aluminum tolerant alfalfa line may be a hybrid or inbred line. In certain specific embodiments, the less-aluminum-tolerant alfalfa line is any commercial variety that is well known to one skilled in the art.

In some aspects a less-aluminum-tolerant alfalfa parent plant or line may contribute loci that enhance aluminum tolerance in progeny lines. For example, in some cases, the less-aluminum-tolerant alfalfa parent plant is a *Medicago sativa* NECS-141 plant. Loci contributing to aluminum tolerance that may be introgressed from such a parent plant include, but are not limited to, chromosomal loci mapping between BF228-153 and AL81-228 on linkage group 1;

between 1a09ggt5-1-252B and BG171-192, Mstri10127-123 and BF71-229, Mstri11701-17389 and 1g05tct12-1-277, or RCS4310-272B and MTIC332-1485860 on linkage group 4; or between MTIC250-133 and 3d03.atc.5-1-239B244 on linkage group 6.

In some aspects, a more-aluminum-tolerant plant is another member of the *Medicago* genus, other than *Medicago sativa* L., such as *Medicago truncatula* or *Medicago trifolium*. The plant may be a wild plant, or a hybrid or inbred line. In certain embodiments, the more-aluminum-tolerant alfalfa plant is *Medicago sativa* ssp. *caerulea* accession PI464724-25. In certain other embodiments the more-aluminum-tolerant alfalfa plant is a plant other than *Medicago sativa* ssp. *caerulea* accession PI464724-25. Loci contributing to aluminum tolerance that may be introgressed from a more aluminum tolerant parent plant include, but are not limited to, chromosomal loci mapping between MTIC95-146A and BG285-309A, MtBA36F01F1-126A and BG181-164A, or MTIC84-18793 and BG234-251A on linkage group 1; between RCS5744-229B33 and 1e04.tatc.4-1-232A or MTIC124-179B and MTIC169-113 on linkage group 3; between MTIC94-13538B and Mstir12038-216, AW347-324A and BF184-28404, or AL84-156A64A and Mstir11989-111 on linkage group 4; between TC105099-111 and 2c12.gga.5-1-165A, TC106861 and Mstri10743-120, Mstir10801-446A and Mstri10743-120, or AW389-482 and BG157-154 on linkage group 5; between B198-15458A and 8E92-199 on linkage group 6; or between BG119-270 and MTIC183-170B or AW212-245A65 and BF26-289A96A04A on linkage group 7.

In a further aspect, there is provided a method for introgressing aluminum tolerance into an alfalfa line by marker-assisted selection using a marker linked to a chromosomal locus that contributes to aluminum tolerance in an alfalfa plant. In certain embodiments, the marker may be a marker that detects chromosomal insertions, deletions or other polymorphisms, such as simple sequence repeats and single nucleotide polymorphisms (SNPs). In certain embodiments, a marker for use according to the invention is between markers MTIC95-146A and BG285-309A, MtBA36F01F1-126A and BG181-164A, BF228-153 and AL81-228, or MTIC84-18793 and BG234-251A on linkage group 1; between RCS5744-229B33 and 1e04.tatc.4-1-232A or MTIC124-179B and MTIC169-113 on linkage group 3; between MTIC94-13538B and Mstir12038-216, AW347-324A and BF184-28404, 1a09ggt5-1-252B and BG171-192, Mstri10127-123 and BF71-229, Mstri11701-17389 and 1g05tct12-1-277, RCS4310-272B and MTIC332-1485860, or AL84-156A64A and Mstir11989-111 on linkage group 4; between TC105099-111 and 2c12.gga.5-1-165A, TC106861 and Mstri10743-120, Mstir10801-446A and Mstri10743-120, or AW389-482 and BG157-154 on linkage group 5; between BI98-15458A and 8E92-199 or MTIC250-133 and 3d03.atc.5-1-239B244 on linkage group 6; or between BG119-270 and MTIC183-170B or AW212-245A65 and BF26-289A96A04A on linkage group 7. For example, the marker may be one of the markers detectable by one of the primer pairs provided in Table 1 or Table 5 (SEQ ID NOs:1-560).

In still a further aspect, there is provided an alfalfa line produced by methods according to the invention, wherein the line comprises aluminum tolerance and is agronomically elite. Progeny of such plants comprising aluminum tolerance and an agronomically elite phenotype are also included as part of the invention.

In yet a further aspect, the invention provides an alfalfa plant comprising aluminum tolerance wherein the plant is agronomically elite. For example, the alfalfa plant may be an inbred or hybrid plant. A tolerant alfalfa plant may display a reduction in one or more symptom of aluminum toxicity. Symptoms that may be reduced in a tolerant plant include, but are not limited to, reduction or inhibition of root growth, increase in susceptibility to drought, nutrient deficiency, decreased yield, and leaf chlorosis and/or necrosis. Progeny of such plants comprising aluminum tolerance and an agronomically elite phenotype are also included as part of the invention. Likewise, seeds of plants according to the invention are also provided wherein the seeds produce agronomically elite plants comprising aluminum tolerance. Transgenic alfalfa plants are also provided as part of the instant invention. In certain embodiments, the invention provides parts of a plant according to the invention. Plant parts included but are not limited to a leaf, an ovule, pollen or a cell.

Plants according to the invention may be homozygous or heterozygous for a chromosomal locus linked to an aluminum tolerance phenotype. In further embodiments, the invention provides a seed of a plant according to the invention wherein the seed comprises a chromosomal locus linked to aluminum tolerance.

In still a further aspect, an alfalfa plant according to the instant invention comprises at least one additional trait of agronomic interest.

In yet another aspect, a tissue culture of regenerable cells of an alfalfa plant according to the invention is provided. The tissue culture may be capable of regenerating alfalfa plants capable of expressing all of the physiological and morphological characteristics of the starting plant (e.g., aluminum tolerance), and of regenerating plants having substantially the same genotype as the starting plant. The regenerable cells in such tissue cultures may be derived, for example, from embryos, meristems, cotyledons, pollen, leaves, anthers, roots, root tips, pistil, flower, seed, or stalks. In still further embodiments, the invention provides alfalfa plants regenerated from a tissue culture of the invention wherein the plants comprise aluminum tolerance.

In a further aspect, the present invention provides a method of producing progeny of a plant according to the invention, the method comprising the steps of: (a) preparing a progeny plant derived from an aluminum tolerant plant, wherein said preparing comprises crossing a plant according to the invention with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce further progeny plants. The derived plant may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, an aluminum tolerant plant is obtained which possesses some of the desirable traits of the line/hybrid as well as potentially other selected traits.

In still a further aspect there is provided a method of vegetatively propagating an alfalfa plant according to the invention comprising the steps of: (a) collecting tissue capable of being propagated from a plant according to the invention; (b) cultivating said tissue to obtain proliferated shoots; (c) rooting said proliferated shoots to obtain rooted plantlets; and, optionally, (d) growing plants from the rooted plantlets.

In certain aspects, the present invention provides a method of producing food or feed comprising: (a) obtaining a plant according to the invention, wherein the plant has been cultivated to maturity, and (b) collecting plant tissue from the plant. Plants according to the invention comprise, in certain aspects, a commercial alfalfa variety comprising aluminum tolerance. Accordingly, alfalfa produced from such plants may be of any variety.

In further aspects, the invention provides a method of making a commercial product comprising obtaining alfalfa according the invention and producing a commercial product therefrom.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan, however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A-I: Consensus linkage map and QTLs from Altet-4 chromosomes 1, 3 to 7, and NECS-141 chromosomes 1, 4, and 6. Linkage map sections represent QTL regions identified from the callus bio-assay, whole plant assay in media, and soil-based assay (as indicated) identified from interval mapping. QTL likelihood plots based on significant LOD scores are shown for the following phenotypic assays: Callus-AVG=average of callus growth ratio; Al50=Relative root length in whole plant assay in media (pH7Al−/pH4Al+), with Al+ 50 µM; Al1K=Relative root length in whole plant assay in media (pH7Al−/pH4Al+) with Al+ 1 mM); Rdmr=Relative root biomass in soil-based assay (experiment 1=Rdmr1, and experiment 2=Rdmr2). X-axis=LOD score, Y axis, position in cM.

FIG. 6A-D: FIG. 6A, Altet-4: Mean callus growth ratio of QTL genotypes on chromosome 3 (74 cM) from callus bioassay. FIG. 6B, Altet-4: Mean relative dry matter of roots of QTL genotypes on chromosome 4 (4 cM) from soil-based evaluations (Experiment 2, un-limed/limed). FIG. 6C, Altet-4: Mean relative dry matter of roots of QTL genotypes on chromosome 4 (38 cM) from soil-based evaluations (Experiment 1, un-limed/limed). FIG. 6D, Altet-4: Mean relative root growth (pH4Al+ 50 µM/pH7Al−) of QTL genotypes on chromosome 7 (70 cM) from whole plant assay in media.

FIG. 7A-C: FIG. 7A, NECS-141: Mean relative root growth (pH4Al+ 1 mM/pH7 Al−) of QTL genotypes on chromosome 1 (98 cM) from whole plant assay in media. FIG. 7B, NECS-141: Mean relative root growth (pH4Al+ 50 µM/pH7 Al−) of QTL genotypes on chromosome 1 (98 cM) from whole plant assay in media. FIG. 7C, NECS-141: Mean relative dry matter of roots from QTL genotypes on chromosome 4 (32 cM) based on soil-based evaluations (Experiment 2, un-limed/limed).

FIG. 9A-B: Al tolerance QTL on LG 1 explained 20.8% of the phenotypic variation for total callus weight ratio (TCWR) from the callus bio-assay. A) Composite map of LG 1 from Altet-4 and QTL likelihood plot. B) QTL allele effects at a given loci are based on the mean TCWR score of six possible allelic combinations. Error bars represent an average of the standard errors of all genotypes within each allelic combination. White numbers above the QTL genotype indicate the number of individuals with each allelic combination.

FIG. 10A-B: Al tolerance QTL on LG 4 of Altet-4 explained 15.2% of the phenotypic variation for total root length ratio (TRLR) in the whole plant assay in media. A) Composite map of LG 4 from Altet-4 and QTL likelihood plot. B) QTL allele effects at a given loci are based on the mean TRLR score of six possible allelic combinations. Error bars represent an average of the standard errors of all genotypes within each allelic combination. White numbers above the QTL genotype indicate the number of individuals with each allelic combination.

FIG. 11A-B: Al tolerance QTL on LG 7 of NECS-141 explained 21.7% of the phenotypic variation for total root length ratio (TRLR) from the whole plant assay in media. A) Composite map of LG 7 from NECS-141 and QTL likelihood plot. B) QTL allele effects at a given loci are based on the mean TRLR score of six possible allelic combinations. Error bars represent an average of the standard errors of all genotypes within each allelic combination. White numbers above the QTL genotype indicate the number of individuals with each allelic combination.

DETAILED DESCRIPTION OF THE INVENTION

Figure 1:
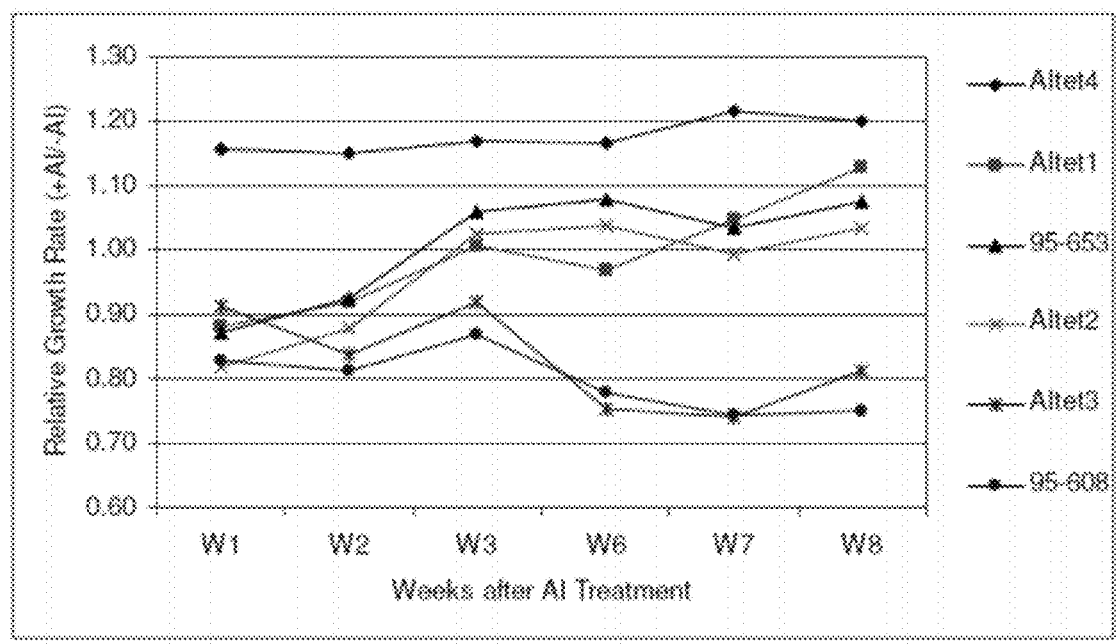
FIG. 1: Callus relative growth ratio (callus growth in medium with aluminum/callus growth in medium without aluminum) of six genotypes grown in Blaydes callus induction medium with and without aluminum.

The invention provides alfalfa exhibiting tolerance or enhanced tolerance to aluminum. Such plants can be referred to as aluminum tolerant alfalfa varieties. Methods of producing aluminum tolerant alfalfa plants are also provided. Also disclosed herein are methods of use and derivatives of the aluminum tolerant alfalfa plants. These findings can be used to enable implementation of effective molecular breeding strategies through SNP genotyping and other high-throughput platforms to accelerate the development of alfalfa cultivars with desirable agronomic characteristics that are adapted to a range of growing conditions, and are productive in acid and Al toxic soils.

The aluminum tolerant *Medicago sativa* alfalfa plants of the invention may bear one or more alleles conferring aluminum tolerance that have been introduced from other members of the *Medicago* genus employing techniques described herein. According to the invention, such traits may be introduced, for the first time, into agronomically elite varieties. Likewise, loci that contribute to aluminum tolerance have been identified in less-aluminum-tolerant plants. These loci can be introgressed or maintained in a line to enhance aluminum tolerance. Aluminum tolerant alfalfa plants of the present invention may thus display vigorous growth and other desirable properties for cultivation.

The invention also provides methods for introgression of aluminum tolerance into an alfalfa line. Through multiple rounds of backcrossing, chromosomal loci linked to aluminum tolerance may be introgressed into any other genotype according to the invention. This allows production of agronomically elite plants with aluminum tolerance. The backcrossing allows recovery of a starting genotype together with the desired aluminum tolerance alleles. For example, aluminum tolerant lines may comprise a genome that is 80%, 85%, 90%, 95%, 98%, or more *Medicago sativa* L. sequence from any particular background. Aluminum tolerant plants according to the invention may be defined, in certain embodiments, as "locus converted plants," wherein essentially all of the desired morphological and physiological characteristics of a variety are recovered in addition to the characteristics of the single locus transferred into the variety via a backcrossing or by genetic transformation. Such lines may be heterozygous for chromosomal loci linked to aluminum tolerance or may be homozygous for such loci. Homozygous lines may have particular use, for example, as parents for selfing to produce inbred seed or crossing with a second elite alfalfa line for generating hybrid alfalfa seed.

Introgression of aluminum tolerance in accordance with the invention may be affected by marker-assisted selection. In particular, the invention provides genetic markers genetically linked to alleles conferring aluminum tolerance. Thus, tracking of markers linked to these loci allows efficient identification of progeny plants harboring aluminum tolerance. High-throughput breeding techniques using marker-assisted selection can be used to rapidly introgress loci into an agronomically elite background and thereby produce commercially viable aluminum tolerant lines. Introgression of aluminum tolerance in alfalfa may also be performed by genomic selection. Genomic selection (GS) predicts the breeding values of lines in a population by analyzing their phenotypes and marker scores (Heffner et al., *Crop Sci.* 49:1-12, 2009). GS incorporates all marker information in the prediction model, thus avoiding biased estimates of the marker effect and capturing more of the variation due to small effect quantitative trait loci (QTL).

As used herein, an "agronomically elite" alfalfa plant or line refers to plants or varieties exhibiting traits appropriate for commercial production, which are well known to those of skill in the art. For example, agronomically elite plants are capable of producing a commercial scale hay or silage yield. In certain aspects, agronomically elite plants and lines produce alfalfa of uniform size, color and quality. Agronomically elite lines may also exhibit desirable hardiness traits, such as disease resistance, cold tolerance, environmental stress tolerance, persistence, forage quality, and nutrient utilization, or use traits such as improved harvestability.

As used herein, a "control alfalfa plant" is any alfalfa plant susceptible to aluminum (aluminum susceptible), including typical commercially available and wild relatives of modern alfalfa plants. A control alfalfa plant is also grown under similar environmental conditions to a test plant according to the present disclosure.

As used herein, a "hybrid alfalfa plant" includes a plant resulting directly or indirectly from crosses between populations, breeds or cultivars within the species *Medicago sativa*. This also refers to plants resulting directly or indirectly from crosses between different species within the *Medicago* genus (e.g., interspecific hybrids resulting from crosses between *Medicago sativa* and *Medicago truncatula* or crosses between *Medicago sativa* and *Medicago trifolium*).

As used herein an "aluminum tolerant alfalfa plant" displays an increased tolerance to aluminum, or a decrease in the development of symptoms of aluminum susceptibility, when compared to the parental *Medicago sativa* plant or a control alfalfa line grown under similar environmental conditions.

As used herein, a descendent or progeny of a particular plant includes not only, without limitation, the products of any initial cross (be it a backcross or otherwise) between two plants, but all descendants whose pedigree traces back to the original cross. In an aspect of the present invention, the descendent contains about 50%, 25%, 12.5%, 6%, 3%, 1%, or less nuclear DNA from an aluminum tolerant alfalfa plant and expresses that genetic material to provide at least a portion of the plant's aluminum tolerance.

Aluminum tolerant alfalfa plants also include alfalfa cultivars, lines or varieties having tolerance to aluminum, referred to herein as aluminum tolerant alfalfa cultivars, aluminum tolerant alfalfa lines, or aluminum tolerant alfalfa varieties respectively. Aluminum tolerant alfalfa cultivars, aluminum tolerant alfalfa lines, or aluminum tolerant alfalfa varieties may have been bred and selected for at least aluminum tolerance and may also have been selected for other desirable traits.

As used herein, a "female parent" refers to an alfalfa plant that is the recipient of pollen from a male donor line, which successfully pollinates an egg. A female parent can be any alfalfa plant that is the recipient of pollen. Such female parents can be male sterile, for example, because of genetic male sterility, cytoplasmic male sterility, or because they have been subject to emasculation of the stamens. Genetic or cytoplasmic male sterility can be manifested in different manners, such as sterile pollen, malformed or stamenless flowers, positional sterility, and functional sterility.

As used herein, "cytoplasmic male sterility" refers to plants that are not usually capable of breeding from self-pollination, but are capable of breeding from cross-pollination.

As used herein, "linkage" or "genetic linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), simple sequence length polymorphisms (SSLPs), insertion(s)/deletion(s) (INDEL(s)), and random amplified polymorphic DNA (RAPD) sequences. A marker may be codominant and completely heritable (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with aluminum tolerance. A "molecular marker" as used herein means a nucleic acid molecule that is capable of being a marker for detecting a polymorphism, phenotype, or both associated with aluminum tolerance. Genetic maps and markers for use in alfalfa are known in the art (Brummer et al., *Theor Appl Genet* 86:329-332, 1993; Echt et al., *Genome* 37:61-71 1993; Kiss et al., *Mol Gen Genet* 238:129-137, 1993; Brower et al., *Crop Sci* 40:1387-1396, 2000; Robins et al., *Crop Sci* 48:1780-1786, 2008; Robins et al., *Crop Sci* 47 1-10, 2007).

As used herein, a "desirable trait" or "desirable traits" that may be introduced into aluminum tolerant alfalfa plants by breeding may be directed to the alfalfa plant. Desirable alfalfa plant traits that may be independently selected include, but are not limited to, plant vigor, leaf shape, leaf length, leaf color, plant height, time to maturity, adaptation to field growth, persistance, forage quality, and resistance to one or more diseases or disease causing organisms. Any combination of desirable alfalfa traits may be combined with aluminum tolerance.

The present invention provides for one or more aluminum tolerant alfalfa plants. The aluminum tolerance of any alfalfa plant provided herein can be a tolerance to high concentrations of aluminum or a tolerance to low concentrations of aluminum, wherein either the high or low concentration of aluminum would cause symptoms in a non-aluminum-tolerant alfalfa plant. The aluminum tolerance of an alfalfa plant provided herein can be measured by any means available in the art.

In one aspect, the aluminum tolerance of an alfalfa plant is determined using a callus or tissue culture assay. The assay may comprise inducing callus formation, transferring one part of the induced callus to a growth medium comprising aluminum, and a second part of the callus to a growth medium which does not comprise aluminum. The growth medium may be Blaydes callus induction medium, and the callus may be grown in controlled growth chambers at 25° C. and with an 18-hour light photoperiod. The assay may further comprise weighing the callus. The assay may further comprise comparing the relative weights or amount of growth between the two parts of the callus.

In another aspect, the aluminum tolerance of an alfalfa plant is determined using a whole-plant culture media assay. The assay may comprise growing vegetatively propagated alfalfa clones or stem cuttings in culture media comprising 400 μM $CaCl_2$, 1.4% gel rite, 0 or 50 μM $Al^{+3}$ in the form of $AlCl_3$, and pH 7.0 or 4.0 adjusted using 1 N HCl, and the alfalfa may be grown in controlled-environment growth chambers at 25° C. with an 18-hour light photoperiod.

Root growth may be quantified using winRHIZO® software (Regent Instruments, Québec, Canada) to determine aluminum tolerance. For example, total root length, lateral root numbers, and branching may be quantified. The absolute root growth and ratio of root characteristics (biomass, length, and branching) after 3 weeks of growth in either aluminum-containing media or aluminum-free media may also be used for determining aluminum tolerance.

In another aspect, the alfalfa plants and lines provided herein demonstrate little or no aluminum toxicity symptoms after treatment with aluminum. In some aspects, an aluminum tolerant alfalfa genotype demonstrates aluminum toxicity symptoms in less than 10%, 9%, 8%, 7%, 6%, 5%, 4%, 3% 2%, or 1% of alfalfa plants of that genotype.

Aluminum tolerant alfalfa plants may exhibit a delay in the onset of aluminum toxicity symptoms relative to a non-tolerant control alfalfa plant. In some embodiments, the aluminum tolerant alfalfa plants exhibit a delay of 1, 2, 3, 4, 5, 6, 7, 8, 9, 10, 11, 12, 13, 14, or more days in the onset of aluminum toxicity symptoms relative to a control alfalfa plant. In other embodiments, the aluminum tolerant alfalfa plants exhibit a delay of at least 7 or more days, 10 or more days, or 14 or more days in the onset of aluminum toxicity symptoms relative to a control alfalfa plant.

In one aspect, the alfalfa plant is a seedling at the time of aluminum exposure. In some aspects, the alfalfa plant is a seedling at the trifoliate leaf stage of development at the time of aluminum exposure. In one aspect, aluminum toxicity symptoms can be measured at any time after aluminum exposure of an alfalfa plant. In other aspects, symptoms can be measured 2, 3, 4, 5, 6, 7, 8, 9, 10, 11, 12, 13, 14, 15, 16, 17, 18, 19, 20, 21, or more days after exposure. In another aspect, the alfalfa plant is any age of plant at the time of exposure.

In another aspect, the alfalfa plant is a callus at the time of aluminum exposure. In some aspects, the callus has been allowed to form for about two weeks in Blaydes callus induction medium before exposure. In one aspect, aluminum toxicity symptoms can be measured at any time after aluminum exposure of an alfalfa callus. In other aspects, symptoms can be measured 2, 3, 4, 5, 6, 7, 8, 9, 10, 11, 12, 13, 14, 15, 16, 17, 18, 19, 20, 21, or more weeks after exposure. In another aspect, the alfalfa callus is any age of callus at the time of exposure.

In another aspect, the alfalfa plant is a vegetatively propagated alfalfa clone or stem cutting at the time of aluminum exposure. In some aspects, the vegetatively propagated alfalfa clone or stem cutting has been allowed to develop in medium comprising 400 μM $CaCl_2$, 1.4% gel rite, 0 or 50 μM $Al^{+3}$ in the form of $AlCl_3$ before exposure. In one aspect, aluminum toxicity symptoms can be measured at any time after aluminum exposure of an alfalfa plant. In other aspects, symptoms can be measured 2, 3, 4, 5, 6, 7, 8, 9, 10, 11, 12, 13, 14, 15, 16, 17, 18, 19, 20, 21, or more days after exposure. In another aspect, the alfalfa plant is any age of plant at the time of exposure.

Aluminum tolerant alfalfa plants of the present invention may exhibit an increase in callus relative growth ratios after exposure to aluminum when compared to the relative growth rate of a control alfalfa callus exposed to aluminum. In one aspect, the aluminum tolerant alfalfa callus exhibit a 1%, 2%, 5%, 10%, 15%, 20%, or more increase in callus relative growth ratio relative to a control alfalfa plant after exposure to aluminum.

The present invention provides for a seed of an alfalfa plant capable of producing an aluminum tolerant alfalfa plant. In one aspect, the aluminum tolerant alfalfa plant can be an open-pollinated variety, a hybrid parent inbred line, or a male sterile line.

The aluminum tolerant alfalfa plants of the present invention can be aluminum tolerant alfalfa lines adapted for field alfalfa production or any other growing environment. In one aspect, the aluminum tolerant alfalfa plants of the present invention are adapted for open field alfalfa production.

The present invention also provides for an intra-specific hybrid alfalfa plant having aluminum tolerance developed from aluminum tolerant alfalfa plants. In another aspect, those intra-specific hybrid alfalfa plants exhibit aluminum tolerance after exposure to aluminum.

Agronomically elite alfalfa plants appropriate for use in a commercial production field represent various aspects of the present invention. In one aspect, certain alfalfa traits, including, for example, hay or silage quality, may be important to the commercial value of the crop.

A further aspect of the invention relates to tissue cultures of the aluminum tolerant alfalfa plants described herein. As used herein, the term "tissue culture" indicates a composition comprising isolated cells of one or more types, or a collection of such cells organized into parts of a plant. Tissue culture includes, but is not limited to, compositions comprising protoplasts and calli. Tissue culture also includes, but is not limited to, compositions comprising plant cells that are present in intact plant tissues, or parts of plants, such as embryo, leaf, peduncle, pedicel, anther, meristem, tip and segments of root, stump and stem, explants, and the like. In one aspect, a tissue culture comprises embryos, protoplasts, meristematic cells, pollen, leaves, anthers, or cells derived from immature tissues of these plant parts. Means for preparing and maintaining plant tissue cultures are well known in the art. Examples of processes of tissue culturing and regeneration of alfalfa are described in, for example, Parrot and Bouton, *Crop Sci.*, (1990) 30:387-389. In some aspects, tissue culture of the aluminum tolerant alfalfa plants described herein relates to the culture of protoplasts, calli, or plant cells, that are isolated from, or present in, intact parts of the aluminum tolerant alfalfa plants described herein. In another aspect, tissue culture refers to the culture of protoplasts, calli, or plant cells, that are isolated from, or present in, intact parts of one or more aluminum tolerant plants selected from the group consisting of Altet1, Altet2, Altet3, and/or Altet4, and aluminum tolerant descendants thereof, including those produced by crosses or backcrosses. In yet another aspect, tissue culture of the aluminum tolerant alfalfa plants described herein relates to the culture of protoplasts, calli, or plant cells, that are isolated from, or present in, intact parts of the aluminum tolerant plants described herein.

Once aluminum tolerant alfalfa plants are produced, the plants themselves can be cultivated in accordance with conventional procedures. Aluminum tolerant descendants of aluminum tolerant alfalfa plants may be obtained through sexual reproduction. The seeds resulting from sexual reproduction can be recovered from the aluminum tolerant alfalfa plants and planted or otherwise grown as a means of propagation. Aluminum tolerant descendents may also be obtained from aluminum tolerant alfalfa plants through asexual reproduction. Protoplast or propagules (e.g., cuttings, scions, or rootstocks) can be recovered from aluminum tolerant alfalfa plants, or parts thereof, and may be employed to propagate aluminum tolerant alfalfa plants.

The present invention also provides for and includes a container of alfalfa seeds in which alfalfa plants grown from greater than 50% of the seeds have resistance or partial aluminum tolerance. In another aspect, alfalfa plants grown from greater than 55%, 60%, 65%, 70%, 75%, 80%, 85%, 90%, 95%, 98%, or 99% of the alfalfa seeds in the container have aluminum tolerance. Another aspect of the invention relates to seeds from an alfalfa plant selected from the group consisting of Altet1, Altet2, Altet3, Altet4, and aluminum tolerant descendents thereof, wherein alfalfa plants grown from about 50%, or greater than 50%, of the seeds have resistance or partial aluminum tolerance.

The container of alfalfa seeds can contain any number, weight or volume of seeds. For example, a container can contain about, or greater than about, 10, 25, 50, 100, 200, 300, 400, 500, 600, 700, 800, 900, 1000, 1500, 2000, 2500, 3000, 3500, 4000, or more seeds. In another aspect, a container can contain about, or greater than about, 1 gram, 5, 10, 15, 20, 25, 50, 100, 250, 500, or 1,000 grams of seeds. Alternatively, the container can contain about or at least, or greater than, about 1 ounce, 2, 3, 4, 5, 6, 7, 8, 9, 10 ounces, 1 pound, 2, 3, 4, 5, 6, 7, 8, 9, 10, 11, 12 pounds or more of seeds.

Containers of alfalfa seeds can be any container available in the art. For example, a container can be a box, a bag, a packet, a pouch, a tape roll, a foil, a pail, or a tube.

One aspect of the invention relates to dried, or otherwise processed alfalfa hay, produced by an alfalfa plant having a genome that comprises at least one genetic locus giving rise to aluminum tolerance when expressed in an alfalfa plant. Processed alfalfa can be in the form of, but is not limited to, hay, silage, haylage, fermented hay, or greenchop. In some aspects, the dried, or otherwise processed alfalfa, is from an alfalfa plant selected from one or more of the group consisting of Altet1, Altet2, Altet3 and/or Altet4, and aluminum tolerant descendents thereof.

The present invention includes and provides for *Medicago sativa* plants having at least one allele for an aluminum tolerance trait. The aluminum tolerant alfalfa plants can be either heterozygous or homozygous for the aluminum tolerance trait. In one embodiment, the aluminum tolerance trait can be linked to variations in a single gene (e.g., linked to one or more alleles of a single gene). In another embodiment, the aluminum tolerance trait can be linked to variations at one or one or more quantitative trait loci (QTL). In a yet another embodiment, the aluminum tolerant alfalfa plants are homozygous for the aluminum tolerance trait. In one aspect, the genetic loci derived from an aluminum tolerant alfalfa plant can be identified using genetic markers.

The present invention provides for an aluminum tolerant alfalfa plant having less than or equal to 50% of its genome derived from a non-*M. sativa* aluminum tolerant plant that can be crossed directly, or indirectly (e.g., through tissue culture manipulation, or through the use of a bridging species) with *Medicago sativa*. The present invention also provides for descendents of alfalfa plants having aluminum tolerance.

One aspect of the present invention provides for an aluminum tolerant alfalfa plant that contains a genetic marker or a complement to a genetic marker linked to one or more aluminum tolerance loci. Another aspect of the invention is an alfalfa plant that contains at least 1, 2, 3, or 4 sequences complementary to markers linked to an aluminum tolerance locus. In another aspect, an alfalfa plant can contain sequence complementary to any combination of markers linked to the aluminum tolerance locus.

As used herein linkage of two loci, including a marker sequence and an allele imparting a desired trait such as aluminum tolerance, may be genetic or physical or both. In one aspect of the invention, a nucleic acid marker and genetic locus conferring aluminum tolerance are genetically linked and, for example, are located less than 50 cM from one another. In particular embodiments, the marker and locus may exhibit a LOD score of greater than 2.0, as judged by interval mapping for the aluminum tolerance trait based on maximum likelihood methods described by Lander and Botstein, *Genetics,* 121:185-199 (1989), and implemented in the software package MAPMAKER (default parameters). In other embodiments, the marker and region conferring aluminum tolerance are genetically linked and exhibit a LOD score of greater than 3.0, or a LOD score of greater than 3.5, or a LOD score of about 4.0 based upon interval mapping.

In another aspect, the nucleic acid marker is genetically linked at a distance of between about 0 and about 49 centimorgans (cM) to the aluminum tolerance locus. In other embodiments, the distance between the nucleic acid marker and the aluminum tolerance locus is between about 0 and about 30 cM, or between about 0 and about 20 cM, or between about 0 and about 15 cM, or between about 0 and about 10 cM, or between about 0 and about 5 cM, or less. See, for example, FIG. 5 which provided relative distance in cM between identified loci.

In another aspect, the nucleic acid molecule may be physically linked to an aluminum tolerance locus. In some aspects, the nucleic acid marker specifically hybridizes to a nucleic acid molecule having a sequence that is within about 30 Mbp, or about 20 Mbp, or about 15 Mbp, or about 10 Mbp, or about 5 Mbp of an aluminum tolerance locus.

As used herein, two nucleic acid molecules are said to be capable of hybridizing to one another if the two molecules are capable of forming an anti-parallel, double-stranded nucleic acid structure. Conventional stringency conditions are described by Sambrook et al., Molecular Cloning, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0x sodium chloride/sodium citrate (SSC) at about 45° C., followed by a wash of 2.0xSSC at 50° C., are known to those skilled in the art or can be found in *Current Protocols in Molecular Biology*, John Wiley & Sons, N.Y. (1989), 6.3.1-6.3.6. In some embodiments, hybridization conditions can be high, moderate or low stringency conditions. High stringency conditions, for example, typically include a wash step at 65° C. in 0.2xSSC.

The specificity of hybridization can be affected by post-hybridization washes. For example, the salt concentration in the wash step can be selected from a low stringency of about 2.0xSSC at 50° C. to a moderate stringency of about 1.0xSSC at 50° C. to a high stringency of about 0.2xSSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid plant produced using that plant as a parent. For example, if an inbred plant having a known genetic marker profile and phenotype is crossed with a second inbred plant having a known genetic marker profile and phenotype, it is possible to predict the phenotype of the $F_1$ hybrid based on the combined genetic marker profiles of the parent inbred plants. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, or isozymes.

Additional markers, such as SSRs, AFLP markers, RFLP markers, RAPD markers, phenotypic markers, SNPs, isozyme markers, or microarray transcription profiles that are genetically linked to or correlated with aluminum tolerance can be utilized (Walton, *Seed World* 22-29 (July, 1993); Burow and Blake, *Molecular Dissection of Complex Traits,* 13-29, Eds. Paterson, CRC Press, New York (1988)). Methods to isolate such markers are known in the art. For example, locus-specific SSRs can be obtained by screening an alfalfa genomic library for SSRs, sequencing of "positive" clones, designing primers which flank the repeats, and amplifying genomic DNA with these primers.

The genetic linkage of marker molecules to aluminum tolerance can be established by a gene mapping model such as, without limitation, the flanking marker model reported by Lander and Botstein, *Genetics,* 121:185-199 (1989), and the interval mapping, based on maximum likelihood methods described by Lander and Botstein, *Genetics,* 121:185-199 (1989), and implemented in the software package MAPMAKER.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein, *Genetics,* 121:185-199 (1989), and further described by Ars and Moreno-Gonzalez, *Plant Breeding*, Hayward, Bosemark, Romagosa (eds.) Chapman & Hall, London, pp. 314-331 (1993).

Selection of appropriate mapping or segregation populations is important in trait mapping. The choice of appropriate mapping population depends on the type of marker systems employed (Tanksley et al., *Molecular mapping plant chromosomes. Chromosome structure and function: Impact of* new concepts, J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

The present application provides a genetic complement of the alfalfa lines described herein. Further provided is a hybrid genetic complement, wherein the complement is formed by the combination of a haploid genetic complement from elite inbred alfalfa lines described herein and another haploid genetic complement. Means for determining such a genetic complement are well known in the art.

As used herein, the phrase "genetic complement" means an aggregate of nucleotide sequences, the expression of which defines the phenotype of a plant, such as a *Medicago sativa* alfalfa plant or a cell or tissue of that plant. By way of example, a *Medicago sativa* alfalfa plant is genotyped to determine a representative sample of the inherited markers it possesses. Markers may be inherited in codominant fashion so that the presence of both alleles at a diploid or tetraploid locus is readily detectable, and they are free of environmental variation, i.e., their heritability is close to, or equal to, 1. This genotyping is may be performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified $F_2$ population using a codominant marker system (Mather, Measurement of Linkage in Heredity: Methuen and Co., (1938)). An $F_2$ population is the first generation of self or sib pollination after the hybrid seed is produced. Usually, a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals in the preceding generation. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single-plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., linkage disequilibrium).

Recombinant inbred lines (RILs) (genetically related lines; usually >$F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci. (U.S.A.)* 89:1477-1481, 1992). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., *Proc. Natl. Acad. Sci. (U.S.A.)* 89:1477-1481, 1992).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci are polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., *Proc. Natl. Acad. Sci. (U.S.A.)* 88:9828-9832, 1991). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing an aluminum tolerant alfalfa plant comprising: (a) crossing an aluminum tolerant alfalfa line with a second alfalfa line lacking aluminum tolerance to form a segregating population; (b) screening the population for aluminum tolerance; and (c) selecting one or more members of the population having said aluminum tolerance. In one aspect, plants are identified as aluminum tolerant prior to conducting one or more crosses. In one aspect, plants can be selected on the basis of partial or complete aluminum tolerance. In one aspect, the segregating population is self-crossed and the subsequent population is screened for resistance.

In another aspect, the present invention provides a method of introgressing aluminum tolerance into an alfalfa plant comprising: (a) crossing at least a first aluminum tolerant alfalfa line with a second alfalfa line to form a segregating population; (b) screening said population for aluminum tolerance; and (c) selecting at least one member of said population exhibiting aluminum tolerance. In one aspect, plants are identified as aluminum tolerant prior to conducting one or more crosses. In one aspect, the segregating population is self-crossed and the subsequent population is screened for resistance.

Aluminum tolerant alfalfa plants of the present invention can be part of, or generated from, a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches for breeding the plants of the present invention are set forth below. A breeding program can be enhanced using marker-assisted selection, or marker-assisted backcrossing, of the descendents of any cross. It is further understood that any commercial and non-commercial cultivars can be utilized in a breeding program. Factors such as, for example, emergence vigor, vegetative vigor, stress tolerance, disease resistance, branching, flowering, seed size, forage quality, and/or forage yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In some embodiments a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better performance estimate. A breeder can select and cross two or more parental lines, followed by repeated self or sib pollinating and selection, producing many new genetic combinations.

The development of new alfalfa lines requires the preparation and selection of alfalfa varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of an aluminum tolerant alfalfa plant may be conducted where the other parent (second alfalfa plant) is aluminum tolerant or the other parent is not aluminum tolerant.

Alfalfa plants generated of the invention may be generated using a single-seed descent procedure. The single-seed descent procedure, in the strict sense, refers to planting a segregating population, then selecting one plant in this and each subsequent generation to self and create the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the F$_2$ plants originally sampled in the population will be represented by a progeny when generation advance is completed.

Descriptions of other breeding methods that are commonly used for different traits and crops can be found in reference texts (e.g., Fehr, *Principles of Cultivar Development* Vol. 1, pp. 2-3, 1987).

In one aspect of the present invention, the source of aluminum tolerance trait for use in a breeding program is derived from a plant selected from the group consisting of Altet1, Altet2, Altet3, Altet4 and aluminum tolerant descendants thereof. In another aspect, the source of the aluminum tolerance trait for use in a breeding program is derived from a plant selected from the group consisting of Altet4 and aluminum tolerant descendants thereof.

Another aspect of the invention is directed to an inbred alfalfa plant, wherein said resistance is exhibited when said plant is in contact with aluminum. In one embodiment the inbred plant is an aluminum tolerant alfalfa plant. Also included in the invention is an alfalfa plant having a genome, wherein said genome comprises one or more genetic loci conferring aluminum tolerance, wherein said one or more genetic loci associated with one or more genetic markers linked thereto.

In one aspect, additional sources of aluminum tolerance for use in a breeding program can be identified by screening alfalfa germplasm for aluminum tolerance. In a yet another aspect, alfalfa plants can be screened for aluminum tolerance by identifying germplasm exhibiting reduced aluminum toxicity relative to a control alfalfa plant after inoculation or infection. In one aspect, alfalfa plants can be screened for aluminum tolerance using a method as described in Example 2. In another aspect, alfalfa plants can be screened for aluminum tolerance using a method as described in Example 3.

In another aspect, additional sources of aluminum tolerance for use in a breeding program can be identified by screening with one or more molecular markers linked to a genetic locus conferring aluminum tolerance.

In another aspect, aluminum tolerant alfalfa plants, varieties, lines or cultivars can be used in breeding programs to combine aluminum tolerance with additional traits of interest. In one aspect, aluminum tolerance can be combined with any additional trait, including other disease resistant traits, yield traits, and hay quality traits. Breeding programs can also be used to combine aluminum tolerance with one or more disease resistant traits. In another aspect, the traits that are combined can be co-inherited in subsequent crosses.

The present invention also provides for parts of the aluminum tolerant alfalfa plants produced by a method of the present invention. Parts of alfalfa plants, without limitation, include plant cells or parts of plant cells, seed, endosperm, meristem, flower, anther, ovule, pollen, callus, flowers, stems, roots, stalks or leaves, scions, and root stocks. In one embodiment of the present invention, the plant part is a seed.

The invention further provides for parts of an aluminum tolerant alfalfa plant having a genome, which comprises at least one genetic locus giving rise to aluminum tolerance in the alfalfa plant. In another embodiment, parts of alfalfa plants are derived from an alfalfa plant selected from the group consisting of Altet1, Altet2, Altet3 and Altet4, and aluminum tolerant descendants thereof.

One aspect of the invention includes a aluminum tolerant alfalfa plant, or the hay or seeds thereof, wherein the alfalfa plant, or the hay or seeds thereof, expresses one, or two, or three, or more independently selected desirable traits in addition to aluminum tolerance. In other aspects of the invention, the plants bearing one or more desirable traits in addition to aluminum tolerance display a greater than 10%, or a greater than 30%, or a greater than 60%, or a greater than 80% reduction in of aluminum toxicity symptoms relative to a non-resistant control plant upon exposure to aluminum. Another aspect of the present invention is directed to a method of producing an aluminum tolerant alfalfa plant comprising: crossing an aluminum tolerant alfalfa plant, or a plant from an aluminum tolerant alfalfa line, cultivar or variety with a second plant lacking aluminum tolerance but capable of donating one or more of the aforementioned desirable traits.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Plant Materials

The diploid Al-tolerant alfalfa Al-4 (Narasimhamoorthy et al., *Theor Appl Genet* 114:901-91, 2007b) was crossed with individual genotypes from the synthetic non-dormant tetraploid variety CUF 101 (Lehman et al., *Crop Sci* 23 398-399, 1983) to produce seeds from Altet-1 through Altet-4. Altet-4 (Al-tolerant) was manually crossed in the greenhouse with NECS-141 (semi-dormant breeding line developed in Iowa and derived from a strain cross between 5454, Oneida VR, and Apica). A total of 185 individuals from the NECS141Altet4 population were used for phenotyping and mapping. Of these, 110 F$_1$ progeny were derived from Altet-4 as the maternal parent and 75 individuals had NECS-141 as the maternal parent. Individual F$_1$ seeds were stored for 72 h at −20 C.°, scarified using sand-paper, and planted in a germination mix in the greenhouse. Stem cuttings of individual genotypes were collected from the greenhouse and sterilized using 70% EtOH for 5 min followed by rinsing 3X with sterilized double distilled water for 5 min. All genotypes were clonally propagated in modified MS medium (Murashige and Skoog, *Physiol Plant* 15:473-797, 1962) containing the MS basal salt mixture (PhytoTechnology Laboratories, product number M524) containing 2 mg/l of Indole-3-butyric acid (IBA) and 2% sucrose (Invitrogen, catalog number 15503-022) using the axillary and terminal meristems.

Example 2

Callus Bioassay Assay (CBA) for Evaluating Aluminum Tolerance

Individuals from the NECS141Altet4 population, NECS-141, Altet-1 through Altet-4, and the CUF101-derived genotypes 95-608 and 95-653, were evaluated for their Al-tolerance response using Blaydes medium (ALB) to induce callus formation (Parrot and Bouton, 1990). Half of a single 2-week-old callus was transferred to Blaydes media with Al ("ALB+" with 400 µM of Al supplied by $AlCl_3$, pH 4.0) and the other half was transferred to Blaydes medium without Al ("ALB−" at pH 4.0) as previously described (Parrot and Bouton, *Crop Sci* 30:387-389, 1990). Individual calli were weighed and transferred to fresh ALB+ and ALB− media at one week intervals for 8 weeks to determine the relative growth rate of each genotype. The experimental design was a randomized complete block design with three replications, each of which consisted of five individual calli per genotype per treatment.

Example 3

Whole-Plant Assay (WPA) for Evaluating Aluminum Tolerance

Vegetatively propagated alfalfa clones (stem cuttings) from each individual in the mapping population were used to evaluate the same genotype across replications and treatments using a culture media adapted from Ma et al., (*Nature* 390:569-570, 1997) containing 200 µM $CaCl_2$, 1.4% Gelzan, either 0, 50 µM or 1 mM Al supplied as $AlCl_3$, and pH 7.0 or 4.0 adjusted using 1 N HCl. Apical stem cuttings were rooted in least macro salt (LMS) medium which consisted of 0.1 mM $CaCl_2$, 500 µM $KNO_3$ and 500 µM $MgSO_4$ and 1.2% Gelzan. Cuttings with visually uniform root size and lateral root number were transferred to $CaCl_2$ medium −Al and +Al (1 mM $AlCl_3$). Plant evaluations using both the callus bioassay and the whole plant assay in media were conducted in controlled-environment growth chambers at 25° C. and 18 h light photoperiod. Quantification of total root length, lateral root numbers, and branching was performed using the winRHIZO® software (Regent Instruments, Québec, Canada) commonly used to identify quantitative differences in root branching and length (Jahufer et al., *Crop Sci.* 48:487-494, 2008; Zhu et al., *Funct. Plant Biol.* 32:749-762, 2005). The absolute root growth and ratio of root characteristics (biomass, length, and branching) after 2 weeks of growth in Al+ and Al− media were used as quantitative measurements to determine Al tolerance.

Example 4

Genotyping and QTL Identification

Genomic DNA from each individual from the NECS141Altet4 mapping population was extracted separately using DNeasy™ Plant Mini Kit (QIAGEN, Cat. No. 69104, Valencia, USA). A total of 1024 EST-SSR primer pairs distributed throughout the alfalfa linkage groups (Sledge et al., *Theor Appl Genet* 111:980-992, 2005) and those developed from alfalfa trichome ESTs (Mtri) were used to evaluate polymorphism between Altet-4, 95-608, and NECS-141 and genotyping as previously described (Zhang et al., *Plant Methods* 4:19, 2008). A total of 538 polymorphic SSR primers pairs were used for genotyping and to identify any selfed progeny (exemplary primers are provided in Table 1). Genes implicated in the Al tolerance response in other species, including those involved in organic acid synthesis (malate dehydrogenase, aluminum-activated malate transporter (ALMT), citrate synthase, citrate dehydrogenase, isocitrate dehydrogenase, oxalate oxidase, superoxide dismutase, acid phosphatases, peroxidases), signal transduction pathways, oxidative stress (phosphoenolpyruvate carboxylase, PEPC), and transporters (Ermolayev et al., *Exp Bot* 54:2745-2756, 2003; Maron et al., 2008; Tesfaye et al., *Pl. Physiol.* 127:1836-1844, 2001) were used to identify homologous genes in *M. truncatula* and to design molecular markers. Additional gene targets for marker development included Al responsive genes identified from transcript profiling in *Medicago truncatula* (Chandran et al., 2008).

Amplicons obtained using microsatellites were visualized and scored using GeneMapper™ 3.7 software. PCR reactions producing single amplification products using primers designed from putative orthologs of candidate genes implicated in Al tolerance were used to identify length polymorphism or sequenced with the BigDye® terminator v3.1 cycle sequencing kit (Applied Biosystems) and analyzed using an ABI3730 genetic analyzer to confirm amplification of the target sequence and identify candidate SNPs. Polymorphic amplicons segregating in the population were scored as described by Hackett et al. (*J Hered* 94:358-359, 2003). Simplex (1:1), duplex (5:1), and double simplex (3:1) markers were scored based on their segregation ratio in the population to achieve maximum resolution on the parental linkage map. Recombination frequencies and clustering of markers into linkage groups (LGs) was performed using the software TetraploidMap (Hackett et al., *Genetics* 159:1819-1832, 2001; Hackett et al., *J. Hered.* 98:727-729, 2007) previously used for mapping in alfalfa (Julier et al., *BMC Plant Biol.* 3:9, 2003; Robins et al., *Crop Sci.* 48:1780-1786, 2008; Robins et al., *Crop Sci.* 47:11-16, 2007). MapChart (Voorrips, *J. Hered.* 93:77-78, 2002) was used to construct the resulting linkage groups (LG). Interval mapping for autotetraploid species was implemented for QTL analysis as described by (Hackett et al., *Genetics* 159:1819-1832, 2001). The 'TetraploidMap' software program (Hackett and Luo, *J Hered* 94:358-359, 2003) was used for all analytical procedures for QTL interval mapping. Multiple regression analysis for each of the identified QTLs was performed to determine the allelic effect at each QTL region.

TABLE 1

Alfalfa genomic and trichome EST-SSRs used to genotype the mapping populations.

| Primer ID | Reverse primer sequence | Forward primer sequence |
|---|---|---|
| 122161-41 | CCACGTTGTTGAACAGTGGAAATG (SEQ ID NO: 1) | TGTAAAACGACGGCCAGTGCGAACTTGTTTCCGATGATGC (SEQ ID NO: 2) |
| 1a07.aac.5-1 | GAGCCATGTTGTTGGTGTTG (SEQ ID NO: 3) | TGTAAAACGACGGCCAGTTTGGTTGGTGGGGTTATCAT (SEQ ID NO: 4) |
| 1a09.ggt.5-1 | TCTCTGGTCAGCACCAACTG (SEQ ID NO: 5) | TGTAAAACGACGGCCAGTGCATGGTGAGAGACGTCGTA (SEQ ID NO: 6) |

TABLE 1-continued

Alfalfa genomic and trichome EST-SSRs used to genotype the mapping populations.

| Primer ID | Reverse primer sequence | Forward primer sequence |
|---|---|---|
| 1b08.aga.7-1 | TGGAGGGAAATGATTTAGCG (SEQ ID NO: 7) | TGTAAAACGACGGCCAGTAACGAAAACGAAAACGAACG (SEQ ID NO: 8) |
| 1b11.gtg.6-1 | AACCTCCTCGACAACATTGG (SEQ ID NO: 9) | TGTAAAACGACGGCCAGTACCTGGGATTGGGTTAGGAC (SEQ ID NO: 10) |
| 1b12.ttc.5-1 | GTCGTCGTAGAGTGGGGTGT (SEQ ID NO: 11) | TGTAAAACGACGGCCAGTGAGTGGCCATGGATTCAAAC (SEQ ID NO: 12) |
| 1c06.tta.6-1 | CAAATGAGAGCACGTTGTGAA (SEQ ID NO: 13) | TGTAAAACGACGGCCAGTATCATATTGGCTTGGTGCAA (SEQ ID NO: 14) |
| 1c09.gat.6-1 | TTTTCCATTCCCACCTACCA (SEQ ID NO: 15) | TGTAAAACGACGGCCAGTTTTGGAAAACACTTGCCCAC (SEQ ID NO: 16) |
| 1c11.tgg.5-1 | TTGCCCTTTTGTCCAAGAAC (SEQ ID NO: 17) | TGTAAAACGACGGCCAGTGACGAGAGTCCCATCAGAGC (SEQ ID NO: 18) |
| 1c12.tgt.5-1 | TTACGATCTGGCTTGGAACC (SEQ ID NO: 19) | TGTAAAACGACGGCCAGTCTCGACCTGCACGACAATTA (SEQ ID NO: 20) |
| 1d06.gaa.6-1 | GAAGGTTTTGGGTGGTGATG (SEQ ID NO: 21) | TGTAAAACGACGGCCAGTCCATGGCTCTTTCCTACCAA (SEQ ID NO: 22) |
| 1e04.aaat.4-1 | GACCGGGATTGATGGATATG (SEQ ID NO: 23) | TGTAAAACGACGGCCAGTAACAAGAGATGGGAGGAAAAA (SEQ ID NO: 24) |
| 1e04.tatc.4-1 | TGTTTCTGATCAGGGCATTG (SEQ ID NO: 25) | TGTAAAACGACGGCCAGTTCTAGGTATTCGCTGGCGTT (SEQ ID NO: 26) |
| 1e08.gat.5-1 | ACTTCCTGACGGTCCTCCTT (SEQ ID NO: 27) | TGTAAAACGACGGCCAGTGGCGCATAATCACCATTACC (SEQ ID NO: 28) |
| 1e08.tttc.4-1 | TCCTTCTGGACAAGAAACCG (SEQ ID NO: 29) | TGTAAAACGACGGCCAGTTCCATCACGACATATTTCACTTTT (SEQ ID NO: 30) |
| 1f02.tat.6-1 | TGATGCTGTCCTATGCCAAG (SEQ ID NO: 31) | TGTAAAACGACGGCCAGTTGGAAAAGGCTTTGACTGTTG (SEQ ID NO: 32) |
| 1f08.att.6-1 | TGATGGATGCAATAGGGGAT (SEQ ID NO: 33) | TGTAAAACGACGGCCAGTTGACATCATATGCACGGTCC (SEQ ID NO: 34) |
| 1f08.tat.6-1 | ATGAAGGTCATTGCAAGGCT (SEQ ID NO: 35) | TGTAAAACGACGGCCAGTCTGCTGACTTCTGTCTGGCA (SEQ ID NO: 36) |
| 1f10.ttg.6-1 | AGTGCCGCTATGCTGCTATT (SEQ ID NO: 37) | TGTAAAACGACGGCCAGTTTGATCCATGTAGCCAACCC (SEQ ID NO: 38) |
| 1f11.aatt.4-1 | TTGAAAAGACACGGGGAAGT (SEQ ID NO: 39) | TGTAAAACGACGGCCAGTCCACAAAAGCAGATGGTTGA (SEQ ID NO: 40) |
| 1f11.caa.5-1 | TTGGTGAGAGCTGGTGATTG (SEQ ID NO: 41) | TGTAAAACGACGGCCAGTTTACCGCTTTTGGATTCTGG (SEQ ID NO: 42) |
| 1g03.gaa.5-1 | TTTATCGGCGAAGAAGATCG (SEQ ID NO: 43) | TGTAAAACGACGGCCAGTTCCCGCTTCACTTCACTTTC (SEQ ID NO: 44) |
| 1g05.cata.17-1 | CCCTAAATCAGGGGTTCAAA (SEQ ID NO: 45) | TGTAAAACGACGGCCAGTCACTCATTGCTGAGGGCATA (SEQ ID NO: 46) |
| 1g05.tct.12-1 | TCAGAAATTCCCTCCCATTG (SEQ ID NO: 47) | TGTAAAACGACGGCCAGTAAGAATGACGAAGAGGCGAA (SEQ ID NO: 48) |
| 1h03.aatt.4-1 | TGATTCAAGGATGGGAAAGC (SEQ ID NO: 49) | TGTAAAACGACGGCCAGTTGTCTTCCGTGGTCTCACTG (SEQ ID NO: 50) |
| 1h03.ata.9-1 | GAGTTTCTGAATTCGCCGTC (SEQ ID NO: 51) | TGTAAAACGACGGCCAGTTCGGCATCAATCATGTCATC (SEQ ID NO: 52) |
| 1h09.aat.11-1 | CGATAATTCACCCCCATGAC (SEQ ID NO: 53) | TGTAAAACGACGGCCAGTCACAATCAAATGCATAGCCG (SEQ ID NO: 54) |
| 2a03.aga.5-1 | TCGAGAGCTCGGTATTCGAT (SEQ ID NO: 55) | TGTAAAACGACGGCCAGTATCCAAGGGCGGTAGAAGAC (SEQ ID NO: 56) |

TABLE 1-continued

Alfalfa genomic and trichome EST-SSRs used to genotype the mapping populations.

| Primer ID | Reverse primer sequence | Forward primer sequence |
|---|---|---|
| 2a03.gaa.8-1 | TCGAGAGCTCGGTATTCGAT(SEQ ID NO: 57) | TGTAAAACGACGGCCAGTGTGTGGAAGAGACCGGAGAA (SEQ ID NO: 58) |
| 2a03.tga.5-1 | AAGCACTCTGAGCCACCATT(SEQ ID NO: 59) | TGTAAAACGACGGCCAGTTGAGGAAATTCTTGGGAGGA (SEQ ID NO: 60) |
| 2a07.tatt.4-1 | GCAGGGACGAAACCAGAATA (SEQ ID NO: 61) | TGTAAAACGACGGCCAGTTTGCACTTCCACTAAATGACTTG (SEQ ID NO: 62) |
| 2a09.aac.6-1 | CCCTCCAATCAAGAAACAGC (SEQ ID NO: 63) | TGTAAAACGACGGCCAGTCCCAATTCCAAACCAGAAAA (SEQ ID NO: 64) |
| 2a09.ttta.4-1 | GACCATTGATCATGTCTCACG (SEQ ID NO: 65) | TGTAAAACGACGGCCAGTCCAGATTGCTTACCAGGGAC (SEQ ID NO: 66) |
| 2c06.ctc.8-1 | AACAACCAAACTTGGCCTTG (SEQ ID NO: 67) | TGTAAAACGACGGCCAGTTGGTCGAAGGAAGCAGAGAT(SEQ ID NO: 68) |
| 2c06.gat.6-1 | ACTTCCATTGCCGCTTCTAA (SEQ ID NO: 69) | TGTAAAACGACGGCCAGTTGTGGCGAAGTAACGAAGAA (SEQ ID NO: 70) |
| 2c06.tta.9-1 | AAACCAATGATATCAAACTCCCTT(SEQ ID NO: 71) | TGTAAAACGACGGCCAGTAAAAAGTCATGCTACAAATCATAAAAA (SEQ ID NO: 72) |
| 2c12.gga.5-1 | AAATGGATTCGAACTCACGC (SEQ ID NO: 73) | TGTAAAACGACGGCCAGTAAGAAGAAAAATGGCAGGAGG (SEQ ID NO: 74) |
| 2c12.tta.5-1 | AGCCTCAAGCAGTCGTTGAC (SEQ ID NO: 75) | TGTAAAACGACGGCCAGTGGAGGGGAGCAAATCTCTTT(SEQ ID NO: 76) |
| 3c02.ata.9-1 | ACTCGCTCCCTAGGGTTTGT(SEQ ID NO: 77) | TGTAAAACGACGGCCAGTCCCCCAAATCCAAGAAGATT(SEQ ID NO: 78) |
| 3d03.atc.5-1 | TGTGAACATCAGGAGGTGGA (SEQ ID NO: 79) | TGTAAAACGACGGCCAGTGTGAATGGTGGTCGTCTTCA (SEQ ID NO: 80) |
| 3d03.cat.6-1 | AACCATGCGGTGGTTAGGTA (SEQ ID NO: 81) | TGTAAAACGACGGCCAGTCGTCATCATCATCATCACCA (SEQ ID NO: 82) |
| 3d03.cat.7-1 | TGAATGGAATCATGCAGAGG (SEQ ID NO: 83) | TGTAAAACGACGGCCAGTAACGGGTGGTCTTGTGATTG (SEQ ID NO: 84) |
| 3d03.tca.5-1 | TTTTCGATCATGCCATTTGA (SEQ ID NO: 85) | TGTAAAACGACGGCCAGTTTTGCACCAATGGGTAGTTC (SEQ ID NO: 86) |
| 3e10.cag.6-1 | AGCATTTGCAGTGCTAGGGT(SEQ ID NO: 87) | TGTAAAACGACGGCCAGTACAGCAACAGCAACAACAGC (SEQ ID NO: 88) |
| 3f10.gtt.8-1 | GAAGCTATTTGGGCGAGCTT(SEQ ID NO: 89) | TGTAAAACGACGGCCAGTCATTATGGCGTCATTTGATCC (SEQ ID NO: 90) |
| 3g06.aga.9-1 | GACACCGTTTTCGGTGATTT(SEQ ID NO: 91) | TGTAAAACGACGGCCAGTTGAAACACGTTCCCACAAAG (SEQ ID NO: 92) |
| AA04 | GAACTATCACCTTTCCCTTGGA (SEQ ID NO: 93) | TGTAAAACGACGGCCAGTATTCCGGTCGTCAGAATCAG (SEQ ID NO: 94) |
| AA06 | AGCAGGTGGAAGAATTGGTG (SEQ ID NO: 95) | TGTAAAACGACGGCCAGTCGCGTGTGTTTAGAGAGAGAGA (SEQ ID NO: 96) |
| AC126014 | TTCTTCTTGGACTTGCACCA (SEQ ID NO: 97) | TGTAAAACGACGGCCAGTTAAGGATGACCCAACCAAGC (SEQ ID NO: 98) |
| AC155884 | TTCTTAGCTTGAAGGGCACG (SEQ ID NO: 99) | TGTAAAACGACGGCCAGTCCATTCCTGGTTGTCAGTCC (SEQ ID NO: 100) |
| AFct11 | TTGTGTGGAAAGAATAGGAA (SEQ ID NO: 101) | TGTAAAACGACGGCCAGTGGACAGAGCAAAAGAACAAT(SEQ ID NO: 102) |
| AFct45 | GCCATCTTTTCTTTTGCTTC (SEQ ID NO: 103) | TGTAAAACGACGGCCAGTTAAAAAACGGAAAGAGTTGGTTAG (SEQ ID NO: 104) |
| AI01 | TTGAAAATTGGGAACGGAAA (SEQ ID NO: 105) | TGTAAAACGACGGCCAGTGTTGGAGTGGGAAATTGCAG (SEQ ID NO: 106) |
| AJ02 | GGAAGAGGGAGAAGGAGATGA (SEQ ID NO: 107) | TGTAAAACGACGGCCAGTTCAATGGCGAACACTTTCAC (SEQ ID NO: 108) |
| AL111 | TGCAGCCAGGTGAATAACAA (SEQ ID NO: 109) | TGTAAAACGACGGCCAGTCATCTGATGGTGGTGATTGG (SEQ ID NO: 110) |

TABLE 1-continued

Alfalfa genomic and trichome EST-SSRs used to genotype the mapping populations.

| Primer ID | Reverse primer sequence | Forward primer sequence |
|---|---|---|
| AL64 | CCAATATGTCACTCCTTGCTGA (SEQ ID NO: 111) | TGTAAAACGACGGCCAGTAGGTGGCAAGCCTAACTGAA (SEQ ID NO: 112) |
| AL79 | TCCTCAACCAACCACTTCCT (SEQ ID NO: 113) | TGTAAAACGACGGCCAGTCCCCATTGACGCATTCTTAC (SEQ ID NO: 114) |
| AL81 | GTGGTGGAGAAGGAGCAATC (SEQ ID NO: 115) | TGTAAAACGACGGCCAGTCAATCCTCCACCATCACCTT (SEQ ID NO: 116) |
| AL83 | CGTTACCGTCACTGTCGTTG (SEQ ID NO: 117) | TGTAAAACGACGGCCAGTCAAACCTGATTCCGACCCTA (SEQ ID NO: 118) |
| AL84 | CTGCACCCCCTAAAAATCAA (SEQ ID NO: 119) | TGTAAAACGACGGCCAGTCTCATTGCCCTTCTCACACA (SEQ ID NO: 120) |
| AL92 | TGACTCTTGCATGCAGTTCC (SEQ ID NO: 121) | TGTAAAACGACGGCCAGTTGCTCCTCCTCTGCTTCTTC (SEQ ID NO: 122) |
| AL96 | GCCCCCTCACGTTTTTATTT (SEQ ID NO: 123) | TGTAAAACGACGGCCAGTCAATTTTGGTTGGTTATGCTCA (SEQ ID NO: 124) |
| AL97 | TCCCTCTTACACCTCTCATGC (SEQ ID NO: 125) | TGTAAAACGACGGCCAGTTCTCCTTGGAATTGAACCTG (SEQ ID NO: 126) |
| AL99 | CAGAAATTTCCATGCCAAAA (SEQ ID NO: 127) | TGTAAAACGACGGCCAGTAGTTGTGGATTGGGTGAAGC (SEQ ID NO: 128) |
| AW107 | AAACATCGGCTTCGGAAGTA (SEQ ID NO: 129) | TGTAAAACGACGGCCAGTTTTTTGAGCAGTGTAATGGTGTAA (SEQ ID NO: 130) |
| AW108 | CCATGGCGTCTACCCATTAT (SEQ ID NO: 131) | TGTAAAACGACGGCCAGTTTTTTCACAGCACTGAAGAGG (SEQ ID NO: 132) |
| AW11 | GACATTTGCAGACCACCATT (SEQ ID NO: 133) | TGTAAAACGACGGCCAGTATTCGCAGTGAGCTGATCCT (SEQ ID NO: 134) |
| AW123 | CATGTTTCCGGTTCTGGTTT (SEQ ID NO: 135) | TGTAAAACGACGGCCAGTAGTCCCTGCAAAATCCCTTC (SEQ ID NO: 136) |
| AW134 | TGGAAACAGCAAAACCACCT (SEQ ID NO: 137) | TGTAAAACGACGGCCAGTTCCGAAATCTGAAACCAACC (SEQ ID NO: 138) |
| AW150 | TCCACAAATGTCTAAAACCAACA (SEQ ID NO: 139) | TGTAAAACGACGGCCAGTTTTTTGTGTAGGGATGCAAAGG (SEQ ID NO: 140) |
| AW16 | GTGGGGTTGGTGAGAGTGTT (SEQ ID NO: 141) | TGTAAAACGACGGCCAGTATCGTCCCCACTGTGTCTTC (SEQ ID NO: 142) |
| AW177 | CAGCAAAATCCAATCCTTCAG (SEQ ID NO: 143) | TGTAAAACGACGGCCAGTTTCTCATCGTCACTCCAAAGAA (SEQ ID NO: 144) |
| AW186 | TGCTTGAACTTTGAGTCTTGGA (SEQ ID NO: 145) | TGTAAAACGACGGCCAGTTCTCTCCATCATCACCATCATC (SEQ ID NO: 146) |
| AW193 | GACAGAACCTTTGCCGATTTT (SEQ ID NO: 147) | TGTAAAACGACGGCCAGTGCACCAGCAGAGTAGAAGTAGC (SEQ ID NO: 148) |
| AW196 | AACTCGCAGGTGTTTTATCGTT (SEQ ID NO: 149) | TGTAAAACGACGGCCAGTAATCTCAACCGCAACAAACTCT (SEQ ID NO: 150) |
| AW199 | CATGGAGAAGCAGAACTGGAG (SEQ ID NO: 151) | TGTAAAACGACGGCCAGTCCAAACAACAACCAACTCTCTG (SEQ ID NO: 152) |
| AW201 | CCGTCTTTACATGAATCCACAA (SEQ ID NO: 153) | TGTAAAACGACGGCCAGTCACAGTCATCATCCTTGCTCTC (SEQ ID NO: 154) |
| AW212 | GGTTAGGGTTTTGGGTTTGAA (SEQ ID NO: 155) | TGTAAAACGACGGCCAGTGTCGAAATGGTTGCTTCTCTTT (SEQ ID NO: 156) |
| AW213 | CATGTACGGGGATTGTTGTTTT (SEQ ID NO: 157) | TGTAAAACGACGGCCAGTACCCTTGTGGGTTCTTCTTCTT (SEQ ID NO: 158) |
| AW220 | TGCTGCTGTGCCGTAGTAGATA (SEQ ID NO: 159) | TGTAAAACGACGGCCAGTGCCACAATTTTCTCATCATCAC (SEQ ID NO: 160) |
| AW232 | AGCACTTTGTTCATCGTTCTGA (SEQ ID NO: 161) | TGTAAAACGACGGCCAGTAAGAGAGTATCGTGGAGCCGTA (SEQ ID NO: 162) |
| AW252 | CTTGAGAAAGCGAAGGTTTTGT (SEQ ID NO: 163) | TGTAAAACGACGGCCAGTCTCGTTCATTAGCAGTTGCAGT (SEQ ID NO: 164) |
| AW254 | CACATCTTCGTCATCATCTTCA (SEQ ID NO: 165) | TGTAAAACGACGGCCAGTTATATGCTTGTTGAGGCCACTG (SEQ ID NO: 166) |

TABLE 1-continued

Alfalfa genomic and trichome EST-SSRs used to genotype the mapping populations.

| Primer ID | Reverse primer sequence | Forward primer sequence |
| --- | --- | --- |
| AW255 | TGCTTGAACTTTGAGTCTTGGA (SEQ ID NO: 167) | TGTAAAACGACGGCCAGTTCTCTCCATCATCACCATCATC (SEQ ID NO: 168) |
| AW258 | GAGTATCGGAAGAGGGTTGTTG (SEQ ID NO: 169) | TGTAAAACGACGGCCAGTAATTGGAACCTATCGTTGTCGT (SEQ ID NO: 170) |
| AW260 | GCATAGGAACCAGCTCTAATGG (SEQ ID NO: 171) | TGTAAAACGACGGCCAGTACGAGGGATTGTTGTTTGAGAT (SEQ ID NO: 172) |
| AW285 | CAACTGTGAACGCAAATCTCTC (SEQ ID NO: 173) | TGTAAAACGACGGCCAGTAACGACGCTCTTCGACTACTTC (SEQ ID NO: 174) |
| AW289 | GGTGCTTTCATTACATCCCATA (SEQ ID NO: 175) | TGTAAAACGACGGCCAGTACGAGGCACACACTCTCTCTCT (SEQ ID NO: 176) |
| AW306 | GTGTTCGTCGCATATCACCTC (SEQ ID NO: 177) | TGTAAAACGACGGCCAGTGCATTTCCCTCTCTTTCCATAA (SEQ ID NO: 178) |
| AW310 | CAATGCAAGAAACCCTAAAAGC (SEQ ID NO: 179) | TGTAAAACGACGGCCAGTCCACTCAACCTCATCTCTCTACC (SEQ ID NO: 180) |
| AW317 | TTTTCGATTAGGTCGTGGATCT (SEQ ID NO: 181) | TGTAAAACGACGGCCAGTACGCACATTTCCATTCTCATTC (SEQ ID NO: 182) |
| AW325 | GCTTGTTGTTGTTGATGCT (SEQ ID NO: 183) | TGTAAAACGACGGCCAGTTCTGTAAGAGGGTCACTGCGTA (SEQ ID NO: 184) |
| AW326 | GCATATCCATTCCAAGTTCATC (SEQ ID NO: 185) | TGTAAAACGACGGCCAGTACTTTCTTCCTCATTGCTCTGC (SEQ ID NO: 186) |
| AW329771 | ATCCCATTCAAGGAAACACC (SEQ ID NO: 187) | TGTAAAACGACGGCCAGTGGAATAATGCTGGTGGAAGC (SEQ ID NO: 188) |
| AW334 | CGATGTTTGTTTGAGCTAGTGA (SEQ ID NO: 189) | TGTAAAACGACGGCCAGTGAGAGAGAGAGAGAGCATTGAGC (SEQ ID NO: 190) |
| AW347 | GAACGGGTTTGCGATCTTT (SEQ ID NO: 191) | TGTAAAACGACGGCCAGTCCATGTCTCTCAATCTTCGTCA (SEQ ID NO: 192) |
| AW352 | ATCTCCTCGTGTATTCCTTCCA (SEQ ID NO: 193) | TGTAAAACGACGGCCAGTACGTTCCTCCTTCATCTCGTAA (SEQ ID NO: 194) |
| AW359 | TTCAAGGATCTGGTGATGATGA (SEQ ID NO: 195) | TGTAAAACGACGGCCAGTGAGGAAGAGGAAGAGGAGGAAG (SEQ ID NO: 196) |
| AW365 | TGTTGGTAATGTTCAAGCTCCA (SEQ ID NO: 197) | TGTAAAACGACGGCCAGTCACCACTATCTCTTCCCTCACC (SEQ ID NO: 198) |
| AW369 | AGAATTGAGACATGGCAGAGG (SEQ ID NO: 199) | TGTAAAACGACGGCCAGTGCGCTCATCATCTTCATCTAAA (SEQ ID NO: 200) |
| AW379 | TTCTCGAAATCTTCTGCTCTCG (SEQ ID NO: 201) | TGTAAAACGACGGCCAGTGTCTCTCTCTATTCTCTTCCCTTTTC (SEQ ID NO: 202) |
| AW389 | GCAGCCTTCAAATCTCCATAAC (SEQ ID NO: 203) | TGTAAAACGACGGCCAGTTCACTCTCTCACCAATCACCAC (SEQ ID NO: 204) |
| AW64 | CATGTTTCCGGTTCTGGTTT (SEQ ID NO: 205) | TGTAAAACGACGGCCAGTAGTCCCTGCAAAATCCCTTC (SEQ ID NO: 206) |
| AW86 | TTGTTGCAGCAATTAAGGAAGA (SEQ ID NO: 207) | TGTAAAACGACGGCCAGTATTGCCATTGCCTCTCTCAT (SEQ ID NO: 208) |
| AW97 | ACAAAAACTCTCCCGGCTTT (SEQ ID NO: 209) | TGTAAAACGACGGCCAGTCAAAACAATCAAACCAAAGATTG (SEQ ID NO: 210) |
| AW98 | ATTCATCCTTGCTCGTTTCG (SEQ ID NO: 211) | TGTAAAACGACGGCCAGTGATCAATTCGTGCAGAAGCA (SEQ ID NO: 212) |
| BE105 | AAGGGCAAAACCGTAAAAGAGT (SEQ ID NO: 213) | TGTAAAACGACGGCCAGTATCACCCCAAACCACATCTATC (SEQ ID NO: 214) |
| BE112 | AGCGAGATAGATTTCACCGAAG (SEQ ID NO: 215) | TGTAAAACGACGGCCAGTTTCATTTCATAGTTTTCCATTGC (SEQ ID NO: 216) |
| BE118 | TGCAAACTTCACCGAATAGATG (SEQ ID NO: 217) | TGTAAAACGACGGCCAGTCTCCTTTGTAACGCAACAGCAG (SEQ ID NO: 218) |

TABLE 1-continued

Alfalfa genomic and trichome EST-SSRs used to genotype the mapping populations.

| Primer ID | Reverse primer sequence | Forward primer sequence |
| --- | --- | --- |
| BE120 | CATCATCCTTCATTTCCGATCT (SEQ ID NO: 219) | TGTAAAACGACGGCCAGTTCTCACATTCACATTCCATTCC (SEQ ID NO: 220) |
| BE123 | TTGATGGGTAAAGGAGAAGGTG (SEQ ID NO: 221) | TGTAAAACGACGGCCAGTATCACAAGCCTCAACAGCCATA (SEQ ID NO: 222) |
| BE41 | ACGCCTCTCTTTCCGATCTT (SEQ ID NO: 223) | TGTAAAACGACGGCCAGTTCACTCACACTCAACACACAACA (SEQ ID NO: 224) |
| BE67 | CACCAGCCTCTAAGCTCATTTT (SEQ ID NO: 225) | TGTAAAACGACGGCCAGTCTCCATTCTCCATTTCAATACC (SEQ ID NO: 226) |
| BE74 | GCACAAGCAGCCATATTGATAG (SEQ ID NO: 227) | TGTAAAACGACGGCCAGTTACTGTCCCAATCTTCACAACG (SEQ ID NO: 228) |
| BE76 | TGAAAGTTGAAGGATCTGGTGA (SEQ ID NO: 229) | TGTAAAACGACGGCCAGTGAGGAAGAGGAAGAGGAGGAAG (SEQ ID NO: 230) |
| BE84 | TGGGATACTGATTTTCTGCTTC (SEQ ID NO: 231) | TGTAAAACGACGGCCAGTTCCGAACCCTACTTCCAAATTA (SEQ ID NO: 232) |
| BE85 | CTGATTCGAGATTGGGATTGAT (SEQ ID NO: 233) | TGTAAAACGACGGCCAGTTTTCCTCTTATTATTCTTTCATACCC (SEQ ID NO: 234) |
| BE92 | GATGAGGATGATGATGAATTGG (SEQ ID NO: 235) | TGTAAAACGACGGCCAGTAGTTCAAACCCTTACCCTTCA (SEQ ID NO: 236) |
| BF106 | GTTTTCCTGGATATTTGGATGG (SEQ ID NO: 237) | TGTAAAACGACGGCCAGTTTCAATCTTCTCCTTTGATTGC (SEQ ID NO: 238) |
| BF111 | TCAGTGAGAAGGTCGTTCATGT (SEQ ID NO: 239) | TGTAAAACGACGGCCAGTTGAGAGAGAGTTCGTGGGTTG (SEQ ID NO: 240) |
| BF119 | GTGATGAAGCATTGGTGATGAT (SEQ ID NO: 241) | TGTAAAACGACGGCCAGTAATGGCGAACACTTTCACTCTT (SEQ ID NO: 242) |
| BF120 | ATTTCAGAGGCAGATGGTGAAT (SEQ ID NO: 243) | TGTAAAACGACGGCCAGTTAGCAAAATGGGTCAACAAGTG (SEQ ID NO: 244) |
| BF132 | AATCCAGCTTTGGAAGACTCAA (SEQ ID NO: 245) | TGTAAAACGACGGCCAGTTTCTTGTGGTGGTGATGAAAAC (SEQ ID NO: 246) |
| BF142 | GTGTGTTCCCCAGTTCTCAGTT (SEQ ID NO: 247) | TGTAAAACGACGGCCAGTCATACCCTTCAAATCCAACCAT (SEQ ID NO: 248) |
| BF147 | GATTGTTCTTTGGTAAGCCTCA (SEQ ID NO: 249) | TGTAAAACGACGGCCAGTACTGCAAGTGAAGAGGGAGAGA (SEQ ID NO: 250) |
| BF149 | GCTTCTTTGGCTTTCTCTTCAA (SEQ ID NO: 251) | TGTAAAACGACGGCCAGTCGTTTCCCTCTCTCACTCACTT (SEQ ID NO: 252) |
| BF150 | ATCAGAAACAGAAGCATCAGCA (SEQ ID NO: 253) | TGTAAAACGACGGCCAGTCTCCAAAACTCAAACTCAACCA (SEQ ID NO: 254) |
| BF184 | CTAGACTTGCCGCTACTTTGG (SEQ ID NO: 255) | TGTAAAACGACGGCCAGTCAACAATCACCACACACATTGA (SEQ ID NO: 256) |
| BF215 | GGAAACATAGATGAAGCAGCAA (SEQ ID NO: 257) | TGTAAAACGACGGCCAGTAGCAAGCAAAGAACAATCACAA (SEQ ID NO: 258) |
| BF218 | TCGGATTTGGTTTTGAGTTTTC (SEQ ID NO: 259) | TGTAAAACGACGGCCAGTCTCAGGAGGTGCTGTTCTTCTT (SEQ ID NO: 260) |
| BF220 | TGAGTTTTCAGATTCAGCAGGA (SEQ ID NO: 261) | TGTAAAACGACGGCCAGTATCATCGTCGTCGTGTTTATTG (SEQ ID NO: 262) |
| BF225 | TTTTCATCTGTGCCCTGTAATG (SEQ ID NO: 263) | TGTAAAACGACGGCCAGTTCACTCACACTCAACACACAACA (SEQ ID NO: 264) |
| BF228 | ATTAGAAGCTCCGTTACCGTCA (SEQ ID NO: 265) | TGTAAAACGACGGCCAGTATAACCAACTCCAAACCACACC (SEQ ID NO: 266) |
| BF24 | TTGAAAATTGGGAACGGAAA (SEQ ID NO: 267) | TGTAAAACGACGGCCAGTGTTGGAGTGGGAAATTGCAG (SEQ ID NO: 268) |
| BF257 | ATGCCAGGATGGTGATACATCT (SEQ ID NO: 269) | TGTAAAACGACGGCCAGTGGATTTGGGCGTGAGACTATAC (SEQ ID NO: 270) |

TABLE 1-continued

Alfalfa genomic and trichome EST-SSRs used to genotype the mapping populations.

| Primer ID | Reverse primer sequence | Forward primer sequence |
|---|---|---|
| BF26 | TCAAAGTTGTTGTTCTGCTTGAA (SEQ ID NO: 271) | TGTAAAACGACGGCCAGTTCTCACACCCCAAAAACACA (SEQ ID NO: 272) |
| BF56 | TCAAAGTTGTTGTTCTGCTTGAA (SEQ ID NO: 273) | TGTAAAACGACGGCCAGTTCTCACACCCCAAAAACACA (SEQ ID NO: 274) |
| BF65 | AAGAGCAGAAGAAGGTTTGTCG (SEQ ID NO: 275) | TGTAAAACGACGGCCAGTACCTAAGCAAGCAAGGCAAA (SEQ ID NO: 276) |
| BF71 | CGGTGAAATGGTGGAAGAAG (SEQ ID NO: 277) | TGTAAAACGACGGCCAGTTAACAAAACCCAACCCCATC (SEQ ID NO: 278) |
| BF79 | GGTGTGGAGAGGGAGGGTAG (SEQ ID NO: 279) | TGTAAAACGACGGCCAGTCGAGGGATATTCTTTCCCTTAAA (SEQ ID NO: 280) |
| BF97 | CTACCTCCAGCAGAACCATGTC (SEQ ID NO: 281) | TGTAAAACGACGGCCAGTGTAACCATCCTTTGAGTTCGTCTG (SEQ ID NO: 282) |
| BG115 | TGCATTTGTTAACGAGTGTGAA (SEQ ID NO: 283) | TGTAAAACGACGGCCAGTCCACAGAAGAAAGAAGAACTTGC (SEQ ID NO: 284) |
| BG119 | TCGAGGCCAATAGAAGACCTAA (SEQ ID NO: 285) | TGTAAAACGACGGCCAGTGGTTCTCTTCCAATCCCTTCTT (SEQ ID NO: 286) |
| BG134 | TTTTCAAGGAGGAGAAGATCCA (SEQ ID NO: 287) | TGTAAAACGACGGCCAGTACCCCACCTAACCCTCTACAGT (SEQ ID NO: 288) |
| BG142 | TGTGGTGAAGAAACGGATAGAA (SEQ ID NO: 289) | TGTAAAACGACGGCCAGTAGTATCAATCTTTGGCGCTACC (SEQ ID NO: 290) |
| BG143 | GGTAATCGTTGGCGTTGTTTAT (SEQ ID NO: 291) | TGTAAAACGACGGCCAGTTCAGGTAGTTGACGACGAAGAA (SEQ ID NO: 292) |
| BG157 | CAACGCCTCCTCTTTCTCTGTA (SEQ ID NO: 293) | TGTAAAACGACGGCCAGTCTCAAAACCCTAACTTCTTCAACC (SEQ ID NO: 294) |
| BG166 | CAACTGTGAACGCAAATCTCTC (SEQ ID NO: 295) | TGTAAAACGACGGCCAGTAACGACGCTCTTCGACTACTTC (SEQ ID NO: 296) |
| BG171 | GGATCCAACCGAATTTCTTTC (SEQ ID NO: 297) | TGTAAAACGACGGCCAGTACCTAGCAACCCAAATCAGAAG (SEQ ID NO: 298) |
| BG172 | CCTCGAAAAGATTACCGAACAC (SEQ ID NO: 299) | TGTAAAACGACGGCCAGTCGCCTTCTTCTTCAACACACTA (SEQ ID NO: 300) |
| BG178 | TTCTCCTTGACCAACCTTGATT (SEQ ID NO: 301) | TGTAAAACGACGGCCAGTACCCACTCAACTCAACACACAC (SEQ ID NO: 302) |
| BG180 | AGAAGGTGGAACACGTCTCTTC (SEQ ID NO: 303) | TGTAAAACGACGGCCAGTCTACAAGCCCAGATTTCAAAGG (SEQ ID NO: 304) |
| BG181 | TTCGCAGTTCTTGAGTAGGTCA (SEQ ID NO: 305) | TGTAAAACGACGGCCAGTTACTTCATGTACCCCACAACCA (SEQ ID NO: 306) |
| BG186 | TTGTCGATGAGTTCAACGTTTC (SEQ ID NO: 307) | TGTAAAACGACGGCCAGTACAACAAAACACAATGGGTGAC (SEQ ID NO: 308) |
| BG208 | AGTAACCGCGAACCAAAGAGTA (SEQ ID NO: 309) | TGTAAAACGACGGCCAGTACACCTCGAACAAGATTCATCC (SEQ ID NO: 310) |
| BG218 | ACCATATCCACAGGCATAATCC (SEQ ID NO: 311) | TGTAAAACGACGGCCAGTAATCCATACTCAAACCCACCAG (SEQ ID NO: 312) |
| BG222 | ATCACGAGAACCGCCATAAGAT (SEQ ID NO: 313) | TGTAAAACGACGGCCAGTAGGGCTGATGAGGTGGATAAT (SEQ ID NO: 314) |
| BG229 | GAACGGGTTTGCGATCTTT (SEQ ID NO: 315) | TGTAAAACGACGGCCAGTCCATGTCTCTCAATCTTCGTCA (SEQ ID NO: 316) |
| BG231 | GCATGTATGATTTACAGCTCCAAG (SEQ ID NO: 317) | TGTAAAACGACGGCCAGTCCACAGTTTCATTTTCTGTCCA (SEQ ID NO: 318) |
| BG232 | TGCCTTTGATTAGTGCTGACAT (SEQ ID NO: 319) | TGTAAAACGACGGCCAGTCTCTGCTCCCATCTACTTCACA (SEQ ID NO: 320) |
| BG234 | GCAACATACCATCCCCTAAAAG (SEQ ID NO: 321) | TGTAAAACGACGGCCAGTGCTGGAATACACCAAGCATGA (SEQ ID NO: 322) |

TABLE 1-continued

Alfalfa genomic and trichome EST-SSRs used to genotype the mapping populations.

| Primer ID | Reverse primer sequence | Forward primer sequence |
|---|---|---|
| BG248 | ACATAAGCGACTGGAACAAACC (SEQ ID NO: 323) | TGTAAAACGACGGCCAGTGGATACAAAATCCACAAGCACA (SEQ ID NO: 324) |
| BG249 | ACATAAGCGACTGGAACAAACC (SEQ ID NO: 325) | TGTAAAACGACGGCCAGTGGATACAAAATCCACAAGCACA (SEQ ID NO: 326) |
| BG257 | ATTTCAGAGGCAGATGGTGAAT (SEQ ID NO: 327) | TGTAAAACGACGGCCAGTTAGCAAAATGGGTCAACAAGTG (SEQ ID NO: 328) |
| BG272 | CAGGGGAATCAATCAGTCAAAG (SEQ ID NO: 329) | TGTAAAACGACGGCCAGTAAACAGAGAGACAGGAATTTGGA (SEQ ID NO: 330) |
| BG280 | TGTTGAAGTTGGAGTTTTGGTG (SEQ ID NO: 331) | TGTAAAACGACGGCCAGTTCAGCAGTTAGTTTTGGTATGC (SEQ ID NO: 332) |
| BG281 | GGTTGGAAACAAAGTCAGAACC (SEQ ID NO: 333) | TGTAAAACGACGGCCAGTACATCATCAACAGCAAAACCAG (SEQ ID NO: 334) |
| BG285 | TGCTTCTTGGTTTCTCATCATC (SEQ ID NO: 335) | TGTAAAACGACGGCCAGTATGGTTATGTGGGTTGTGTTCA (SEQ ID NO: 336) |
| BG82 | TTCCCATATGCAACAGACCTT (SEQ ID NO: 337) | TGTAAAACGACGGCCAGTAACGGTGGTGTGTTTATTGCT (SEQ ID NO: 338) |
| BG89 | GGCAGGAACAGATCCTTGAA (SEQ ID NO: 339) | TGTAAAACGACGGCCAGTCGTAAACAAAGAAAAGCTTGAGAG (SEQ ID NO: 340) |
| BG96 | TTAACGAGGGTGGTGATGGT (SEQ ID NO: 341) | TGTAAAACGACGGCCAGTTCGATGTTATGGTAGCAGCAA (SEQ ID NO: 342) |
| BI107 | AGCAGTGATGTCTTGGCTATGT (SEQ ID NO: 343) | TGTAAAACGACGGCCAGTGTTTCCGGTTCTTTGTCGTTC (SEQ ID NO: 344) |
| BI113 | AACATCGTAATGAGGAGGAGGA (SEQ ID NO: 345) | TGTAAAACGACGGCCAGTACAGTATCAGCAACACCAGCAG (SEQ ID NO: 346) |
| BI116 | TCAACCCTTCAGATTTTCTTCC (SEQ ID NO: 347) | TGTAAAACGACGGCCAGTCACACTTTCTCGTTTGCTCTCT (SEQ ID NO: 348) |
| BI122 | CAATTTCCTTAGTGGCCGTTAC (SEQ ID NO: 349) | TGTAAAACGACGGCCAGTTTATTAGCTGGGCTTTTCTTCG (SEQ ID NO: 350) |
| BI68 | ATCAGCGTAAATTCTGGCCTTA (SEQ ID NO: 351) | TGTAAAACGACGGCCAGTCCATTCCAATCCACACTATCG (SEQ ID NO: 352) |
| BI75 | CGTAGGAAGAAGGATCGAGTTC (SEQ ID NO: 353) | TGTAAAACGACGGCCAGTCCCAATTCAAAACGAAGAACC (SEQ ID NO: 354) |
| BI86 | CGTCGAAGTCAAAATCAATCTC (SEQ ID NO: 355) | TGTAAAACGACGGCCAGTGAAAAGAAATCACCCCGAAGAT (SEQ ID NO: 356) |
| BI96 | CTCATTCACCCAACCAAAATGT (SEQ ID NO: 357) | TGTAAAACGACGGCCAGTGGCTAATTCACCTGTTTCTGCT (SEQ ID NO: 358) |
| BI98 | TCAACAGCCAACTCAAAGTGAT (SEQ ID NO: 359) | TGTAAAACGACGGCCAGTCATCAATCAACCCTTTCGTTTC (SEQ ID NO: 360) |
| MSCWSNP0386 | TTAGAGATGGTAATTGCAGTGGAC (SEQ ID NO: 361) | TTGGTGGAAGTCATGTTTGG (SEQ ID NO: 362) |
| MSCWSNP0406 | AACAGGACTGTGTTGCACGTA (SEQ ID NO: 363) | CTGCTTCTGCTGATGGACAA (SEQ ID NO: 364) |
| MSCWSNP0407 | CCCACTGAGGGTACTCATGC (SEQ ID NO: 365) | AGCTGCAACAACTCCTCCAT (SEQ ID NO: 366) |
| MSCWSNP0453 | GAAACTCAAAGGGCGATCACT (SEQ ID NO: 367) | AAGCGATATCAGAGGGTGGA (SEQ ID NO: 368) |
| Mstir10581 | CCTTGGCAGCTACAGGTACAG (SEQ ID NO: 369) | TGTAAAACGACGGCCAGTGTCTGCTGCTCCAGCTAAGAA (SEQ ID NO: 370) |
| Mstir10584 | TCACATCAGCCCTAACATTCC (SEQ ID NO: 371) | TGTAAAACGACGGCCAGTCCAAATATCTTCGCTCTTCCA (SEQ ID NO: 372) |
| Mstir10649 | GGATATCCTGGTGGAGGGTAA (SEQ ID NO: 373) | TGTAAAACGACGGCCAGTACAACCCCATTTCCAACTTTC (SEQ ID NO: 374) |

TABLE 1-continued

Alfalfa genomic and trichome EST-SSRs used to genotype the mapping populations.

| Primer ID | Reverse primer sequence | Forward primer sequence |
| --- | --- | --- |
| Mstir10665 | CCTCCAGGTCTAAGTCCCATT (SEQ ID NO: 375) | TGTAAAACGACGGCCAGTCCAATGCAGTTCGGTAATCC (SEQ ID NO: 376) |
| Mstir10801 | GGAGCAAACATTCTACCACCA (SEQ ID NO: 377) | TGTAAAACGACGGCCAGTTCACAAAACAAACCCTTCTTCT (SEQ ID NO: 378) |
| Mstir11087 | TGACTTAGACACCACCGGAGT (SEQ ID NO: 379) | TGTAAAACGACGGCCAGTTCATCCATTCATTAAAACGCA (SEQ ID NO: 380) |
| Mstir11314 | ATACACCATAGCACGAGACGC (SEQ ID NO: 381) | TGTAAAACGACGGCCAGTTAATTCGAGGAGGATTGTGGA (SEQ ID NO: 382) |
| Mstir11442 | GGATCCATTACCAGACAGTGC (SEQ ID NO: 383) | TGTAAAACGACGGCCAGTTGATTTCACTTTAGCATCTTGTG (SEQ ID NO: 384) |
| Mstir11470 | GGAGATGAAGAAGGAGATGGG (SEQ ID NO: 385) | TGTAAAACGACGGCCAGTTTGAAATAGTGCAAGAAGAACCC (SEQ ID NO: 386) |
| Mstir11523 | TGTCACTTGTTCTGGTCCTTCT (SEQ ID NO: 387) | TGTAAAACGACGGCCAGTGGAGAGAGCAAAGTCTCTTCAA (SEQ ID NO: 388) |
| Mstir11989 | CAGGAACATAACTGTGACCCG (SEQ ID NO: 389) | TGTAAAACGACGGCCAGTTCCTAATACCCCATTCATTGGT (SEQ ID NO: 390) |
| Mstir12038 | GCCTTTAGGCCAATCAGAGAC (SEQ ID NO: 391) | TGTAAAACGACGGCCAGTAAGATTAGGGTTTGAGTAAGGGAA (SEQ ID NO: 392) |
| Mstir7231 | ACATCTTCTGGAAGACCCGTT (SEQ ID NO: 393) | TGTAAAACGACGGCCAGTGGTAGTACTTCCTTCACTCTTCT (SEQ ID NO: 394) |
| Mstir7729 | ATCTGGGAAGTGTGACCTCCT (SEQ ID NO: 395) | TGTAAAACGACGGCCAGTTCAAAACCTTGGTGTTGGTTG (SEQ ID NO: 396) |
| Mstir7771 | CATACTATGGTGGTGGTTGGG (SEQ ID NO: 397) | TGTAAAACGACGGCCAGTCTCTTTAAGATTGCTTCTCTTGC (SEQ ID NO: 398) |
| Mstir8491 | GGACGGTTTCGAACTTCTAGC (SEQ ID NO: 399) | TGTAAAACGACGGCCAGTCGAGGCATCTTCATCTTCAAC (SEQ ID NO: 400) |
| Mstir8637 | GATAAAGCTCCCACAGTTCCC (SEQ ID NO: 401) | TGTAAAACGACGGCCAGTCTCTTTTCTCTTCAATTTTCAAT (SEQ ID NO: 402) |
| Mstir8931 | TACAGTTGCCCATACAGGAGG (SEQ ID NO: 403) | TGTAAAACGACGGCCAGTCAAACAGGTGACGAGGTGAAT (SEQ ID NO: 404) |
| Mstir9329 | ATCAAGATCGACTGAACCACG (SEQ ID NO: 405) | TGTAAAACGACGGCCAGTTTGGCTTTGATTGCTTCAACT (SEQ ID NO: 406) |
| Mstir9849 | TGAGGCTTAACCTTAGGAGGC (SEQ ID NO: 407) | TGTAAAACGACGGCCAGTTTTCAAATCCAAGTGGTGGAG (SEQ ID NO: 408) |
| Mstri10127 | GGGAAACCATTTCGTACCCTA (SEQ ID NO: 409) | TGTAAAACGACGGCCAGTAATTCCCAATTCTCATTCGTG (SEQ ID NO: 410) |
| Mstri10235 | TTGCCATCGTAGAAAATGGTC (SEQ ID NO: 411) | TGTAAAACGACGGCCAGTCCTTAACACATTTTTGCTTCA (SEQ ID NO: 412) |
| Mstri10456 | TGTCGTCTTTTGACCATTTCC (SEQ ID NO: 413) | TGTAAAACGACGGCCAGTTTATCATGTGCAGACAATACC (SEQ ID NO: 414) |
| Mstri10592 | GATTAAACATACATGCAACATTGA (SEQ ID NO: 415) | TGTAAAACGACGGCCAGTGGTTGAAATCGACATGAGAGG (SEQ ID NO: 416) |
| Mstri10686 | CCAACACTTTAAGCCTCCAAA (SEQ ID NO: 417) | TGTAAAACGACGGCCAGTTGTTCTCCTCTCTTCGTCTCTTG (SEQ ID NO: 418) |
| Mstri10743 | CCGGTTCTGTTTGGTAGTGAA (SEQ ID NO: 419) | TGTAAAACGACGGCCAGTAACCAGAGAAAAATCCAACCA (SEQ ID NO: 420) |
| Mstri10866 | CCTTAGGCACATTGAAAACCA (SEQ ID NO: 421) | TGTAAAACGACGGCCAGTTAAGGGTTCATGCTCACCATC (SEQ ID NO: 422) |
| Mstri11061 | AACATGCACAATTAAGCATTCAA (SEQ ID NO: 423) | TGTAAAACGACGGCCAGTACCTGAAAGGCCACAAAAGAT (SEQ ID NO: 424) |

TABLE 1-continued

Alfalfa genomic and trichome EST-SSRs used to genotype the mapping populations.

| Primer ID | Reverse primer sequence | Forward primer sequence |
| --- | --- | --- |
| Mstri11067 | AATTCGGGTGGAATAACAAGC (SEQ ID NO: 425) | TGTAAAACGACGGCCAGTTTGCCTCGGATTATTACTTGTG (SEQ ID NO: 426) |
| Mstri11090 | GCAATCACCTTAGCATTTTGG (SEQ ID NO: 427) | TGTAAAACGACGGCCAGTGCCAGTTTTGGGCAATTTTAT (SEQ ID NO: 428) |
| Mstri11131 | GTTCAAGCATGGAAAGTTTGG (SEQ ID NO: 429) | TGTAAAACGACGGCCAGTGGGACCTAATATGATGAACTTACA (SEQ ID NO: 430) |
| Mstri11311 | TGACAGTTTCCACAATCCTCC (SEQ ID NO: 431) | TGTAAAACGACGGCCAGTGACGAACTCTTTTCTTTTCTGACA (SEQ ID NO: 432) |
| Mstri11419 | ACAAGAAGAAGATTGCGACGA (SEQ ID NO: 433) | TGTAAAACGACGGCCAGTTGAAGGAAGAAGGAAGAAGGAA (SEQ ID NO: 434) |
| Mstri11460 | AATTTGGACTTTGATTGTGCG (SEQ ID NO: 435) | TGTAAAACGACGGCCAGTCAAGAACCAGATCATCAACAACA (SEQ ID NO: 436) |
| Mstri11539 | AAATTTCTTTCCATTGGCTCC (SEQ ID NO: 437) | TGTAAAACGACGGCCAGTTTCATGAATTTGCTTCTATTGCAT (SEQ ID NO: 438) |
| Mstri11701 | AGCTTTTTCAACGAGTTCAGC (SEQ ID NO: 439) | TGTAAAACGACGGCCAGTTTTCATCAACATCAAACACCG (SEQ ID NO: 440) |
| Mstri11744 | TTCTTGGCTTCGACTTCTTCA (SEQ ID NO: 441) | TGTAAAACGACGGCCAGTCCGATTGGACTCGGAACTT (SEQ ID NO: 442) |
| Mstri11748 | GGATTTCGTTTGGGTTCATTT (SEQ ID NO: 443) | TGTAAAACGACGGCCAGTTCTGTAACACAGGCAGAGTCG (SEQ ID NO: 444) |
| Mstri7274 | CACACATCAAAGCCCCTAAAA (SEQ ID NO: 445) | TGTAAAACGACGGCCAGTACTCCATCAACTGGTTCACCG (SEQ ID NO: 446) |
| Mstri7698 | CAGTTGATGCATAGAAACGCA (SEQ ID NO: 447) | TGTAAAACGACGGCCAGTAAGCGATTTCATTAGTAGTTGT (SEQ ID NO: 448) |
| Mstri7807 | TCACCAGCACATGAATCAAAA (SEQ ID NO: 449) | TGTAAAACGACGGCCAGTAACAACCTAGATTTTCTCGACC (SEQ ID NO: 450) |
| Mstri8119 | AGGGTTGATGCAGATGTTACG (SEQ ID NO: 451) | TGTAAAACGACGGCCAGTATTGCAATCATCTTCTCCCCT (SEQ ID NO: 452) |
| Mstri8616 | AACAATATGATCTGGCATGTCG (SEQ ID NO: 453) | TGTAAAACGACGGCCAGTGGAAGATCACCATTTTGTCCA (SEQ ID NO: 454) |
| Mstri8733 | AGGTACAAGCCATGATGTCCA (SEQ ID NO: 455) | TGTAAAACGACGGCCAGTTTTCCAAACTTTCCTTCTTTTG (SEQ ID NO: 456) |
| Mstri8791 | ACAAGAAGAAGATTGCGACGA (SEQ ID NO: 457) | TGTAAAACGACGGCCAGTTGAAGGAAGAAGGAAGAAGGAA (SEQ ID NO: 458) |
| Mstri8899 | CGCAGCACATGTAACTTGAAA (SEQ ID NO: 459) | TGTAAAACGACGGCCAGTCACATTCTCTTCGTGCCCTC (SEQ ID NO: 460) |
| Mstri8923 | TCCGAAAAGGTGACAGATTG (SEQ ID NO: 461) | TGTAAAACGACGGCCAGTGGCTCACAACAACAACAAAAT (SEQ ID NO: 462) |
| Mstri8930 | CCAAACAGATCTAAAGTTCCCA (SEQ ID NO: 463) | TGTAAAACGACGGCCAGTTGCTTGATTATTGCTAATCGG (SEQ ID NO: 464) |
| Mstri8949 | TAAATGCAAGGTAGGTGGTGG (SEQ ID NO: 465) | TGTAAAACGACGGCCAGTCGAGGACGAGTTCTGGTCAA (SEQ ID NO: 466) |
| Mstri9154 | AAGACCAAGAGGAATCACCGT (SEQ ID NO: 467) | TGTAAAACGACGGCCAGTTAATTTCATTCGCGATCACAC (SEQ ID NO: 468) |
| Mstri9223 | TGAATGTGAGGAAGTGGGTTT (SEQ ID NO: 469) | TGTAAAACGACGGCCAGTCCGCCTCAAATAGTTATAAACTTC (SEQ ID NO: 470) |
| Mstri9326 | AGTACTATTGCAATGGCGTGG (SEQ ID NO: 471) | TGTAAAACGACGGCCAGTGGTTTCGCTTGGAATTCTGAT (SEQ ID NO: 472) |
| Mstri9544 | ATTTTTCCACTTCTGGTGGGA (SEQ ID NO: 473) | TGTAAAACGACGGCCAGTCAACACAATCATTTTGGGAGC (SEQ ID NO: 474) |

TABLE 1-continued

Alfalfa genomic and trichome EST-SSRs used to genotype the mapping populations.

| Primer ID | Reverse primer sequence | Forward primer sequence |
|---|---|---|
| Mstri9820 | TCTTGTTGATATAATCTACGGAA (SEQ ID NO: 475) | TGTAAAACGACGGCCAGTCCTGATGGTCATCACTAAGCC (SEQ ID NO: 476) |
| Mstri9857 | GGGACCCAATAACCGAAAATA (SEQ ID NO: 477) | TGTAAAACGACGGCCAGTTTTGATAAACCAATCTCCCACA (SEQ ID NO: 478) |
| Mt1D06 | GAAGGTTTTGGGTGGTGATG (SEQ ID NO: 479) | TGTAAAACGACGGCCAGTCCATGGCTCTTTCCTACCAA (SEQ ID NO: 480) |
| Mt1G03 | TGGTTGATCAATGTTCCTCCT (SEQ ID NO: 481) | TGTAAAACGACGGCCAGTAAAGAGATTGGGTCGGTGAA (SEQ ID NO: 482) |
| MtBA36F01F1 | AATAAACACAGATTCCAAATCCA (SEQ ID NO: 483) | TGTAAAACGACGGCCAGTTCTTCATCGCTTTCTTCTATTTCA (SEQ ID NO: 484) |
| MtBC01G06F3 | TCAGGACAAACTGCCATTTC (SEQ ID NO: 485) | TGTAAAACGACGGCCAGTTGCATTGAAGCAAATTAACGA (SEQ ID NO: 486) |
| MTIC107 | TACGTAGCCCCTTGCTCATT (SEQ ID NO: 487) | TGTAAAACGACGGCCAGTCAAACCATTTCCTCCATTGTG (SEQ ID NO: 488) |
| MTIC124 | TTGGGTTGTCAATAATGCTCA (SEQ ID NO: 489) | TGTAAAACGACGGCCAGTTTGTCACGAGTGTTGGAATTTT (SEQ ID NO: 490) |
| MTIC169 | GCGTGCTAGGTTTGAGAGGA (SEQ ID NO: 491) | TGTAAAACGACGGCCAGTTCAAAACCCTAAAACCCTTTCTC (SEQ ID NO: 492) |
| MTIC183 | TTCTCTTCAAGTGGGAGGTA (SEQ ID NO: 493) | TGTAAAACGACGGCCAGTAAATGGAAGAAAGTGTCACG (SEQ ID NO: 494) |
| MTIC19 | TGCAACAGAAGAAGCAAAACA (SEQ ID NO: 495) | TGTAAAACGACGGCCAGTTCTAGAAAAGCAATGATGTGAGA (SEQ ID NO: 496) |
| MTIC233 | AAGGAACAATCCCAGTTTTT (SEQ ID NO: 497) | TGTAAAACGACGGCCAGTGCGTAACGTAACAACATTCA (SEQ ID NO: 498) |
| MTIC238 | CCTTAGCCAAGCAAGTAAAA (SEQ ID NO: 499) | TGTAAAACGACGGCCAGTTTCTTCTTCTAGGAATTTGGAG (SEQ ID NO: 500) |
| MTIC247 | TGAGAGCATTGATTTTTGTG (SEQ ID NO: 501) | TGTAAAACGACGGCCAGTTTCGCAGAACCTAAATTCAT (SEQ ID NO: 502) |
| MTIC248 | GGATTGTGATGAAGAAATGG (SEQ ID NO: 503) | TGTAAAACGACGGCCAGTTATCTCCCTTCTCCTTCTCC (SEQ ID NO: 504) |
| MTIC249 | GTGGGTGAGGATGTGTGTAT (SEQ ID NO: 505) | TGTAAAACGACGGCCAGTTAGGTCATGGCTATTGCTTC (SEQ ID NO: 506) |
| MTIC250 | CGTTGATGATGTTCTTGATG (SEQ ID NO: 507) | TGTAAAACGACGGCCAGTGCCTGAACTATTGTGAATGG (SEQ ID NO: 508) |
| MTIC258 | TGAAATTCACATCAACTGGA (SEQ ID NO: 509) | TGTAAAACGACGGCCAGTCACCACCTTCACCTAAGAAA (SEQ ID NO: 510) |
| MTIC304 | AGCGTAAAGTAAAACCCTTTC (SEQ ID NO: 511) | TGTAAAACGACGGCCAGTTTGGGCTTAATTTGACTGAT (SEQ ID NO: 512) |
| MTIC332 | GGTCATACGAGCTCCTCCAT (SEQ ID NO: 513) | TGTAAAACGACGGCCAGTCCCTGGGTTTTTGATCCAG (SEQ ID NO: 514) |
| MTIC338 | CATTGGTGGACGAGGTCTCT (SEQ ID NO: 515) | TGTAAAACGACGGCCAGTTCCCCTTAAGCTTCACTCTTTTC (SEQ ID NO: 516) |
| MTIC343 | CCATTGCGGTGGCTACTCT (SEQ ID NO: 517) | TGTAAAACGACGGCCAGTTCCGATCTTGCGTCCTAACT (SEQ ID NO: 518) |
| MTIC35 | GGCAGGAACAGATCCTTGAA (SEQ ID NO: 519) | TGTAAAACGACGGCCAGTGAAGAAGAAAAAGAGATAGATCTGTGG (SEQ ID NO: 520) |
| MTIC354 | AACCTACGCTAGGGTTGCAG (SEQ ID NO: 521) | TGTAAAACGACGGCCAGTAAGTGCCAAAGAACAGGGTTT (SEQ ID NO: 522) |
| MTIC452 | TCACAAAAACTGCATAAAGC (SEQ ID NO: 523) | TGTAAAACGACGGCCAGTCTAGTGCCAACACAAAAACA (SEQ ID NO: 524) |
| MTIC470 | CCCTTCACAGAATGATTGAT (SEQ ID NO: 525) | TGTAAAACGACGGCCAGTGGTTCGTGTATTTGTTCGAT (SEQ ID NO: 526) |
| MTIC51 | ACAAAAACTCTCCCGGCTTT (SEQ ID NO: 527) | TGTAAAACGACGGCCAGTAGTATAGTGATGAAGTGGTAGTGAACA (SEQ ID NO: 528) |
| MTIC84 | GGGAAAAGGTGTAGCCATTG (SEQ ID NO: 529) | TGTAAAACGACGGCCAGTTCTGAGAGAGAGACAAACAAAACAA (SEQ ID NO: 530) |

TABLE 1-continued

Alfalfa genomic and trichome EST-SSRs used to genotype the mapping populations.

| Primer ID | Reverse primer sequence | Forward primer sequence |
|---|---|---|
| MTIC94 | CAGGGTCAGAGCAACAATCA (SEQ ID NO: 531) | TGTAAAACGACGGCCAGTGCTACAACAGCGCTACATCG (SEQ ID NO: 532) |
| MTIC95 | AGGAAGGAGAGGGACGAAAG (SEQ ID NO: 533) | TGTAAAACGACGGCCAGTAAAGGTGTTGGGTTTTGTGG (SEQ ID NO: 534) |
| RCS0121 | CTGCTTTGGTTTGGAAGAAA (SEQ ID NO: 535) | TGTAAAACGACGGCCAGTGGAAAGAATATGCAATTTCTCGAT (SEQ ID NO: 536) |
| RCS1209 | TGAACTTTGAAGCCACATTGA (SEQ ID NO: 537) | TGTAAAACGACGGCCAGTAAAATCCAGAAGCACGAGTGA (SEQ ID NO: 538) |
| RCS2510 | GCCCTAAAAGTTGAAAGAGCA (SEQ ID NO: 539) | TGTAAAACGACGGCCAGTCACGAGGGAACACTTCATCA (SEQ ID NO: 540) |
| RCS2936 | CCAATGCAATTCGGTAATCC (SEQ ID NO: 541) | TGTAAAACGACGGCCAGTCGTTATTTATCCCTCCGGGT (SEQ ID NO: 542) |
| RCS4209 | TCACAATGGGCACCTAATCA (SEQ ID NO: 543) | TGTAAAACGACGGCCAGTCAATTTTCGCTGACTGACCA (SEQ ID NO: 544) |
| RCS4310 | GCCATTTGCTTCAACCTTGT (SEQ ID NO: 545) | TGTAAAACGACGGCCAGTGCCATTGCTGGAATCGTAAT (SEQ ID NO: 546) |
| RCS5452 | GGGCAAAACAGGAAATGAAA (SEQ ID NO: 547) | TGTAAAACGACGGCCAGTATTCGATAAGGATGGCGATG (SEQ ID NO: 548) |
| RCS5744 | TGTCGTCGTATCATTTCCGA (SEQ ID NO: 549) | TGTAAAACGACGGCCAGTGGAGATATGCTCATTCCCCA (SEQ ID NO: 550) |
| SNP1111 | TTGAAAGCACAAGGTTTCAGC (SEQ ID NO: 551) | GTGACTTTGATGCCGGAGTT (SEQ ID NO: 552) |
| TC105099 | AGATAGGAATTTGGGTCGGG (SEQ ID NO: 553) | TGTAAAACGACGGCCAGTACAACCATGATGTGGGAATG (SEQ ID NO: 554) |
| TC106861 | GCAGGGCTGAGACTCCAGTA (SEQ ID NO: 555) | TGTAAAACGACGGCCAGTAGCCCTGCTTTTTCTCCTCT (SEQ ID NO: 556) |
| TC85780-1 | AAAGTGACATGATCCACAGG (SEQ ID NO: 557) | TGTAAAACGACGGCCAGTGCTAAGAAAGCATGGGGTTGTTGG (SEQ ID NO: 558) |
| TC96233 | GTGGCGTTTCAAATCCTTGT (SEQ ID NO: 559) | TGTAAAACGACGGCCAGTTTGACTCAAACACACCCCAA (SEQ ID NO: 560) |

Example 5

Evaluation of Aluminum Tolerance Using the Callus Bioassay

The parental clones Altet-4 and NECS-141, and 185 $F_1$ genotypes were evaluated for their Al-tolerance response using Blaydes medium (ALB) as previously described (Parrot and Bouton, Crop Sci 30:387-389, 1990). Leaves and petioles from the individual genotypes were used for callus induction. Half of a single 2-week old callus was transferred to Blaydes medium with Al (+ALB, pH 4.0 with 400 µM of Al supplied by $AlCl_3$) and the other half was transferred to Blaydes medium without Al (−ALB, pH 4.0). Individual calli were weighed and transferred to fresh +ALB and −ALB medium at one week intervals for 8 weeks to determine the relative growth rate of each genotype. The experimental design for the callus bioassay using ALB medium included three replications with five individual calli per genotype per replication. Al tolerance (+ALB/−ALB) was estimated using the total callus weight ratio (TCWR) of each genotype grown in medium +Al and −Al.

The relative growth rate of Altet-4 calli in media Al+ vs. Al− was consistently higher than any other genotype evaluated, including the other Altet genotypes (FIG. 1). Therefore, Altet-4 was used as the Al-tolerant parent to develop the population NECS141Altet4 segregating for Al tolerance.

Figure 2:
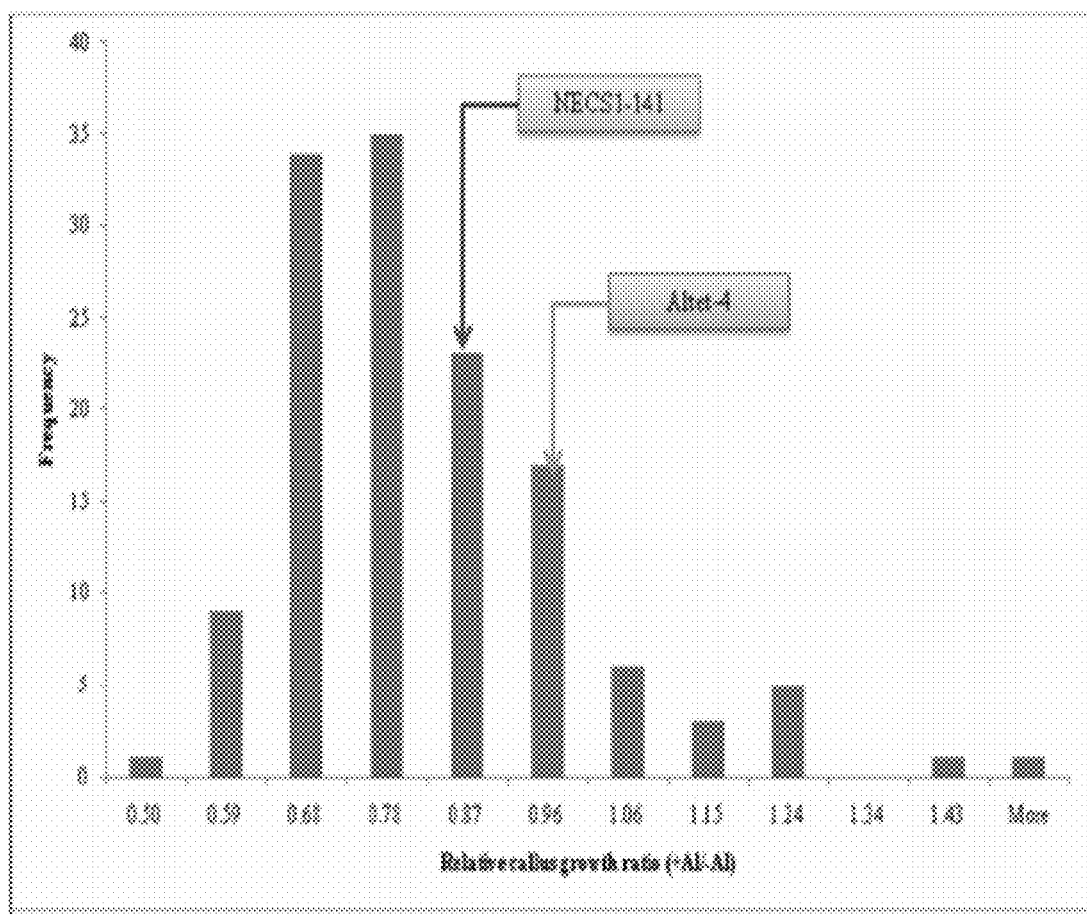
FIG. 2: Distribution of an aluminum-tolerant phenotype of the NECS141Altet4 mapping population. The phenotype graphed is the relative callus growth ratio at 8 weeks of growth in the callus bioassay.

The phenotypic evaluations of Al tolerance in the NECS141Altet4 population using the callus bioassay exhibited a continuous and normal distribution consistent with polygenic inheritance (FIG. 2). The relative growth rates of the progeny ranged from 0.5 to >1.7 suggesting transgressive segregation for Al tolerance in this population.

Statistical analysis. Variation for Al tolerance from phenotypic evaluations in the callus bioassay and whole plant assay in media, and the correlations between phenotyping systems were determined using SAS 9.1 (SAS, Cary, N.C.). Statistical differences between genotypes were determined using PROC GLM and LSMEANS with genotype treated as a random variable and replication as fixed effect. PROC CORR was used to evaluate the correlation between callus growth and root growth in both assays. The normality of the Al tolerance phenotypic data from the segregating population was evaluated with the Shapiro-Wilk test (Shapiro and Wilk, Biometrika 52:591-611, 1965) using PROC UNIVARIATE.

Results.

Phenotypic evaluations of Al tolerance in the mapping population using the callus bioassay exhibited a continuous and normal distribution based on a Shapiro-Wilk (W) score of 0.92 (P<0.001) (FIG. 1A). The TCWR of Altet-4 (0.91) was higher than the TCWR of NECS-141 (0.74). The mean TCWR of the $F_1$ progeny ranged from 0.50 to 1.70, with a population mean of 0.78 (sd=0.17) suggesting transgressive segregation for Al tolerance in this population.

Example 6

Evaluation of Aluminum Tolerance Using the Whole-Plant Culture Media Assay

Clonally propagated alfalfa (stem cuttings) from each individual in the mapping population were evaluated for Al-tolerance using the whole plant assay as previously described by Khu et al. (2011a, *Crop Sci* 52. doi:10.2135/cropsci2011.2105.0256). Briefly, the $CaCl_2$ medium contains 200 μM 4 $CaCl_2$, 1.4% Gelzan (G3251, PhytoTechnology Laboratories), and either 0 (pH 7 and pH 4) or 1 mM $AlCl_3$ (pH 4). The pH was adjusted to pH 3 and pH 10.5 to obtain media with pH 4 and 7, respectively, after autoclaving due to the lack of buffering capacity. Apical stem cuttings were rooted in least macro salt (LMS) medium which consisted of 0.1 mM $CaCl_2$, 500 μM $KNO_3$ and 500 μM $MgSO_4$ and 1.2% Gelzan. Cuttings with visually uniform root size and lateral root number were transferred to $CaCl_2$ medium −Al and +Al (1 mM $AlCl_3$). The experimental design included five replications with a single rooted cutting per replication and treatment combination (pH 7 −Al, pH 4 −Al, and pH 4 +Al). The total root length of each clone was measured after 14 d of growth in medium with pH 7 −Al, pH 4 −Al, and pH 4 +Al using the winRHIZO® software (Regent Instruments, Québec, Canada). Al tolerance (pH 4 +Al/pH 7 −Al) was estimated using the average total root length ratio (TRLR) of each genotype grown in media at pH 7 −Al and pH 4 +Al.

Figure 3:
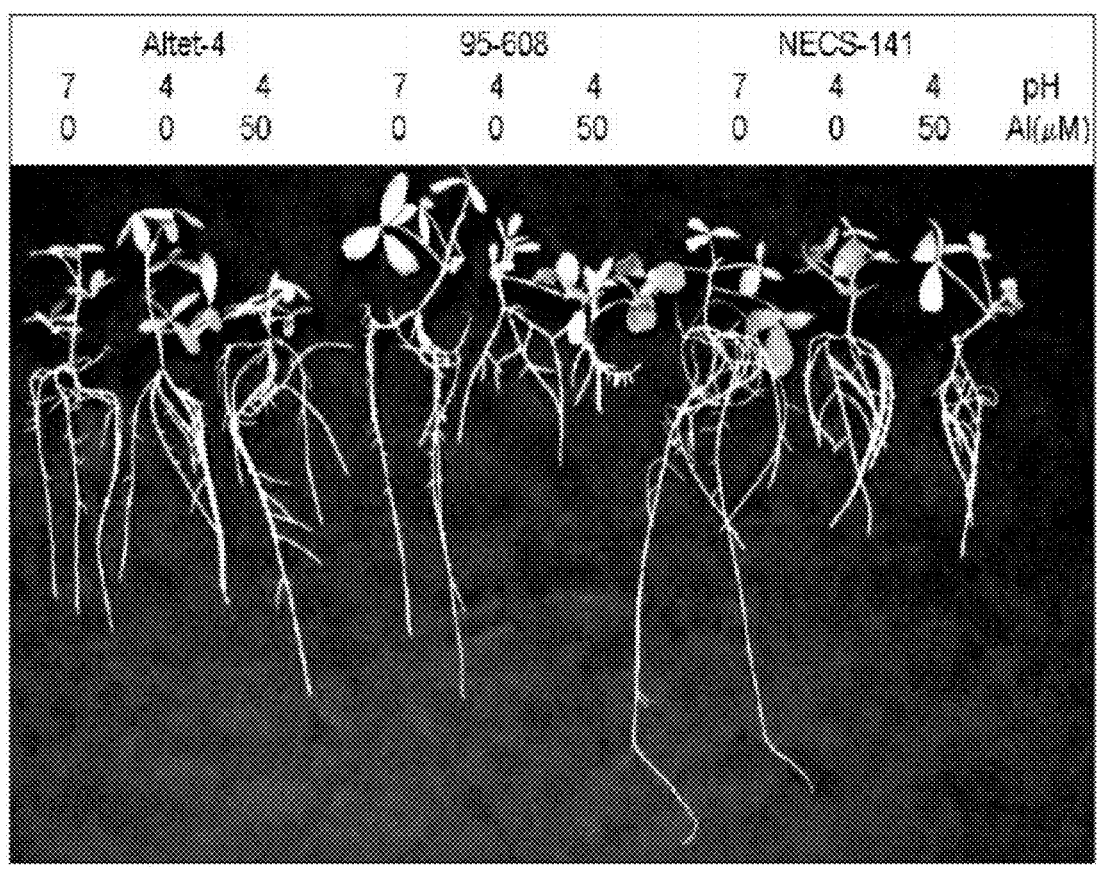
FIG. 3: Phenotypes of three genotypes of tetraploid alfalfa after 18 days of growth in the whole-plant culture media assay.
Figure 4:
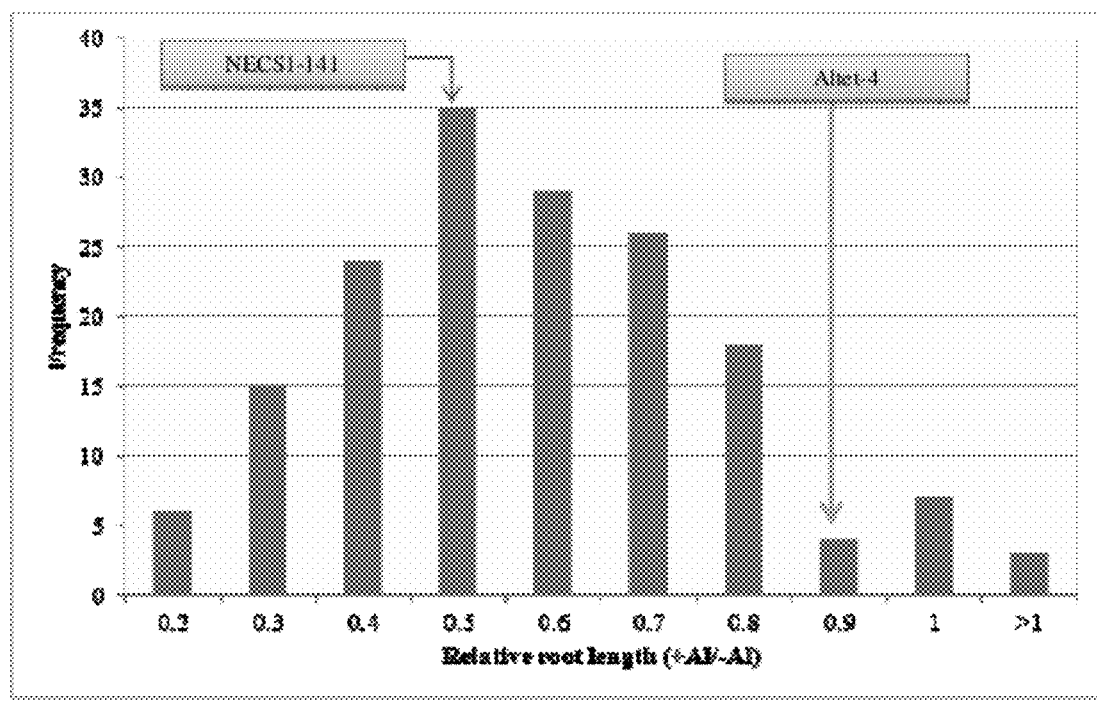
FIG. 4: Frequency distribution of Al tolerance based on relative root growth from the NECSAltet4 population from the whole plant assay in media.

The relative root length (pH7/pH4Al+) of Altet-4 and NECS-141 resulting from WPA evaluations in media (FIGS. 3 & 4) was 0.93 and 0.43, respectively. The phenotypic evaluations of Al tolerance in the NECS141Altet4 population using the WPA also exhibited a continuous and normal distribution consistent with polygenic inheritance (FIG. 4). The relative root length of the progeny ranged from 0.23 to >1.26 again indicating transgressive segregation for Al tolerance in this population and confirming the ability of the assay to detect quantitative differences in Al tolerance. $F_1$ progeny individuals with higher Al tolerance than the Al tolerant parent were observed in both the CBA and the WPA in media assays suggesting that both parents may be contributing positive alleles for Al tolerance.

Example 7

DNA Isolation and Genotyping

Genomic DNA from each $F_1$ progeny in the mapping population was extracted separately using the DNeasy Plant Mini Kit (QIAGEN, Cat. No. 69104, Valencia, USA). A total of 755 SSR primer pairs from *M. truncatula* EST-SSRs (Eujayl et al. *Theor Appl Genet* 108:414-422, 2004; Julier et al. BMC Plant Biol 3:9, 2003; Sledge et al. *Theor Appl Genet* 111:980-992, 2005) and alfalfa genomic SSRs (Diwan et al. *Theor Appl Genet* 101:165-172, 2000), were used to screen for polymorphism between Altet-4 and NECS-141 as previously described by Zhang et al (*Plant Methods* 4:19, 2008). In addition to previously used SSR markers, 269 SSR primers developed from alfalfa trichome unigene sequences were used to screen for polymorphism between the two parents. Briefly, the total 4,485 *Medicago sativa* trichome unigenes, consisting of 3,406 singletons and 1,079 contigs or tentative consensus (TC) sequences, assembled from two EST libraries (MS_TRI1 and MS_TRI2) of glandular trichomes isolated from *Medicago sativa* stems and one EST library (MS_FAL_SSH) of cold-treated *Medicago falcata* L. subsp. *falcata* leaves were downloaded from the TrichOME database (Dai et al. *Pl Physiol* 152:44-54, 2010). Candidate SSRs were identified from the downloaded unigenes using the SSRIT Perl scripts (Kantety et al. *Plant Mol Biol* 48:501-510, 2002) for perfect SSR identification and the Sputnik software (espressosoftware.com/sputnik/index.html; Verified Aug. 8 2011) for imperfect SSR identification as previously described (Zhang et al. *Plant Methods* 4:19, 2008). PCR primers were designed using Primer3 (Rozen and Skaletsky, Primer3 on the WWW for general users and for biologist programmers. In: Misener S, Krawetz S A (eds) Bioinformatics Methods and Protocols. Humana Press, pp 365-386, 1999) to amplify the identified candidate SSR regions. PCR reactions were prepared in a 10 μl volume and contained 20 ng of template DNA, 2.5 mM $MgCl_2$, 1×PCR buffer II (Applied Biosystems, Foster City, Calif., USA), 0.15 mM dNTPs, 1.0 pmol each of the reverse primer with an additional 18 nucleotides from the M13 forward sequencing universal primer (e.g. Schuelke *Nature Biotechnol*. 18:233-234, 2000) appended to the 5'end, 0.25 pmol of the forward primer (see Table 5), and 0.5 U GoTaq® DNA polymerase (Promega, Madison, Wis., USA). The M13 nucleotide sequences were labeled either with blue (6-FAM), green (HEX), yellow (NED) or red (PET) fluorescent tags. PCR products with different fluorescent labels and with different fragment sizes were pooled for detection. A total of 1.6 μl of pooled PCR products were combined with 12 μl of deionized formamide and 0.5 μl of GeneScan-500 LIZ internal size standard and analyzed on the ABI PRISM® 3730 Genetic Analyzer (Applied Biosystems, Foster City, Calif., USA). GeneMapper 3.7 software was used to analyze the DNA amplicons and assign allele scores.

Example 8

Genotype and QTL Identification

A total of 305 primers from the total legume SSR primer pairs evaluated were polymorphic between the parental genotypes Altet-4 and NECS-141. 212 SSR loci from Altet-4 and 226 loci from NECS-141 were captured in the genetic linkage map, which consists of eight consensus LGs representing the eight chromosomes in the alfalfa genome. The consensus map length of Altet-4 was 826 cM and 745 cM for NECS-141. The consensus parental maps were constructed from the 32 co-segregation groups for each parental genome. These co-segregation groups provide a more precise view of linkage relationships among marker alleles and facilitate identification of positive alleles for QTLs. Single factor analysis of variance (SF-ANOVA) and the non-parametric Kruskal-Wallis test identified significant markers associated with Al tolerance from the CBA on LGs 1, 3, 4, 5, 6, and 8 in the NECS141Altet4 population (Table 2). Interval mapping was performed for all Al tolerance screening methods utilized in this study. Based on phenotypic data from the CBA, whole plant assay in media and whole plant assay in soil, Al tolerance QTLs were identified on six LGs (Table 2 & FIG. 5).

TABLE 2

Single factor analysis for Al tolerance from the callus bioassay.

| Markers | Linkage group | Average progeny callus growth ratio (Al+/Al−) absent | Average progeny callus growth ratio (Al+/Al−) present | Standard error | P value of ANOVA | P value of Kruskal-Wallis test |
|---|---|---|---|---|---|---|
| 608Altet4 population | | | | | | |
| MTIC233-135 | 1 | 0.98 | 0.91 | 0.031 | 0.037 | 0.043 |
| MTIC247-130 | 1 | 0.89 | 0.97 | 0.031 | 0.02 | 0.015 |
| MTIC19-154-2 | 2 | 0.96 | 0.90 | 0.031 | 0.026 | 0.035 |
| MTIC51-146 | 3 | 1.24 | 0.92 | 0.068 | 0.002 | 0.000 |
| AW289-312 | 4 | 0.91 | 0.99 | 0.032 | 0.028 | 0.011 |
| 2c12gga5-1-171 | 5 | 0.86 | 0.96 | 0.036 | 0.003 | 0.007 |
| 2c06ctc8-1-200 | 5 | 1.02 | 0.92 | 0.038 | 0.018 | 0.008 |
| 3d03atc5-1-246 | 6 | 0.88 | 0.97 | 0.033 | 0.002 | 0.008 |
| AW64-202 | 7 | 0.90 | 0.98 | 0.031 | 0.019 | 0.010 |
| 1b11caa6-1-273 | 7 | 0.97 | 0.91 | 0.031 | 0.043 | 0.050 |
| AW166-203 | Un-linked | 1.05 | 0.91 | 0.040 | 0.011 | 0.001 |
| RCS5743-222 | Un-linked | 0.91 | 0.98 | 0.031 | 0.029 | 0.015 |
| RCS1812-142 | Un-linked | 0.97 | 0.89 | 0.031 | 0.007 | 0.005 |
| NECS141Altet4 population | | | | | | |
| u-MTIC233-145 | 1 | 0.85 | 0.76 | 0.042 | 0.037 | 0.039 |
| 1c09gat6-1-211 | 3 | 0.87 | 0.76 | 0.041 | 0.026 | 0.008 |
| 1h09aat11-1-233 | 4 | 0.75 | 0.84 | 0.034 | 0.031 | 0.009 |
| MTIC249-125 | 4 | 1.09 | 0.77 | 0.123 | 0.019 | 0.010 |
| 2c06gat6-1-128 | 5 | 0.83 | 0.74 | 0.031 | 0.024 | 0.011 |
| MTIC250-133 | 6 | 0.74 | 0.82 | 0.030 | 0.031 | 0.010 |
| BF26-306 | 7 | 0.82 | 0.73 | 0.030 | 0.01 | 0.006 |

TABLE 3

Al tolerance QTLs identified in the NECS141Altet4 population based on interval mapping from three phenotypic assays (callus bioassay, whole plant assay in media, and soil-based assay).

| LG | Parents | Callus bio-assay Position (cM) | Callus bio-assay R²† | Whole plant assay Position | Whole plant assay R² | Soil-based assay Position | Soil-based assay R² |
|---|---|---|---|---|---|---|---|
| 1 | Altet-4 | | | | | 72 (Rdmr1) | 9.6 |
|   |         | 4 | 10.9 | | | 14 (Rdmr2) | 7.7 |
|   | NECS-141 | | | 98 (Al50) | 17.3 | | |
|   |          | 100 | 14.2 | 98 (Al1K) | 26.9 | | |
| 3 | Altet-4 | 74 | 25.2 | | | | |
| 4 | Altet-4 | | | | | 38 (Rdmr1) | 29.7 |
|   |         | | | | | 4 (Rdmr2) | 20.2 |
|   | NECS-141 | 98 | 15.9 | | | | |
|   |          | | | | | 32 (Rdmr2) | 20.6 |
| 5 | Altet-4 | 62 | 14.1 | | | | |
| 6 | Altet-4 | | | | | 102 (Rdmr2) | 13.1 |
|   | NECS-141 | 8 | 7.8 | | | | |
| 7 | Altet-4 | | | 70 (Al50) | 19.5 | | |
|   |         | 52 | 16.2 | 72 (Al1K) | 9.9 | | |

$R^{2\dagger}$ = % variance explained;
Al50 = Relative root length in whole plant assay in media (pH 7Al−/pH 4Al+), with 50 μM Al;
Al1K = Relative root length in whole plant assay in media (pH 7Al−/pH 4Al+) with 1 mM Al;
Rdmr1: relative dry matter of roots between limed and un-limed soil from soil-based experiment 1;
Rdmr2: relative dry matter of roots between limed and un-limed soil in soil-based experiment 2.

Figure 5B:
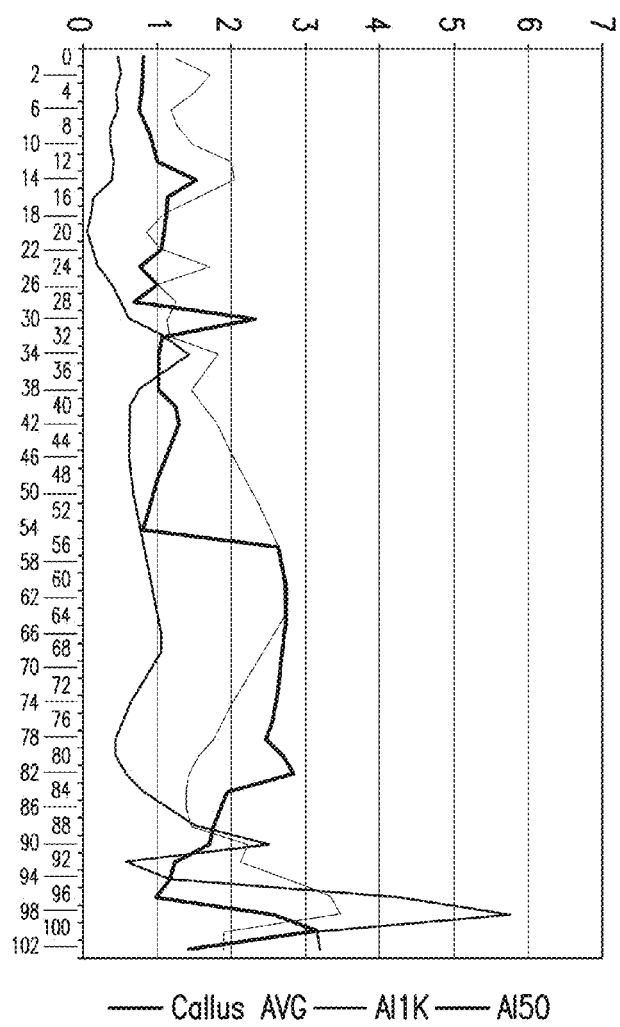
Figure 5D:
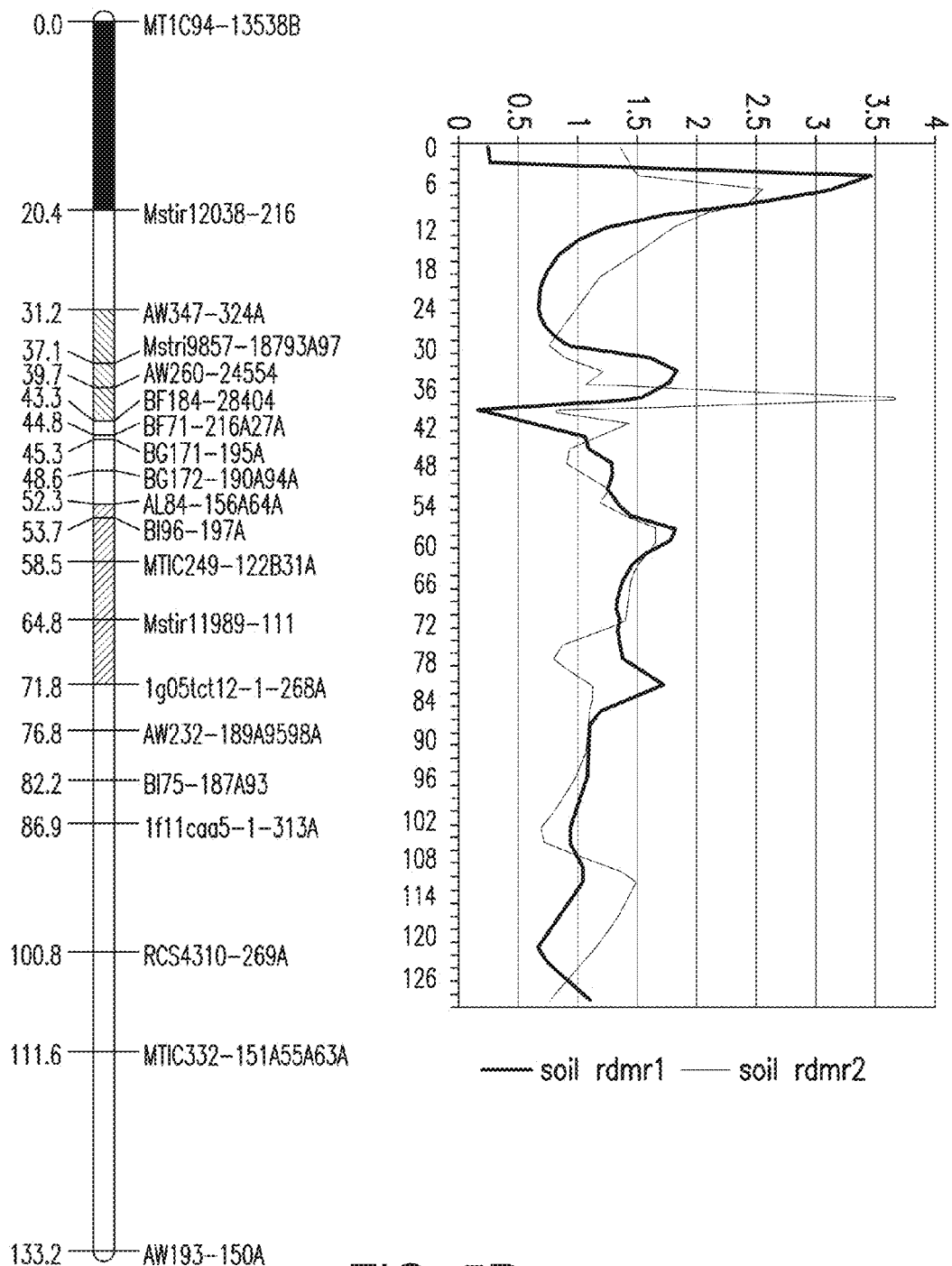
Figure 5F:
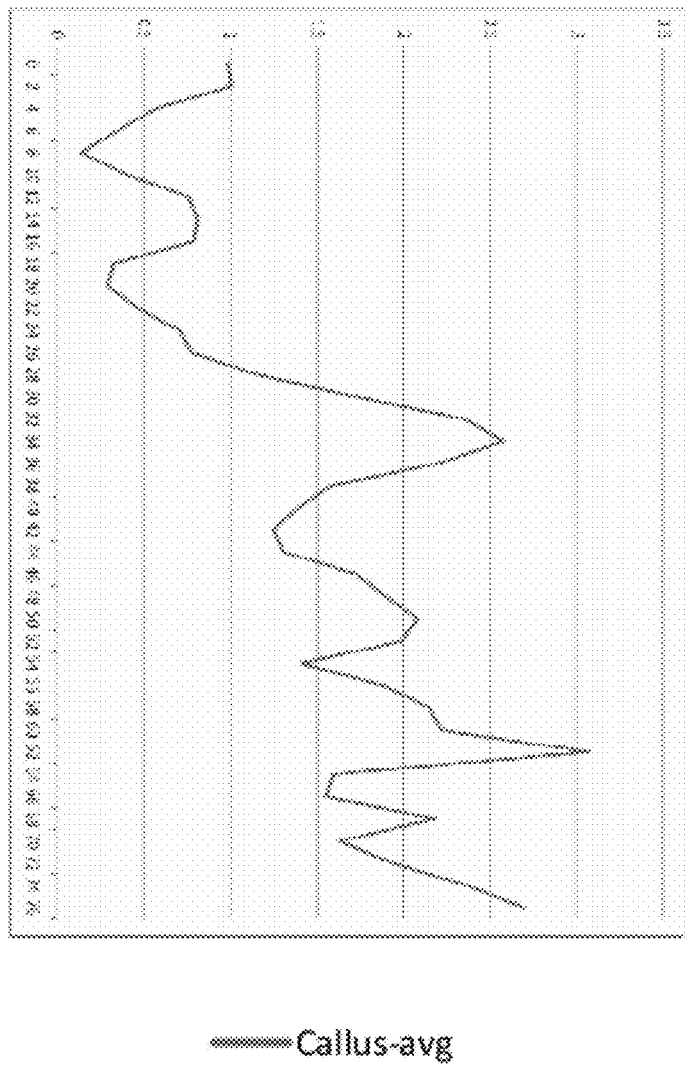
Figure 5H:
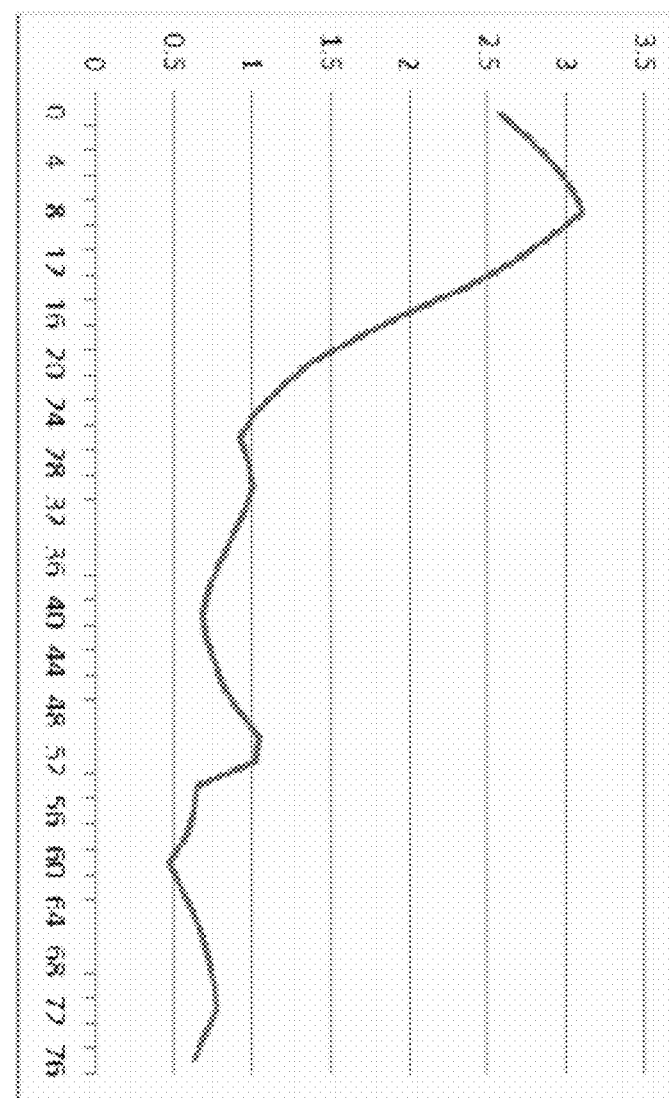
Figure 5I:
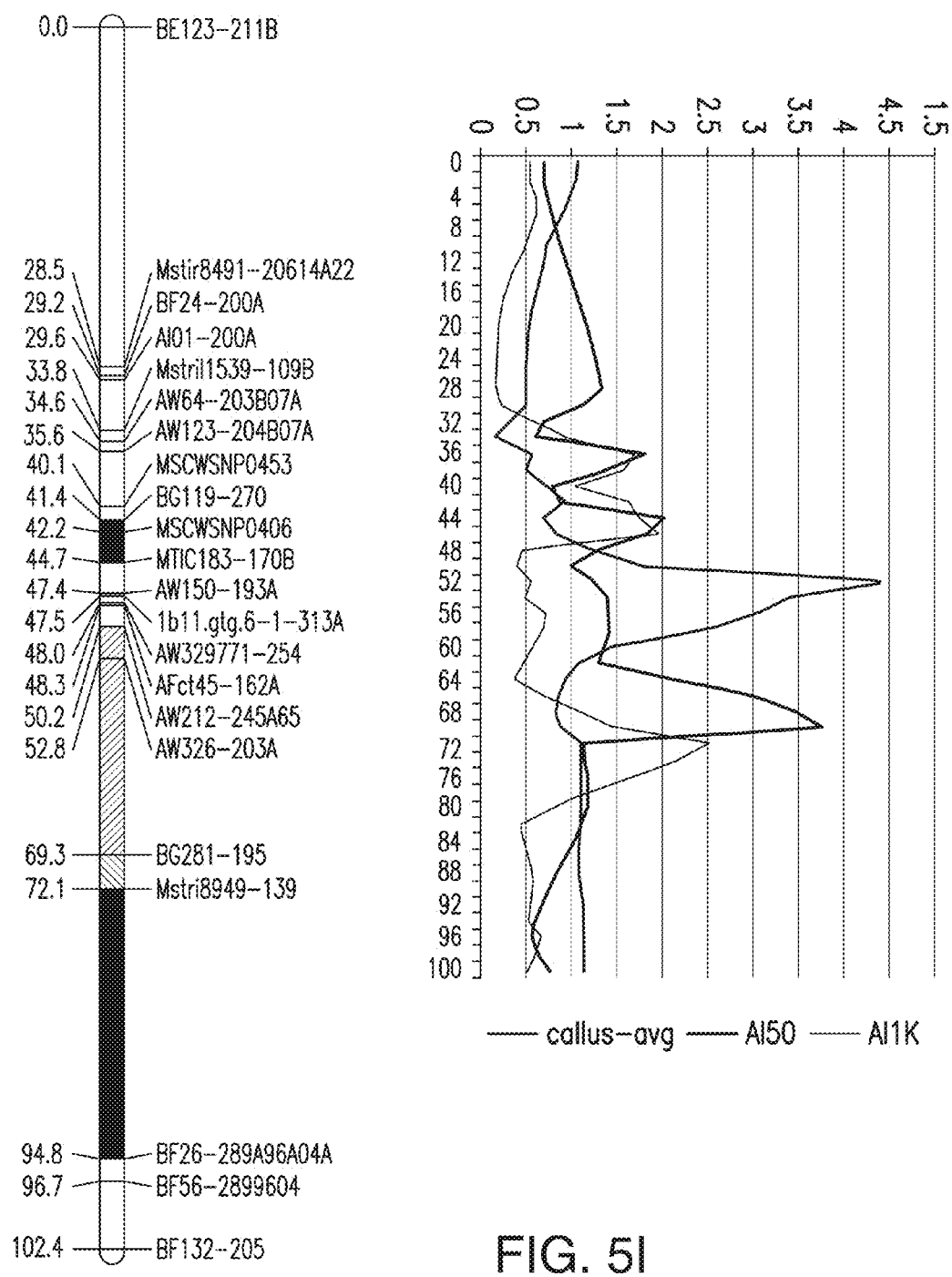
Figure 6A:
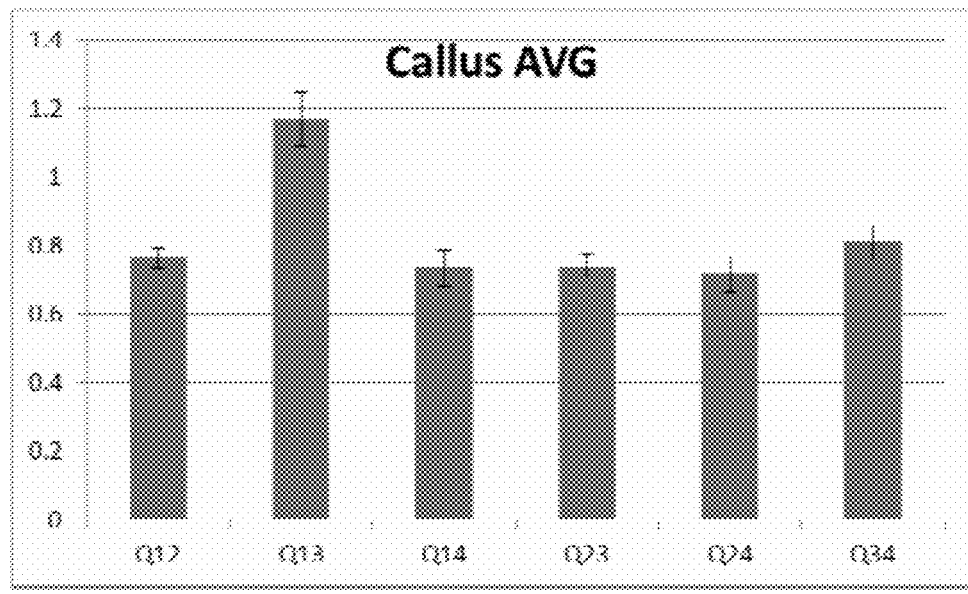

Significant QTLs for Al tolerance on LGs 1, 3, 4, 5 and 7 were identified in which Altet-4 contributed the positive allele (FIG. 5). In the callus bioassay ("CBA"), the QTL for Al tolerance on LG-3 (74 cM) explained 25.2% of the variation in the Al tolerance response. Using interval mapping, a QTL for callus growth was also identified at 90 cM on LG 1 from Altet-4. This QTL explained 20.8% of the phenotypic variation for total callus weight ("TCWR"). The allelic effect at each Al tolerance QTL was estimated using the mean phenotypic value for all progeny with a given allele at a particular locus and used to evaluate the performance of individuals with a given allelic composition (FIG. 6). For the Al tolerance QTL on LG-3, the allelic combination '$Q_{13}$' at 74 cM from homologous chromosomes H1 and H3 contributed by Altet-4, has higher Al tolerance compared to all other possible allelic combinations at this loci (FIG. 6A). A QTL for Al tolerance based on the CBA and the whole plant assay ("WPA") was identified on LG-7 and explains 19.5% of the variation observed in relative root length (Table 3 & FIG. 5I). In this case, Altet-4 contributes the positive alleles and '$Q_{13}$' represents the most desirable allelic combination (FIG. 6D). This QTL for Al tolerance was significant at both Al concentrations used in the WPA (Al50 and Al1K) suggesting a potential mechanism of tolerance independent of Al concentration.

Three Al tolerance QTLs were identified on chromosomes 1, 4, and 6 in the NECS-141 parental linkage map. Although NECS-141 has lower phenotypic values than Altet-4 (FIGS. 2 & 3; Table 4), positive alleles for Al tolerance from NECS-141 were identified (FIG. 5B, 5E, 5H). These findings indicate that while NECS-141 is phenotypically poor, it may posses some alleles capable of increasing the trait value. A previous study in diploid alfalfa also identified Al tolerance QTLs from the Al sensitive parent (Sledge et al., *Crop Sci* 42:1121-1128, 2002). Others have also identified QTL alleles enhancing the trait value from a phenotypically inferior parent (Tanksley and Nelson, *Theor Appl Genet* 92:191-203, 1996; Ali et al., *Theor Appl Genet* 101:756-7662000; Lou et al., *Euphytica* 158:87-94, 2007). The QTL for Al tolerance from NECS-141 located on chromosome 1 (98 cM) explain 26.9% of the variation in relative root length (Table 3). The mean relative root growth with QTL genotypes from the WPA at two different Al concentrations indicates that 'Q34' is the most desirable allelic combination at this locus (FIGS. 7A & 7B).

TABLE 4

Al tolerance of alfalfa genotypes obtained from soil-based assay and whole plant assay in media.

| Genotypes | Whole plant assay† | Soil-based assay‡ |
|---|---|---|
| 95-608 | 0.56 (2)§ | 0.54 (2) |
| NECS-141 | 0.52 (3) | 0.31 (3) |
| Altet-4 | 0.97 (1) | 0.71 (1) |

†Ratio of total root length (pH 7 Al−/pH 4 Al+ at 50 μM)
‡Ratio of root dry matter (unlimed/limed)
§Rankings of genotypes based on performance, 1: most Al tolerant; 3: least Al tolerant.

Figure 6B:
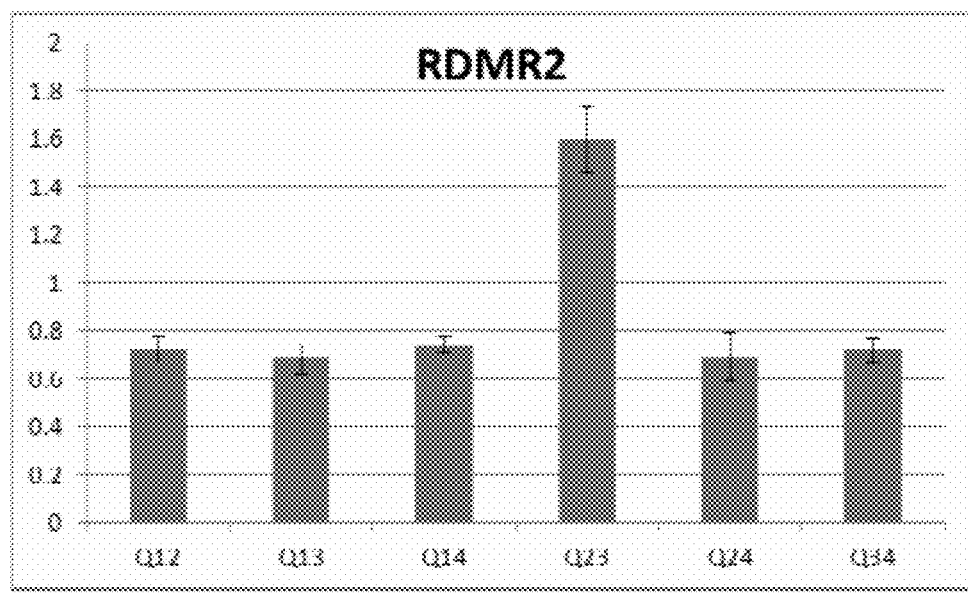

Soil-based assays were performed twice in the greenhouse using replicates in time (experiment 1 and experiment 2). The two experiments showed significant covariance (data not shown) and thus each set of experimental data was analyzed separately. Soil-based phenotypic data from experiment 1 and 2 was used to identify two QTLs for Al tolerance on chromosome 1 and 4 from Altet-4 (Table 3, FIG. 5A & FIG. 5D). In experiment 2, QTLs for Al tolerance were identified on chromosomes 1, 4 and 6 (Table 3). In all three cases, Altet-4 contributed the positive allele for Al tolerance. The most desirable allelic combination at both Al tolerance QTLs identified on chromosome 4 is 'Q23' (FIG. 6B & FIG. 6C).

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the invention as disclosed.

Example 9

Linkage Map Construction and QTL Analysis

Linkage and QTL analysis were performed using the TetraploidMap software (Hackett et al., *J Hered* 98:727-729, 2007) previously used for mapping in tetraploid alfalfa (Julier et al., *BMC Plant Biol* 3:9, 2003; Robins et al., *Crop Sci* 47 1-10, 2007; Robins et al., *Crop Sci* 48:1780-1786, 2008) and tetraploid potato (Bradshaw et al., *Theor Appl Genet* 116:193-211, 2008; Khu et al., *Am J Potato Res* 85:129-139, 2008). The parental genotypes were determined based on the observed parent and offspring marker score (Luo et al., *Theor Appl Genet* 100:1067-1073, 2000). Markers were assigned to a given LG based on the location of previously mapped SSR markers (Julier et al., *BMC Plant Biol* 3:9, 2003; Narasimhamoorthy et al., *Theor Appl Genet* 114:901-91, 2007b; Robins et al., *Crop Sci* 47 1-10, 2007) and simplex coupling linkages. The EM algorithm was used to calculate the recombination frequency and LOD score to identify the most likely phase of markers on the same LG (Luo et al., *Genetics* 157:1369-1385, 2001). A simulated annealing algorithm (Hackett and Luo, *J Hered* 94:358-359, 2003) was used to identify the most accurate order of markers and distance between markers.

Multi-allelic SSR markers with either three or four alleles representing different homologous chromosomes were used to identify $F_1$ genotypes that inherited products of double reduction. Once the allelic combination of each $F_1$ genotype was identified, markers located in the interval between this locus and the distal end of the chromosome were evaluated to confirm double reduction in that $F_1$ genotype. The 27 $F_1$ genotypes resulting from double reduction identified in this study were not included in the corresponding linkage map and QTL analysis because a reliable model for analyzing double reduction is not available (Bradshaw et al., *Theor Appl Genet* 116:193-211, 2008).

Single-factor analysis of variance (SF-ANOVA) and interval mapping were performed using the TetraploidMap software as described by Hackett et al. (*Genetics* 159:1819-1832, 2001) and Bradshaw et al. (*Theor Appl Genet* 116: 193-211, 2008). The inheritance of each marker allele in the $F_1$ progeny representing homologous chromosomes i and j from the parental genotypes were denoted using $Q_{ij}$. For each marker allele combination, the mean value of all genotypes containing the allele was compared to the mean value of the individuals without the allele. A maximum-likelihood approach for fitting QTL models was evaluated with separate means for each of the possible QTL genotypes (gametes $Q_1Q_2$, $Q_1Q_3$, $Q_1Q_4$, $Q_2Q_3$, $Q_2Q_4$, and $Q_3Q_4$) using a 2 cM window along the chromosome as previously described (Hackett, 2001). Significant QTLs were identified based on LOD scores greater than 3.0 and a threshold value determined using 500 permutations. After the significant QTLs were identified, four models were evaluated using the simplex allele (absent $Q_i$ versus present $Q_i$) and six models were evaluated for the dominant duplex allele on the pairs of homologous chromosomes (e.g., $Q_1Q_2+Q_1Q_{3+}$ $Q_1Q_{4+}$ $Q_2Q_{3+}$ $Q_2Q_4$ versus $Q_3Q_4$) and compared them using the likelihood ratio test. Biallelic genotypes are reported for each marker combination with less than 5% missing data points. Interval mapping was performed using the permutation test with 500 iterations to declare significance (P<0.05).

A total of 257 primer pairs (Table 5) from the 1,024 legume SSR primer pairs evaluated were polymorphic between the parental genotypes Altet-4 and NECS-141. For Altet-4, 283 SSR alleles were scored (Table 6). Of these, 198 were segregating in a 1:1 ratio (simplex) and 59 segregated in a 5:1 ratio (duplex). Among these, 70 co-dominant SSR combinations were identified by significant repulsion linkage and clustering analysis. For NECS-141, 231 SSR alleles segregated in a 1:1 ratio and 48 segregated in a 5:1 ratio. Among these, a total of 64 co-dominant SSR combinations were identified. SSR markers were used to construct linkage maps for the eight LGs corresponding to the eight alfalfa chromosomes. A total of 185 SSR loci from Altet-4 and 205 loci from NECS-141 were captured in the parental genetic linkage maps, with 115 loci in common between the two parental maps. The consensus maps covered 761 cM for Altet-4 and 721 cM for NECS-141, and included the 32 co-segregating homologous chromosomes (4 homologs for each of the eight chromosomes) for each parental genome (FIG. 9). Each homologous linkage group contained, on average, eleven SSR loci. The linkage maps generated in this study include multi-allelic co-dominant SSR markers not previously included in any tetraploid alfalfa linkage maps (Brouwer and Osborn, *Crop Sci* 40:1387-1396, 1999; Julier et al., *BMC Plant Biol* 3:9, 2003; Robins et al., *Crop Sci* 47 1-10, 2007; Sledge et al., *Theor Appl Genet* 111:980-992, 2005). Twenty-six double simplex markers (segregating in a 3:1 ratio) associated with a simplex coupling linkage group were identified in both parental simplex LGs. Segregation distortion was identified in 27% of the markers scored in this population, which is similar to levels of distortion in other alfalfa mapping studies performed using $F_1$ mapping populations (Julier et al., *BMC Plant Biol* 3:9, 2003; Robins et al., *Crop Sci* 47 1-10, 2007).

TABLE 5

List of SSR primer pairs used for linkage mapping and QTL identification in alfalfa

| Primer ID | Reverse primer sequence | Forward primer sequence | LG | Amplicon size range |
| --- | --- | --- | --- | --- |
| 122161-41 | CCACGTTGTTGAACAGTGGAAATG (SEQ ID NO: 1) | GCGAACTTGTTTCCGATGATGC (SEQ ID NO: 2) | 1 | 413-447 |
| 1a07aac5-1 | GAGCCATGTTGTTGGTGTTG (SEQ ID NO: 3) | TTGGTTGGTGGGGTTATCAT (SEQ ID NO: 4) | 3 | 144-162 |
| 1a09ggt5-1 | TCTCTGGTCAGCACCAACTG (SEQ ID NO: 5) | GCATGGTGAGAGACGTCGTA (SEQ ID NO: 6) | 4 | 250-252 |
| 1b08aga7-1 | TGGAGGGAAATGATTTAGCG (SEQ ID NO: 7) | AACGAAAACGAAAACGAACG (SEQ ID NO: 8) | 8 | 175-190 |
| 1b11caa6-1 | AACCTCCTCGACAACATTGG (SEQ ID NO: 9) | AACTCAAACCCGAACAATGC (SEQ ID NO: 561) | 7 | 254-281 |
| 1b11gtg6-1 | AACCTCCTCGACAACATTGG (SEQ ID NO: 9) | ACCTGGGATTGGGTTAGGAC (SEQ ID NO: 10) | 7 | 313-328 |
| 1b12ttc5-1 | GTCGTCGTAGAGTGGGGTGT (SEQ ID NO: 11) | GAGTGGCCATGGATTCAAAC (SEQ ID NO: 12) | 4 | 245-248 |
| 1c06tta6-1 | CAAATGAGAGCACGTTGTGAA (SEQ ID NO: 13) | ATCATATTGGCTTGGTGCAA (SEQ ID NO: 14) | 6 | 214-265 |
| 1c09gat6-1 | TTTTCCATTCCCACCTACCA (SEQ ID NO: 15) | TTTGGAAAACACTTGCCCAC (SEQ ID NO: 16) | 3 | 202-211 |
| 1c11tgg5-1 | TTGCCCTTTTGTCCAAGAAC (SEQ ID NO: 17) | GACGAGAGTCCCATCAGAGC (SEQ ID NO: 18) | 5 | 116-169 |
| 1c12tgt5-1 | TTACGATCTGGCTTGGAACC (SEQ ID NO: 19) | CTCGACCTGCACGACAATTA (SEQ ID NO: 20) | 5 | 100-235 |
| 1d06gaa6-1 | GAAGGTTTTGGGTGGTGATG (SEQ ID NO: 21) | CCATGGCTCTTTCCTACCAA (SEQ ID NO: 22) | 2 | 189-192 |
| 1e04aaat4-1 | GACCGGGATTGATGGATATG (SEQ ID NO: 23) | AACAAGAGATGGGAGGAAAAA (SEQ ID NO: 24) | 3 | 162-166 |
| 1e04tatc4-1 | TGTTTCTGATCAGGGCATTG (SEQ ID NO: 25) | TCTAGGTATTCGCTGGCGTT (SEQ ID NO: 26) | 3 | 232-244 |
| 1e08gat5-1 | ACTTCCTGACGGTCCTCCTT (SEQ ID NO: 27) | GGCGCATAATCACCATTACC (SEQ ID NO: 28) | 8 | 238-244 |
| 1e08tttc4-1 | TCCTTCTGGACAAGAAACCG (SEQ ID NO: 29) | TCCATCACGACATATTTCACTTTT (SEQ ID NO: 30) | 8 | 342-343 |
| 1f02tat6-1 | TGATGCTGTCCTATGCCAAG (SEQ ID NO: 31) | TGGAAAAGGCTTTGACTGTTG (SEQ ID NO: 32) | 5 | 321-335 |
| 1f08att6-1 | TGATGGATGCAATAGGGGAT (SEQ ID NO: 33) | TGACATCATATGCACGGTCC (SEQ ID NO: 34) | 6 | 116-119 |
| 1f08tat6-1 | ATGAAGGTCATTGCAAGGCT (SEQ ID NO: 35) | CTGCTGACTTCTGTCTGGCA (SEQ ID NO: 36) | 4 | 262-324 |
| 1f10ttg6-1 | AGTGCCGCTATGCTGCTATT (SEQ ID NO: 37) | TTGATCCATGTAGCCAACCC (SEQ ID NO: 38) | 5 | 210-263 |
| 1f11aatt4-1 | TTGAAAAGACACGGGGAAGT (SEQ ID NO: 39) | CCACAAAAGCAGATGGTTGA (SEQ ID NO: 40) | 6 | 192-195 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| 1f11caa5-1 | TTGGTGAGAGCTGGTGATTG (SEQ ID NO: 41) | TTACCGCTTTTGGATTCTGG (SEQ ID NO: 42) | 4 | 313-317 |
| 1g03gaa5-1 | TTTATCGGCGAAGAAGATCG (SEQ ID NO: 43) | TCCCGCTTCACTTCACTTTC (SEQ ID NO: 44) | 8 | 155-220 |
| 1g05cata17-1 | CCCTAAATCAGGGGTTCAAA (SEQ ID NO: 45) | CACTCATTGCTGAGGGCATA (SEQ ID NO: 46) | 2 | 139-173 |
| 1g05tct12-1 | TCAGAAATTCCCTCCCATTG (SEQ ID NO: 47) | AAGAATGACGAAGAGGCGAA (SEQ ID NO: 48) | 4 | 268-277 |
| 1h03aatt4-1 | TGATTCAAGGATGGGAAAGC (SEQ ID NO: 49) | TGTCTTCCGTGGTCTCACTG (SEQ ID NO: 50) | 1 | 202-229 |
| 1h03ata9-1 | GAGTTTCTGAATTCGCCGTC (SEQ ID NO: 51) | TCGGCATCAATCATGTCATC (SEQ ID NO: 52) | 1 | 300-303 |
| 1h09aat11-1 | CGATAATTCACCCCCATGAC (SEQ ID NO: 53) | CACAATCAAATGCATAGCCG (SEQ ID NO: 54) | 4 | 218-237 |
| 2a03aga5-1 | TCGAGAGCTCGGTATTCGAT (SEQ ID NO: 55) | ATCCAAGGGCGGTAGAAGAC (SEQ ID NO: 56) | 4 | 279-284 |
| 2a03gaa8-1 | TCGAGAGCTCGGTATTCGAT (SEQ ID NO: 57) | GTGTGGAAGAGACCGGAGAA (SEQ ID NO: 58) | 4 | 230-236 |
| 2a03tga5-1 | AAGCACTCTGAGCCACCATT (SEQ ID NO: 59) | TGAGGAAATTCTTGGGAGGA (SEQ ID NO: 60) | 8 | 277-292 |
| 2a07tatt4-1 | GCAGGGACGAAACCAGAATA (SEQ ID NO: 61) | TTGCACTTCCACTAAATGACTTG (SEQ ID NO: 62) | 5 | 316-318 |
| 2a09aac6-1 | CCCTCCAATCAAGAAACAGC (SEQ ID NO: 63) | CCCAATTCCAAACCAGAAAA (SEQ ID NO: 64) | 8 | 256-282 |
| 2a09ttta4-1 | GACCATTGATCATGTCTCACG (SEQ ID NO: 65) | CCAGATTGCTTACCAGGGAC (SEQ ID NO: 66) | 3 | 276-303 |
| 2c06ctc8-1 | AACAACCAAACTTGGCCTTG (SEQ ID NO: 67) | TGGTCGAAGGAAGCAGAGAT (SEQ ID NO: 68) | 5 | 173-200 |
| 2c06gat6-1 | ACTTCCATTGCCGCTTCTAA (SEQ ID NO: 69) | TGTGGCGAAGTAACGAAGAA (SEQ ID NO: 70) | 5 | 128-137 |
| 2c06tta9-1 | AAACCAATGATATCAAACTCCCTT (SEQ ID NO: 71) | AAAAAGTCATGCTACAAATCATAAAAA (SEQ ID NO: 72) | 3 | 244-304 |
| 2c12gga5-1 | AAATGGATTCGAACTCACGC (SEQ ID NO: 73) | AAGAAGAAAAATGGCAGGAGG (SEQ ID NO: 74) | 5 | 165-174 |
| 2c12tta5-1 | AGCCTCAAGCAGTCGTTGAC (SEQ ID NO: 75) | GGAGGGGAGCAAATCTCTTT (SEQ ID NO: 76) | 5 | 316-319 |
| 3d03atc5-1 | TGTGAACATCAGGAGGTGGA (SEQ ID NO: 79) | GTGAATGGTGGTCGTCTTCA (SEQ ID NO: 80) | 6 | 206-268 |
| 3d03cat6-1 | AACCATGCGGTGGTTAGGTA (SEQ ID NO: 81) | CGTCATCATCATCATCACCA (SEQ ID NO: 82) | 6 | 175-181 |
| 3d03cat7-1 | TGAATGGAATCATGCAGAGG (SEQ ID NO: 83) | AACGGGTGGTCTTGTGATTG (SEQ ID NO: 84) | 6 | 284-313 |
| 3d03tca5-1 | TTTTCGATCATGCCATTTGA (SEQ ID NO: 85) | TTTGCACCAATGGGTAGTTC (SEQ ID NO: 86) | 6 | 207-226 |
| 3e10cag6-1 | AGCATTTGCAGTGCTAGGGT (SEQ ID NO: 87) | ACAGCAACAGCAACAACAGC (SEQ ID NO: 88) | 1 | 187-196 |
| 3f10gtt8-1 | GAAGCTATTTGGGCGAGCTT (SEQ ID NO: 89) | CATTATGGCGTCATTTGATCC (SEQ ID NO: 90) | 4 | 190-197 |
| 3g06aga9-1 | GACACCGTTTTCGGTGATTT (SEQ ID NO: 91) | TGAAACACGTTCCCACAAAG (SEQ ID NO: 92) | 2 | 295-301 |
| AA04 | GAACTATCACCTTTCCCTTGGA (SEQ ID NO: 93) | ATTCCGGTCGTCAGAATCAG (SEQ ID NO: 94) | 4 | 306-315 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| AA06 | AGCAGGTGGAAGAATTGGTG (SEQ ID NO: 95) | CGCGTGTGTTTAGAGAGAGA (SEQ ID NO: 96) | 5 | 177-179 |
| AC126014 | TTCTTCTTGGACTTGCACCA (SEQ ID NO: 97) | TAAGGATGACCCAACCAAGC (SEQ ID NO: 98) | 4 | 301-308 |
| AC155884 | TTCTTAGCTTGAAGGGCACG (SEQ ID NO: 99) | CCATTCCTGGTTGTCAGTCC (SEQ ID NO: 100) | 2 | 154-162 |
| AFct11 | TTGTGTGGAAAGAATAGGAA (SEQ ID NO: 101) | GGACAGAGCAAAAGAACAAT (SEQ ID NO: 102) | 6 | 203-210 |
| AFct45 | GCCATCTTTTCTTTTGCTTC (SEQ ID NO: 103) | TAAAAACGGAAAGAGTTGGTTAG (SEQ ID NO: 104) | 7 | 153-162 |
| AI01 | TTGAAAATTGGGAACGGAAA (SEQ ID NO: 105) | GTTGGAGTGGGAAATTGCAG (SEQ ID NO: 106) | 7 | 196-200 |
| AJ02 | GGAAGAGGGAGAAGGAGATGA (SEQ ID NO: 107) | TCAATGGCGAACACTTTCAC (SEQ ID NO: 108) | 1 | 222-231 |
| AL111 | TGCAGCCAGGTGAATAACAA (SEQ ID NO: 109) | CATCTGATGGTGGTGATTGG (SEQ ID NO: 110) | 8 | 197-200 |
| AL64 | CCAATATGTCACTCCTTGCTGA (SEQ ID NO: 111) | AGGTGGCAAGCCTAACTGAA (SEQ ID NO: 112) | 8 | 237-240 |
| AL79 | TCCTCAACCAACCACTTCCT (SEQ ID NO: 113) | CCCCATTGACGCATTCTTAC (SEQ ID NO: 114) | 8 | 259-268 |
| AL81 | GTGGTGGAGAAGGAGCAATC (SEQ ID NO: 115) | CAATCCTCCACCATCACCTT (SEQ ID NO: 116) | 1 | 228-257 |
| AL83 | CGTTACCGTCACTGTCGTTG (SEQ ID NO: 117) | CAAACCTGATTCCGACCCTA (SEQ ID NO: 118) | 1 | 153-159 |
| AL84 | CTGCACCCCCTAAAAATCAA (SEQ ID NO: 119) | CTCATTGCCCTTCTCACACA (SEQ ID NO: 120) | 4 | 156-164 |
| AL92 | TGACTCTTGCATGCAGTTCC (SEQ ID NO: 121) | TGCTCCTCCTCTGCTTCTTC (SEQ ID NO: 122) | 8 | 201-209 |
| AL96 | GCCCCCTCACGTTTTTATTT (SEQ ID NO: 123) | CAATTTTGGTTGGTTATGCTCA (SEQ ID NO: 124) | 8 | 150-155 |
| AL97 | TCCCTCTTACACCTCTCATGC (SEQ ID NO: 125) | TCTCCTTGGAATTGAACCTG (SEQ ID NO: 126) | 6 | 144-194 |
| AL99 | CAGAAATTTCCATGCCAAAA (SEQ ID NO: 127) | AGTTGTGGATTGGGTGAAGC (SEQ ID NO: 128) | 2 | 167-176 |
| AW107 | AAACATCGGCTTCGGAAGTA (SEQ ID NO: 129) | TTTTTGAGCAGTGTAATGGTGTAA (SEQ ID NO: 130) | 3 | 203-205 |
| AW108 | CCATGGCGTCTACCCATTAT (SEQ ID NO: 131) | TTTTTCACAGCACTGAAGAGG (SEQ ID NO: 132) | 3 | 220-223 |
| AW11 | GACATTTGCAGACCACCATT (SEQ ID NO: 133) | ATTCGCAGTGAGCTGATCCT (SEQ ID NO: 134) | 8 | 214-237 |
| AW123 | CATGTTTCCGGTTCTGGTTT (SEQ ID NO: 135) | AGTCCCTGCAAAATCCCTTC (SEQ ID NO: 136) | 7 | 200-207 |
| AW134 | TGGAAACAGCAAAACCACCT (SEQ ID NO: 137) | TCCGAAATCTGAAACCAACC (SEQ ID NO: 138) | 4 | 201-227 |
| AW150 | TCCACAAATGTCTAAAACCAACA (SEQ ID NO: 139) | TTTTGTGTAGGGATGCAAAGG (SEQ ID NO: 140) | 7 | 186-193 |
| AW16 | GTGGGGTTGGTGAGAGTGTT (SEQ ID NO: 141) | ATCGTCCCCACTGTGTCTTC (SEQ ID NO: 142) | 2 | 207-234 |
| AW177 | CAGCAAAATCCAATCCTTCAG (SEQ ID NO: 143) | TTCTCATCGTCACTCCAAAGAA (SEQ ID NO: 144) | 7 | 288-291 |
| AW186 | TGCTTGAACTTTGAGTCTTGGA (SEQ ID NO: 145) | TCTCTCCATCATCACCATCATC (SEQ ID NO: 146) | 8 | 237-240 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| AW196 | AACTCGCAGGTGTTTTATCGTT (SEQ ID NO: 149) | AATCTCAACCGCAACAAACTCT (SEQ ID NO: 150) | 5 | 209-217 |
| AW199 | CATGGAGAAGCAGAACTGGAG (SEQ ID NO: 151) | CCAAACAACAACCAACTCTCTG (SEQ ID NO: 152) | 1 | 318-333 |
| AW201 | CCGTCTTTACATGAATCCACAA (SEQ ID NO: 153) | CACAGTCATCATCCTTGCTCTC (Nucleotides 19 through 40 of SEQ ID NO: 154) | 8 | 286-299 |
| AW212 | GGTTAGGGTTTTGGGTTTGAA (SEQ ID NO: 155) | GTCGAAATGGTTGCTTCTCTTT (Nucleotides 19 through 40 of SEQ ID NO: 156) | 7 | 242-272 |
| AW213 | CATGTACGGGGATTGTTGTTTT (SEQ ID NO: 157) | ACCCTTGTGGGTTCTTCTTCTT (Nucleotides 19 through 40 of SEQ ID NO: 158) | 3 | 262-270 |
| AW232 | AGCACTTTGTTCATCGTTCTGA (SEQ ID NO: 161) | AAGAGAGTATCGTGGAGCCGTA (Nucleotides 19 through 40 of SEQ ID NO: 162) | 4 | 189-198 |
| AW252 | CTTGAGAAAGCGAAGGTTTTGT (SEQ ID NO: 163) | CTCGTTCATTAGCAGTTGCAGT (Nucleotides 19 through 40 of SEQ ID NO: 164) | 7 | 142-144 |
| AW254 | CACATCTTCGTCATCATCTTCA (SEQ ID NO: 165) | TATATGCTTGTTGAGGCCACTG (Nucleotides 19 through 40 of SEQ ID NO: 166) | 7 | 210-216 |
| AW255 | TGCTTGAACTTTGAGTCTTGGA (SEQ ID NO: 167) | TCTCTCCATCATCACCATCATC (Nucleotides 19 through 40 of SEQ ID NO: 168) | 8 | 234-243 |
| AW258 | GAGTATCGGAAGAGGGTTGTTG (SEQ ID NO: 169) | AATTGGAACCTATCGTTGTCGT (Nucleotides 19 through 40 of SEQ ID NO: 170) | 8 | 240-243 |
| AW285 | CAACTGTGAACGCAAATCTCTC (SEQ ID NO: 173) | AACGACGCTCTTCGACTACTTC (Nucleotides 19 through 40 of SEQ ID NO: 174) | 4 | 119-140 |
| AW289 | GGTGCTTTCATTACATCCCATA (SEQ ID NO: 175) | ACGAGGCACACACTCTCTCTCT (Nucleotides 19 through 40 of SEQ ID NO: 176) | 4 | 301-307 |
| AW306 | GTGTTCGTCGCATATCACCTC (SEQ ID NO: 177) | GCATTTCCCTCTCTTTCCATAA (Nucleotides 19 through 40 of SEQ ID NO: 178) | 3 | 242-247 |
| AW310 | CAATGCAAGAAACCCTAAAAGC (SEQ ID NO: 179) | CCACTCAACCTCATCTCTCTACC (Nucleotides 19 through 41 of SEQ ID NO: 180) | 2 | 327-353 |
| AW325 | GCTTGTTGTTGTTGTTGATGCT (SEQ ID NO: 183) | TCTGTAAGAGGGTCACTGCGTA (Nucleotides 19 through 40 of SEQ ID NO: 184) | 8 | 160-172 |
| AW326 | GCATATCCATTCCAAGTTCATC (SEQ ID NO: 185) | ACTTTCTTCCTCATTGCTCTGC (Nucleotides 19 through 40 of SEQ ID NO: 186) | 7 | 199-206 |
| AW329771 | ATCCCATTCAAGGAAACACC (SEQ ID NO: 187) | GGAATAATGCTGGTGGAAGC (Nucleotides 19 through 38 of SEQ ID NO: 188) | 7 | 244-254 |
| AW334 | CGATGTTTGTTTGAGCTAGTGA (SEQ ID NO: 189) | GAGAGAGAGAGAGAGCATTGAGC (Nucleotides 19 through 41 of SEQ ID NO: 190) | 8 | 240-247 |
| AW347 | GAACGGGTTTGCGATCTTT (SEQ ID NO: 191) | CCATGTCTCTCAATCTTCGTCA (Nucleotides 19 through 40 of SEQ ID NO: 192) | 4 | 321-324 |
| AW352 | ATCTCCTCGTGTATTCCTTCCA (SEQ ID NO: 193) | ACGTTCCTCCTTCATCTCGTAA (Nucleotides 19 through 40 of SEQ ID NO: 194) | 7 | 207-212 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| AW359 | TTCAAGGATCTGGTGATGATGA (SEQ ID NO: 195) | GAGGAAGAGGAAGAGGAGGAAG (Nucleotides 19 through 40 of SEQ ID NO: 196) | 5 | 175-184 |
| AW365 | TGTTGGTAATGTTCAAGCTCCA (SEQ ID NO: 197) | CACCACTATCTCTTCCCTCACC (Nucleotides 19 through 40 of SEQ ID NO: 198) | 1 | 261-273 |
| AW369 | AGAATTGAGACATGGCAGAGG (SEQ ID NO: 199) | GCGCTCATCATCTTCATCTAAA (Nucleotides 19 through 40 of SEQ ID NO: 200) | 5 | 103-169 |
| AW379 | TTCTCGAAATCTTCTGCTCTCG (SEQ ID NO: 201) | GTCTCTCTCTATTCTCTTCCCTTTTC (Nucleotides 19 through 44 of SEQ ID NO: 202) | 3 | 165-174 |
| AW389 | GCAGCCTTCAAATCTCCATAAC (SEQ ID NO: 203) | TCACTCTCTCACCAATCACCAC (Nucleotides 19 through 40 of SEQ ID NO: 204) | 5 | 482-497 |
| AW64 | CATGTTTCCGGTTCTGGTTT (SEQ ID NO: 205) | AGTCCCTGCAAAATCCCTTC (Nucleotides 19 through 38 of SEQ ID NO: 206) | 7 | 200-207 |
| AW86 | TTGTTGCAGCAATTAAGGAAGA (SEQ ID NO: 207) | ATTGCCATTGCCTCTCTCAT (Nucleotides 19 through 38 of SEQ ID NO: 208) | 1 | 174-222 |
| AW97 | ACAAAAACTCTCCCGGCTTT (SEQ ID NO: 209) | CAAAACAATCAAACCAAAGATTG (Nucleotides 19 through 41 of SEQ ID NO: 210) | 3 | 220-232 |
| AW98 | ATTCATCCTTGCTCGTTTCG (SEQ ID NO: 211) | GATCAATTCGTGCAGAAGCA (Nucleotides 19 through 38 of SEQ ID NO: 212) | 2 | 205-232 |
| BE105 | AAGGGCAAAACCGTAAAAGAGT (SEQ ID NO: 213) | ATCACCCCAAACCACATCTATC (Nucleotides 19 through 40 of SEQ ID NO: 214) | 1 | 236-242 |
| BE114 | ATGAAGCTGTTGTTGTTGCAGT (SEQ ID NO: 562) | CCACCTCATCACTCCGTAAAA (SEQ ID NO: 563) | 3 | 198-220 |
| BE118 | TGCAAACTTCACCGAATAGATG (SEQ ID NO: 217) | CTCCTTTGTAACGCAACAGCAG (Nucleotides 19 through 40 of SEQ ID NO: 218) | 8 | 233-241 |
| BE120 | CATCATCCTTCATTTCCGATCT (SEQ ID NO: 219) | TCTCACATTCACATTCCATTCC (Nucleotides 19 through 40 of SEQ ID NO: 220) | 5 | 234-234 |
| BE123 | TTGATGGGTAAAGGAGAAGGTG (SEQ ID NO: 221) | ATCACAAGCCTCAACAGCCATA (Nucleotides 19 through 40 of SEQ ID NO: 222) | 7 | 211-229 |
| BE41 | ACGCCTCTCTTTCCGATCTT (SEQ ID NO: 223) | TCACTCACACTCAACACACAACA (Nucleotides 19 through 41 of SEQ ID NO: 224) | 3 | 212-223 |
| BE67 | CACCAGCCTCTAAGCTCATTTT (SEQ ID NO: 225) | CTCCATTCTCCATTTCAATACC (Nucleotides 19 through 40 of SEQ ID NO: 226) | 3 | 167-182 |
| BE74 | GCACAAGCAGCCATATTGATAG (SEQ ID NO: 227) | TACTGTCCCAATCTTCACAACG (Nucleotides 19 through 40 of SEQ ID NO: 228) | 7 | 238-267 |
| BE76 | TGAAAGTTGAAGGATCTGGTGA (SEQ ID NO: 229) | GAGGAAGAGGAAGAGGAGGAAG (Nucleotides 19 through 40 of SEQ ID NO: 230) | 5 | 182-191 |
| BE84 | TGGGATACTGATTTTCTGCTTC (SEQ ID NO: 231) | TCCGAACCCTACTTCCAAATTA (Nucleotides 19 through 40 of SEQ ID NO: 232) | 4 | 223-229 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| BE85 | CTGATTCGAGATTGGGATTGAT (SEQ ID NO: 233) | TTTCCTCTTATTATTCTTTCATACCC (Nucleotides 19 through 44 of SEQ ID NO: 234) | 3 | 233-246 |
| BE92 | GATGAGGATGATGATGAATTGG (SEQ ID NO: 235) | AGTTCAAACCCTTACCCTTCA (Nucleotides 19 through 39 of SEQ ID NO: 236) | 6 | 190-199 |
| BF106 | GTTTTCCTGGATATTTGGATGG (SEQ ID NO: 237) | TTCAATCTTCTCCTTTGATTGC (Nucleotides 19 through 40 of SEQ ID NO: 238) | 5 | 214-218 |
| BF111 | TCAGTGAGAAGGTCGTTCATGT (SEQ ID NO: 239) | TGAGAGAGAGTTCGTGGGTTG (Nucleotides 19 through 39 of SEQ ID NO: 240) | 2 | 170-205 |
| BF119 | GTGATGAAGCATTGGTGATGAT (SEQ ID NO: 241) | AATGGCGAACACTTTCACTCTT (Nucleotides 19 through 40 of SEQ ID NO: 242) | 1 | 119-159 |
| BF120 | ATTTCAGAGGCAGATGGTGAAT (SEQ ID NO: 243) | TAGCAAAATGGGTCAACAAGTG (Nucleotides 19 through 40 of SEQ ID NO: 244) | 3 | 224-226 |
| BF132 | AATCCAGCTTTGGAAGACTCAA (SEQ ID NO: 245) | TTCTTGTGGTGGTGATGAAAAC (Nucleotides 19 through 40 of SEQ ID NO: 246) | 7 | 205-214 |
| BF142 | GTGTGTTCCCCAGTTCTCAGTT (SEQ ID NO: 247) | CATACCCTTCAAATCCAACCAT (Nucleotides 19 through 40 of SEQ ID NO: 248) | 7 | 263-266 |
| BF147 | GATTGTTCTTTGGTAAGCCTCA (SEQ ID NO: 249) | ACTGCAAGTGAAGAGGGAGAGA (Nucleotides 19 through 40 of SEQ ID NO: 250) | 5 | 147-150 |
| BF149 | GCTTCTTTGGCTTTCTCTTCAA (SEQ ID NO: 251) | CGTTTCCCTCTCTCACTCACTT (Nucleotides 19 through 40 of SEQ ID NO: 252) | 6 | 103-113 |
| BF150 | ATCAGAAACAGAAGCATCAGCA (SEQ ID NO: 253) | CTCCAAAACTCAAACTCAACCA (Nucleotides 19 through 40 of SEQ ID NO: 254) | 2 | 274-277 |
| BF184 | CTAGACTTGCCGCTACTTTGG (SEQ ID NO: 255) | CAACAATCACCACACACATTGA (Nucleotides 19 through 40 of SEQ ID NO: 256) | 4 | 284-304 |
| BF215 | GGAAACATAGATGAAGCAGCAA (SEQ ID NO: 257) | AGCAAGCAAAGAACAATCACAA (Nucleotides 19 through 40 of SEQ ID NO: 258) | 2 | 230-237 |
| BF218 | TCGGATTTGGTTTTGAGTTTTC (SEQ ID NO: 259) | CTCAGGAGGTGCTGTTCTTCTT (Nucleotides 19 through 40 of SEQ ID NO: 260) | 8 | 243-245 |
| BF220 | TGAGTTTTCAGATTCAGCAGGA (SEQ ID NO: 261) | ATCATCGTCGTCGTGTTTATTG (Nucleotides 19 through 40 of SEQ ID NO: 262) | 3 | 287-308 |
| BF223 | AATAGGGTTTGATTGAGGAGCA (SEQ ID NO: 564) | CGACGAACAGAAGCTAAGAGATG (SEQ ID NO: 565) | 4 | 124-136 |
| BF225 | TTTTCATCTGTGCCCTGTAATG (SEQ ID NO: 263) | TCACTCACACTCAACACACAACA (Nucleotides 19 through 41 of SEQ ID NO: 264) | 3 | 190-201 |
| BF228 | ATTAGAAGCTCCGTTACCGTCA (SEQ ID NO: 265) | ATAACCAACTCCAAACCACACC (Nucleotides 19 through 40 of SEQ ID NO: 266) | 1 | 143-153 |
| BF24 | TTGAAAATTGGGAACGGAAA (SEQ ID NO: 267) | GTTGGAGTGGGAAATTGCAG (Nucleotides 19 through 38 of SEQ ID NO: 268) | 7 | 196-200 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| BF257 | ATGCCAGGATGGTGATACATCT (SEQ ID NO: 269) | GGATTTGGGCGTGAGACTATAC (Nucleotides 19 through 40 of SEQ ID NO: 270) | 3 | 412-430 |
| BF26 | TCAAAGTTGTTGTTCTGCTTGAA (SEQ ID NO: 271) | TCTCACACCCCAAAAACACA (Nucleotides 19 through 38 of SEQ ID NO: 272) | 7 | 289-306 |
| BF71 | CGGTGAAATGGTGGAAGAAG (SEQ ID NO: 277) | TAACAAAACCCAACCCCATC (Nucleotides 19 through 38 of SEQ ID NO: 278) | 4 | 216-229 |
| BF79 | GGTGTGGAGAGGGAGGGTAG (SEQ ID NO: 279) | CGAGGGATATTCTTTCCCTTAAA (Nucleotides 19 through 41 of SEQ ID NO: 280) | 3 | 182-197 |
| BF97 | CTACCTCCAGCAGAACCATGTC (SEQ ID NO: 281) | GTAACCATCCTTTGAGTTCGTCTG (Nucleotides 19 through 42 of SEQ ID NO: 282) | 8 | 249-252 |
| BG115 | TGCATTTGTTAACGAGTGTGAA (SEQ ID NO: 283) | CCACAGAAGAAAGAAGAACTTGC (Nucleotides 19 through 41 of SEQ ID NO: 284) | 3 | 208-230 |
| BG119 | TCGAGGCCAATAGAAGACCTAA (SEQ ID NO: 285) | GGTTCTCTTCCAATCCCTTCTT (Nucleotides 19 through 40 of SEQ ID NO: 286) | 7 | 265-281 |
| BG134 | TTTTCAAGGAGGAGAAGATCCA (SEQ ID NO: 287) | ACCCCACCTAACCCTCTACAGT (Nucleotides 19 through 40 of SEQ ID NO: 288) | 5 | 190-203 |
| BG137 | CAGAGCAATAAGAACACCAGGA (SEQ ID NO: 566) | ACTCTTCCTCGCCACTTCAAC (SEQ ID NO: 567) | 1 | 320-323 |
| BG143 | GGTAATCGTTGGCGTTGTTTAT (SEQ ID NO: 291) | TCAGGTAGTTGACGACGAAGAA (Nucleotides 19 through 40 of SEQ ID NO: 292) | 2 | 125-134 |
| BG157 | CAACGCCTCCTCTTTCTCTGTA (SEQ ID NO: 293) | CTCAAAACCCTAACTTCTTCAACC (Nucleotides 19 through 42 of SEQ ID NO: 294) | 5 | 146-154 |
| BG166 | CAACTGTGAACGCAAATCTCTC (SEQ ID NO: 295) | AACGACGCTCTTCGACTACTTC (Nucleotides 19 through 40 of SEQ ID NO: 296) | 4 | 120-141 |
| BG171 | GGATCCAACCGAATTTCTTTC (SEQ ID NO: 297) | ACCTAGCAACCCAAATCAGAAG (Nucleotides 19 through 40 of SEQ ID NO: 298) | 4 | 192-195 |
| BG172 | CCTCGAAAAGATTACCGAACAC (SEQ ID NO: 299) | CGCCTTCTTCTTCAACACACTA (Nucleotides 19 through 40 of SEQ ID NO: 300) | 4 | 190-194 |
| BG178 | TTCTCCTTGACCAACCTTGATT (SEQ ID NO: 301) | ACCCACTCAACTCAACACACAC (Nucleotides 19 through 40 of SEQ ID NO: 302) | 7 | 212-226 |
| BG180 | AGAAGGTGGAACACGTCTCTTC (SEQ ID NO: 303) | CTACAAGCCCAGATTTCAAAGG (Nucleotides 19 through 40 of SEQ ID NO: 304) | 1 | 159-172 |
| BG181 | TTCGCAGTTCTTGAGTAGGTCA (SEQ ID NO: 305) | TACTTCATGTACCCCACAACCA (Nucleotides 19 through 40 of SEQ ID NO: 306) | 1 | 162-167 |
| BG186 | TTGTCGATGAGTTCAACGTTTC (SEQ ID NO: 307) | ACAACAAAACACAATGGGTGAC (Nucleotides 19 through 40 of SEQ ID NO: 308) | 8 | 166-189 |
| BG208 | AGTAACCGCGAACCAAAGAGTA (SEQ ID NO: 309) | ACACCTCGAACAAGATTCATCC (Nucleotides 19 through 40 of SEQ ID NO: 310) | 1 | 220-226 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| BG218 | ACCATATCCACAGGCATAATCC (SEQ ID NO: 311) | AATCCATACTCAAACCCACCAG (Nucleotides 19 through 40 of SEQ ID NO: 312) | 2 | 285-301 |
| BG222 | ATCACGAGAACCGCCATAAGAT (SEQ ID NO: 313) | AGGGCTGATGAGGTGGATAAT (Nucleotides 19 through 39 of SEQ ID NO: 314) | 4 | 228-237 |
| BG229 | GAACGGGTTTGCGATCTTT (SEQ ID NO: 315) | CCATGTCTCTCAATCTTCGTCA (Nucleotides 19 through 40 of SEQ ID NO: 316) | 4 | 321-323 |
| BG231 | GCATGTATGATTTACAGCTCCAAG (SEQ ID NO: 317) | CCACAGTTTCATTTTCTGTCCA (Nucleotides 19 through 40 of SEQ ID NO: 318) | 2 | 383-399 |
| BG232 | TGCCTTTGATTAGTGCTGACAT (SEQ ID NO: 319) | CTCTGCTCCCATCTACTTCACA (Nucleotides 19 through 40 of SEQ ID NO: 320) | 8 | 167-172 |
| BG234 | GCAACATACCATCCCCTAAAAG (SEQ ID NO: 321) | GCTGGAATACACCAAGCATGA (Nucleotides 19 through 40 of SEQ ID NO: 322) | 1 | 217-251 |
| BG248 | ACATAAGCGACTGGAACAAACC (SEQ ID NO: 323) | GGATACAAAATCCACAAGCACA (Nucleotides 19 through 40 of SEQ ID NO: 324) | 1 | 284-348 |
| BG257 | ATTTCAGAGGCAGATGGTGAAT (SEQ ID NO: 327) | TAGCAAAATGGGTCAACAAGTG (Nucleotides 19 through 40 of SEQ ID NO: 328) | 3 | 223-230 |
| BG272 | CAGGGGAATCAATCAGTCAAAG (SEQ ID NO: 329) | AAACAGAGAGACAGGAATTTGGA (Nucleotides 19 through 41 of SEQ ID NO: 330) | 3 | 446-456 |
| BG280 | TGTTGAAGTTGGAGTTTTGGTG (SEQ ID NO: 331) | TCAGCAGTTAGTTTTGGTATGC (Nucleotides 19 through 40 of SEQ ID NO: 332) | 2 | 126-149 |
| BG281 | GGTTGGAAACAAAGTCAGAACC (SEQ ID NO: 333) | ACATCATCAACAGCAAAACCAG (Nucleotides 19 through 40 of SEQ ID NO: 334) | 7 | 195-198 |
| BG285 | TGCTTCTTGGTTTCTCATCATC (SEQ ID NO: 335) | ATGGTTATGTGGGTTGTGTTCA (Nucleotides 19 through 40 of SEQ ID NO: 336) | 1 | 309-316 |
| BG82 | TTCCCATATGCAACAGACCTT (SEQ ID NO: 337) | AACGGTGGTGTGTTTATTGCT (Nucleotides 19 through 39 of SEQ ID NO: 338) | 3 | 195-204 |
| BG96 | TTAACGAGGGTGGTGATGGT (SEQ ID NO: 341) | TCGATGTTATGGTAGCAGCAA (Nucleotides 19 through 39 of SEQ ID NO: 342) | 3 | 184-191 |
| BI107 | AGCAGTGATGTCTTGGCTATGT (SEQ ID NO: 343) | GTTTCCGGTTCTTTGTCGTTC (Nucleotides 19 through 39 of SEQ ID NO: 344) | 5 | 354-429 |
| BI113 | AACATCGTAATGAGGAGGAGGA (SEQ ID NO: 345) | ACAGTATCAGCAACACCAGCAG (Nucleotides 19 through 40 of SEQ ID NO: 346) | 8 | 241-253 |
| BI116 | TCAACCCTTCAGATTTTCTTCC (SEQ ID NO: 347) | CACACTTTCTCGTTTGCTCTCT (Nucleotides 19 through 40 of SEQ ID NO: 348) | 8 | 218-226 |
| BI122 | CAATTTCCTTAGTGGCCGTTAC (SEQ ID NO: 349) | TTATTAGCTGGGCTTTTCTTCG (Nucleotides 19 through 40 of SEQ ID NO: 350) | 7 | 366-369 |
| BI68 | ATCAGCGTAAATTCTGGCCTTA (SEQ ID NO: 351) | CCATTCCAATCCACACTATCG (Nucleotides 19 through 39 of SEQ ID NO: 352) | 5 | 261-276 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| BI75 | CGTAGGAAGAAGGATCGAGTTC (SEQ ID NO: 353) | CCCAATTCAAAACGAAGAACC (Nucleotides 19 through 39 of SEQ ID NO: 344) | 4 | 187-193 |
| BI86 | CGTCGAAGTCAAAATCAATCTC (SEQ ID NO: 355) | GAAAAGAAATCACCCCGAAGAT (Nucleotides 19 through 40 of SEQ ID NO: 356) | 8 | 223-249 |
| BI96 | CTCATTCACCCAACCAAAATGT (SEQ ID NO: 357) | GGCTAATTCACCTGTTTCTGCT (Nucleotides 19 through 40 of SEQ ID NO: 358) | 4 | 195-197 |
| BI98 | TCAACAGCCAACTCAAAGTGAT (SEQ ID NO: 359) | CATCAATCAACCCTTTCGTTTC (Nucleotides 19 through 40 of SEQ ID NO: 360) | 6 | 154-164 |
| MsTri7698 | CAGTTGATGCATAGAAACGCA (SEQ ID NO: 447) | AAGCGATTTCATTAGTAGTTGT (Nucleotides 19 through 40 of SEQ ID NO: 448) | 8 | 194-196 |
| MsTri7729 | ATCTGGGAAGTGTGACCTCCT (SEQ ID NO: 395) | TCAAAACCTTGGTGTTGGTTG (Nucleotides 19 through 39 of SEQ ID NO: 396) | 4 | 295-300 |
| MsTri7771 | CATACTATGGTGGTGGTTGGG (SEQ ID NO: 397) | CTCTTTAAGATTGCTTCTCTTGC (Nucleotides 19 through 41 of SEQ ID NO: 398) | 8 | 368-393 |
| MsTri7807 | TCACCAGCACATGAATCAAAA (SEQ ID NO: 449) | AACAACCTAGATTTTCTCGACC (Nucleotides 19 through 40 of SEQ ID NO: 450) | 8 | 238-242 |
| MsTri8119 | AGGGTTGATGCAGATGTTACG (SEQ ID NO: 451) | ATTGCAATCATCTTCTCCCCT (Nucleotides 19 through 39 of SEQ ID NO: 452) | 3 | 270-282 |
| MsTri8491 | GGACGGTTTCGAACTTCTAGC (SEQ ID NO: 399) | CGAGGCATCTTCATCTTCAAC (Nucleotides 19 through 39 of SEQ ID NO: 400) | 7 | 206-222 |
| MsTri8616 | AACAATATGATCTGGCATGTCG (SEQ ID NO: 453) | GGAAGATCACCATTTTGTCCA (Nucleotides 19 through 39 of SEQ ID NO: 454) | 7 | 274-281 |
| MsTri8637 | GATAAAGCTCCCACAGTTCCC (SEQ ID NO: 401) | CTCTTTTCTCTTCAATTTTCAAT (Nucleotides 19 through 41 of SEQ ID NO: 402) | 3 | 232-238 |
| MsTri8733 | AGGTACAAGCCATGATGTCCA (SEQ ID NO: 455) | TTTCCAAACTTTCCTTCTTTTG (Nucleotides 19 through 40 of SEQ ID NO: 456) | 6 | 188-205 |
| MsTri8791 | ACAAGAAGAAGATTGCGACGA (SEQ ID NO: 457) | TGAAGGAAGAAGGAAGAAGGAA (Nucleotides 19 through 40 of SEQ ID NO: 458) | 6 | 178-180 |
| MsTri8899 | CGCAGCACATGTAACTTGAAA (SEQ ID NO: 459) | CACATTCTCTTCGTGCCCTC (Nucleotides 19 through 38 of SEQ ID NO: 460) | 8 | 340-397 |
| MsTri8923 | TCCGAAAAGGTGACAGATTG (SEQ ID NO: 461) | GGCTCACAACAACAACAAAAT (Nucleotides 19 through 39 of SEQ ID NO: 462) | 8 | 168-192 |
| MsTri8930 | CCAAACAGATCTAAAGTTCCCA (SEQ ID NO: 463) | TGCTTGATTATTGCTAATCGG (Nucleotides 19 through 39 of SEQ ID NO: 464) | 3 | 103-112 |
| MsTri8931 | TACAGTTGCCCATACAGGAGG (SEQ ID NO: 403) | CAAACAGGTGACGAGGTGAAT (Nucleotides 19 through 39 of SEQ ID NO: 404) | 3 | 131-150 |
| MsTri8949 | TAAATGCAAGGTAGGTGGTGG (SEQ ID NO: 465) | CGAGGACGAGTTCTGGTCAA (Nucleotides 19 through 38 of SEQ ID NO: 466) | 7 | 100-145 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| MsTri9154 | AAGACCAAGAGGAATCACCGT (SEQ ID NO: 467) | TAATTTCATTCGCGATCACAC (Nucleotides 19 through 39 of SEQ ID NO: 468) | 1 | 157-166 |
| MsTri9223 | TGAATGTGAGGAAGTGGGTTT (SEQ ID NO: 469) | CCGCCTCAAATAGTTATAAACTTC (Nucleotides 19 through 42 of SEQ ID NO: 470) | 8 | 140-162 |
| MsTri9326 | AGTACTATTGCAATGGCGTGG (SEQ ID NO: 471) | GGTTTCGCTTGGAATTCTGAT (Nucleotides 19 through 39 of SEQ ID NO: 472) | 3 | 105-107 |
| MsTri9329 | ATCAAGATCGACTGAACCACG (SEQ ID NO: 405) | TTGGCTTTGATTGCTTCAACT (Nucleotides 19 through 39 of SEQ ID NO: 406) | 2 | 117-123 |
| MsTri9475 | TGCATGTAATATCTATCTTTGGAA (SEQ ID NO: 568) | CCAAACCCTAGGAGTCTGAGGT (SEQ ID NO: 569) | 6 | 146-146 |
| MsTri9544 | ATTTTTCCACTTCTGGTGGGA (SEQ ID NO: 473) | CAACACAATCATTTTGGGAGC (Nucleotides 19 through 39 of SEQ ID NO: 474) | 5 | 159-177 |
| MsTri9820 | TCTTGTTGATATAATCTACGGAA (SEQ ID NO: 475) | CCTGATGGTCATCACTAAGCC (Nucleotides 19 through 39 of SEQ ID NO: 476) | 8 | 116-120 |
| MsTri9849 | TGAGGCTTAACCTTAGGAGGC (SEQ ID NO: 407) | TTTCAAATCCAAGTGGTGGAG (Nucleotides 19 through 39 of SEQ ID NO: 408) | 5 | 161-167 |
| MsTri10127 | GGGAAACCATTTCGTACCCTA (SEQ ID NO: 409) | AATTCCCAATTCTCATTCGTG (Nucleotides 19 through 39 of SEQ ID NO: 410) | 4 | 123-134 |
| MsTri10235 | TTGCCATCGTAGAAAATGGTC (SEQ ID NO: 411) | CCTTAACACATTTTTGCTTCA (Nucleotides 19 through 39 of SEQ ID NO: 412) | 2 | 353-368 |
| MsTri10456 | TGTCGTCTTTTGACCATTTCC (SEQ ID NO: 413) | TTATCATGTGCAGACAATACC (Nucleotides 19 through 39 of SEQ ID NO: 414) | 1 | 283-296 |
| MsTri10581 | CCTTGGCAGCTACAGGTACAG (SEQ ID NO: 369) | GTCTGCTGCTCCAGCTAAGAA (Nucleotides 19 through 39 of SEQ ID NO: 370) | 7 | 306-316 |
| MsTri10592 | GATTAAACATACATGCAACATTGA (SEQ ID NO: 415) | GGTTGAAATCGACATGAGAGG (Nucleotides 19 through 39 of SEQ ID NO: 416) | 8 | 151-161 |
| MsTri10649 | GGATATCCTGGTGGAGGGTAA (SEQ ID NO: 373) | ACAACCCCATTTCCAACTTTC (Nucleotides 19 through 39 of SEQ ID NO: 374) | 1 | 293-317 |
| MsTri10686 | CCAACACTTTAAGCCTCCAAA (SEQ ID NO: 417) | TGTTCTCCTCTCTTCGTCTCTTG (Nucleotides 19 through 41 of SEQ ID NO: 418) | 5 | 126-132 |
| MsTri10743 | CCGGTTCTGTTTGGTAGTGAA (SEQ ID NO: 419) | AACCAGAGAAAAATCCAACCA (Nucleotides 19 through 39 of SEQ ID NO: 420) | 5 | 111-120 |
| MsTri10801 | GGAGCAAACATTCTACCACCA (SEQ ID NO: 377) | TCACAAAACAAACCCTTCTTCT (Nucleotides 19 through 40 of SEQ ID NO: 378) | 5 | 432-448 |
| MsTri10866 | CCTTAGGCACATTGAAAACCA (SEQ ID NO: 421) | TAAGGGTTCATGCTCACCATC (Nucleotides 19 through 39 of SEQ ID NO: 422) | 3 | 334-340 |
| MsTri11061 | AACATGCACAATTAAGCATTCAA (SEQ ID NO: 423) | ACCTGAAAGGCCACAAAAGAT (Nucleotides 19 through 39 of SEQ ID NO: 424) | 5 | 100-111 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| MsTri11067 | AATTCGGGTGGAATAACAAGC (SEQ ID NO: 425) | TTGCCTCGGATTATTACTTGTG (Nucleotides 19 through 40 of SEQ ID NO: 426) | 3 | 137-171 |
| MsTri11087 | TGACTTAGACACCACCGGAGT (SEQ ID NO: 379) | TCATCCATTCATTAAAACGCA (Nucleotides 19 through 39 of SEQ ID NO: 380) | 3 | 209-219 |
| MsTri11090 | GCAATCACCTTAGCATTTTGG (SEQ ID NO: 427) | GCCAGTTTTGGGCAATTTTAT (Nucleotides 19 through 39 of SEQ ID NO: 428) | 2 | 187-189 |
| MsTri11131 | GTTCAAGCATGGAAAGTTTGG (SEQ ID NO: 429) | GGGACCTAATATGATGAACTTACA (Nucleotides 19 through 42 of SEQ ID NO: 430) | 8 | 180-188 |
| MsTri11311 | TGACAGTTTCCACAATCCTCC (SEQ ID NO: 431) | GACGAACTCTTTTCTTTTCTGACA (Nucleotides 19 through 42 of SEQ ID NO: 432) | 5 | 305-317 |
| MsTri11314 | ATACACCATAGCACGAGACGC (SEQ ID NO: 381) | TAATTCGAGGAGGATTGTGGA (Nucleotides 19 through 39 of SEQ ID NO: 382) | 5 | 131-137 |
| MsTri11419 | ACAAGAAGAAGATTGCGACGA (SEQ ID NO: 433) | TGAAGGAAGAAGGAAGAAGGAA (Nucleotides 19 through 40 of SEQ ID NO: 434) | 6 | 177-180 |
| MsTri11460 | AATTTGGACTTTGATTGTGCG (SEQ ID NO: 435) | CAAGAACCAGATCATCAACAACA (Nucleotides 19 through 41 of SEQ ID NO: 436) | 7 | 295-306 |
| MsTri11470 | GGAGATGAAGAAGGAGATGGG (SEQ ID NO: 385) | TTGAAATAGTGCAAGAAGAACCC (Nucleotides 19 through 41 of SEQ ID NO: 386) | 8 | 306-319 |
| MsTri11523 | TGTCACTTGTTCTGGTCCTTCT (SEQ ID NO: 387) | GGAGAGAGCAAAGTCTCTTCAA (Nucleotides 19 through 40 of SEQ ID NO: 388) | 2 | 136-142 |
| MsTri11701 | AGCTTTTTCAACGAGTTCAGC (SEQ ID NO: 439) | TTTCATCAACATCAAACACCG (Nucleotides 19 through 39 of SEQ ID NO: 440) | 4 | 173-189 |
| MsTri11744 | TTCTTGGCTTCGACTTCTTCA (SEQ ID NO: 441) | CCGATTGGACTCGGAACTT (Nucleotides 19 through 37 of SEQ ID NO: 442) | 2 | 330-373 |
| MsTri11748 | GGATTTCGTTTGGGTTCATTT (SEQ ID NO: 443) | TCTGTAACACAGGCAGAGTCG (Nucleotides 19 through 39 of SEQ ID NO: 444) | 4 | 310-316 |
| MsTri11989 | CAGGAACATAACTGTGACCCG (SEQ ID NO: 389) | TCCTAATACCCCATTCATTGGT (Nucleotides 19 through 40 of SEQ ID NO: 390) | 4 | 111-112 |
| MsTri12038 | GCCTTTAGGCCAATCAGAGAC (SEQ ID NO: 391) | AAGATTAGGGTTTGAGTAAGGGAA (Nucleotides 19 through 42 of SEQ ID NO: 392) | 4 | 211-216 |
| Mt1D06 | GAAGGTTTTGGGTGGTGATG (SEQ ID NO: 479) | CCATGGCTCTTTCCTACCAA (Nucleotides 19 through 38 of SEQ ID NO: 480) | 7 | 167-189 |
| Mt1G03 | TGGTTGATCAATGTTCCTCCT (SEQ ID NO: 481) | AAAGAGATTGGGTCGGTGAA (Nucleotides 19 through 38 of SEQ ID NO: 482) | 8 | 238-269 |
| MtBA36F01F1 | AATAAACACAGATTCCAAATCCA (SEQ ID NO: 483) | TCTTCATCGCTTTCTTCTATTTCA (Nucleotides 19 through 42 of SEQ ID NO: 484) | 1 | 126-145 |
| MtBC01G06F3 | TCAGGACAAACTGCCATTTC (SEQ ID NO: 485) | TGCATTGAAGCAAATTAACGA (Nucleotides 19 through 39 of SEQ ID NO: 486) | 1 | 177-189 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| MTIC107 | TACGTAGCCCCTTGCTCATT (SEQ ID NO: 487) | CAAACCATTTCCTCCATTGTG (Nucleotides 19 through 39 of SEQ ID NO: 488) | 1 | 170-184 |
| MTIC124 | TTGGGTTGTCAATAATGCTCA (SEQ ID NO: 489) | TTGTCACGAGTGTTGGAATTTT (Nucleotides 19 through 40 of SEQ ID NO: 490) | 3 | 135-192 |
| MTIC169 | GCGTGCTAGGTTTGAGAGGA (SEQ ID NO: 491) | TCAAAACCCTAAAACCCTTTCTC (Nucleotides 19 through 41 of SEQ ID NO: 492) | 3 | 99-113 |
| MTIC19 | TGCAACAGAAGAAGCAAAACA (SEQ ID NO: 495) | TCTAGAAAAAGCAATGATGTGAGA (Nucleotides 19 through 42 of SEQ ID NO: 496) | 2 | 149-166 |
| MTIC233 | AAGGAACAATCCCAGTTTTT (SEQ ID NO: 497) | GCGTAACGTAACAACATTCA (Nucleotides 19 through 38 of SEQ ID NO: 498) | 1 | 145-170 |
| MTIC238 | CCTTAGCCAAGCAAGTAAAA (SEQ ID NO: 499) | TTCTTCTTCTAGGAATTTGGAG (Nucleotides 19 through 40 of SEQ ID NO: 500) | 5 | 140-144 |
| MTIC247 | TGAGAGCATTGATTTTTGTG (SEQ ID NO: 501) | TTCGCAGAACCTAAATTCAT (Nucleotides 19 through 38 of SEQ ID NO: 502) | 1 | 125-131 |
| MTIC248 | GGATTGTGATGAAGAAATGG (SEQ ID NO: 503) | TATCTCCCTTCTCCTTCTCC (Nucleotides 19 through 38 of SEQ ID NO: 504) | 8 | 137-154 |
| MTIC249 | GTGGGTGAGGATGTGTGTAT (SEQ ID NO: 505) | TAGGTCATGGCTATTGCTTC (Nucleotides 19 through 38 of SEQ ID NO: 506) | 4 | 122-131 |
| MTIC250 | CGTTGATGATGTTCTTGATG (SEQ ID NO: 507) | GCCTGAACTATTGTGAATGG (Nucleotides 19 through 38 of SEQ ID NO: 508) | 6 | 133-136 |
| MTIC258 | TGAAATTCACATCAACTGGA (SEQ ID NO: 509) | CACCACCTTCACCTAAGAAA (Nucleotides 19 through 38 of SEQ ID NO: 510) | 1 | 147-151 |
| MTIC304 | AGCGTAAAGTAAAACCCTTTC (SEQ ID NO: 511) | TTGGGCTTAATTTGACTGAT (Nucleotides 19 through 38 of SEQ ID NO: 512) | 2 | 159-175 |
| MTIC332 | GGTCATACGAGCTCCTCCAT (SEQ ID NO: 513) | CCCTGGGTTTTTGATCCAG (Nucleotides 19 through 37 of SEQ ID NO: 514) | 4 | 148-163 |
| MTIC338 | CATTGGTGGACGAGGTCTCT (SEQ ID NO: 515) | TCCCCTTAAGCTTCACTCTTTTC (Nucleotides 19 through 41 of SEQ ID NO: 516) | 3 | 181-196 |
| MTIC343 | CCATTGCGGTGGCTACTCT (SEQ ID NO: 517) | TCCGATCTTGCGTCCTAACT (Nucleotides 19 through 38 of SEQ ID NO: 518) | 6 | 140-160 |
| MTIC35 | GGCAGGAACAGATCCTTGAA (SEQ ID NO: 519) | GAAGAAGAAAAAGAGATAGATCTGTGG (Nucleotides 19 through 45 of SEQ ID NO: 520) | 7 | 129-132 |
| MTIC354 | AACCTACGCTAGGGTTGCAG (SEQ ID NO: 521) | AAGTGCCAAAGAACAGGGTTT (Nucleotides 19 through 39 of SEQ ID NO: 522) | 2 | 244-257 |
| MTIC452 | TCACAAAAACTGCATAAAGC (SEQ ID NO: 523) | CTAGTGCCAACACAAAAACA (Nucleotides 19 through 38 of SEQ ID NO: 524) | 2 | 114-126 |
| MTIC51 | ACAAAAACTCTCCCGGCTTT (SEQ ID NO: 527) | AGTATAGTGATGAAGTGGTAGTGAACA (Nucleotides 19 through 45 of SEQ ID NO: 528) | 3 | 141-154 |

TABLE 5-continued

List of SSR primer pairs used for linkage mapping and QTL identification in alfalfa

| Primer ID | Reverse primer sequence | Forward primer sequence | LG | Amplicon size range |
|---|---|---|---|---|
| MTIC82 | GAGAGGATTTCGGTGATGT (SEQ ID NO: 570) | CACTTTCCACACTCAAACCA (SEQ ID NO: 571) | 7 | 138-142 |
| MTIC84 | GGGAAAAGGTGTAGCCATTG (SEQ ID NO: 529) | TCTGAGAGAGAGACAAACAAAACAA (Nucleotides 19 through 43 of SEQ ID NO: 530) | 1 | 183-193 |
| MTIC95 | AGGAAGGAGAGGGACGAAAG (SEQ ID NO: 533) | AAAGGTGTTGGGTTTTGTGG (Nucleotides 19 through 38 of SEQ ID NO: 534) | 1 | 146-148 |
| RCS0121 | CTGCTTTGGTTTGGAAGAAA (SEQ ID NO: 535) | GGAAAGAATATGCAATTTCTCGAT (Nucleotides 19 through 42 of SEQ ID NO: 536) | 2 | 92-100 |
| RCS1209 | TGAACTTTGAAGCCACATTGA (SEQ ID NO: 537) | AAAATCCAGAAGCACGAGTGA (Nucleotides 19 through 39 of SEQ ID NO: 538) | 4 | 109-111 |
| RCS2510 | GCCCTAAAAGTTGAAAGAGCA (SEQ ID NO: 539) | CACGAGGGAACACTTCATCA (Nucleotides 19 through 38 of SEQ ID NO: 540) | 6 | 122-220 |
| RCS2936 | CCAATGCAATTCGGTAATCC (SEQ ID NO: 541) | CGTTATTTATCCCTCCGGGT (Nucleotides 19 through 38 of SEQ ID NO: 542) | 8 | 141-376 |
| RCS4209 | TCACAATGGGCACCTAATCA (SEQ ID NO: 543) | CAATTTTCGCTGACTGACCA (Nucleotides 19 through 38 of SEQ ID NO: 544) | 2 | 157-158 |
| RCS4310 | GCCATTTGCTTCAACCTTGT (SEQ ID NO: 545) | GCCATTGCTGGAATCGTAAT (Nucleotides 19 through 38 of SEQ ID NO: 546) | 4 | 269-272 |
| TC105099 | AGATAGGAATTTGGGTCGGG (SEQ ID NO: 553) | ACAACCATGATGTGGGAATG (Nucleotides 19 through 38 of SEQ ID NO: 554) | 5 | 111-117 |
| TC106861 | GCAGGGCTGAGACTCCAGTA (SEQ ID NO: 555) | AGCCCTGCTTTTTCTCCTCT (Nucleotides 19 through 38 of SEQ ID NO: 556) | 5 | 245-247 |
| TC85780-1 | AAAGTGACATGATCCACAGG (SEQ ID NO: 557) | GCTAAGAAAGCATGGGGTTGTTGG (Nucleotides 19 through 42 of SEQ ID NO: 558) | 5 | 276-283 |

TABLE 6

Number of simplex, duplex, double simplex and co-dominant SSR markers used to construct tetraploid linkage maps in each of the parental alfalfa genotypes.

| | Altet-4 | | | | NECS-141 | | | |
|---|---|---|---|---|---|---|---|---|
| LG | 1:1 | 5:1 | 3:1 | Co-dominant | 1:1 | 5:1 | 3:1 | Co-dominant |
| 1 | 20 | 12 | 4 | 7 | 23 | 9 | 4 | 5 |
| 2 | 23 | 14 | 3 | 9 | 26 | 2 | 3 | 6 |
| 3 | 19 | 5 | 7 | 8 | 41 | 8 | 7 | 13 |
| 4 | 38 | 8 | 5 | 17 | 24 | 3 | 5 | 8 |
| 5 | 33 | 3 | 6 | 10 | 22 | 7 | 6 | 7 |
| 6 | 29 | 2 | 1 | 11 | 19 | 2 | 1 | 4 |
| 7 | 22 | 2 | 0 | 5 | 28 | 11 | 0 | 8 |
| 8 | 14 | 13 | 0 | 3 | 48 | 6 | 0 | 13 |
| Total | 198 | 59 | 26 | 70 | 231 | 48 | 26 | 64 |

Example 10

Further QTL Analysis Using SF-ANOVA from Callus and Whole Plant Assays

Twenty markers associated with the response to Al in the callus bioassay were identified using SF-ANOVA (Table 7). Of these markers, 14 were associated with decreasing total callus weight ratio (TCWR) and six with increasing TCWR. Forty-one markers relevant to Al tolerance in the whole plant assay were also found using SF-ANOVA. Of these, 21 markers were associated with increasing total root length ratio (TRLR) and 20 markers were associated with decreasing TRLR.

Using interval mapping, a QTL for callus growth was identified at 90 cM on LG 1 from Altet-4 (FIG. 9A). This QTL explained 20.8% of the phenotypic variation for TCWR. The average TCWR score of the allelic combination $Q_{12}$ (0.97) was higher than the other possible allelic combinations at this locus, which had an average TCWR score of 0.75 (FIG. 9B). All allelic combinations were represented by at least 16 individuals. These results suggest that a recessive allele providing increased Al-tolerance is present on homologues 1 and 2 in a duplex condition. The SF-ANOVA did not identify a marker with a positive association for TCWR in LG 1 of Altet-4, likely due to the lack of a duplex marker associated with $Q_1$ and $Q_2$ in the QTL region. However, two simplex markers on homolog H3 in the region of the QTL decreased TCWR (Table 7).

Two QTLs for Al tolerance were identified based on interval mapping of the root growth differences in the whole plant assay on LG 4 of Altet-4 (FIG. 10) and LG 7 of NECS-14 (FIG. 11). These QTL explained 15.2% and 21.7% of the variation, respectively, and again suggested the presence of recessive alleles that improve Al tolerance. For the Al tolerance QTL from Altet-4 located on LG 4 (FIG. 10B), the average TRLR of allelic combination $Q_{34}$ (0.72) was higher than the average TRLR from all other allelic combinations (0.52). The results from the SF-ANOVA show that among the Altet-4 markers on LG 4, five simplex markers on homologs H3 and H4 were positively associated with Al tolerance, while one simplex marker on homolog H1 and one duplex marker bridging homolog H1 and H2 were negatively associated with Al tolerance (Table 7).

Interval mapping was used to identify additional QTLs for Al tolerance on LGs 4 and 7 (FIGS. 10-11) from evaluations at the whole plant level. Soil-based evaluations of the Altet-4×NECS-141 population identified a QTL for root dry weight ratio that represents the relative root growth in unlimed vs limed soil conditions associated with the same markers on LG 4 (data not shown). These represent novel Al tolerance QTLs not previously identified in diploids using the callus bioassay. These QTL are apparently relevant at the whole plant level but not in callus. The lack of correlation between Al tolerance responses in the callus bioassay and whole plant assay suggests that although similar stress responses may be involved, these systems capture different tolerance mechanisms. Al tolerance evaluations at the whole plant level may thus capture defense mechanisms at the cell level as well as complex organ responses, including changes in root growth. The primary effects of growth inhibition due to $Al^{+3}$ occur at or near the root tip (Kochian et al. *Ann Rev. Pl. Biol.* 55:459-493, 2004). Alternatively, the additional Al tolerance QTL may have been identified due to the increase in marker density compared to the relatively sparse genetic map used in a diploid mapping study (Narasimhamoorthy et al. *TAG* 114:901-909, 2007), or they represent QTL that are only relevant at the tetraploid level due to allelic interactions or gene expression changes. Additionally, the tetraploid and diploid populations used to identify Al tolerance QTL differ in their genetic background. The identification of QTLs may vary on the genetic background of the populations used (Monteros et al. *Crop Sci.* 48:2223-2234, 2008; Tang and Scarth *Pl. Breeding* 123:254-261, 2004). In *Oryza sativa* L., the effect of genetic background on QTLs identified was greater than the environmental effects (Liao et al. *TAG* 103:104-111, 2001).

Figure 8:
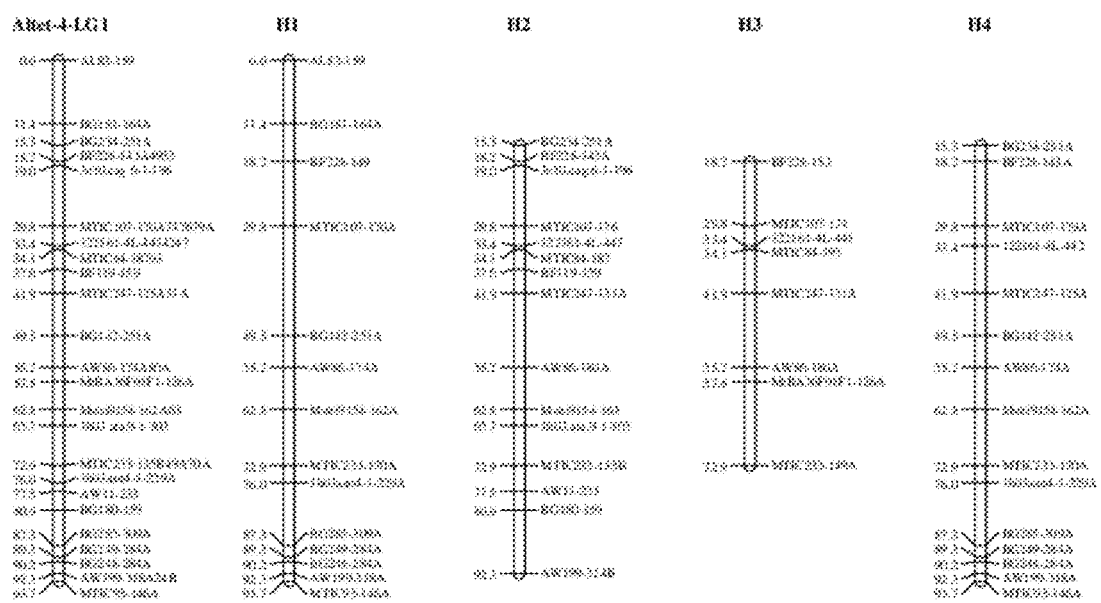
FIG. 8: Genetic linkage maps of Altet-4 and NECS-141. Consensus linkage maps (left) and the four homologous linkage groups (H1-H4) (right) are shown for Chromosomes 1 through 8.
Figure 8:
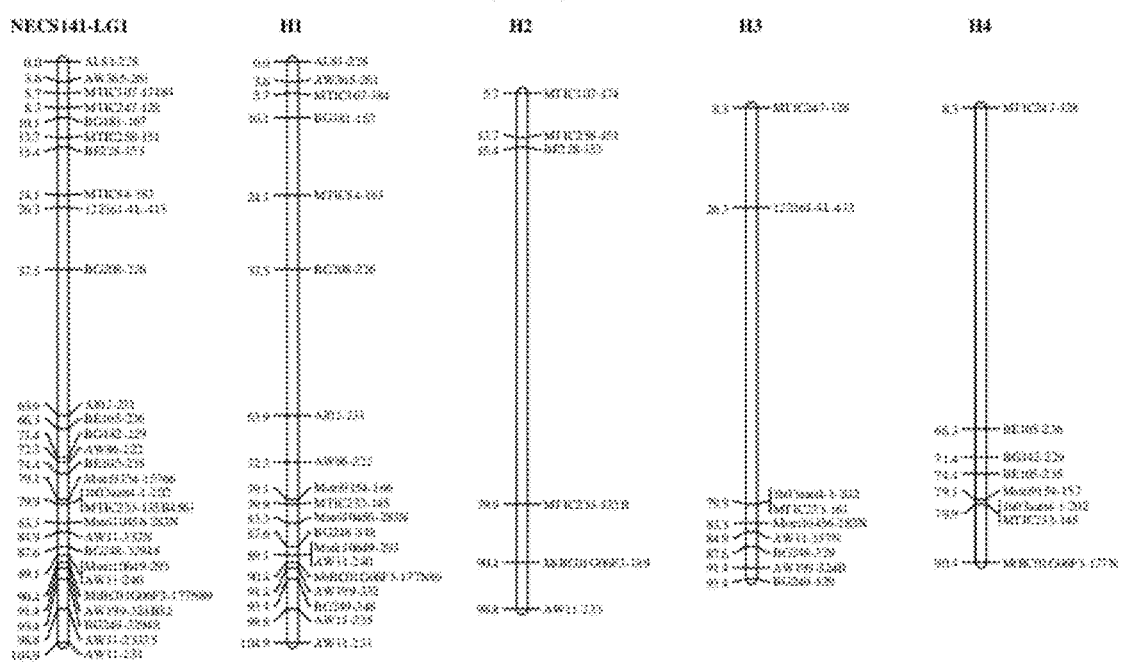
Figure 8:
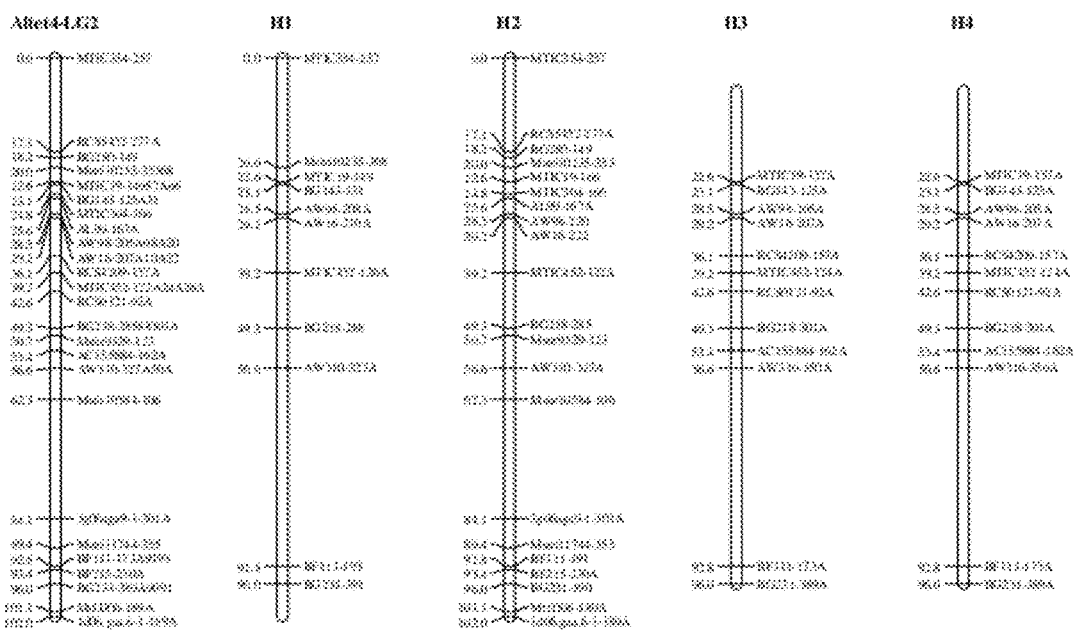
Figure 8:
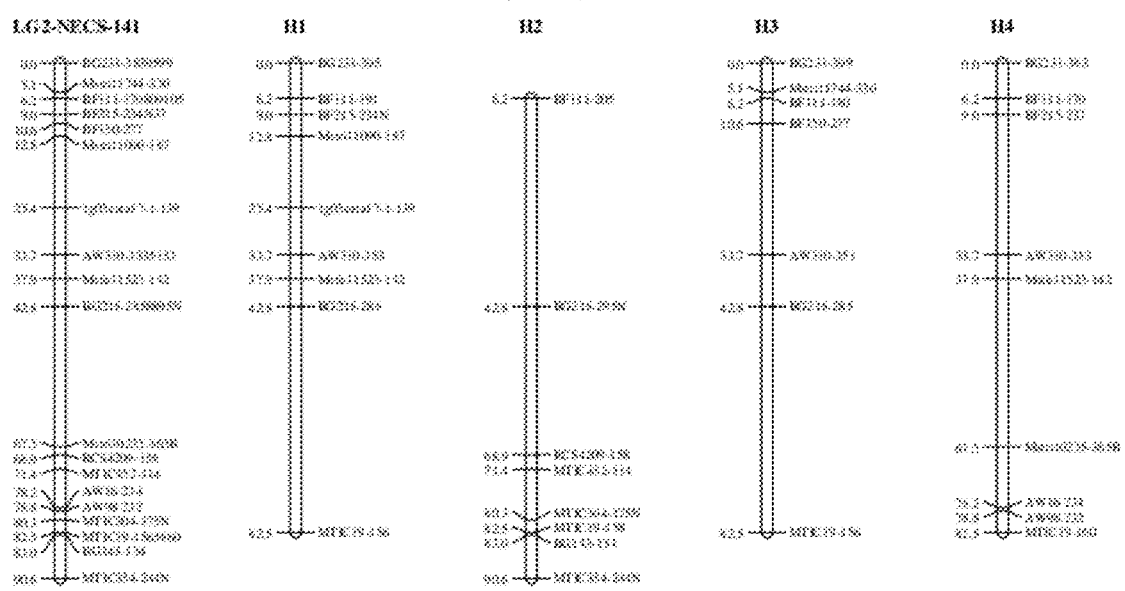
Figure 8:
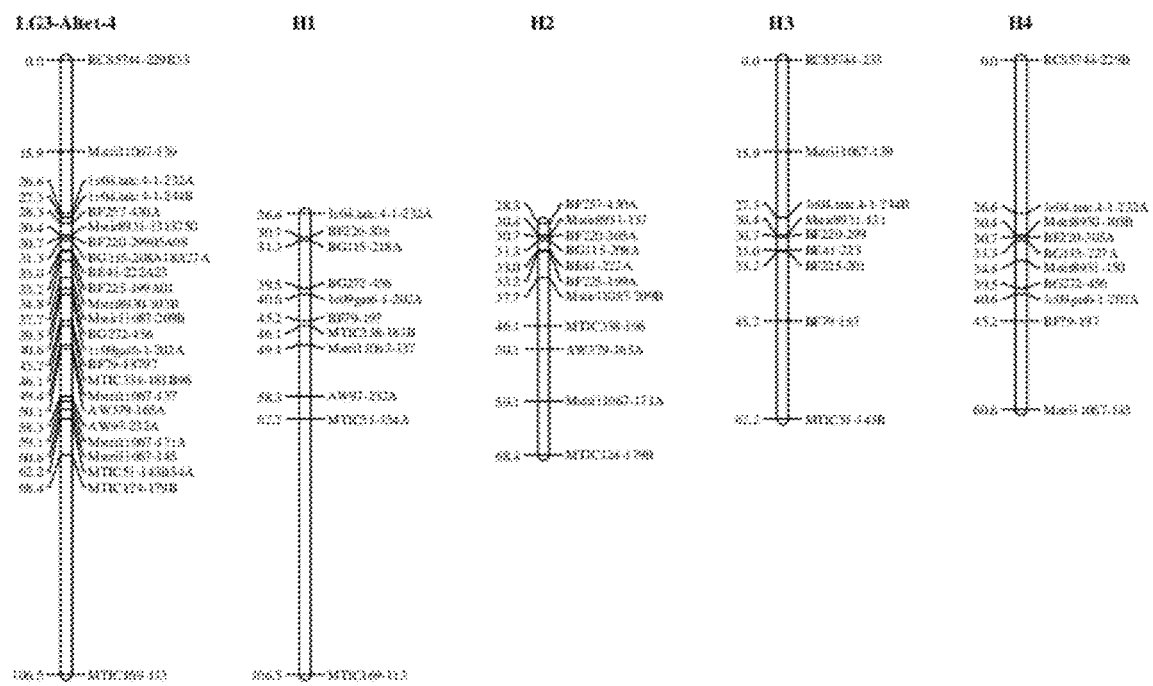
Figure 8:
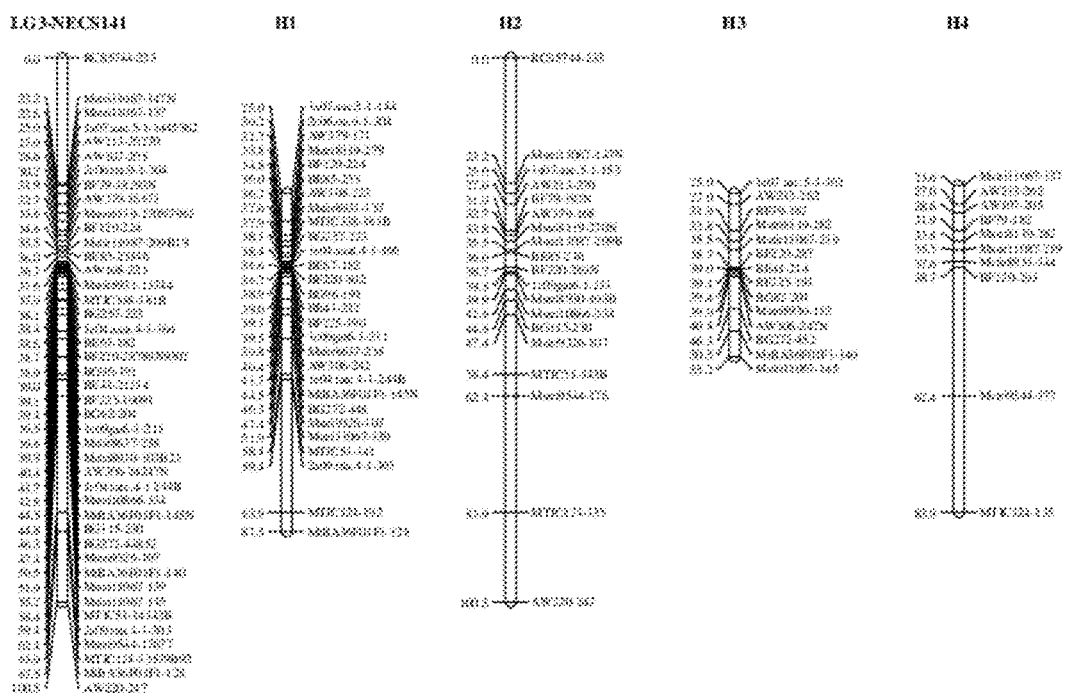
Figure 8:
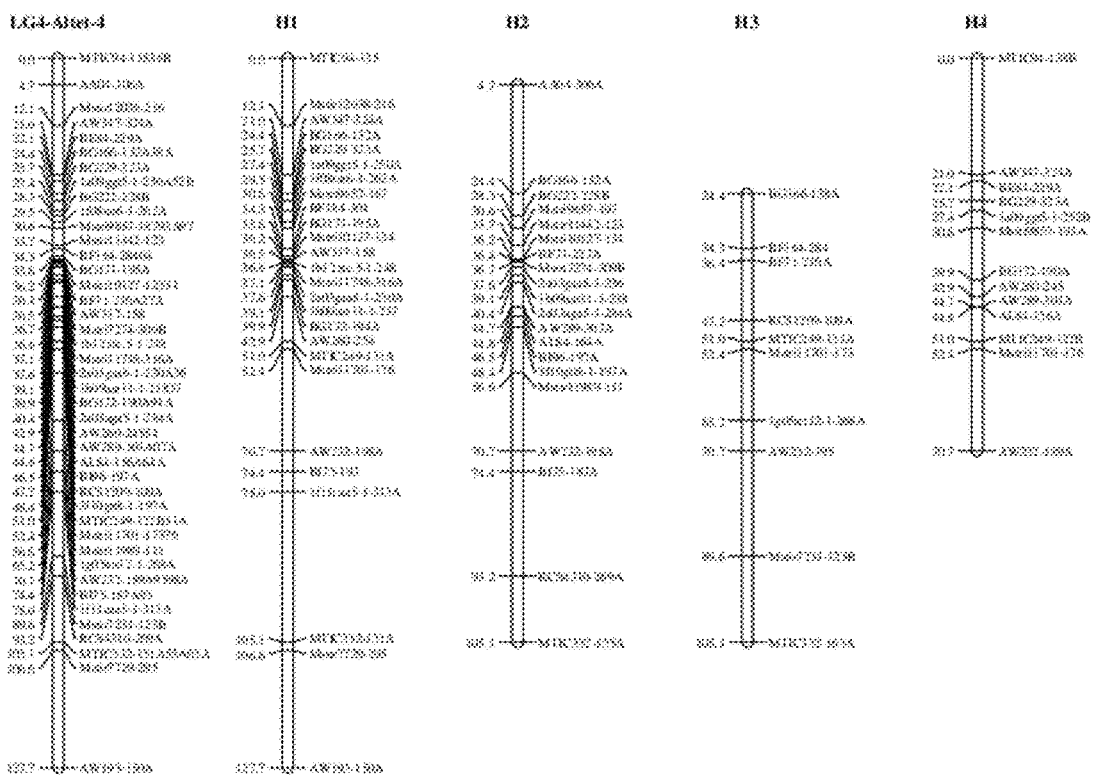
Figure 8:
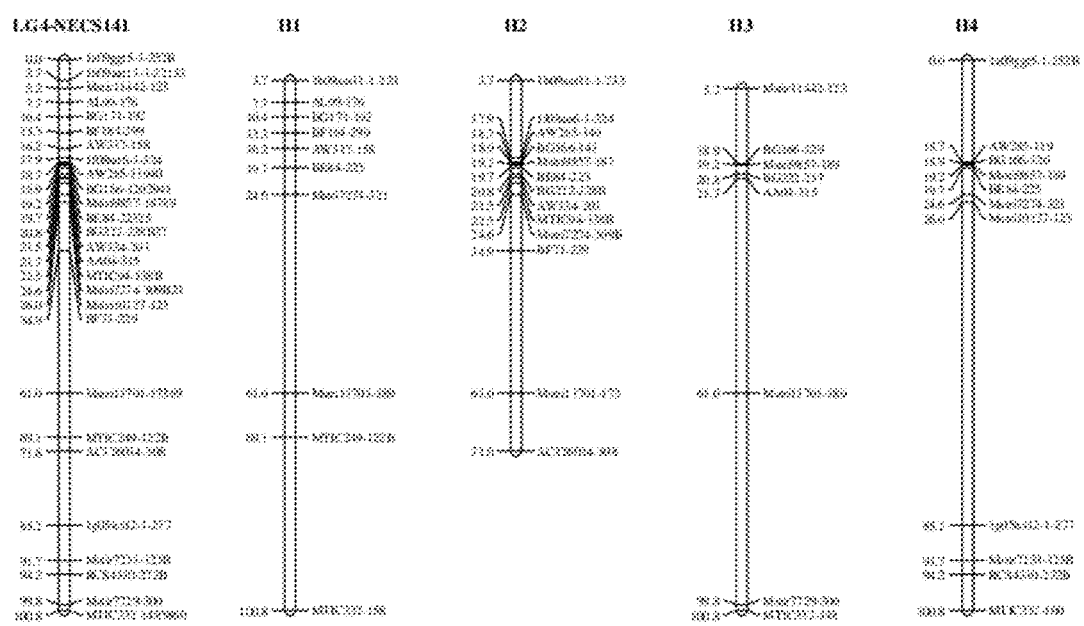
Figure 8:
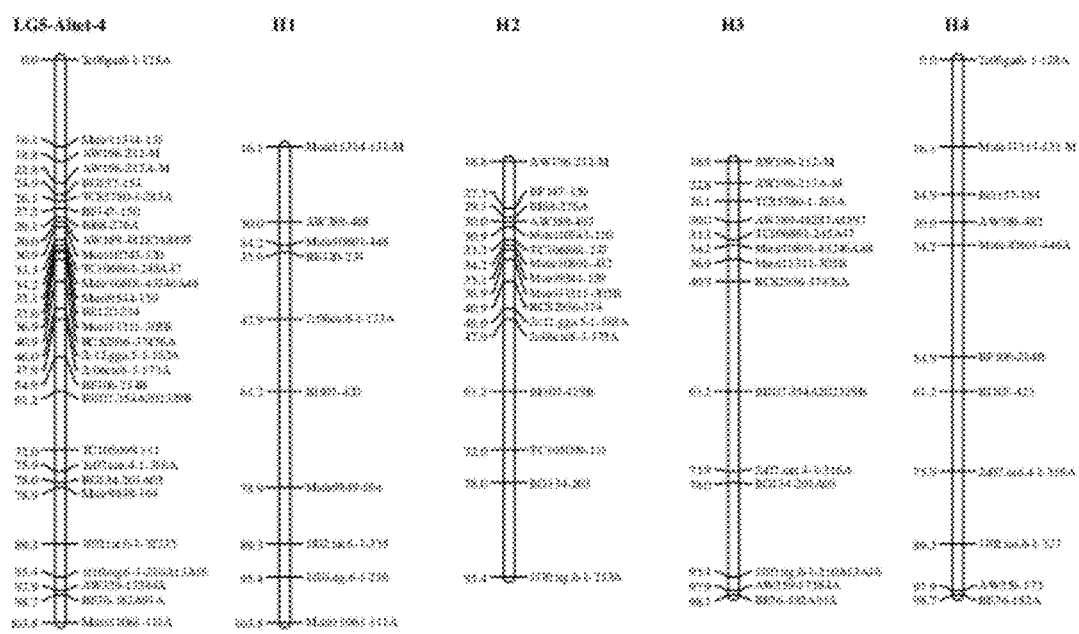
Figure 8:
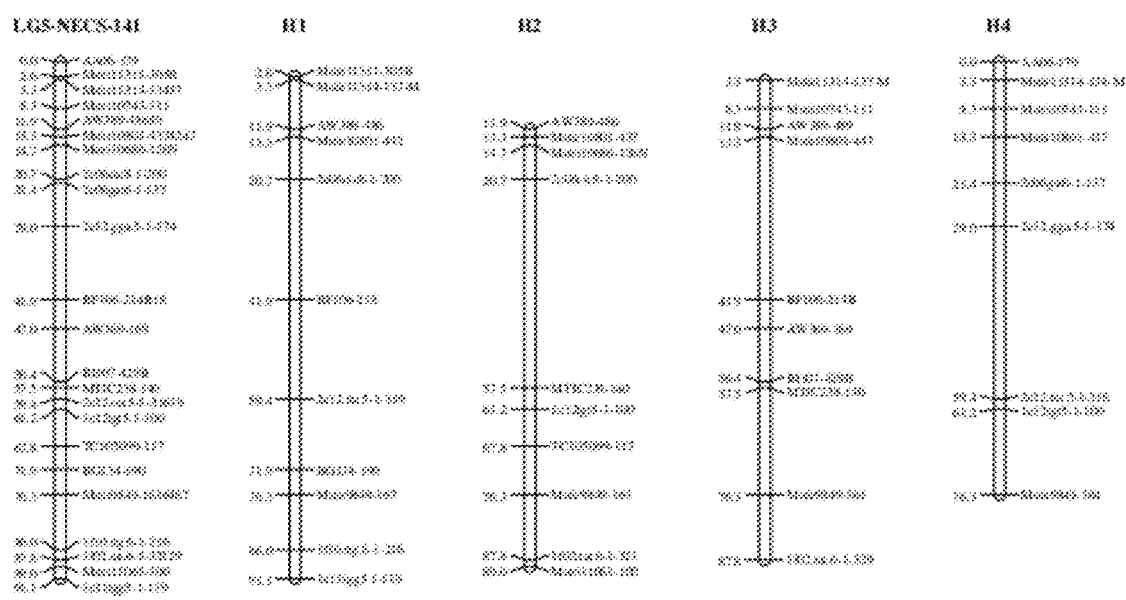
Figure 8:
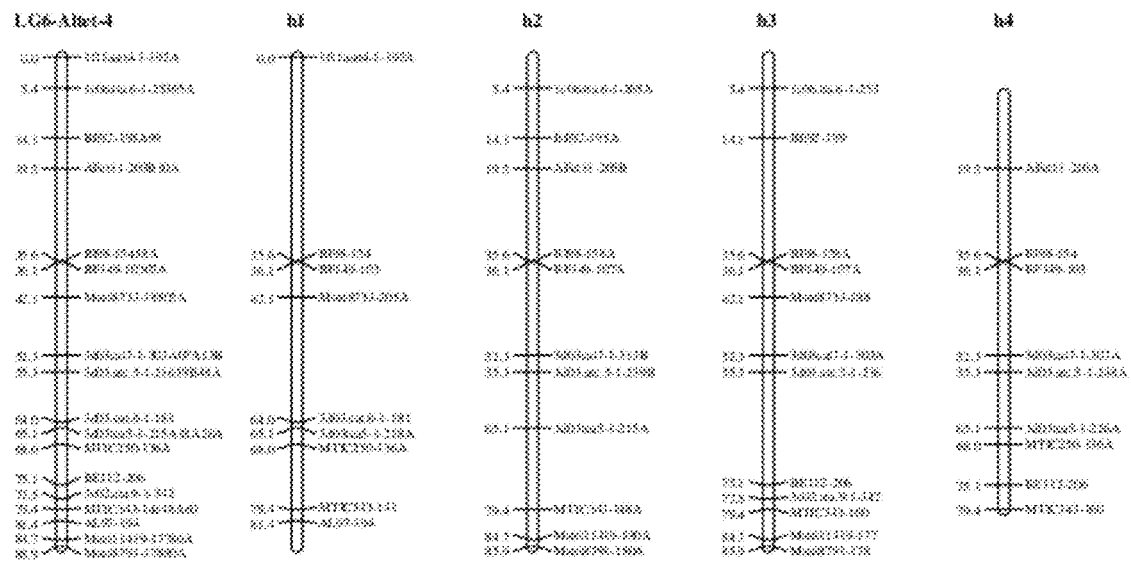
Figure 8:
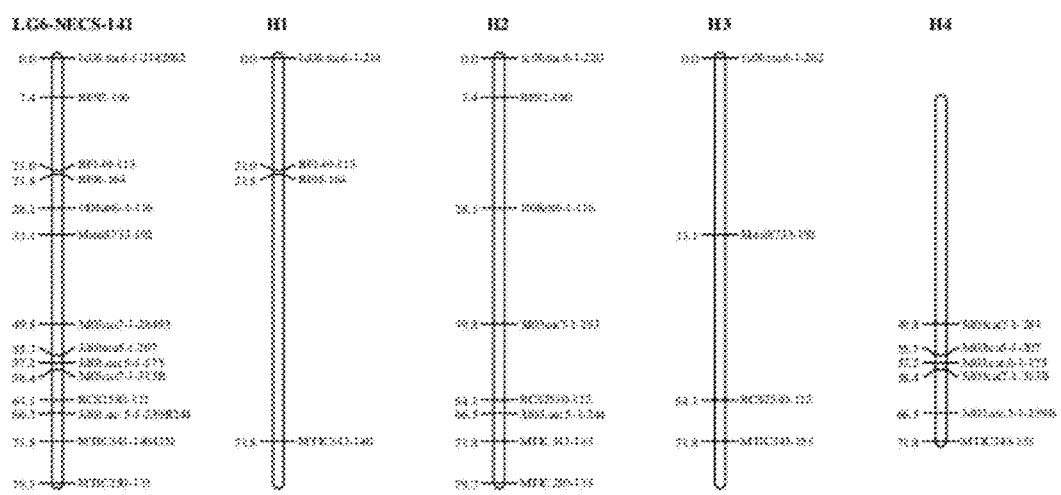
Figure 8:
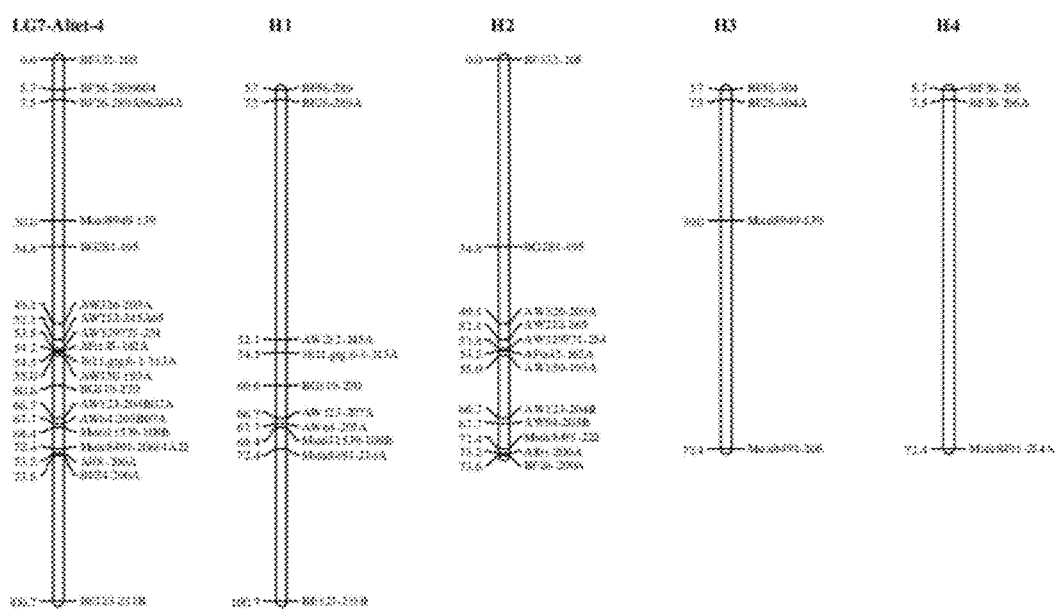
Figure 8:
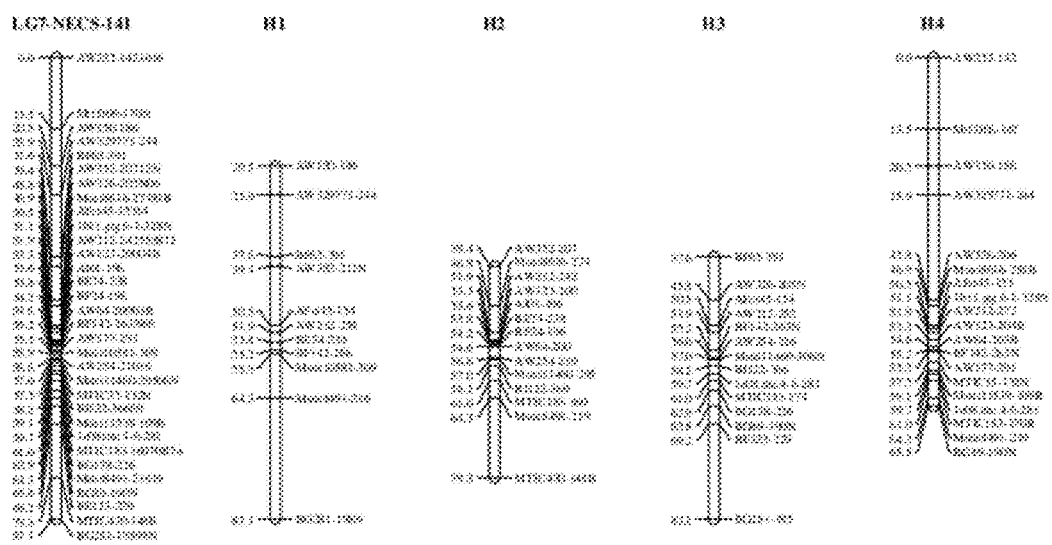
Figure 8:
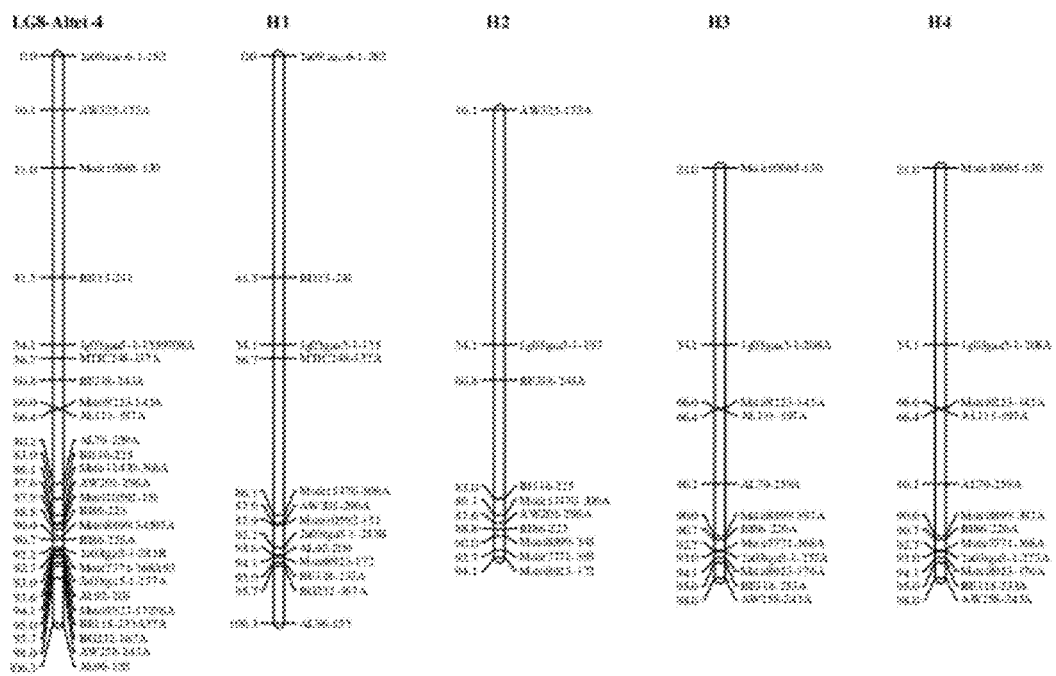
Figure 8:
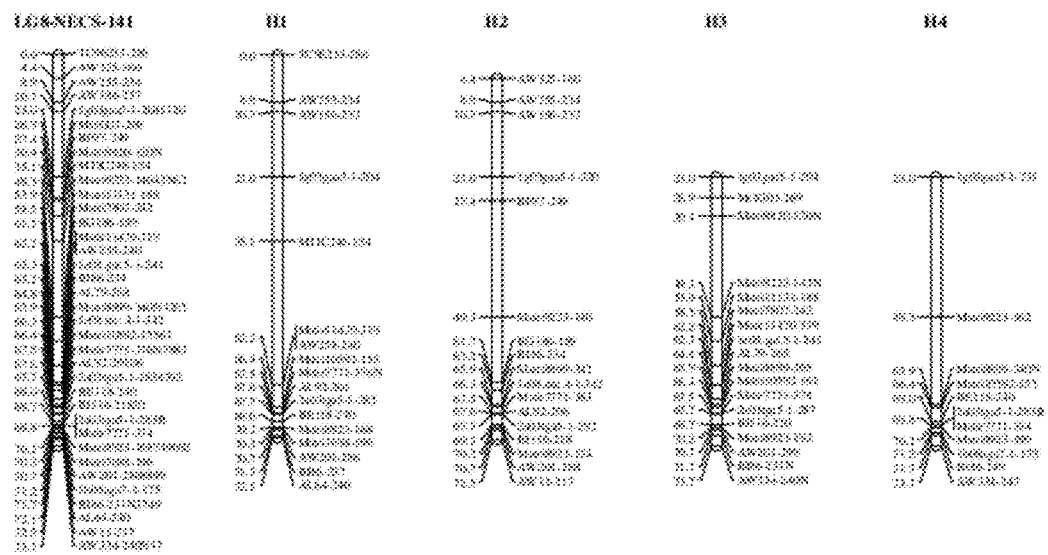

Al tolerance QTL on LG 7 of NECS-141 explained 21.7% of the phenotypic variation for total root length ratio (TRLR) from the whole plant assay in media. For the Al tolerance QTL identified from the whole plant assay on LG 7 from NECS-141, the average TRLR of the allelic combination $Q_{23}$ (0.75), was higher than the average TRLR of all other allelic combinations (0.50) (FIG. 11B). No marker significantly associated with the Al tolerance phenotype on LG 7 was identified in the SF-ANOVA, likely due to the absence of markers covering homologs H2 and H3 of NECS-141 in this region (e.g. FIG. 8). However, four simplex markers on homologous chromosome H1 were negatively associated with TRLR thus providing additional evidence showing that the recessive allele on H2 and H3 increases Al tolerance at the whole plant level (Table 7).

TABLE 7

Additional significant markers associated with Al tolerance in alfalfa from the callus bioassay (CBA) and whole plant assay in media (WPA-M) based on single-factor ANOVA ($p < 0.05$).

| $LG^a$ | $H^b$ | cM | Parent | Marker | Effect$^c$ | Mean(0)$^d$ | Mean(1)$^e$ | SED$^f$ | p value |
|---|---|---|---|---|---|---|---|---|---|
| \multicolumn{10}{c}{Callus bioassay} |
| LG1 | H3 | 75.7 | Altet-4 | MTIC233-149A | − | 0.817 | 0.745 | 0.035 | 0.041 |
|  | H3 | 57.1 | Altet-4 | MtBA36F01F1-126A | − | 0.828 | 0.740 | 0.034 | 0.011 |
| LG3 | H12 | 50.1 | NECS-141 | 1c09gat6-1-211 | − | 0.878 | 0.772 | 0.047 | 0.025 |
|  | H12 | 59.8 | NECS-141 | MsTri9326-107 | − | 0.863 | 0.771 | 0.044 | 0.039 |
| LG4 | H1 | 41.1 | Altet-4 | 1h09aat11-1-237 | − | 0.825 | 0.752 | 0.035 | 0.041 |
|  | H14 | 55.2 | Altet-4 | MsTri11701-176 | − | 0.908 | 0.774 | 0.054 | 0.015 |
|  | H2 | 25.3 | NECS-141 | 1h09aat11-1-233 | + | 0.756 | 0.831 | 0.036 | 0.037 |
| LG5 | H4 | 0 | Altet-4 | 2c06gat6-1-128A | − | 0.847 | 0.751 | 0.034 | 0.006 |
|  | H4 | 21.3 | Altet-4 | BG157-154 | − | 0.829 | 0.737 | 0.034 | 0.008 |
|  | H4 | 88.1 | NECS-141 | 2c06gat6-1-137 | + | 0.754 | 0.827 | 0.034 | 0.036 |
| LG6 | H2 | 67.9 | NECS-141 | 3d03atc5-1-244 | + | 0.752 | 0.829 | 0.034 | 0.025 |
|  | H2 | 77.5 | NECS-141 | MTIC250-133 | + | 0.751 | 0.823 | 0.034 | 0.039 |
|  | H1 | 72.1 | NECS-141 | MTIC343-140 | − | 0.823 | 0.737 | 0.034 | 0.015 |
|  | H2 | 72.1 | NECS-141 | MTIC343-143 | + | 0.749 | 0.838 | 0.034 | 0.009 |
| LG7 | H1 | 56.2 | Altet-4 | 1b11gtg6-1-313A | + | 0.762 | 0.832 | 0.035 | 0.048 |
|  | H4 | 8.4 | Altet-4 | BF26-296A | − | 0.824 | 0.752 | 0.034 | 0.036 |
|  | H4 | 6.5 | Altet-4 | BF56-296A | − | 0.824 | 0.752 | 0.034 | 0.036 |
|  | H2 | 53.4 | Altet-4 | AW212-265 | − | 0.829 | 0.732 | 0.035 | 0.007 |
|  | H1 | 1.0 | NECS-141 | BF26-306 | − | 0.839 | 0.740 | 0.033 | 0.004 |
|  | H1 | 0.1 | NECS-141 | BF56-306 | − | 0.837 | 0.743 | 0.033 | 0.006 |
| \multicolumn{10}{c}{Whole plant assay in media} |
| LG1 | H24 | 68.6 | NECS-141 | BG137-323 | − | 0.582 | 0.481 | 0.041 | 0.013 |
|  | H1 | 90.7 | NECS-141 | BG248-348 | + | 0.469 | 0.527 | 0.029 | 0.046 |
| LG2 | H34 | 90.9 | Altet-4 | BF111-173A | − | 0.629 | 0.530 | 0.044 | 0.025 |
|  | H4 | 10.9 | NECS-141 | AW16-234 | − | 0.580 | 0.510 | 0.035 | 0.046 |
|  | H4 | 8.2 | NECS-141 | MTIC19-160 | − | 0.585 | 0.507 | 0.035 | 0.026 |
| LG3 | H3 | 8.1 | Altet-4 | BE41-223 | + | 0.469 | 0.528 | 0.029 | 0.044 |
|  | H3 | 5.4 | Altet-4 | BF220-299 | + | 0.468 | 0.531 | 0.029 | 0.031 |

TABLE 7-continued

Additional significant markers associated with Al tolerance in alfalfa from the callus bioassay (CBA) and whole plant assay in media (WPA-M) based on single-factor ANOVA (p < 0.05).

| LG[a] | H[b] | cM | Parent | Marker | Effect[c] | Mean(0)[d] | Mean(1)[e] | SED[f] | p value |
|---|---|---|---|---|---|---|---|---|---|
|  | H3 | 8.5 | Altet-4 | BF225-201 | + | 0.469 | 0.528 | 0.029 | 0.044 |
|  | H4 | 6.2 | Altet-4 | BG115-227A | − | 0.527 | 0.459 | 0.029 | 0.021 |
|  | H3 | 5.0 | Altet-4 | MsTri8931-131 | + | 0.470 | 0.531 | 0.029 | 0.038 |
|  | H14 | 16.6 | Altet-4 | BG272-456 | − | 0.582 | 0.469 | 0.036 | 0.002 |
|  | H1 | 55.5 | NECS-141 | BF120-224 | + | 0.469 | 0.530 | 0.029 | 0.039 |
|  | H3 | 61.6 | NECS-141 | MtBA36F01F1-140 | − | 0.522 | 0.458 | 0.030 | 0.032 |
| LG4 | H3 | 67.5 | Altet-4 | 1g05tct12-1-268A | + | 0.463 | 0.537 | 0.029 | 0.013 |
|  | H3 | 73.1 | Altet-4 | AW232-195 | + | 0.463 | 0.535 | 0.029 | 0.014 |
|  | H1 | 26.3 | Altet-4 | AW260-254 | − | 0.532 | 0.456 | 0.029 | 0.009 |
|  | H4 | 24.8 | Altet-4 | BE84-229A | + | 0.462 | 0.530 | 0.029 | 0.022 |
|  | H12 | 27.3 | Altet-4 | BG166-132A | − | 0.589 | 0.478 | 0.039 | 0.005 |
|  | H4 | 31.5 | Altet-4 | MsTri9857-193A | + | 0.468 | 0.526 | 0.029 | 0.049 |
|  | H3 | 48.7 | Altet-4 | RCS1209-109A | + | 0.467 | 0.538 | 0.029 | 0.016 |
| LG5 | H14 | 16.2 | Altet-4 | MsTri11314-131 | − | 0.547 | 0.479 | 0.034 | 0.048 |
|  | H4 | 54.6 | NECS-141 | 2c12tta5-1-316 | − | 0.525 | 0.456 | 0.029 | 0.021 |
|  | H3 | 62.3 | NECS-141 | AW369-169 | + | 0.451 | 0.536 | 0.029 | 0.004 |
|  | H12 | 96.7 | NECS-141 | AW389-486 | − | 0.569 | 0.480 | 0.039 | 0.025 |
|  | H3 | 96.7 | NECS-141 | AW389-489 | + | 0.460 | 0.526 | 0.029 | 0.026 |
|  | H3 | 95.7 | NECS-141 | MsTri10801-447 | + | 0.454 | 0.532 | 0.029 | 0.007 |
| LG6 | H1 | 0 | Altet-4 | 1f11aatt4-1-192A | − | 0.533 | 0.471 | 0.030 | 0.037 |
|  | H3 | 51.2 | Altet-4 | 3d03cat7-1-303A | + | 0.441 | 0.516 | 0.033 | 0.024 |
|  | H23 | 28.4 | Altet-4 | BF149-107A | + | 0.431 | 0.511 | 0.037 | 0.033 |
|  | H14 | 66.0 | Altet-4 | MTIC250-136A | − | 0.544 | 0.476 | 0.032 | 0.034 |
|  | H3 | 72.3 | Altet-4 | MTIC343-160 | + | 0.410 | 0.509 | 0.043 | 0.023 |
|  | H1 | 0 | NECS-141 | 1c06tta6-1-214 | − | 0.525 | 0.463 | 0.029 | 0.034 |
|  | H2 | 67.9 | NECS-141 | 3d03atc5-1-244 | + | 0.466 | 0.527 | 0.029 | 0.038 |
|  | H1 | 26.4 | NECS-141 | BI98-164 | − | 0.523 | 0.463 | 0.029 | 0.045 |
| LG7 | H1 | 57.4 | NECS-141 | BF142-266 | − | 0.528 | 0.459 | 0.029 | 0.019 |
|  | H1 | 1.0 | NECS-141 | BF26-306 | − | 0.533 | 0.459 | 0.029 | 0.011 |
|  | H1 | 0.1 | NECS-141 | BF56-306 | − | 0.529 | 0.462 | 0.029 | 0.023 |
| LG8 | H2 | 87.3 | Altet-4 | BI86-223 | + | 0.460 | 0.522 | 0.030 | 0.038 |
|  | H12 | 21.3 | NECS-141 | AW186-237 | + | 0.379 | 0.500 | 0.058 | 0.042 |
|  | H12 | 20.3 | NECS-141 | AW255-234 | + | 0.376 | 0.503 | 0.062 | 0.046 |
|  | H13 | 75.2 | NECS-141 | MsTri11470-319 | − | 0.579 | 0.463 | 0.063 | 0.069 |

[a]Linkage group
[b]Homologous chromosome number
[c]Effect: (+) presence of the marker increases the trait value; (−) absence of the marker increases the trait value
[d]Mean of individuals with marker genotype 0 (absent)
[e]Mean of individuals with marker genotype 1 (present)
[f]standard error of the difference between marker class means

---

What is claimed is:

1. A method for increasing the aluminum tolerance of an alfalfa line, said method comprising introgressing at least one chromosomal locus contributing to aluminum tolerance from a parent alfalfa plant into a selected alfalfa line, wherein said chromosomal locus maps between loci Mstri9857-18793A97 and AW260-24554 on linkage group 4.

2. The method of claim 1, wherein the aluminum tolerant alfalfa plant is an agronomically elite plant.

3. The method of claim 1, wherein the aluminum tolerant alfalfa plant is a hybrid or inbred plant.

4. The method of claim 1, wherein the introgressing is by marker-assisted selection using at least a first genetic marker linked to said chromosomal locus.

5. The method of claim 4, wherein the marker is selected from one of those detectable using a primer pair in Table 1.

6. The method of claim 1, wherein the parent alfalfa plant is Altet-4.

7. The method of claim 1, wherein the parent alfalfa plant is a *Medicago sativa* NECS-141 plant.

8. The method of claim 1, wherein the parent alfalfa plant exhibits at least a 50% reduction in aluminum sensitivity relative to the less aluminum tolerant alfalfa line.

9. The method of claim 8, wherein the parent alfalfa plant displays at least a 75% reduction in aluminum sensitivity relative to the less aluminum tolerant alfalfa line.

10. The method of claim 1 further comprising producing an alfalfa seed by crossing the aluminum tolerant plant with itself or a second alfalfa plant and allowing seed to form.

11. A method for obtaining an alfalfa plant comprising an allele conferring aluminum tolerance, said method comprising:
   a) obtaining nucleic acids from an alfalfa plant comprising at least a first allele that confers aluminum tolerance, wherein said allele maps between loci Mstri9857-18793A97 and AW260-24554 on linkage group 4;
   b) assaying said nucleic acids for the presence of at least a first genetic marker that is genetically linked to said allele; and
   c) selecting the alfalfa plant based on the presence of said genetic marker.

12. The method of claim 11, wherein the alfalfa plant is a progeny of a plant of Altet-4.

13. The method of claim 11, wherein the alfalfa plant is a progeny of a plant of a *Medicago sativa* NECS-141 plant.

* * * * *

SEQUENCE LISTING

<160> NUMBER OF SEQ ID NOS: 571

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
ccacgttgtt gaacagtgga aatg                                          24

<210> SEQ ID NO 2
<211> LENGTH: 40
<212> TYPE: DNA
<213> ORGANISM: Artificial Sequence
<220> FEATURE:
<223> OTHER INFORMATION: PCR primer

<400> SEQUENCE: 2
tgtaaaacga cggccagtgc gaacttgttt ccgatgatgc                          40

<210> SEQ ID NO 3

```
<211> LENGTH: 20
<212> TYPE: DNA
<213> ORGANISM: Artificial Sequence
<220> FEATURE:
<223> OTHER INFORMATION: PCR primer

<400> SEQUENCE: 3
gagccatgtt gttggtgttg                                             20

<210> SEQ ID NO 4
<211> LENGTH: 38
<212> TYPE: DNA
<213> ORGANISM: Artificial Sequence
<220> FEATURE:
<223> OTHER INFORMATION: PCR primer

<400> SEQUENCE: 4
tgtaaaacga cggccagttt ggttggtggg gttatcat                         38

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
tctctggtca gcaccaactg                                             20

<210> SEQ ID NO 6
<211> LENGTH: 38
<212> TYPE: DNA
<213> ORGANISM: Artificial Sequence
<220> FEATURE:
<223> OTHER INFORMATION: PCR primer

<400> SEQUENCE: 6
tgtaaaacga cggccagtgc atggtgagag acgtcgta                         38

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
tggagggaaa tgatttagcg                                             20

<210> SEQ ID NO 8
<211> LENGTH: 38
<212> TYPE: DNA
<213> ORGANISM: Artificial Sequence
<220> FEATURE:
<223> OTHER INFORMATION: PCR primer

<400> SEQUENCE: 8
tgtaaaacga cggccagtaa cgaaaacgaa aacgaacg                         38

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
```

```
aacctcctcg acaacattgg                                              20

<210> SEQ ID NO 10
<211> LENGTH: 38
<212> TYPE: DNA
<213> ORGANISM: Artificial Sequence
<220> FEATURE:
<223> OTHER INFORMATION: PCR primer

<400> SEQUENCE: 10
tgtaaaacga cggccagtac ctgggattgg gttaggac                          38

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
gtcgtcgtag agtggggtgt                                              20

<210> SEQ ID NO 12
<211> LENGTH: 38
<212> TYPE: DNA
<213> ORGANISM: Artificial Sequence
<220> FEATURE:
<223> OTHER INFORMATION: PCR primer

<400> SEQUENCE: 12
tgtaaaacga cggccagtga gtggccatgg attcaaac                          38

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
caaatgagag cacgttgtga a                                            21

<210> SEQ ID NO 14
<211> LENGTH: 38
<212> TYPE: DNA
<213> ORGANISM: Artificial Sequence
<220> FEATURE:
<223> OTHER INFORMATION: PCR primer

<400> SEQUENCE: 14
tgtaaaacga cggccagtat catattggct tggtgcaa                          38

<210> SEQ ID NO 15
<211> LENGTH: 20
<212> TYPE: DNA
<213> ORGANISM: Artificial Sequence
<220> FEATURE:
<223> OTHER INFORMATION: PCR primer

<400> SEQUENCE: 15
ttttccattc ccacctacca                                              20

<210> SEQ ID NO 16
<211> LENGTH: 38
<212> TYPE: DNA
```

```
<213> ORGANISM: Artificial Sequence
<220> FEATURE:
<223> OTHER INFORMATION: PCR primer

<400> SEQUENCE: 16
tgtaaaacga cggccagttt tggaaaacac ttgcccac                    38

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17 ttgcccttttt gtccaagaac                                       20

<210> SEQ ID NO 18
<211> LENGTH: 38
<212> TYPE: DNA
<213> ORGANISM: Artificial Sequence
<220> FEATURE:
<223> OTHER INFORMATION: PCR primer

<400> SEQUENCE: 18
tgtaaaacga cggccagtga cgagagtccc atcagagc                    38

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
ttacgatctg gcttggaacc                                        20

<210> SEQ ID NO 20
<211> LENGTH: 38
<212> TYPE: DNA
<213> ORGANISM: Artificial Sequence
<220> FEATURE:
<223> OTHER INFORMATION: PCR primer

<400> SEQUENCE: 20
tgtaaaacga cggccagtct cgacctgcac gacaatta                    38

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
gaaggttttg ggtggtgatg                                        20

<210> SEQ ID NO 22
<211> LENGTH: 38
<212> TYPE: DNA
<213> ORGANISM: Artificial Sequence
<220> FEATURE:
<223> OTHER INFORMATION: PCR primer

<400> SEQUENCE: 22
tgtaaaacga cggccagtcc atggctcttt cctaccaa                    38
```

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
gaccgggatt gatggatatg                                              20

<210> SEQ ID NO 24
<211> LENGTH: 39
<212> TYPE: DNA
<213> ORGANISM: Artificial Sequence
<220> FEATURE:
<223> OTHER INFORMATION: PCR primer

<400> SEQUENCE: 24
tgtaaaacga cggccagtaa caagagatgg gaggaaaaa                         39

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
tgtttctgat cagggcattg                                              20

<210> SEQ ID NO 26
<211> LENGTH: 38
<212> TYPE: DNA
<213> ORGANISM: Artificial Sequence
<220> FEATURE:
<223> OTHER INFORMATION: PCR primer

<400> SEQUENCE: 26
tgtaaaacga cggccagttc taggtattcg ctggcgtt                          38

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
acttcctgac ggtcctcctt                                              20

<210> SEQ ID NO 28
<211> LENGTH: 38
<212> TYPE: DNA
<213> ORGANISM: Artificial Sequence
<220> FEATURE:
<223> OTHER INFORMATION: PCR primer

<400> SEQUENCE: 28
tgtaaaacga cggccagtgg cgcataatca ccattacc                          38

<210> SEQ ID NO 29
<211> LENGTH: 20
<212> TYPE: DNA
<213> ORGANISM: Artificial Sequence
<220> FEATURE:

<223> OTHER INFORMATION: PCR primer

<400> SEQUENCE: 29
tccttctgga caagaaaccg					20

<210> SEQ ID NO 30
<211> LENGTH: 42
<212> TYPE: DNA
<213> ORGANISM: Artificial Sequence
<220> FEATURE:
<223> OTHER INFORMATION: PCR primer

<400> SEQUENCE: 30
tgtaaaacga cggccagttc catcacgaca tatttcactt tt					42

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
tgatgctgtc ctatgccaag					20

<210> SEQ ID NO 32
<211> LENGTH: 39
<212> TYPE: DNA
<213> ORGANISM: Artificial Sequence
<220> FEATURE:
<223> OTHER INFORMATION: PCR primer

<400> SEQUENCE: 32
tgtaaaacga cggccagttg gaaaaggctt tgactgttg					39

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
tgatggatgc aatagggat					20

<210> SEQ ID NO 34
<211> LENGTH: 38
<212> TYPE: DNA
<213> ORGANISM: Artificial Sequence
<220> FEATURE:
<223> OTHER INFORMATION: PCR primer

<400> SEQUENCE: 34
tgtaaaacga cggccagttg acatcatatg cacggtcc					38

<210> SEQ ID NO 35
<211> LENGTH: 20
<212> TYPE: DNA
<213> ORGANISM: Artificial Sequence
<220> FEATURE:
<223> OTHER INFORMATION: PCR primer

<400> SEQUENCE: 35
atgaaggtca ttgcaaggct					20

<210> SEQ ID NO 36
<211> LENGTH: 38
<212> TYPE: DNA
<213> ORGANISM: Artificial Sequence
<220> FEATURE:
<223> OTHER INFORMATION: PCR primer

<400> SEQUENCE: 36
tgtaaaacga cggccagtct gctgacttct gtctggca                    38

<210> SEQ ID NO 37
<211> LENGTH: 20
<212> TYPE: DNA
<213> ORGANISM: Artificial Sequence
<220> FEATURE:
<223> OTHER INFORMATION: PCR primer

<400> SEQUENCE: 37
agtgccgcta tgctgctatt                                        20

<210> SEQ ID NO 38
<211> LENGTH: 38
<212> TYPE: DNA
<213> ORGANISM: Artificial Sequence
<220> FEATURE:
<223> OTHER INFORMATION: PCR primer

<400> SEQUENCE: 38
tgtaaaacga cggccagttt gatccatgta gccaaccc                    38

<210> SEQ ID NO 39
<211> LENGTH: 20
<212> TYPE: DNA
<213> ORGANISM: Artificial Sequence
<220> FEATURE:
<223> OTHER INFORMATION: PCR primer

<400> SEQUENCE: 39
ttgaaaagac acggggaagt                                        20

<210> SEQ ID NO 40
<211> LENGTH: 38
<212> TYPE: DNA
<213> ORGANISM: Artificial Sequence
<220> FEATURE:
<223> OTHER INFORMATION: PCR primer

<400> SEQUENCE: 40
tgtaaaacga cggccagtcc acaaaagcag atggttga                    38

<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
ttggtgagag ctggtgattg                                        20

<210> SEQ ID NO 42
<211> LENGTH: 38
<212> TYPE: DNA
<213> ORGANISM: Artificial Sequence
<220> FEATURE:
<223> OTHER INFORMATION: PCR primer

<400> SEQUENCE: 42
tgtaaaacga cggccagttt accgcttttg gattctgg                                38

<210> SEQ ID NO 43
<211> LENGTH: 20
<212> TYPE: DNA
<213> ORGANISM: Artificial Sequence
<220> FEATURE:
<223> OTHER INFORMATION: PCR primer

<400> SEQUENCE: 43
tttatcggcg aagaagatcg                                                    20

<210> SEQ ID NO 44
<211> LENGTH: 38
<212> TYPE: DNA
<213> ORGANISM: Artificial Sequence
<220> FEATURE:
<223> OTHER INFORMATION: PCR primer

<400> SEQUENCE: 44
tgtaaaacga cggccagttc ccgcttcact tcactttc                                38

<210> SEQ ID NO 45
<211> LENGTH: 20
<212> TYPE: DNA
<213> ORGANISM: Artificial Sequence
<220> FEATURE:
<223> OTHER INFORMATION: PCR primer

<400> SEQUENCE: 45
ccctaaatca ggggttcaaa                                                    20

<210> SEQ ID NO 46
<211> LENGTH: 38
<212> TYPE: DNA
<213> ORGANISM: Artificial Sequence
<220> FEATURE:
<223> OTHER INFORMATION: PCR primer

<400> SEQUENCE: 46
tgtaaaacga cggccagtca ctcattgctg agggcata                                38

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
tcagaaattc cctcccattg                                                    20

<210> SEQ ID NO 48
<211> LENGTH: 38
<212> TYPE: DNA
<213> ORGANISM: Artificial Sequence
<220> FEATURE:
<223> OTHER INFORMATION: PCR primer

<400> SEQUENCE: 48
tgtaaaacga cggccagtaa gaatgacgaa gaggcgaa                                38

<210> SEQ ID NO 49
<211> LENGTH: 20

```
<212> TYPE: DNA
<213> ORGANISM: Artificial Sequence
<220> FEATURE:
<223> OTHER INFORMATION: PCR primer

<400> SEQUENCE: 49
tgattcaagg atgggaaagc                                           20

<210> SEQ ID NO 50
<211> LENGTH: 38
<212> TYPE: DNA
<213> ORGANISM: Artificial Sequence
<220> FEATURE:
<223> OTHER INFORMATION: PCR primer

<400> SEQUENCE: 50
tgtaaaacga cggccagttg tcttccgtgg tctcactg                       38

<210> SEQ ID NO 51
<211> LENGTH: 20
<212> TYPE: DNA
<213> ORGANISM: Artificial Sequence
<220> FEATURE:
<223> OTHER INFORMATION: PCR primer

<400> SEQUENCE: 51
gagtttctga attcgccgtc                                           20

<210> SEQ ID NO 52
<211> LENGTH: 38
<212> TYPE: DNA
<213> ORGANISM: Artificial Sequence
<220> FEATURE:
<223> OTHER INFORMATION: PCR primer

<400> SEQUENCE: 52
tgtaaaacga cggccagttc ggcatcaatc atgtcatc                       38

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
cgataattca cccccatgac                                           20

<210> SEQ ID NO 54
<211> LENGTH: 38
<212> TYPE: DNA
<213> ORGANISM: Artificial Sequence
<220> FEATURE:
<223> OTHER INFORMATION: PCR primer

<400> SEQUENCE: 54
tgtaaaacga cggccagtca caatcaaatg catagccg                       38

<210> SEQ ID NO 55
<211> LENGTH: 20
<212> TYPE: DNA
<213> ORGANISM: Artificial Sequence
<220> FEATURE:
<223> OTHER INFORMATION: PCR primer

<400> SEQUENCE: 55
```
tcgagagctc ggtattcgat               20

<210> SEQ ID NO 56
<211> LENGTH: 38
<212> TYPE: DNA
<213> ORGANISM: Artificial Sequence
<220> FEATURE:
<223> OTHER INFORMATION: PCR primer

<400> SEQUENCE: 56
tgtaaaacga cggccagtat ccaagggcgg tagaagac               38

<210> SEQ ID NO 57
<211> LENGTH: 20
<212> TYPE: DNA
<213> ORGANISM: Artificial Sequence
<220> FEATURE:
<223> OTHER INFORMATION: PCR primer

<400> SEQUENCE: 57
tcgagagctc ggtattcgat               20

<210> SEQ ID NO 58
<211> LENGTH: 38
<212> TYPE: DNA
<213> ORGANISM: Artificial Sequence
<220> FEATURE:
<223> OTHER INFORMATION: PCR primer

<400> SEQUENCE: 58
tgtaaaacga cggccagtgt gtggaagaga ccggagaa               38

<210> SEQ ID NO 59
<211> LENGTH: 20
<212> TYPE: DNA
<213> ORGANISM: Artificial Sequence
<220> FEATURE:
<223> OTHER INFORMATION: PCR primer

<400> SEQUENCE: 59
aagcactctg agccaccatt               20

<210> SEQ ID NO 60
<211> LENGTH: 38
<212> TYPE: DNA
<213> ORGANISM: Artificial Sequence
<220> FEATURE:
<223> OTHER INFORMATION: PCR primer

<400> SEQUENCE: 60
tgtaaaacga cggccagttg aggaaattct tgggagga               38

<210> SEQ ID NO 61
<211> LENGTH: 20
<212> TYPE: DNA
<213> ORGANISM: Artificial Sequence
<220> FEATURE:
<223> OTHER INFORMATION: PCR primer

<400> SEQUENCE: 61
gcagggacga aaccagaata               20

<210> SEQ ID NO 62
<211> LENGTH: 41
<212> TYPE: DNA
<213> ORGANISM: Artificial Sequence

```
<220> FEATURE:
<223> OTHER INFORMATION: PCR primer

<400> SEQUENCE: 62
tgtaaaacga cggccagttt gcacttccac taaatgactt g        41

<210> SEQ ID NO 63
<211> LENGTH: 20
<212> TYPE: DNA
<213> ORGANISM: Artificial Sequence
<220> FEATURE:
<223> OTHER INFORMATION: PCR primer

<400> SEQUENCE: 63
ccctccaatc aagaaacagc                                 20

<210> SEQ ID NO 64
<211> LENGTH: 38
<212> TYPE: DNA
<213> ORGANISM: Artificial Sequence
<220> FEATURE:
<223> OTHER INFORMATION: PCR primer

<400> SEQUENCE: 64
tgtaaaacga cggccagtcc caattccaaa ccagaaaa             38

<210> SEQ ID NO 65
<211> LENGTH: 21
<212> TYPE: DNA
<213> ORGANISM: Artificial Sequence
<220> FEATURE:
<223> OTHER INFORMATION: PCR primer

<400> SEQUENCE: 65
gaccattgat catgtctcac g                               21

<210> SEQ ID NO 66
<211> LENGTH: 38
<212> TYPE: DNA
<213> ORGANISM: Artificial Sequence
<220> FEATURE:
<223> OTHER INFORMATION: PCR primer

<400> SEQUENCE: 66
tgtaaaacga cggccagtcc agattgctta ccagggac             38

<210> SEQ ID NO 67
<211> LENGTH: 20
<212> TYPE: DNA
<213> ORGANISM: Artificial Sequence
<220> FEATURE:
<223> OTHER INFORMATION: PCR primer

<400> SEQUENCE: 67
aacaaccaaa cttggccttg                                 20

<210> SEQ ID NO 68
<211> LENGTH: 38
<212> TYPE: DNA
<213> ORGANISM: Artificial Sequence
<220> FEATURE:
<223> OTHER INFORMATION: PCR primer

<400> SEQUENCE: 68
tgtaaaacga cggccagttg gtcgaaggaa gcagagat             38
```

<210> SEQ ID NO 69
<211> LENGTH: 20
<212> TYPE: DNA
<213> ORGANISM: Artificial Sequence
<220> FEATURE:
<223> OTHER INFORMATION: PCR primer

<400> SEQUENCE: 69
acttccattg ccgcttctaa                                        20

<210> SEQ ID NO 70
<211> LENGTH: 38
<212> TYPE: DNA
<213> ORGANISM: Artificial Sequence
<220> FEATURE:
<223> OTHER INFORMATION: PCR primer

<400> SEQUENCE: 70
tgtaaaacga cggccagttg tggcgaagta acgaagaa                    38

<210> SEQ ID NO 71
<211> LENGTH: 24
<212> TYPE: DNA
<213> ORGANISM: Artificial Sequence
<220> FEATURE:
<223> OTHER INFORMATION: PCR primer

<400> SEQUENCE: 71
aaaccaatga tatcaaactc cctt                                   24

<210> SEQ ID NO 72
<211> LENGTH: 45
<212> TYPE: DNA
<213> ORGANISM: Artificial Sequence
<220> FEATURE:
<223> OTHER INFORMATION: PCR primer

<400> SEQUENCE: 72
tgtaaaacga cggccagtaa aaagtcatgc tacaaatcat aaaaa            45

<210> SEQ ID NO 73
<211> LENGTH: 20
<212> TYPE: DNA
<213> ORGANISM: Artificial Sequence
<220> FEATURE:
<223> OTHER INFORMATION: PCR primer

<400> SEQUENCE: 73
aaatggattc gaactcacgc                                        20

<210> SEQ ID NO 74
<211> LENGTH: 39
<212> TYPE: DNA
<213> ORGANISM: Artificial Sequence
<220> FEATURE:
<223> OTHER INFORMATION: PCR primer

<400> SEQUENCE: 74
tgtaaaacga cggccagtaa gaagaaaaat ggcaggagg                   39

<210> SEQ ID NO 75
<211> LENGTH: 20
<212> TYPE: DNA
<213> ORGANISM: Artificial Sequence
<220> FEATURE:
<223> OTHER INFORMATION: PCR primer

<400> SEQUENCE: 75
agcctcaagc agtcgttgac                                            20

<210> SEQ ID NO 76
<211> LENGTH: 38
<212> TYPE: DNA
<213> ORGANISM: Artificial Sequence
<220> FEATURE:
<223> OTHER INFORMATION: PCR primer

<400> SEQUENCE: 76
tgtaaaacga cggccagtgg aggggagcaa atctcttt                        38

<210> SEQ ID NO 77
<211> LENGTH: 20
<212> TYPE: DNA
<213> ORGANISM: Artificial Sequence
<220> FEATURE:
<223> OTHER INFORMATION: PCR primer

<400> SEQUENCE: 77
actcgctccc tagggtttgt                                            20

<210> SEQ ID NO 78
<211> LENGTH: 38
<212> TYPE: DNA
<213> ORGANISM: Artificial Sequence
<220> FEATURE:
<223> OTHER INFORMATION: PCR primer

<400> SEQUENCE: 78
tgtaaaacga cggccagtcc cccaaatcca agaagatt                        38

<210> SEQ ID NO 79
<211> LENGTH: 20
<212> TYPE: DNA
<213> ORGANISM: Artificial Sequence
<220> FEATURE:
<223> OTHER INFORMATION: PCR primer

<400> SEQUENCE: 79
tgtgaacatc aggaggtgga                                            20

<210> SEQ ID NO 80
<211> LENGTH: 38
<212> TYPE: DNA
<213> ORGANISM: Artificial Sequence
<220> FEATURE:
<223> OTHER INFORMATION: PCR primer

<400> SEQUENCE: 80
tgtaaaacga cggccagtgt gaatggtggt cgtcttca                        38

<210> SEQ ID NO 81
<211> LENGTH: 20
<212> TYPE: DNA
<213> ORGANISM: Artificial Sequence
<220> FEATURE:
<223> OTHER INFORMATION: PCR primer

<400> SEQUENCE: 81
aaccatgcgg tggttaggta                                            20

<210> SEQ ID NO 82

<210> SEQ ID NO 82
<211> LENGTH: 38
<212> TYPE: DNA
<213> ORGANISM: Artificial Sequence
<220> FEATURE:
<223> OTHER INFORMATION: PCR primer

<400> SEQUENCE: 82
tgtaaaacga cggccagtcg tcatcatcat catcacca         38

<210> SEQ ID NO 83
<211> LENGTH: 20
<212> TYPE: DNA
<213> ORGANISM: Artificial Sequence
<220> FEATURE:
<223> OTHER INFORMATION: PCR primer

<400> SEQUENCE: 83
tgaatggaat catgcagagg         20

<210> SEQ ID NO 84
<211> LENGTH: 38
<212> TYPE: DNA
<213> ORGANISM: Artificial Sequence
<220> FEATURE:
<223> OTHER INFORMATION: PCR primer

<400> SEQUENCE: 84
tgtaaaacga cggccagtaa cgggtggtct tgtgattg         38

<210> SEQ ID NO 85
<211> LENGTH: 20
<212> TYPE: DNA
<213> ORGANISM: Artificial Sequence
<220> FEATURE:
<223> OTHER INFORMATION: PCR primer

<400> SEQUENCE: 85
ttttcgatca tgccatttga         20

<210> SEQ ID NO 86
<211> LENGTH: 38
<212> TYPE: DNA
<213> ORGANISM: Artificial Sequence
<220> FEATURE:
<223> OTHER INFORMATION: PCR primer

<400> SEQUENCE: 86
tgtaaaacga cggccagttt tgcaccaatg ggtagttc         38

<210> SEQ ID NO 87
<211> LENGTH: 20
<212> TYPE: DNA
<213> ORGANISM: Artificial Sequence
<220> FEATURE:
<223> OTHER INFORMATION: PCR primer

<400> SEQUENCE: 87
agcatttgca gtgctagggt         20

<210> SEQ ID NO 88
<211> LENGTH: 38
<212> TYPE: DNA
<213> ORGANISM: Artificial Sequence
<220> FEATURE:
<223> OTHER INFORMATION: PCR primer

<400> SEQUENCE: 88
tgtaaaacga cggccagtac agcaacagca acaacagc        38

<210> SEQ ID NO 89
<211> LENGTH: 20
<212> TYPE: DNA
<213> ORGANISM: Artificial Sequence
<220> FEATURE:
<223> OTHER INFORMATION: PCR primer

<400> SEQUENCE: 89
gaagctattt gggcgagctt        20

<210> SEQ ID NO 90
<211> LENGTH: 39
<212> TYPE: DNA
<213> ORGANISM: Artificial Sequence
<220> FEATURE:
<223> OTHER INFORMATION: PCR primer

<400> SEQUENCE: 90
tgtaaaacga cggccagtca ttatggcgtc atttgatcc        39

<210> SEQ ID NO 91
<211> LENGTH: 20
<212> TYPE: DNA
<213> ORGANISM: Artificial Sequence
<220> FEATURE:
<223> OTHER INFORMATION: PCR primer

<400> SEQUENCE: 91
gacaccgttt tcggtgattt        20

<210> SEQ ID NO 92
<211> LENGTH: 38
<212> TYPE: DNA
<213> ORGANISM: Artificial Sequence
<220> FEATURE:
<223> OTHER INFORMATION: PCR primer

<400> SEQUENCE: 92
tgtaaaacga cggccagttg aaacacgttc ccacaaag        38

<210> SEQ ID NO 93
<211> LENGTH: 22
<212> TYPE: DNA
<213> ORGANISM: Artificial Sequence
<220> FEATURE:
<223> OTHER INFORMATION: PCR primer

<400> SEQUENCE: 93
gaactatcac ctttcccttg ga        22

<210> SEQ ID NO 94
<211> LENGTH: 38
<212> TYPE: DNA
<213> ORGANISM: Artificial Sequence
<220> FEATURE:
<223> OTHER INFORMATION: PCR primer

<400> SEQUENCE: 94
tgtaaaacga cggccagtat tccggtcgtc agaatcag        38

<210> SEQ ID NO 95
<211> LENGTH: 20
<212> TYPE: DNA

-continued

```
<213> ORGANISM: Artificial Sequence
<220> FEATURE:
<223> OTHER INFORMATION: PCR primer

<400> SEQUENCE: 95
agcaggtgga agaattggtg                                                    20

<210> SEQ ID NO 96
<211> LENGTH: 40
<212> TYPE: DNA
<213> ORGANISM: Artificial Sequence
<220> FEATURE:
<223> OTHER INFORMATION: PCR primer

<400> SEQUENCE: 96
tgtaaaacga cggccagtcg cgtgtgttta gagagagaga                              40

<210> SEQ ID NO 97
<211> LENGTH: 20
<212> TYPE: DNA
<213> ORGANISM: Artificial Sequence
<220> FEATURE:
<223> OTHER INFORMATION: PCR primer

<400> SEQUENCE: 97
ttcttcttgg acttgcacca                                                    20

<210> SEQ ID NO 98
<211> LENGTH: 38
<212> TYPE: DNA
<213> ORGANISM: Artificial Sequence
<220> FEATURE:
<223> OTHER INFORMATION: PCR primer

<400> SEQUENCE: 98
tgtaaaacga cggccagtta aggatgaccc aaccaagc                                38

<210> SEQ ID NO 99
<211> LENGTH: 20
<212> TYPE: DNA
<213> ORGANISM: Artificial Sequence
<220> FEATURE:
<223> OTHER INFORMATION: PCR primer

<400> SEQUENCE: 99
ttcttagctt gaagggcacg                                                    20

<210> SEQ ID NO 100
<211> LENGTH: 38
<212> TYPE: DNA
<213> ORGANISM: Artificial Sequence
<220> FEATURE:
<223> OTHER INFORMATION: PCR primer

<400> SEQUENCE: 100
tgtaaaacga cggccagtcc attcctggtt gtcagtcc                                38

<210> SEQ ID NO 101
<211> LENGTH: 20
<212> TYPE: DNA
<213> ORGANISM: Artificial Sequence
<220> FEATURE:
<223> OTHER INFORMATION: PCR primer

<400> SEQUENCE: 101
ttgtgtggaa agaataggaa                                                    20
```

<210> SEQ ID NO 102
<211> LENGTH: 38
<212> TYPE: DNA
<213> ORGANISM: Artificial Sequence
<220> FEATURE:
<223> OTHER INFORMATION: PCR primer

<400> SEQUENCE: 102
tgtaaaacga cggccagtgg acagagcaaa agaacaat                    38

<210> SEQ ID NO 103
<211> LENGTH: 20
<212> TYPE: DNA
<213> ORGANISM: Artificial Sequence
<220> FEATURE:
<223> OTHER INFORMATION: PCR primer

<400> SEQUENCE: 103 gccatcttttt cttttgcttc                                       20

<210> SEQ ID NO 104
<211> LENGTH: 42
<212> TYPE: DNA
<213> ORGANISM: Artificial Sequence
<220> FEATURE:
<223> OTHER INFORMATION: PCR primer

<400> SEQUENCE: 104
tgtaaaacga cggccagtta aaaaacggaa agagttggtt ag                42

<210> SEQ ID NO 105
<211> LENGTH: 20
<212> TYPE: DNA
<213> ORGANISM: Artificial Sequence
<220> FEATURE:
<223> OTHER INFORMATION: PCR primer

<400> SEQUENCE: 105
ttgaaaattg ggaacggaaa                                        20

<210> SEQ ID NO 106
<211> LENGTH: 38
<212> TYPE: DNA
<213> ORGANISM: Artificial Sequence
<220> FEATURE:
<223> OTHER INFORMATION: PCR primer

<400> SEQUENCE: 106
tgtaaaacga cggccagtgt tggagtggga aattgcag                    38

<210> SEQ ID NO 107
<211> LENGTH: 21
<212> TYPE: DNA
<213> ORGANISM: Artificial Sequence
<220> FEATURE:
<223> OTHER INFORMATION: PCR primer

<400> SEQUENCE: 107
ggaagaggga gaaggagatg a                                      21

<210> SEQ ID NO 108
<211> LENGTH: 38
<212> TYPE: DNA
<213> ORGANISM: Artificial Sequence
<220> FEATURE:

<223> OTHER INFORMATION: PCR primer

<400> SEQUENCE: 108
tgtaaaacga cggccagttc aatggcgaac actttcac                              38

<210> SEQ ID NO 109
<211> LENGTH: 20
<212> TYPE: DNA
<213> ORGANISM: Artificial Sequence
<220> FEATURE:
<223> OTHER INFORMATION: PCR primer

<400> SEQUENCE: 109
tgcagccagg tgaataacaa                                                  20

<210> SEQ ID NO 110
<211> LENGTH: 38
<212> TYPE: DNA
<213> ORGANISM: Artificial Sequence
<220> FEATURE:
<223> OTHER INFORMATION: PCR primer

<400> SEQUENCE: 110
tgtaaaacga cggccagtca tctgatggtg gtgattgg                              38

<210> SEQ ID NO 111
<211> LENGTH: 22
<212> TYPE: DNA
<213> ORGANISM: Artificial Sequence
<220> FEATURE:
<223> OTHER INFORMATION: PCR primer

<400> SEQUENCE: 111
ccaatatgtc actccttgct ga                                               22

<210> SEQ ID NO 112
<211> LENGTH: 38
<212> TYPE: DNA
<213> ORGANISM: Artificial Sequence
<220> FEATURE:
<223> OTHER INFORMATION: PCR primer

<400> SEQUENCE: 112
tgtaaaacga cggccagtag gtggcaagcc taactgaa                              38

<210> SEQ ID NO 113
<211> LENGTH: 20
<212> TYPE: DNA
<213> ORGANISM: Artificial Sequence
<220> FEATURE:
<223> OTHER INFORMATION: PCR primer

<400> SEQUENCE: 113
tcctcaacca accacttcct                                                  20

<210> SEQ ID NO 114
<211> LENGTH: 38
<212> TYPE: DNA
<213> ORGANISM: Artificial Sequence
<220> FEATURE:
<223> OTHER INFORMATION: PCR primer

<400> SEQUENCE: 114
tgtaaaacga cggccagtcc ccattgacgc attcttac                              38

```
<210> SEQ ID NO 115
<211> LENGTH: 20
<212> TYPE: DNA
<213> ORGANISM: Artificial Sequence
<220> FEATURE:
<223> OTHER INFORMATION: PCR primer

<400> SEQUENCE: 115
gtggtggaga aggagcaatc                                               20

<210> SEQ ID NO 116
<211> LENGTH: 38
<212> TYPE: DNA
<213> ORGANISM: Artificial Sequence
<220> FEATURE:
<223> OTHER INFORMATION: PCR primer

<400> SEQUENCE: 116
tgtaaaacga cggccagtca atcctccacc atcacctt                           38

<210> SEQ ID NO 117
<211> LENGTH: 20
<212> TYPE: DNA
<213> ORGANISM: Artificial Sequence
<220> FEATURE:
<223> OTHER INFORMATION: PCR primer

<400> SEQUENCE: 117
cgttaccgtc actgtcgttg                                               20

<210> SEQ ID NO 118
<211> LENGTH: 38
<212> TYPE: DNA
<213> ORGANISM: Artificial Sequence
<220> FEATURE:
<223> OTHER INFORMATION: PCR primer

<400> SEQUENCE: 118
tgtaaaacga cggccagtca aacctgattc cgacccta                           38

<210> SEQ ID NO 119
<211> LENGTH: 20
<212> TYPE: DNA
<213> ORGANISM: Artificial Sequence
<220> FEATURE:
<223> OTHER INFORMATION: PCR primer

<400> SEQUENCE: 119
ctgcaccccc taaaaatcaa                                               20

<210> SEQ ID NO 120
<211> LENGTH: 38
<212> TYPE: DNA
<213> ORGANISM: Artificial Sequence
<220> FEATURE:
<223> OTHER INFORMATION: PCR primer

<400> SEQUENCE: 120
tgtaaaacga cggccagtct cattgccctt ctcacaca                           38

<210> SEQ ID NO 121
<211> LENGTH: 20
<212> TYPE: DNA
<213> ORGANISM: Artificial Sequence
<220> FEATURE:
<223> OTHER INFORMATION: PCR primer
```

<400> SEQUENCE: 121
tgactcttgc atgcagttcc					20

<210> SEQ ID NO 122
<211> LENGTH: 38
<212> TYPE: DNA
<213> ORGANISM: Artificial Sequence
<220> FEATURE:
<223> OTHER INFORMATION: PCR primer

<400> SEQUENCE: 122
tgtaaaacga cggccagttg ctcctcctct gcttcttc					38

<210> SEQ ID NO 123
<211> LENGTH: 20
<212> TYPE: DNA
<213> ORGANISM: Artificial Sequence
<220> FEATURE:
<223> OTHER INFORMATION: PCR primer

<400> SEQUENCE: 123
gccccctcac gttttattt					20

<210> SEQ ID NO 124
<211> LENGTH: 40
<212> TYPE: DNA
<213> ORGANISM: Artificial Sequence
<220> FEATURE:
<223> OTHER INFORMATION: PCR primer

<400> SEQUENCE: 124
tgtaaaacga cggccagtca attttggttg gttatgctca					40

<210> SEQ ID NO 125
<211> LENGTH: 21
<212> TYPE: DNA
<213> ORGANISM: Artificial Sequence
<220> FEATURE:
<223> OTHER INFORMATION: PCR primer

<400> SEQUENCE: 125
tccctcttac acctctcatg c					21

<210> SEQ ID NO 126
<211> LENGTH: 38
<212> TYPE: DNA
<213> ORGANISM: Artificial Sequence
<220> FEATURE:
<223> OTHER INFORMATION: PCR primer

<400> SEQUENCE: 126
tgtaaaacga cggccagttc tccttggaat tgaacctg					38

<210> SEQ ID NO 127
<211> LENGTH: 20
<212> TYPE: DNA
<213> ORGANISM: Artificial Sequence
<220> FEATURE:
<223> OTHER INFORMATION: PCR primer

<400> SEQUENCE: 127
cagaaatttc catgccaaaa					20

<210> SEQ ID NO 128
<211> LENGTH: 38

```
<212> TYPE: DNA
<213> ORGANISM: Artificial Sequence
<220> FEATURE:
<223> OTHER INFORMATION: PCR primer

<400> SEQUENCE: 128
tgtaaaacga cggccagtag ttgtggattg ggtgaagc                              38

<210> SEQ ID NO 129
<211> LENGTH: 20
<212> TYPE: DNA
<213> ORGANISM: Artificial Sequence
<220> FEATURE:
<223> OTHER INFORMATION: PCR primer

<400> SEQUENCE: 129
aaacatcggc ttcggaagta                                                  20

<210> SEQ ID NO 130
<211> LENGTH: 42
<212> TYPE: DNA
<213> ORGANISM: Artificial Sequence
<220> FEATURE:
<223> OTHER INFORMATION: PCR primer

<400> SEQUENCE: 130
tgtaaaacga cggccagttt tttgagcagt gtaatggtgt aa                         42

<210> SEQ ID NO 131
<211> LENGTH: 20
<212> TYPE: DNA
<213> ORGANISM: Artificial Sequence
<220> FEATURE:
<223> OTHER INFORMATION: PCR primer

<400> SEQUENCE: 131
ccatggcgtc tacccattat                                                  20

<210> SEQ ID NO 132
<211> LENGTH: 39
<212> TYPE: DNA
<213> ORGANISM: Artificial Sequence
<220> FEATURE:
<223> OTHER INFORMATION: PCR primer

<400> SEQUENCE: 132
tgtaaaacga cggccagttt tttcacagca ctgaagagg                             39

<210> SEQ ID NO 133
<211> LENGTH: 20
<212> TYPE: DNA
<213> ORGANISM: Artificial Sequence
<220> FEATURE:
<223> OTHER INFORMATION: PCR primer

<400> SEQUENCE: 133
gacatttgca gaccaccatt                                                  20

<210> SEQ ID NO 134
<211> LENGTH: 38
<212> TYPE: DNA
<213> ORGANISM: Artificial Sequence
<220> FEATURE:
<223> OTHER INFORMATION: PCR primer

<400> SEQUENCE: 134
```

```
tgtaaaacga cggccagtat tcgcagtgag ctgatcct                            38

<210> SEQ ID NO 135
<211> LENGTH: 20
<212> TYPE: DNA
<213> ORGANISM: Artificial Sequence
<220> FEATURE:
<223> OTHER INFORMATION: PCR primer

<400> SEQUENCE: 135
catgtttccg gttctggttt                                               20

<210> SEQ ID NO 136
<211> LENGTH: 38
<212> TYPE: DNA
<213> ORGANISM: Artificial Sequence
<220> FEATURE:
<223> OTHER INFORMATION: PCR primer

<400> SEQUENCE: 136
tgtaaaacga cggccagtag tccctgcaaa atcccttc                           38

<210> SEQ ID NO 137
<211> LENGTH: 20
<212> TYPE: DNA
<213> ORGANISM: Artificial Sequence
<220> FEATURE:
<223> OTHER INFORMATION: PCR primer

<400> SEQUENCE: 137
tggaaacagc aaaaccacct                                               20

<210> SEQ ID NO 138
<211> LENGTH: 38
<212> TYPE: DNA
<213> ORGANISM: Artificial Sequence
<220> FEATURE:
<223> OTHER INFORMATION: PCR primer

<400> SEQUENCE: 138
tgtaaaacga cggccagttc cgaaatctga aaccaacc                           38

<210> SEQ ID NO 139
<211> LENGTH: 23
<212> TYPE: DNA
<213> ORGANISM: Artificial Sequence
<220> FEATURE:
<223> OTHER INFORMATION: PCR primer

<400> SEQUENCE: 139
tccacaaatg tctaaaacca aca                                           23

<210> SEQ ID NO 140
<211> LENGTH: 39
<212> TYPE: DNA
<213> ORGANISM: Artificial Sequence
<220> FEATURE:
<223> OTHER INFORMATION: PCR primer

<400> SEQUENCE: 140
tgtaaaacga cggccagttt ttgtgtaggg atgcaaagg                          39

<210> SEQ ID NO 141
<211> LENGTH: 20
<212> TYPE: DNA
<213> ORGANISM: Artificial Sequence
```

<220> FEATURE:
<223> OTHER INFORMATION: PCR primer

<400> SEQUENCE: 141
gtggggttgg tgagagtgtt                                              20

<210> SEQ ID NO 142
<211> LENGTH: 38
<212> TYPE: DNA
<213> ORGANISM: Artificial Sequence
<220> FEATURE:
<223> OTHER INFORMATION: PCR primer

<400> SEQUENCE: 142
tgtaaaacga cggccagtat cgtccccact gtgtcttc                          38

<210> SEQ ID NO 143
<211> LENGTH: 21
<212> TYPE: DNA
<213> ORGANISM: Artificial Sequence
<220> FEATURE:
<223> OTHER INFORMATION: PCR primer

<400> SEQUENCE: 143
cagcaaaatc caatccttca g                                            21

<210> SEQ ID NO 144
<211> LENGTH: 40
<212> TYPE: DNA
<213> ORGANISM: Artificial Sequence
<220> FEATURE:
<223> OTHER INFORMATION: PCR primer

<400> SEQUENCE: 144
tgtaaaacga cggccagttt ctcatcgtca ctccaaagaa                        40

<210> SEQ ID NO 145
<211> LENGTH: 22
<212> TYPE: DNA
<213> ORGANISM: Artificial Sequence
<220> FEATURE:
<223> OTHER INFORMATION: PCR primer

<400> SEQUENCE: 145
tgcttgaact ttgagtcttg ga                                           22

<210> SEQ ID NO 146
<211> LENGTH: 40
<212> TYPE: DNA
<213> ORGANISM: Artificial Sequence
<220> FEATURE:
<223> OTHER INFORMATION: PCR primer

<400> SEQUENCE: 146
tgtaaaacga cggccagttc tctccatcat caccatcatc                        40

<210> SEQ ID NO 147
<211> LENGTH: 21
<212> TYPE: DNA
<213> ORGANISM: Artificial Sequence
<220> FEATURE:
<223> OTHER INFORMATION: PCR primer

<400> SEQUENCE: 147
gacagaacct ttgccgattt t                                            21

<210> SEQ ID NO 148
<211> LENGTH: 40
<212> TYPE: DNA
<213> ORGANISM: Artificial Sequence
<220> FEATURE:
<223> OTHER INFORMATION: PCR primer

<400> SEQUENCE: 148
tgtaaaacga cggccagtgc accagcagag tagaagtagc                    40

<210> SEQ ID NO 149
<211> LENGTH: 22
<212> TYPE: DNA
<213> ORGANISM: Artificial Sequence
<220> FEATURE:
<223> OTHER INFORMATION: PCR primer

<400> SEQUENCE: 149
aactcgcagg tgttttatcg tt                                       22

<210> SEQ ID NO 150
<211> LENGTH: 40
<212> TYPE: DNA
<213> ORGANISM: Artificial Sequence
<220> FEATURE:
<223> OTHER INFORMATION: PCR primer

<400> SEQUENCE: 150
tgtaaaacga cggccagtaa tctcaaccgc aacaaactct                    40

<210> SEQ ID NO 151
<211> LENGTH: 21
<212> TYPE: DNA
<213> ORGANISM: Artificial Sequence
<220> FEATURE:
<223> OTHER INFORMATION: PCR primer

<400> SEQUENCE: 151
catggagaag cagaactgga g                                        21

<210> SEQ ID NO 152
<211> LENGTH: 40
<212> TYPE: DNA
<213> ORGANISM: Artificial Sequence
<220> FEATURE:
<223> OTHER INFORMATION: PCR primer

<400> SEQUENCE: 152
tgtaaaacga cggccagtcc aaacaacaac caactctctg                    40

<210> SEQ ID NO 153
<211> LENGTH: 22
<212> TYPE: DNA
<213> ORGANISM: Artificial Sequence
<220> FEATURE:
<223> OTHER INFORMATION: PCR primer

<400> SEQUENCE: 153
ccgtctttac atgaatccac aa                                       22

<210> SEQ ID NO 154
<211> LENGTH: 40
<212> TYPE: DNA
<213> ORGANISM: Artificial Sequence
<220> FEATURE:
<223> OTHER INFORMATION: PCR primer

```
<400> SEQUENCE: 154
tgtaaaacga cggccagtca cagtcatcat ccttgctctc                          40

<210> SEQ ID NO 155
<211> LENGTH: 21
<212> TYPE: DNA
<213> ORGANISM: Artificial Sequence
<220> FEATURE:
<223> OTHER INFORMATION: PCR primer

<400> SEQUENCE: 155
ggttagggtt ttgggtttga a                                              21

<210> SEQ ID NO 156
<211> LENGTH: 40
<212> TYPE: DNA
<213> ORGANISM: Artificial Sequence
<220> FEATURE:
<223> OTHER INFORMATION: PCR primer

<400> SEQUENCE: 156
tgtaaaacga cggccagtgt cgaaatggtt gcttctcttt                          40

<210> SEQ ID NO 157
<211> LENGTH: 22
<212> TYPE: DNA
<213> ORGANISM: Artificial Sequence
<220> FEATURE:
<223> OTHER INFORMATION: PCR primer

<400> SEQUENCE: 157
catgtacggg gattgttgtt tt                                             22

<210> SEQ ID NO 158
<211> LENGTH: 40
<212> TYPE: DNA
<213> ORGANISM: Artificial Sequence
<220> FEATURE:
<223> OTHER INFORMATION: PCR primer

<400> SEQUENCE: 158
tgtaaaacga cggccagtac ccttgtgggt tcttcttctt                          40

<210> SEQ ID NO 159
<211> LENGTH: 22
<212> TYPE: DNA
<213> ORGANISM: Artificial Sequence
<220> FEATURE:
<223> OTHER INFORMATION: PCR primer

<400> SEQUENCE: 159
tgctgctgtg ccgtagtaga ta                                             22

<210> SEQ ID NO 160
<211> LENGTH: 40
<212> TYPE: DNA
<213> ORGANISM: Artificial Sequence
<220> FEATURE:
<223> OTHER INFORMATION: PCR primer

<400> SEQUENCE: 160
tgtaaaacga cggccagtgc cacaattttc tcatcatcac                          40

<210> SEQ ID NO 161
```

```
<210> SEQ ID NO 161
<211> LENGTH: 22
<212> TYPE: DNA
<213> ORGANISM: Artificial Sequence
<220> FEATURE:
<223> OTHER INFORMATION: PCR primer

<400> SEQUENCE: 161
agcactttgt tcatcgttct ga                                             22

<210> SEQ ID NO 162
<211> LENGTH: 40
<212> TYPE: DNA
<213> ORGANISM: Artificial Sequence
<220> FEATURE:
<223> OTHER INFORMATION: PCR primer

<400> SEQUENCE: 162
tgtaaaacga cggccagtaa gagagtatcg tggagccgta                          40

<210> SEQ ID NO 163
<211> LENGTH: 22
<212> TYPE: DNA
<213> ORGANISM: Artificial Sequence
<220> FEATURE:
<223> OTHER INFORMATION: PCR primer

<400> SEQUENCE: 163
cttgagaaag cgaaggtttt gt                                             22

<210> SEQ ID NO 164
<211> LENGTH: 40
<212> TYPE: DNA
<213> ORGANISM: Artificial Sequence
<220> FEATURE:
<223> OTHER INFORMATION: PCR primer

<400> SEQUENCE: 164
tgtaaaacga cggccagtct cgttcattag cagttgcagt                          40

<210> SEQ ID NO 165
<211> LENGTH: 22
<212> TYPE: DNA
<213> ORGANISM: Artificial Sequence
<220> FEATURE:
<223> OTHER INFORMATION: PCR primer

<400> SEQUENCE: 165
cacatcttcg tcatcatctt ca                                             22

<210> SEQ ID NO 166
<211> LENGTH: 40
<212> TYPE: DNA
<213> ORGANISM: Artificial Sequence
<220> FEATURE:
<223> OTHER INFORMATION: PCR primer

<400> SEQUENCE: 166
tgtaaaacga cggccagtta tatgcttgtt gaggccactg                          40

<210> SEQ ID NO 167
<211> LENGTH: 22
<212> TYPE: DNA
<213> ORGANISM: Artificial Sequence
<220> FEATURE:
<223> OTHER INFORMATION: PCR primer

<400> SEQUENCE: 167
```

```
tgcttgaact ttgagtcttg ga                                              22
```

<210> SEQ ID NO 168
<211> LENGTH: 40
<212> TYPE: DNA
<213> ORGANISM: Artificial Sequence
<220> FEATURE:
<223> OTHER INFORMATION: PCR primer

<400> SEQUENCE: 168

```
tgtaaaacga cggccagttc tctccatcat caccatcatc                           40
```

<210> SEQ ID NO 169
<211> LENGTH: 22
<212> TYPE: DNA
<213> ORGANISM: Artificial Sequence
<220> FEATURE:
<223> OTHER INFORMATION: PCR primer

<400> SEQUENCE: 169

```
gagtatcgga agagggttgt tg                                              22
```

<210> SEQ ID NO 170
<211> LENGTH: 40
<212> TYPE: DNA
<213> ORGANISM: Artificial Sequence
<220> FEATURE:
<223> OTHER INFORMATION: PCR primer

<400> SEQUENCE: 170

```
tgtaaaacga cggccagtaa ttggaaccta tcgttgtcgt                           40
```

<210> SEQ ID NO 171
<211> LENGTH: 22
<212> TYPE: DNA
<213> ORGANISM: Artificial Sequence
<220> FEATURE:
<223> OTHER INFORMATION: PCR primer

<400> SEQUENCE: 171

```
gcataggaac cagctctaat gg                                              22
```

<210> SEQ ID NO 172
<211> LENGTH: 40
<212> TYPE: DNA
<213> ORGANISM: Artificial Sequence
<220> FEATURE:
<223> OTHER INFORMATION: PCR primer

<400> SEQUENCE: 172

```
tgtaaaacga cggccagtac gagggattgt tgtttgagat                           40
```

<210> SEQ ID NO 173
<211> LENGTH: 22
<212> TYPE: DNA
<213> ORGANISM: Artificial Sequence
<220> FEATURE:
<223> OTHER INFORMATION: PCR primer

<400> SEQUENCE: 173

```
caactgtgaa cgcaaatctc tc                                              22
```

<210> SEQ ID NO 174
<211> LENGTH: 40
<212> TYPE: DNA

<213> ORGANISM: Artificial Sequence
<220> FEATURE:
<223> OTHER INFORMATION: PCR primer

<400> SEQUENCE: 174
tgtaaaacga cggccagtaa cgacgctctt cgactacttc          40

<210> SEQ ID NO 175
<211> LENGTH: 22
<212> TYPE: DNA
<213> ORGANISM: Artificial Sequence
<220> FEATURE:
<223> OTHER INFORMATION: PCR primer

<400> SEQUENCE: 175
ggtgctttca ttacatccca ta          22

<210> SEQ ID NO 176
<211> LENGTH: 40
<212> TYPE: DNA
<213> ORGANISM: Artificial Sequence
<220> FEATURE:
<223> OTHER INFORMATION: PCR primer

<400> SEQUENCE: 176
tgtaaaacga cggccagtac gaggcacaca ctctctctct          40

<210> SEQ ID NO 177
<211> LENGTH: 21
<212> TYPE: DNA
<213> ORGANISM: Artificial Sequence
<220> FEATURE:
<223> OTHER INFORMATION: PCR primer

<400> SEQUENCE: 177
gtgttcgtcg catatcacct c          21

<210> SEQ ID NO 178
<211> LENGTH: 40
<212> TYPE: DNA
<213> ORGANISM: Artificial Sequence
<220> FEATURE:
<223> OTHER INFORMATION: PCR primer

<400> SEQUENCE: 178
tgtaaaacga cggccagtgc atttccctct ctttccataa          40

<210> SEQ ID NO 179
<211> LENGTH: 22
<212> TYPE: DNA
<213> ORGANISM: Artificial Sequence
<220> FEATURE:
<223> OTHER INFORMATION: PCR primer

<400> SEQUENCE: 179
caatgcaaga aaccctaaaa gc          22

<210> SEQ ID NO 180
<211> LENGTH: 41
<212> TYPE: DNA
<213> ORGANISM: Artificial Sequence
<220> FEATURE:
<223> OTHER INFORMATION: PCR primer

<400> SEQUENCE: 180
tgtaaaacga cggccagtcc actcaacctc atctctctac c          41

<210> SEQ ID NO 181
<211> LENGTH: 22
<212> TYPE: DNA
<213> ORGANISM: Artificial Sequence
<220> FEATURE:
<223> OTHER INFORMATION: PCR primer

<400> SEQUENCE: 181
ttttcgatta ggtcgtggat ct                                              22

<210> SEQ ID NO 182
<211> LENGTH: 40
<212> TYPE: DNA
<213> ORGANISM: Artificial Sequence
<220> FEATURE:
<223> OTHER INFORMATION: PCR primer

<400> SEQUENCE: 182
tgtaaaacga cggccagtac gcacatttcc attctcattc                           40

<210> SEQ ID NO 183
<211> LENGTH: 22
<212> TYPE: DNA
<213> ORGANISM: Artificial Sequence
<220> FEATURE:
<223> OTHER INFORMATION: PCR primer

<400> SEQUENCE: 183
gcttgttgtt gttgttgatg ct                                              22

<210> SEQ ID NO 184
<211> LENGTH: 40
<212> TYPE: DNA
<213> ORGANISM: Artificial Sequence
<220> FEATURE:
<223> OTHER INFORMATION: PCR primer

<400> SEQUENCE: 184
tgtaaaacga cggccagttc tgtaagaggg tcactgcgta                           40

<210> SEQ ID NO 185
<211> LENGTH: 22
<212> TYPE: DNA
<213> ORGANISM: Artificial Sequence
<220> FEATURE:
<223> OTHER INFORMATION: PCR primer

<400> SEQUENCE: 185
gcatatccat tccaagttca tc                                              22

<210> SEQ ID NO 186
<211> LENGTH: 40
<212> TYPE: DNA
<213> ORGANISM: Artificial Sequence
<220> FEATURE:
<223> OTHER INFORMATION: PCR primer

<400> SEQUENCE: 186
tgtaaaacga cggccagtac tttcttcctc attgctctgc                           40

<210> SEQ ID NO 187
<211> LENGTH: 20
<212> TYPE: DNA
<213> ORGANISM: Artificial Sequence
<220> FEATURE:

<223> OTHER INFORMATION: PCR primer

<400> SEQUENCE: 187
atcccattca aggaaacacc                                          20

<210> SEQ ID NO 188
<211> LENGTH: 38
<212> TYPE: DNA
<213> ORGANISM: Artificial Sequence
<220> FEATURE:
<223> OTHER INFORMATION: PCR primer

<400> SEQUENCE: 188
tgtaaaacga cggccagtgg aataatgctg gtggaagc                      38

<210> SEQ ID NO 189
<211> LENGTH: 22
<212> TYPE: DNA
<213> ORGANISM: Artificial Sequence
<220> FEATURE:
<223> OTHER INFORMATION: PCR primer

<400> SEQUENCE: 189
cgatgtttgt ttgagctagt ga                                       22

<210> SEQ ID NO 190
<211> LENGTH: 41
<212> TYPE: DNA
<213> ORGANISM: Artificial Sequence
<220> FEATURE:
<223> OTHER INFORMATION: PCR primer

<400> SEQUENCE: 190
tgtaaaacga cggccagtga gagagagaga gagcattgag c                  41

<210> SEQ ID NO 191
<211> LENGTH: 19
<212> TYPE: DNA
<213> ORGANISM: Artificial Sequence
<220> FEATURE:
<223> OTHER INFORMATION: PCR primer

<400> SEQUENCE: 191
gaacgggttt gcgatcttt                                           19

<210> SEQ ID NO 192
<211> LENGTH: 40
<212> TYPE: DNA
<213> ORGANISM: Artificial Sequence
<220> FEATURE:
<223> OTHER INFORMATION: PCR primer

<400> SEQUENCE: 192
tgtaaaacga cggccagtcc atgtctctca atcttcgtca                    40

<210> SEQ ID NO 193
<211> LENGTH: 22
<212> TYPE: DNA
<213> ORGANISM: Artificial Sequence
<220> FEATURE:
<223> OTHER INFORMATION: PCR primer

<400> SEQUENCE: 193
atctcctcgt gtattccttc ca                                       22

<210> SEQ ID NO 194
<211> LENGTH: 40
<212> TYPE: DNA
<213> ORGANISM: Artificial Sequence
<220> FEATURE:
<223> OTHER INFORMATION: PCR primer

<400> SEQUENCE: 194
tgtaaaacga cggccagtac gttcctcctt catctcgtaa          40

<210> SEQ ID NO 195
<211> LENGTH: 22
<212> TYPE: DNA
<213> ORGANISM: Artificial Sequence
<220> FEATURE:
<223> OTHER INFORMATION: PCR primer

<400> SEQUENCE: 195
ttcaaggatc tggtgatgat ga                              22

<210> SEQ ID NO 196
<211> LENGTH: 40
<212> TYPE: DNA
<213> ORGANISM: Artificial Sequence
<220> FEATURE:
<223> OTHER INFORMATION: PCR primer

<400> SEQUENCE: 196
tgtaaaacga cggccagtga ggaagaggaa gaggaggaag          40

<210> SEQ ID NO 197
<211> LENGTH: 22
<212> TYPE: DNA
<213> ORGANISM: Artificial Sequence
<220> FEATURE:
<223> OTHER INFORMATION: PCR primer

<400> SEQUENCE: 197
tgttggtaat gttcaagctc ca                              22

<210> SEQ ID NO 198
<211> LENGTH: 40
<212> TYPE: DNA
<213> ORGANISM: Artificial Sequence
<220> FEATURE:
<223> OTHER INFORMATION: PCR primer

<400> SEQUENCE: 198
tgtaaaacga cggccagtca ccactatctc ttccctcacc          40

<210> SEQ ID NO 199
<211> LENGTH: 21
<212> TYPE: DNA
<213> ORGANISM: Artificial Sequence
<220> FEATURE:
<223> OTHER INFORMATION: PCR primer

<400> SEQUENCE: 199
agaattgaga catggcagag g                               21

<210> SEQ ID NO 200
<211> LENGTH: 40
<212> TYPE: DNA
<213> ORGANISM: Artificial Sequence
<220> FEATURE:
<223> OTHER INFORMATION: PCR primer

```
<400> SEQUENCE: 200
tgtaaaacga cggccagtgc gctcatcatc ttcatctaaa                              40

<210> SEQ ID NO 201
<211> LENGTH: 22
<212> TYPE: DNA
<213> ORGANISM: Artificial Sequence
<220> FEATURE:
<223> OTHER INFORMATION: PCR primer

<400> SEQUENCE: 201
ttctcgaaat cttctgctct cg                                                 22

<210> SEQ ID NO 202
<211> LENGTH: 44
<212> TYPE: DNA
<213> ORGANISM: Artificial Sequence
<220> FEATURE:
<223> OTHER INFORMATION: PCR primer

<400> SEQUENCE: 202
tgtaaaacga cggccagtgt ctctctctat tctcttccct tttc                         44

<210> SEQ ID NO 203
<211> LENGTH: 22
<212> TYPE: DNA
<213> ORGANISM: Artificial Sequence
<220> FEATURE:
<223> OTHER INFORMATION: PCR primer

<400> SEQUENCE: 203
gcagccttca aatctccata ac                                                 22

<210> SEQ ID NO 204
<211> LENGTH: 40
<212> TYPE: DNA
<213> ORGANISM: Artificial Sequence
<220> FEATURE:
<223> OTHER INFORMATION: PCR primer

<400> SEQUENCE: 204
tgtaaaacga cggccagttc actctctcac caatcaccac                              40

<210> SEQ ID NO 205
<211> LENGTH: 20
<212> TYPE: DNA
<213> ORGANISM: Artificial Sequence
<220> FEATURE:
<223> OTHER INFORMATION: PCR primer

<400> SEQUENCE: 205
catgtttccg gttctggttt                                                    20

<210> SEQ ID NO 206
<211> LENGTH: 38
<212> TYPE: DNA
<213> ORGANISM: Artificial Sequence
<220> FEATURE:
<223> OTHER INFORMATION: PCR primer

<400> SEQUENCE: 206
tgtaaaacga cggccagtag tccctgcaaa atcccttc                                38

<210> SEQ ID NO 207
<211> LENGTH: 22
```

```
<212> TYPE: DNA
<213> ORGANISM: Artificial Sequence
<220> FEATURE:
<223> OTHER INFORMATION: PCR primer

<400> SEQUENCE: 207
ttgttgcagc aattaaggaa ga                                              22

<210> SEQ ID NO 208
<211> LENGTH: 38
<212> TYPE: DNA
<213> ORGANISM: Artificial Sequence
<220> FEATURE:
<223> OTHER INFORMATION: PCR primer

<400> SEQUENCE: 208
tgtaaaacga cggccagtat tgccattgcc tctctcat                             38

<210> SEQ ID NO 209
<211> LENGTH: 20
<212> TYPE: DNA
<213> ORGANISM: Artificial Sequence
<220> FEATURE:
<223> OTHER INFORMATION: PCR primer

<400> SEQUENCE: 209
acaaaaactc tcccggcttt                                                 20

<210> SEQ ID NO 210
<211> LENGTH: 41
<212> TYPE: DNA
<213> ORGANISM: Artificial Sequence
<220> FEATURE:
<223> OTHER INFORMATION: PCR primer

<400> SEQUENCE: 210
tgtaaaacga cggccagtca aaacaatcaa accaaagatt g                         41

<210> SEQ ID NO 211
<211> LENGTH: 20
<212> TYPE: DNA
<213> ORGANISM: Artificial Sequence
<220> FEATURE:
<223> OTHER INFORMATION: PCR primer

<400> SEQUENCE: 211
attcatcctt gctcgtttcg                                                 20

<210> SEQ ID NO 212
<211> LENGTH: 38
<212> TYPE: DNA
<213> ORGANISM: Artificial Sequence
<220> FEATURE:
<223> OTHER INFORMATION: PCR primer

<400> SEQUENCE: 212
tgtaaaacga cggccagtga tcaattcgtg cagaagca                             38

<210> SEQ ID NO 213
<211> LENGTH: 22
<212> TYPE: DNA
<213> ORGANISM: Artificial Sequence
<220> FEATURE:
<223> OTHER INFORMATION: PCR primer

<400> SEQUENCE: 213
```
aagggcaaaa ccgtaaaaga gt                                                   22

<210> SEQ ID NO 214
<211> LENGTH: 40
<212> TYPE: DNA
<213> ORGANISM: Artificial Sequence
<220> FEATURE:
<223> OTHER INFORMATION: PCR primer

<400> SEQUENCE: 214
tgtaaaacga cggccagtat caccccaaac cacatctatc                                40

<210> SEQ ID NO 215
<211> LENGTH: 22
<212> TYPE: DNA
<213> ORGANISM: Artificial Sequence
<220> FEATURE:
<223> OTHER INFORMATION: PCR primer

<400> SEQUENCE: 215
agcgagatag atttcaccga ag                                                   22

<210> SEQ ID NO 216
<211> LENGTH: 41
<212> TYPE: DNA
<213> ORGANISM: Artificial Sequence
<220> FEATURE:
<223> OTHER INFORMATION: PCR primer

<400> SEQUENCE: 216
tgtaaaacga cggccagttt catttcatag ttttccattg c                              41

<210> SEQ ID NO 217
<211> LENGTH: 22
<212> TYPE: DNA
<213> ORGANISM: Artificial Sequence
<220> FEATURE:
<223> OTHER INFORMATION: PCR primer

<400> SEQUENCE: 217
tgcaaacttc accgaataga tg                                                   22

<210> SEQ ID NO 218
<211> LENGTH: 40
<212> TYPE: DNA
<213> ORGANISM: Artificial Sequence
<220> FEATURE:
<223> OTHER INFORMATION: PCR primer

<400> SEQUENCE: 218
tgtaaaacga cggccagtct cctttgtaac gcaacagcag                                40

<210> SEQ ID NO 219
<211> LENGTH: 22
<212> TYPE: DNA
<213> ORGANISM: Artificial Sequence
<220> FEATURE:
<223> OTHER INFORMATION: PCR primer

<400> SEQUENCE: 219
catcatcctt catttccgat ct                                                   22

<210> SEQ ID NO 220
<211> LENGTH: 40
<212> TYPE: DNA
<213> ORGANISM: Artificial Sequence

```
<220> FEATURE:
<223> OTHER INFORMATION: PCR primer

<400> SEQUENCE: 220
tgtaaaacga cggccagttc tcacattcac attccattcc                              40

<210> SEQ ID NO 221
<211> LENGTH: 22
<212> TYPE: DNA
<213> ORGANISM: Artificial Sequence
<220> FEATURE:
<223> OTHER INFORMATION: PCR primer

<400> SEQUENCE: 221
ttgatgggta aaggagaagg tg                                                 22

<210> SEQ ID NO 222
<211> LENGTH: 40
<212> TYPE: DNA
<213> ORGANISM: Artificial Sequence
<220> FEATURE:
<223> OTHER INFORMATION: PCR primer

<400> SEQUENCE: 222
tgtaaaacga cggccagtat cacaagcctc aacagccata                              40

<210> SEQ ID NO 223
<211> LENGTH: 20
<212> TYPE: DNA
<213> ORGANISM: Artificial Sequence
<220> FEATURE:
<223> OTHER INFORMATION: PCR primer

<400> SEQUENCE: 223
acgcctctct ttccgatctt                                                    20

<210> SEQ ID NO 224
<211> LENGTH: 41
<212> TYPE: DNA
<213> ORGANISM: Artificial Sequence
<220> FEATURE:
<223> OTHER INFORMATION: PCR primer

<400> SEQUENCE: 224
tgtaaaacga cggccagttc actcacactc aacacacaac a                            41

<210> SEQ ID NO 225
<211> LENGTH: 22
<212> TYPE: DNA
<213> ORGANISM: Artificial Sequence
<220> FEATURE:
<223> OTHER INFORMATION: PCR primer

<400> SEQUENCE: 225
caccagcctc taagctcatt tt                                                 22

<210> SEQ ID NO 226
<211> LENGTH: 40
<212> TYPE: DNA
<213> ORGANISM: Artificial Sequence
<220> FEATURE:
<223> OTHER INFORMATION: PCR primer

<400> SEQUENCE: 226
tgtaaaacga cggccagtct ccattctcca tttcaatacc                              40
```

<210> SEQ ID NO 227
<211> LENGTH: 22
<212> TYPE: DNA
<213> ORGANISM: Artificial Sequence
<220> FEATURE:
<223> OTHER INFORMATION: PCR primer

<400> SEQUENCE: 227
gcacaagcag ccatattgat ag                                              22

<210> SEQ ID NO 228
<211> LENGTH: 40
<212> TYPE: DNA
<213> ORGANISM: Artificial Sequence
<220> FEATURE:
<223> OTHER INFORMATION: PCR primer

<400> SEQUENCE: 228
tgtaaaacga cggccagtta ctgtcccaat cttcacaacg                           40

<210> SEQ ID NO 229
<211> LENGTH: 22
<212> TYPE: DNA
<213> ORGANISM: Artificial Sequence
<220> FEATURE:
<223> OTHER INFORMATION: PCR primer

<400> SEQUENCE: 229
tgaaagttga aggatctggt ga                                              22

<210> SEQ ID NO 230
<211> LENGTH: 40
<212> TYPE: DNA
<213> ORGANISM: Artificial Sequence
<220> FEATURE:
<223> OTHER INFORMATION: PCR primer

<400> SEQUENCE: 230
tgtaaaacga cggccagtga ggaagaggaa gaggaggaag                           40

<210> SEQ ID NO 231
<211> LENGTH: 22
<212> TYPE: DNA
<213> ORGANISM: Artificial Sequence
<220> FEATURE:
<223> OTHER INFORMATION: PCR primer

<400> SEQUENCE: 231
tgggatactg attttctgct tc                                              22

<210> SEQ ID NO 232
<211> LENGTH: 40
<212> TYPE: DNA
<213> ORGANISM: Artificial Sequence
<220> FEATURE:
<223> OTHER INFORMATION: PCR primer

<400> SEQUENCE: 232
tgtaaaacga cggccagttc cgaaccctac ttccaaatta                           40

<210> SEQ ID NO 233
<211> LENGTH: 22
<212> TYPE: DNA
<213> ORGANISM: Artificial Sequence
<220> FEATURE:
<223> OTHER INFORMATION: PCR primer

<400> SEQUENCE: 233
ctgattcgag attgggattg at                                              22

<210> SEQ ID NO 234
<211> LENGTH: 44
<212> TYPE: DNA
<213> ORGANISM: Artificial Sequence
<220> FEATURE:
<223> OTHER INFORMATION: PCR primer

<400> SEQUENCE: 234
tgtaaaacga cggccagttt tcctcttatt attctttcat accc                      44

<210> SEQ ID NO 235
<211> LENGTH: 22
<212> TYPE: DNA
<213> ORGANISM: Artificial Sequence
<220> FEATURE:
<223> OTHER INFORMATION: PCR primer

<400> SEQUENCE: 235
gatgaggatg atgatgaatt gg                                              22

<210> SEQ ID NO 236
<211> LENGTH: 39
<212> TYPE: DNA
<213> ORGANISM: Artificial Sequence
<220> FEATURE:
<223> OTHER INFORMATION: PCR primer

<400> SEQUENCE: 236
tgtaaaacga cggccagtag ttcaaaccct tacccttca                            39

<210> SEQ ID NO 237
<211> LENGTH: 22
<212> TYPE: DNA
<213> ORGANISM: Artificial Sequence
<220> FEATURE:
<223> OTHER INFORMATION: PCR primer

<400> SEQUENCE: 237
gttttcctgg atatttggat gg                                              22

<210> SEQ ID NO 238
<211> LENGTH: 40
<212> TYPE: DNA
<213> ORGANISM: Artificial Sequence
<220> FEATURE:
<223> OTHER INFORMATION: PCR primer

<400> SEQUENCE: 238
tgtaaaacga cggccagttt caatcttctc ctttgattgc                           40

<210> SEQ ID NO 239
<211> LENGTH: 22
<212> TYPE: DNA
<213> ORGANISM: Artificial Sequence
<220> FEATURE:
<223> OTHER INFORMATION: PCR primer

<400> SEQUENCE: 239
tcagtgagaa ggtcgttcat gt                                              22

<210> SEQ ID NO 240

```
<211> LENGTH: 39
<212> TYPE: DNA
<213> ORGANISM: Artificial Sequence
<220> FEATURE:
<223> OTHER INFORMATION: PCR primer

<400> SEQUENCE: 240
tgtaaaacga cggccagttg agagagagtt cgtgggttg                              39

<210> SEQ ID NO 241
<211> LENGTH: 22
<212> TYPE: DNA
<213> ORGANISM: Artificial Sequence
<220> FEATURE:
<223> OTHER INFORMATION: PCR primer

<400> SEQUENCE: 241
gtgatgaagc attggtgatg at                                                22

<210> SEQ ID NO 242
<211> LENGTH: 40
<212> TYPE: DNA
<213> ORGANISM: Artificial Sequence
<220> FEATURE:
<223> OTHER INFORMATION: PCR primer

<400> SEQUENCE: 242
tgtaaaacga cggccagtaa tggcgaacac tttcactctt                             40

<210> SEQ ID NO 243
<211> LENGTH: 22
<212> TYPE: DNA
<213> ORGANISM: Artificial Sequence
<220> FEATURE:
<223> OTHER INFORMATION: PCR primer

<400> SEQUENCE: 243
atttcagagg cagatggtga at                                                22

<210> SEQ ID NO 244
<211> LENGTH: 40
<212> TYPE: DNA
<213> ORGANISM: Artificial Sequence
<220> FEATURE:
<223> OTHER INFORMATION: PCR primer

<400> SEQUENCE: 244
tgtaaaacga cggccagtta gcaaatggg tcaacaagtg                              40

<210> SEQ ID NO 245
<211> LENGTH: 22
<212> TYPE: DNA
<213> ORGANISM: Artificial Sequence
<220> FEATURE:
<223> OTHER INFORMATION: PCR primer

<400> SEQUENCE: 245
aatccagctt tggaagactc aa                                                22

<210> SEQ ID NO 246
<211> LENGTH: 40
<212> TYPE: DNA
<213> ORGANISM: Artificial Sequence
<220> FEATURE:
<223> OTHER INFORMATION: PCR primer

<400> SEQUENCE: 246
```

```
tgtaaaacga cggccagttt cttgtggtgg tgatgaaaac                    40
```

<210> SEQ ID NO 247
<211> LENGTH: 22
<212> TYPE: DNA
<213> ORGANISM: Artificial Sequence
<220> FEATURE:
<223> OTHER INFORMATION: PCR primer

<400> SEQUENCE: 247

```
gtgtgttccc cagttctcag tt                                       22
```

<210> SEQ ID NO 248
<211> LENGTH: 40
<212> TYPE: DNA
<213> ORGANISM: Artificial Sequence
<220> FEATURE:
<223> OTHER INFORMATION: PCR primer

<400> SEQUENCE: 248

```
tgtaaaacga cggccagtca taccttcaa atccaaccat                     40
```

<210> SEQ ID NO 249
<211> LENGTH: 22
<212> TYPE: DNA
<213> ORGANISM: Artificial Sequence
<220> FEATURE:
<223> OTHER INFORMATION: PCR primer

<400> SEQUENCE: 249

```
gattgttctt tggtaagcct ca                                       22
```

<210> SEQ ID NO 250
<211> LENGTH: 40
<212> TYPE: DNA
<213> ORGANISM: Artificial Sequence
<220> FEATURE:
<223> OTHER INFORMATION: PCR primer

<400> SEQUENCE: 250

```
tgtaaaacga cggccagtac tgcaagtgaa gagggagaga                    40
```

<210> SEQ ID NO 251
<211> LENGTH: 22
<212> TYPE: DNA
<213> ORGANISM: Artificial Sequence
<220> FEATURE:
<223> OTHER INFORMATION: PCR primer

<400> SEQUENCE: 251

```
gcttctttgg ctttctcttc aa                                       22
```

<210> SEQ ID NO 252
<211> LENGTH: 40
<212> TYPE: DNA
<213> ORGANISM: Artificial Sequence
<220> FEATURE:
<223> OTHER INFORMATION: PCR primer

<400> SEQUENCE: 252

```
tgtaaaacga cggccagtcg tttccctctc tcactcactt                    40
```

<210> SEQ ID NO 253
<211> LENGTH: 22
<212> TYPE: DNA

```
<213> ORGANISM: Artificial Sequence
<220> FEATURE:
<223> OTHER INFORMATION: PCR primer

<400> SEQUENCE: 253
atcagaaaca gaagcatcag ca                                              22

<210> SEQ ID NO 254
<211> LENGTH: 40
<212> TYPE: DNA
<213> ORGANISM: Artificial Sequence
<220> FEATURE:
<223> OTHER INFORMATION: PCR primer

<400> SEQUENCE: 254
tgtaaaacga cggccagtct ccaaaactca aactcaacca                           40

<210> SEQ ID NO 255
<211> LENGTH: 21
<212> TYPE: DNA
<213> ORGANISM: Artificial Sequence
<220> FEATURE:
<223> OTHER INFORMATION: PCR primer

<400> SEQUENCE: 255
ctagacttgc cgctactttg g                                               21

<210> SEQ ID NO 256
<211> LENGTH: 40
<212> TYPE: DNA
<213> ORGANISM: Artificial Sequence
<220> FEATURE:
<223> OTHER INFORMATION: PCR primer

<400> SEQUENCE: 256
tgtaaaacga cggccagtca acaatcacca cacacattga                           40

<210> SEQ ID NO 257
<211> LENGTH: 22
<212> TYPE: DNA
<213> ORGANISM: Artificial Sequence
<220> FEATURE:
<223> OTHER INFORMATION: PCR primer

<400> SEQUENCE: 257
ggaaacatag atgaagcagc aa                                              22

<210> SEQ ID NO 258
<211> LENGTH: 40
<212> TYPE: DNA
<213> ORGANISM: Artificial Sequence
<220> FEATURE:
<223> OTHER INFORMATION: PCR primer

<400> SEQUENCE: 258
tgtaaaacga cggccagtag caagcaaaga acaatcacaa                           40

<210> SEQ ID NO 259
<211> LENGTH: 22
<212> TYPE: DNA
<213> ORGANISM: Artificial Sequence
<220> FEATURE:
<223> OTHER INFORMATION: PCR primer

<400> SEQUENCE: 259
tcggatttgg ttttgagttt tc                                              22
```

<210> SEQ ID NO 260
<211> LENGTH: 40
<212> TYPE: DNA
<213> ORGANISM: Artificial Sequence
<220> FEATURE:
<223> OTHER INFORMATION: PCR primer

<400> SEQUENCE: 260
tgtaaaacga cggccagtct caggaggtgc tgttcttctt                          40

<210> SEQ ID NO 261
<211> LENGTH: 22
<212> TYPE: DNA
<213> ORGANISM: Artificial Sequence
<220> FEATURE:
<223> OTHER INFORMATION: PCR primer

<400> SEQUENCE: 261
tgagttttca gattcagcag ga                                            22

<210> SEQ ID NO 262
<211> LENGTH: 40
<212> TYPE: DNA
<213> ORGANISM: Artificial Sequence
<220> FEATURE:
<223> OTHER INFORMATION: PCR primer

<400> SEQUENCE: 262
tgtaaaacga cggccagtat catcgtcgtc gtgtttattg                          40

<210> SEQ ID NO 263
<211> LENGTH: 22
<212> TYPE: DNA
<213> ORGANISM: Artificial Sequence
<220> FEATURE:
<223> OTHER INFORMATION: PCR primer

<400> SEQUENCE: 263
ttttcatctg tgccctgtaa tg                                            22

<210> SEQ ID NO 264
<211> LENGTH: 41
<212> TYPE: DNA
<213> ORGANISM: Artificial Sequence
<220> FEATURE:
<223> OTHER INFORMATION: PCR primer

<400> SEQUENCE: 264
tgtaaaacga cggccagttc actcacactc aacacacaac a                       41

<210> SEQ ID NO 265
<211> LENGTH: 22
<212> TYPE: DNA
<213> ORGANISM: Artificial Sequence
<220> FEATURE:
<223> OTHER INFORMATION: PCR primer

<400> SEQUENCE: 265
attagaagct ccgttaccgt ca                                            22

<210> SEQ ID NO 266
<211> LENGTH: 40
<212> TYPE: DNA
<213> ORGANISM: Artificial Sequence
<220> FEATURE:

<223> OTHER INFORMATION: PCR primer

<400> SEQUENCE: 266
tgtaaaacga cggccagtat aaccaactcc aaaccacacc           40

<210> SEQ ID NO 267
<211> LENGTH: 20
<212> TYPE: DNA
<213> ORGANISM: Artificial Sequence
<220> FEATURE:
<223> OTHER INFORMATION: PCR primer

<400> SEQUENCE: 267
ttgaaaattg ggaacggaaa                                 20

<210> SEQ ID NO 268
<211> LENGTH: 38
<212> TYPE: DNA
<213> ORGANISM: Artificial Sequence
<220> FEATURE:
<223> OTHER INFORMATION: PCR primer

<400> SEQUENCE: 268
tgtaaaacga cggccagtgt tggagtggga aattgcag             38

<210> SEQ ID NO 269
<211> LENGTH: 22
<212> TYPE: DNA
<213> ORGANISM: Artificial Sequence
<220> FEATURE:
<223> OTHER INFORMATION: PCR primer

<400> SEQUENCE: 269
atgccaggat ggtgatacat ct                              22

<210> SEQ ID NO 270
<211> LENGTH: 40
<212> TYPE: DNA
<213> ORGANISM: Artificial Sequence
<220> FEATURE:
<223> OTHER INFORMATION: PCR primer

<400> SEQUENCE: 270
tgtaaaacga cggccagtgg atttgggcgt gagactatac           40

<210> SEQ ID NO 271
<211> LENGTH: 23
<212> TYPE: DNA
<213> ORGANISM: Artificial Sequence
<220> FEATURE:
<223> OTHER INFORMATION: PCR primer

<400> SEQUENCE: 271
tcaaagttgt tgttctgctt gaa                             23

<210> SEQ ID NO 272
<211> LENGTH: 38
<212> TYPE: DNA
<213> ORGANISM: Artificial Sequence
<220> FEATURE:
<223> OTHER INFORMATION: PCR primer

<400> SEQUENCE: 272
tgtaaaacga cggccagttc tcacacccca aaaacaca             38

```
<210> SEQ ID NO 273
<211> LENGTH: 23
<212> TYPE: DNA
<213> ORGANISM: Artificial Sequence
<220> FEATURE:
<223> OTHER INFORMATION: PCR primer

<400> SEQUENCE: 273
tcaaagttgt tgttctgctt gaa                                         23

<210> SEQ ID NO 274
<211> LENGTH: 38
<212> TYPE: DNA
<213> ORGANISM: Artificial Sequence
<220> FEATURE:
<223> OTHER INFORMATION: PCR primer

<400> SEQUENCE: 274
tgtaaaacga cggccagttc tcacacccca aaaacaca                         38

<210> SEQ ID NO 275
<211> LENGTH: 22
<212> TYPE: DNA
<213> ORGANISM: Artificial Sequence
<220> FEATURE:
<223> OTHER INFORMATION: PCR primer

<400> SEQUENCE: 275
aagagcagaa gaaggtttgt cg                                          22

<210> SEQ ID NO 276
<211> LENGTH: 38
<212> TYPE: DNA
<213> ORGANISM: Artificial Sequence
<220> FEATURE:
<223> OTHER INFORMATION: PCR primer

<400> SEQUENCE: 276
tgtaaaacga cggccagtac ctaagcaagc aaggcaaa                         38

<210> SEQ ID NO 277
<211> LENGTH: 20
<212> TYPE: DNA
<213> ORGANISM: Artificial Sequence
<220> FEATURE:
<223> OTHER INFORMATION: PCR primer

<400> SEQUENCE: 277
cggtgaaatg gtggaagaag                                             20

<210> SEQ ID NO 278
<211> LENGTH: 38
<212> TYPE: DNA
<213> ORGANISM: Artificial Sequence
<220> FEATURE:
<223> OTHER INFORMATION: PCR primer

<400> SEQUENCE: 278
tgtaaaacga cggccagtta acaaaaccca accccatc                         38

<210> SEQ ID NO 279
<211> LENGTH: 20
<212> TYPE: DNA
<213> ORGANISM: Artificial Sequence
<220> FEATURE:
<223> OTHER INFORMATION: PCR primer
```

<400> SEQUENCE: 279
ggtgtggaga gggagggtag                                            20

<210> SEQ ID NO 280
<211> LENGTH: 41
<212> TYPE: DNA
<213> ORGANISM: Artificial Sequence
<220> FEATURE:
<223> OTHER INFORMATION: PCR primer

<400> SEQUENCE: 280
tgtaaaacga cggccagtcg agggatattc tttcccttaa a                    41

<210> SEQ ID NO 281
<211> LENGTH: 22
<212> TYPE: DNA
<213> ORGANISM: Artificial Sequence
<220> FEATURE:
<223> OTHER INFORMATION: PCR primer

<400> SEQUENCE: 281
ctacctccag cagaaccatg tc                                         22

<210> SEQ ID NO 282
<211> LENGTH: 42
<212> TYPE: DNA
<213> ORGANISM: Artificial Sequence
<220> FEATURE:
<223> OTHER INFORMATION: PCR primer

<400> SEQUENCE: 282
tgtaaaacga cggccagtgt aaccatcctt tgagttcgtc tg                   42

<210> SEQ ID NO 283
<211> LENGTH: 22
<212> TYPE: DNA
<213> ORGANISM: Artificial Sequence
<220> FEATURE:
<223> OTHER INFORMATION: PCR primer

<400> SEQUENCE: 283
tgcatttgtt aacgagtgtg aa                                         22

<210> SEQ ID NO 284
<211> LENGTH: 41
<212> TYPE: DNA
<213> ORGANISM: Artificial Sequence
<220> FEATURE:
<223> OTHER INFORMATION: PCR primer

<400> SEQUENCE: 284
tgtaaaacga cggccagtcc acagaagaaa gaagaacttg c                    41

<210> SEQ ID NO 285
<211> LENGTH: 22
<212> TYPE: DNA
<213> ORGANISM: Artificial Sequence
<220> FEATURE:
<223> OTHER INFORMATION: PCR primer

<400> SEQUENCE: 285
tcgaggccaa tagaagacct aa                                         22

<210> SEQ ID NO 286
<211> LENGTH: 40

```
<212> TYPE: DNA
<213> ORGANISM: Artificial Sequence
<220> FEATURE:
<223> OTHER INFORMATION: PCR primer

<400> SEQUENCE: 286
tgtaaaacga cggccagtgg ttctcttcca atcccttctt                    40

<210> SEQ ID NO 287
<211> LENGTH: 22
<212> TYPE: DNA
<213> ORGANISM: Artificial Sequence
<220> FEATURE:
<223> OTHER INFORMATION: PCR primer

<400> SEQUENCE: 287
ttttcaagga ggagaagatc ca                                       22

<210> SEQ ID NO 288
<211> LENGTH: 40
<212> TYPE: DNA
<213> ORGANISM: Artificial Sequence
<220> FEATURE:
<223> OTHER INFORMATION: PCR primer

<400> SEQUENCE: 288
tgtaaaacga cggccagtac cccacctaac cctctacagt                    40

<210> SEQ ID NO 289
<211> LENGTH: 22
<212> TYPE: DNA
<213> ORGANISM: Artificial Sequence
<220> FEATURE:
<223> OTHER INFORMATION: PCR primer

<400> SEQUENCE: 289
tgtggtgaag aaacggatag aa                                       22

<210> SEQ ID NO 290
<211> LENGTH: 40
<212> TYPE: DNA
<213> ORGANISM: Artificial Sequence
<220> FEATURE:
<223> OTHER INFORMATION: PCR primer

<400> SEQUENCE: 290
tgtaaaacga cggccagtag tatcaatctt tggcgctacc                    40

<210> SEQ ID NO 291
<211> LENGTH: 22
<212> TYPE: DNA
<213> ORGANISM: Artificial Sequence
<220> FEATURE:
<223> OTHER INFORMATION: PCR primer

<400> SEQUENCE: 291
ggtaatcgtt ggcgttgttt at                                       22

<210> SEQ ID NO 292
<211> LENGTH: 40
<212> TYPE: DNA
<213> ORGANISM: Artificial Sequence
<220> FEATURE:
<223> OTHER INFORMATION: PCR primer

<400> SEQUENCE: 292
```

```
tgtaaaacga cggccagttc aggtagttga cgacgaagaa                              40
```

<210> SEQ ID NO 293
<211> LENGTH: 22
<212> TYPE: DNA
<213> ORGANISM: Artificial Sequence
<220> FEATURE:
<223> OTHER INFORMATION: PCR primer

<400> SEQUENCE: 293

```
caacgcctcc tctttctctg ta                                                22
```

<210> SEQ ID NO 294
<211> LENGTH: 42
<212> TYPE: DNA
<213> ORGANISM: Artificial Sequence
<220> FEATURE:
<223> OTHER INFORMATION: PCR primer

<400> SEQUENCE: 294

```
tgtaaaacga cggccagtct caaaacccta acttcttcaa cc                          42
```

<210> SEQ ID NO 295
<211> LENGTH: 22
<212> TYPE: DNA
<213> ORGANISM: Artificial Sequence
<220> FEATURE:
<223> OTHER INFORMATION: PCR primer

<400> SEQUENCE: 295

```
caactgtgaa cgcaaatctc tc                                                22
```

<210> SEQ ID NO 296
<211> LENGTH: 40
<212> TYPE: DNA
<213> ORGANISM: Artificial Sequence
<220> FEATURE:
<223> OTHER INFORMATION: PCR primer

<400> SEQUENCE: 296

```
tgtaaaacga cggccagtaa cgacgctctt cgactacttc                             40
```

<210> SEQ ID NO 297
<211> LENGTH: 21
<212> TYPE: DNA
<213> ORGANISM: Artificial Sequence
<220> FEATURE:
<223> OTHER INFORMATION: PCR primer

<400> SEQUENCE: 297

```
ggatccaacc gaatttcttt c                                                 21
```

<210> SEQ ID NO 298
<211> LENGTH: 40
<212> TYPE: DNA
<213> ORGANISM: Artificial Sequence
<220> FEATURE:
<223> OTHER INFORMATION: PCR primer

<400> SEQUENCE: 298

```
tgtaaaacga cggccagtac ctagcaaccc aaatcagaag                             40
```

<210> SEQ ID NO 299
<211> LENGTH: 22
<212> TYPE: DNA
<213> ORGANISM: Artificial Sequence

```
<220> FEATURE:
<223> OTHER INFORMATION: PCR primer

<400> SEQUENCE: 299
cctcgaaaag attaccgaac ac                                              22

<210> SEQ ID NO 300
<211> LENGTH: 40
<212> TYPE: DNA
<213> ORGANISM: Artificial Sequence
<220> FEATURE:
<223> OTHER INFORMATION: PCR primer

<400> SEQUENCE: 300
tgtaaaacga cggccagtcg ccttcttctt caacacacta                           40

<210> SEQ ID NO 301
<211> LENGTH: 22
<212> TYPE: DNA
<213> ORGANISM: Artificial Sequence
<220> FEATURE:
<223> OTHER INFORMATION: PCR primer

<400> SEQUENCE: 301
ttctccttga ccaaccttga tt                                              22

<210> SEQ ID NO 302
<211> LENGTH: 40
<212> TYPE: DNA
<213> ORGANISM: Artificial Sequence
<220> FEATURE:
<223> OTHER INFORMATION: PCR primer

<400> SEQUENCE: 302
tgtaaaacga cggccagtac ccactcaact caacacacac                           40

<210> SEQ ID NO 303
<211> LENGTH: 22
<212> TYPE: DNA
<213> ORGANISM: Artificial Sequence
<220> FEATURE:
<223> OTHER INFORMATION: PCR primer

<400> SEQUENCE: 303
agaaggtgga acacgtctct tc                                              22

<210> SEQ ID NO 304
<211> LENGTH: 40
<212> TYPE: DNA
<213> ORGANISM: Artificial Sequence
<220> FEATURE:
<223> OTHER INFORMATION: PCR primer

<400> SEQUENCE: 304
tgtaaaacga cggccagtct acaagcccag atttcaaagg                           40

<210> SEQ ID NO 305
<211> LENGTH: 22
<212> TYPE: DNA
<213> ORGANISM: Artificial Sequence
<220> FEATURE:
<223> OTHER INFORMATION: PCR primer

<400> SEQUENCE: 305
ttcgcagttc ttgagtaggt ca                                              22
```

<210> SEQ ID NO 306
<211> LENGTH: 40
<212> TYPE: DNA
<213> ORGANISM: Artificial Sequence
<220> FEATURE:
<223> OTHER INFORMATION: PCR primer

<400> SEQUENCE: 306
tgtaaaacga cggccagtta cttcatgtac cccacaacca        40

<210> SEQ ID NO 307
<211> LENGTH: 22
<212> TYPE: DNA
<213> ORGANISM: Artificial Sequence
<220> FEATURE:
<223> OTHER INFORMATION: PCR primer

<400> SEQUENCE: 307
ttgtcgatga gttcaacgtt tc        22

<210> SEQ ID NO 308
<211> LENGTH: 40
<212> TYPE: DNA
<213> ORGANISM: Artificial Sequence
<220> FEATURE:
<223> OTHER INFORMATION: PCR primer

<400> SEQUENCE: 308
tgtaaaacga cggccagtac aacaaaacac aatgggtgac        40

<210> SEQ ID NO 309
<211> LENGTH: 22
<212> TYPE: DNA
<213> ORGANISM: Artificial Sequence
<220> FEATURE:
<223> OTHER INFORMATION: PCR primer

<400> SEQUENCE: 309
agtaaccgcg aaccaaagag ta        22

<210> SEQ ID NO 310
<211> LENGTH: 40
<212> TYPE: DNA
<213> ORGANISM: Artificial Sequence
<220> FEATURE:
<223> OTHER INFORMATION: PCR primer

<400> SEQUENCE: 310
tgtaaaacga cggccagtac acctcgaaca agattcatcc        40

<210> SEQ ID NO 311
<211> LENGTH: 22
<212> TYPE: DNA
<213> ORGANISM: Artificial Sequence
<220> FEATURE:
<223> OTHER INFORMATION: PCR primer

<400> SEQUENCE: 311
accatatcca caggcataat cc        22

<210> SEQ ID NO 312
<211> LENGTH: 40
<212> TYPE: DNA
<213> ORGANISM: Artificial Sequence
<220> FEATURE:
<223> OTHER INFORMATION: PCR primer

<400> SEQUENCE: 312
tgtaaaacga cggccagtaa tccatactca aacccaccag      40

<210> SEQ ID NO 313
<211> LENGTH: 22
<212> TYPE: DNA
<213> ORGANISM: Artificial Sequence
<220> FEATURE:
<223> OTHER INFORMATION: PCR primer

<400> SEQUENCE: 313
atcacgagaa ccgccataag at      22

<210> SEQ ID NO 314
<211> LENGTH: 39
<212> TYPE: DNA
<213> ORGANISM: Artificial Sequence
<220> FEATURE:
<223> OTHER INFORMATION: PCR primer

<400> SEQUENCE: 314
tgtaaaacga cggccagtag ggctgatgag gtggataat      39

<210> SEQ ID NO 315
<211> LENGTH: 19
<212> TYPE: DNA
<213> ORGANISM: Artificial Sequence
<220> FEATURE:
<223> OTHER INFORMATION: PCR primer

<400> SEQUENCE: 315
gaacgggttt gcgatcttt      19

<210> SEQ ID NO 316
<211> LENGTH: 40
<212> TYPE: DNA
<213> ORGANISM: Artificial Sequence
<220> FEATURE:
<223> OTHER INFORMATION: PCR primer

<400> SEQUENCE: 316
tgtaaaacga cggccagtcc atgtctctca atcttcgtca      40

<210> SEQ ID NO 317
<211> LENGTH: 24
<212> TYPE: DNA
<213> ORGANISM: Artificial Sequence
<220> FEATURE:
<223> OTHER INFORMATION: PCR primer

<400> SEQUENCE: 317
gcatgtatga tttacagctc caag      24

<210> SEQ ID NO 318
<211> LENGTH: 40
<212> TYPE: DNA
<213> ORGANISM: Artificial Sequence
<220> FEATURE:
<223> OTHER INFORMATION: PCR primer

<400> SEQUENCE: 318
tgtaaaacga cggccagtcc acagtttcat tttctgtcca      40

<210> SEQ ID NO 319

```
<211> LENGTH: 22
<212> TYPE: DNA
<213> ORGANISM: Artificial Sequence
<220> FEATURE:
<223> OTHER INFORMATION: PCR primer

<400> SEQUENCE: 319
tgcctttgat tagtgctgac at                                                  22

<210> SEQ ID NO 320
<211> LENGTH: 40
<212> TYPE: DNA
<213> ORGANISM: Artificial Sequence
<220> FEATURE:
<223> OTHER INFORMATION: PCR primer

<400> SEQUENCE: 320
tgtaaaacga cggccagtct ctgctcccat ctacttcaca                               40

<210> SEQ ID NO 321
<211> LENGTH: 22
<212> TYPE: DNA
<213> ORGANISM: Artificial Sequence
<220> FEATURE:
<223> OTHER INFORMATION: PCR primer

<400> SEQUENCE: 321
gcaacatacc atcccctaaa ag                                                  22

<210> SEQ ID NO 322
<211> LENGTH: 39
<212> TYPE: DNA
<213> ORGANISM: Artificial Sequence
<220> FEATURE:
<223> OTHER INFORMATION: PCR primer

<400> SEQUENCE: 322
tgtaaaacga cggccagtgc tggaatacac caagcatga                                39

<210> SEQ ID NO 323
<211> LENGTH: 22
<212> TYPE: DNA
<213> ORGANISM: Artificial Sequence
<220> FEATURE:
<223> OTHER INFORMATION: PCR primer

<400> SEQUENCE: 323
acataagcga ctggaacaaa cc                                                  22

<210> SEQ ID NO 324
<211> LENGTH: 40
<212> TYPE: DNA
<213> ORGANISM: Artificial Sequence
<220> FEATURE:
<223> OTHER INFORMATION: PCR primer

<400> SEQUENCE: 324
tgtaaaacga cggccagtgg atacaaaatc cacaagcaca                               40

<210> SEQ ID NO 325
<211> LENGTH: 22
<212> TYPE: DNA
<213> ORGANISM: Artificial Sequence
<220> FEATURE:
<223> OTHER INFORMATION: PCR primer

<400> SEQUENCE: 325
```
acataagcga ctggaacaaa cc 22

<210> SEQ ID NO 326
<211> LENGTH: 40
<212> TYPE: DNA
<213> ORGANISM: Artificial Sequence
<220> FEATURE:
<223> OTHER INFORMATION: PCR primer

<400> SEQUENCE: 326
tgtaaaacga cggccagtgg atacaaaatc cacaagcaca 40

<210> SEQ ID NO 327
<211> LENGTH: 22
<212> TYPE: DNA
<213> ORGANISM: Artificial Sequence
<220> FEATURE:
<223> OTHER INFORMATION: PCR primer

<400> SEQUENCE: 327
atttcagagg cagatggtga at 22

<210> SEQ ID NO 328
<211> LENGTH: 40
<212> TYPE: DNA
<213> ORGANISM: Artificial Sequence
<220> FEATURE:
<223> OTHER INFORMATION: PCR primer

<400> SEQUENCE: 328
tgtaaaacga cggccagtta gcaaatggg tcaacaagtg 40

<210> SEQ ID NO 329
<211> LENGTH: 22
<212> TYPE: DNA
<213> ORGANISM: Artificial Sequence
<220> FEATURE:
<223> OTHER INFORMATION: PCR primer

<400> SEQUENCE: 329 cagggggaatc aatcagtcaa ag 22

<210> SEQ ID NO 330
<211> LENGTH: 41
<212> TYPE: DNA
<213> ORGANISM: Artificial Sequence
<220> FEATURE:
<223> OTHER INFORMATION: PCR primer

<400> SEQUENCE: 330
tgtaaaacga cggccagtaa acagagagac aggaatttgg a 41

<210> SEQ ID NO 331
<211> LENGTH: 22
<212> TYPE: DNA
<213> ORGANISM: Artificial Sequence
<220> FEATURE:
<223> OTHER INFORMATION: PCR primer

<400> SEQUENCE: 331
tgttgaagtt ggagttttgg tg 22

<210> SEQ ID NO 332
<211> LENGTH: 40
<212> TYPE: DNA

<213> ORGANISM: Artificial Sequence
<220> FEATURE:
<223> OTHER INFORMATION: PCR primer

<400> SEQUENCE: 332
tgtaaaacga cggccagttc agcagttagt tttggtatgc      40

<210> SEQ ID NO 333
<211> LENGTH: 22
<212> TYPE: DNA
<213> ORGANISM: Artificial Sequence
<220> FEATURE:
<223> OTHER INFORMATION: PCR primer

<400> SEQUENCE: 333
ggttggaaac aaagtcagaa cc      22

<210> SEQ ID NO 334
<211> LENGTH: 40
<212> TYPE: DNA
<213> ORGANISM: Artificial Sequence
<220> FEATURE:
<223> OTHER INFORMATION: PCR primer

<400> SEQUENCE: 334
tgtaaaacga cggccagtac atcatcaaca gcaaaaccag      40

<210> SEQ ID NO 335
<211> LENGTH: 22
<212> TYPE: DNA
<213> ORGANISM: Artificial Sequence
<220> FEATURE:
<223> OTHER INFORMATION: PCR primer

<400> SEQUENCE: 335
tgcttcttgg tttctcatca tc      22

<210> SEQ ID NO 336
<211> LENGTH: 40
<212> TYPE: DNA
<213> ORGANISM: Artificial Sequence
<220> FEATURE:
<223> OTHER INFORMATION: PCR primer

<400> SEQUENCE: 336
tgtaaaacga cggccagtat ggttatgtgg gttgtgttca      40

<210> SEQ ID NO 337
<211> LENGTH: 21
<212> TYPE: DNA
<213> ORGANISM: Artificial Sequence
<220> FEATURE:
<223> OTHER INFORMATION: PCR primer

<400> SEQUENCE: 337
ttcccatatg caacagacct t      21

<210> SEQ ID NO 338
<211> LENGTH: 39
<212> TYPE: DNA
<213> ORGANISM: Artificial Sequence
<220> FEATURE:
<223> OTHER INFORMATION: PCR primer

<400> SEQUENCE: 338
tgtaaaacga cggccagtaa cggtggtgtg tttattgct      39

<210> SEQ ID NO 339
<211> LENGTH: 20
<212> TYPE: DNA
<213> ORGANISM: Artificial Sequence
<220> FEATURE:
<223> OTHER INFORMATION: PCR primer

<400> SEQUENCE: 339
ggcaggaaca gatccttgaa                                               20

<210> SEQ ID NO 340
<211> LENGTH: 42
<212> TYPE: DNA
<213> ORGANISM: Artificial Sequence
<220> FEATURE:
<223> OTHER INFORMATION: PCR primer

<400> SEQUENCE: 340
tgtaaaacga cggccagtcg taaacaaaga aaagcttgag ag                       42

<210> SEQ ID NO 341
<211> LENGTH: 20
<212> TYPE: DNA
<213> ORGANISM: Artificial Sequence
<220> FEATURE:
<223> OTHER INFORMATION: PCR primer

<400> SEQUENCE: 341
ttaacgaggg tggtgatggt                                               20

<210> SEQ ID NO 342
<211> LENGTH: 39
<212> TYPE: DNA
<213> ORGANISM: Artificial Sequence
<220> FEATURE:
<223> OTHER INFORMATION: PCR primer

<400> SEQUENCE: 342
tgtaaaacga cggccagttc gatgttatgg tagcagcaa                          39

<210> SEQ ID NO 343
<211> LENGTH: 22
<212> TYPE: DNA
<213> ORGANISM: Artificial Sequence
<220> FEATURE:
<223> OTHER INFORMATION: PCR primer

<400> SEQUENCE: 343
agcagtgatg tcttggctat gt                                            22

<210> SEQ ID NO 344
<211> LENGTH: 39
<212> TYPE: DNA
<213> ORGANISM: Artificial Sequence
<220> FEATURE:
<223> OTHER INFORMATION: PCR primer

<400> SEQUENCE: 344
tgtaaaacga cggccagtgt ttccggttct ttgtcgttc                          39

<210> SEQ ID NO 345
<211> LENGTH: 22
<212> TYPE: DNA
<213> ORGANISM: Artificial Sequence
<220> FEATURE:

```
<223> OTHER INFORMATION: PCR primer

<400> SEQUENCE: 345
aacatcgtaa tgaggaggag ga                                              22

<210> SEQ ID NO 346
<211> LENGTH: 40
<212> TYPE: DNA
<213> ORGANISM: Artificial Sequence
<220> FEATURE:
<223> OTHER INFORMATION: PCR primer

<400> SEQUENCE: 346
tgtaaaacga cggccagtac agtatcagca acaccagcag                           40

<210> SEQ ID NO 347
<211> LENGTH: 22
<212> TYPE: DNA
<213> ORGANISM: Artificial Sequence
<220> FEATURE:
<223> OTHER INFORMATION: PCR primer

<400> SEQUENCE: 347
tcaacccttc agattttctt cc                                              22

<210> SEQ ID NO 348
<211> LENGTH: 40
<212> TYPE: DNA
<213> ORGANISM: Artificial Sequence
<220> FEATURE:
<223> OTHER INFORMATION: PCR primer

<400> SEQUENCE: 348
tgtaaaacga cggccagtca cactttctcg tttgctctct                           40

<210> SEQ ID NO 349
<211> LENGTH: 22
<212> TYPE: DNA
<213> ORGANISM: Artificial Sequence
<220> FEATURE:
<223> OTHER INFORMATION: PCR primer

<400> SEQUENCE: 349
caatttcctt agtggccgtt ac                                              22

<210> SEQ ID NO 350
<211> LENGTH: 40
<212> TYPE: DNA
<213> ORGANISM: Artificial Sequence
<220> FEATURE:
<223> OTHER INFORMATION: PCR primer

<400> SEQUENCE: 350
tgtaaaacga cggccagttt attagctggg cttttcttcg                           40

<210> SEQ ID NO 351
<211> LENGTH: 22
<212> TYPE: DNA
<213> ORGANISM: Artificial Sequence
<220> FEATURE:
<223> OTHER INFORMATION: PCR primer

<400> SEQUENCE: 351
atcagcgtaa attctggcct ta                                              22
```

```
<210> SEQ ID NO 352
<211> LENGTH: 39
<212> TYPE: DNA
<213> ORGANISM: Artificial Sequence
<220> FEATURE:
<223> OTHER INFORMATION: PCR primer

<400> SEQUENCE: 352
tgtaaaacga cggccagtcc attccaatcc acactatcg                              39

<210> SEQ ID NO 353
<211> LENGTH: 22
<212> TYPE: DNA
<213> ORGANISM: Artificial Sequence
<220> FEATURE:
<223> OTHER INFORMATION: PCR primer

<400> SEQUENCE: 353
cgtaggaaga aggatcgagt tc                                                22

<210> SEQ ID NO 354
<211> LENGTH: 39
<212> TYPE: DNA
<213> ORGANISM: Artificial Sequence
<220> FEATURE:
<223> OTHER INFORMATION: PCR primer

<400> SEQUENCE: 354
tgtaaaacga cggccagtcc caattcaaaa cgaagaacc                              39

<210> SEQ ID NO 355
<211> LENGTH: 22
<212> TYPE: DNA
<213> ORGANISM: Artificial Sequence
<220> FEATURE:
<223> OTHER INFORMATION: PCR primer

<400> SEQUENCE: 355
cgtcgaagtc aaaatcaatc tc                                                22

<210> SEQ ID NO 356
<211> LENGTH: 40
<212> TYPE: DNA
<213> ORGANISM: Artificial Sequence
<220> FEATURE:
<223> OTHER INFORMATION: PCR primer

<400> SEQUENCE: 356
tgtaaaacga cggccagtga aaagaaatca ccccgaagat                             40

<210> SEQ ID NO 357
<211> LENGTH: 22
<212> TYPE: DNA
<213> ORGANISM: Artificial Sequence
<220> FEATURE:
<223> OTHER INFORMATION: PCR primer

<400> SEQUENCE: 357
ctcattcacc caaccaaaat gt                                                22

<210> SEQ ID NO 358
<211> LENGTH: 40
<212> TYPE: DNA
<213> ORGANISM: Artificial Sequence
<220> FEATURE:
<223> OTHER INFORMATION: PCR primer
```

```
<400> SEQUENCE: 358
tgtaaaacga cggccagtgg ctaattcacc tgtttctgct                    40

<210> SEQ ID NO 359
<211> LENGTH: 22
<212> TYPE: DNA
<213> ORGANISM: Artificial Sequence
<220> FEATURE:
<223> OTHER INFORMATION: PCR primer

<400> SEQUENCE: 359
tcaacagcca actcaaagtg at                                       22

<210> SEQ ID NO 360
<211> LENGTH: 40
<212> TYPE: DNA
<213> ORGANISM: Artificial Sequence
<220> FEATURE:
<223> OTHER INFORMATION: PCR primer

<400> SEQUENCE: 360
tgtaaaacga cggccagtca tcaatcaacc ctttcgtttc                    40

<210> SEQ ID NO 361
<211> LENGTH: 24
<212> TYPE: DNA
<213> ORGANISM: Artificial Sequence
<220> FEATURE:
<223> OTHER INFORMATION: PCR primer

<400> SEQUENCE: 361
ttagagatgg taattgcagt ggac                                     24

<210> SEQ ID NO 362
<211> LENGTH: 20
<212> TYPE: DNA
<213> ORGANISM: Artificial Sequence
<220> FEATURE:
<223> OTHER INFORMATION: PCR primer

<400> SEQUENCE: 362
ttggtggaag tcatgtttgg                                          20

<210> SEQ ID NO 363
<211> LENGTH: 21
<212> TYPE: DNA
<213> ORGANISM: Artificial Sequence
<220> FEATURE:
<223> OTHER INFORMATION: PCR primer

<400> SEQUENCE: 363
aacaggactg tgttgcacgt a                                        21

<210> SEQ ID NO 364
<211> LENGTH: 20
<212> TYPE: DNA
<213> ORGANISM: Artificial Sequence
<220> FEATURE:
<223> OTHER INFORMATION: PCR primer

<400> SEQUENCE: 364
ctgcttctgc tgatggacaa                                          20

<210> SEQ ID NO 365
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 365
cccactgagg gtactcatgc                                               20

<210> SEQ ID NO 366
<211> LENGTH: 20
<212> TYPE: DNA
<213> ORGANISM: Artificial Sequence
<220> FEATURE:
<223> OTHER INFORMATION: PCR primer

<400> SEQUENCE: 366
agctgcaaca actcctccat                                               20

<210> SEQ ID NO 367
<211> LENGTH: 21
<212> TYPE: DNA
<213> ORGANISM: Artificial Sequence
<220> FEATURE:
<223> OTHER INFORMATION: PCR primer

<400> SEQUENCE: 367
gaaactcaaa gggcgatcac t                                             21

<210> SEQ ID NO 368
<211> LENGTH: 20
<212> TYPE: DNA
<213> ORGANISM: Artificial Sequence
<220> FEATURE:
<223> OTHER INFORMATION: PCR primer

<400> SEQUENCE: 368
aagcgatatc agagggtgga                                               20

<210> SEQ ID NO 369
<211> LENGTH: 21
<212> TYPE: DNA
<213> ORGANISM: Artificial Sequence
<220> FEATURE:
<223> OTHER INFORMATION: PCR primer

<400> SEQUENCE: 369
ccttggcagc tacaggtaca g                                             21

<210> SEQ ID NO 370
<211> LENGTH: 39
<212> TYPE: DNA
<213> ORGANISM: Artificial Sequence
<220> FEATURE:
<223> OTHER INFORMATION: PCR primer

<400> SEQUENCE: 370
tgtaaaacga cggccagtgt ctgctgctcc agctaagaa                          39

<210> SEQ ID NO 371
<211> LENGTH: 21
<212> TYPE: DNA
<213> ORGANISM: Artificial Sequence
<220> FEATURE:
<223> OTHER INFORMATION: PCR primer

<400> SEQUENCE: 371
```
tcacatcagc cctaacattc c          21

<210> SEQ ID NO 372
<211> LENGTH: 39
<212> TYPE: DNA
<213> ORGANISM: Artificial Sequence
<220> FEATURE:
<223> OTHER INFORMATION: PCR primer

<400> SEQUENCE: 372
tgtaaaacga cggccagtcc aaatatcttc gctcttcca          39

<210> SEQ ID NO 373
<211> LENGTH: 21
<212> TYPE: DNA
<213> ORGANISM: Artificial Sequence
<220> FEATURE:
<223> OTHER INFORMATION: PCR primer

<400> SEQUENCE: 373
ggatatcctg gtggagggta a          21

<210> SEQ ID NO 374
<211> LENGTH: 39
<212> TYPE: DNA
<213> ORGANISM: Artificial Sequence
<220> FEATURE:
<223> OTHER INFORMATION: PCR primer

<400> SEQUENCE: 374
tgtaaaacga cggccagtac aaccccattt ccaactttc          39

<210> SEQ ID NO 375
<211> LENGTH: 21
<212> TYPE: DNA
<213> ORGANISM: Artificial Sequence
<220> FEATURE:
<223> OTHER INFORMATION: PCR primer

<400> SEQUENCE: 375
cctccaggtc taagtcccat t          21

<210> SEQ ID NO 376
<211> LENGTH: 38
<212> TYPE: DNA
<213> ORGANISM: Artificial Sequence
<220> FEATURE:
<223> OTHER INFORMATION: PCR primer

<400> SEQUENCE: 376
tgtaaaacga cggccagtcc aatgcagttc ggtaatcc          38

<210> SEQ ID NO 377
<211> LENGTH: 21
<212> TYPE: DNA
<213> ORGANISM: Artificial Sequence
<220> FEATURE:
<223> OTHER INFORMATION: PCR primer

<400> SEQUENCE: 377
ggagcaaaca ttctaccacc a          21

<210> SEQ ID NO 378
<211> LENGTH: 40
<212> TYPE: DNA
<213> ORGANISM: Artificial Sequence

```
<220> FEATURE:
<223> OTHER INFORMATION: PCR primer

<400> SEQUENCE: 378
tgtaaaacga cggccagttc acaaaacaaa cccttcttct                    40

<210> SEQ ID NO 379
<211> LENGTH: 21
<212> TYPE: DNA
<213> ORGANISM: Artificial Sequence
<220> FEATURE:
<223> OTHER INFORMATION: PCR primer

<400> SEQUENCE: 379
tgacttagac accaccggag t                                         21

<210> SEQ ID NO 380
<211> LENGTH: 39
<212> TYPE: DNA
<213> ORGANISM: Artificial Sequence
<220> FEATURE:
<223> OTHER INFORMATION: PCR primer

<400> SEQUENCE: 380
tgtaaaacga cggccagttc atccattcat taaaacgca                      39

<210> SEQ ID NO 381
<211> LENGTH: 21
<212> TYPE: DNA
<213> ORGANISM: Artificial Sequence
<220> FEATURE:
<223> OTHER INFORMATION: PCR primer

<400> SEQUENCE: 381
atacaccata gcacgagacg c                                         21

<210> SEQ ID NO 382
<211> LENGTH: 39
<212> TYPE: DNA
<213> ORGANISM: Artificial Sequence
<220> FEATURE:
<223> OTHER INFORMATION: PCR primer

<400> SEQUENCE: 382
tgtaaaacga cggccagtta attcgaggag gattgtgga                      39

<210> SEQ ID NO 383
<211> LENGTH: 21
<212> TYPE: DNA
<213> ORGANISM: Artificial Sequence
<220> FEATURE:
<223> OTHER INFORMATION: PCR primer

<400> SEQUENCE: 383
ggatccatta ccagacagtg c                                         21

<210> SEQ ID NO 384
<211> LENGTH: 41
<212> TYPE: DNA
<213> ORGANISM: Artificial Sequence
<220> FEATURE:
<223> OTHER INFORMATION: PCR primer

<400> SEQUENCE: 384
tgtaaaacga cggccagttg atttcacttt agcatcttgt g                   41
```

```
<210> SEQ ID NO 385
<211> LENGTH: 21
<212> TYPE: DNA
<213> ORGANISM: Artificial Sequence
<220> FEATURE:
<223> OTHER INFORMATION: PCR primer

<400> SEQUENCE: 385
ggagatgaag aaggagatgg g                                              21

<210> SEQ ID NO 386
<211> LENGTH: 41
<212> TYPE: DNA
<213> ORGANISM: Artificial Sequence
<220> FEATURE:
<223> OTHER INFORMATION: PCR primer

<400> SEQUENCE: 386
tgtaaaacga cggccagttt gaaatagtgc aagaagaacc c                        41

<210> SEQ ID NO 387
<211> LENGTH: 22
<212> TYPE: DNA
<213> ORGANISM: Artificial Sequence
<220> FEATURE:
<223> OTHER INFORMATION: PCR primer

<400> SEQUENCE: 387
tgtcacttgt tctggtcctt ct                                             22

<210> SEQ ID NO 388
<211> LENGTH: 40
<212> TYPE: DNA
<213> ORGANISM: Artificial Sequence
<220> FEATURE:
<223> OTHER INFORMATION: PCR primer

<400> SEQUENCE: 388
tgtaaaacga cggccagtgg agagagcaaa gtctcttcaa                          40

<210> SEQ ID NO 389
<211> LENGTH: 21
<212> TYPE: DNA
<213> ORGANISM: Artificial Sequence
<220> FEATURE:
<223> OTHER INFORMATION: PCR primer

<400> SEQUENCE: 389
caggaacata actgtgaccc g                                              21

<210> SEQ ID NO 390
<211> LENGTH: 40
<212> TYPE: DNA
<213> ORGANISM: Artificial Sequence
<220> FEATURE:
<223> OTHER INFORMATION: PCR primer

<400> SEQUENCE: 390
tgtaaaacga cggccagttc ctaatacccc attcattggt                          40

<210> SEQ ID NO 391
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 391
gcctttaggc caatcagaga c                                              21

<210> SEQ ID NO 392
<211> LENGTH: 42
<212> TYPE: DNA
<213> ORGANISM: Artificial Sequence
<220> FEATURE:
<223> OTHER INFORMATION: PCR primer

<400> SEQUENCE: 392
tgtaaaacga cggccagtaa gattagggtt tgagtaaggg aa                       42

<210> SEQ ID NO 393
<211> LENGTH: 21
<212> TYPE: DNA
<213> ORGANISM: Artificial Sequence
<220> FEATURE:
<223> OTHER INFORMATION: PCR primer

<400> SEQUENCE: 393
acatcttctg gaagacccgt t                                              21

<210> SEQ ID NO 394
<211> LENGTH: 41
<212> TYPE: DNA
<213> ORGANISM: Artificial Sequence
<220> FEATURE:
<223> OTHER INFORMATION: PCR primer

<400> SEQUENCE: 394
tgtaaaacga cggccagtgg tagtacttcc ttcactcttc t                        41

<210> SEQ ID NO 395
<211> LENGTH: 21
<212> TYPE: DNA
<213> ORGANISM: Artificial Sequence
<220> FEATURE:
<223> OTHER INFORMATION: PCR primer

<400> SEQUENCE: 395
atctgggaag tgtgacctcc t                                              21

<210> SEQ ID NO 396
<211> LENGTH: 39
<212> TYPE: DNA
<213> ORGANISM: Artificial Sequence
<220> FEATURE:
<223> OTHER INFORMATION: PCR primer

<400> SEQUENCE: 396
tgtaaaacga cggccagttc aaaaccttgg tgttggttg                           39

<210> SEQ ID NO 397
<211> LENGTH: 21
<212> TYPE: DNA
<213> ORGANISM: Artificial Sequence
<220> FEATURE:
<223> OTHER INFORMATION: PCR primer

<400> SEQUENCE: 397
catactatgg tggtggttgg g                                              21

<210> SEQ ID NO 398
```

```
<211> LENGTH: 41
<212> TYPE: DNA
<213> ORGANISM: Artificial Sequence
<220> FEATURE:
<223> OTHER INFORMATION: PCR primer

<400> SEQUENCE: 398
tgtaaaacga cggccagtct ctttaagatt gcttctcttg c         41

<210> SEQ ID NO 399
<211> LENGTH: 21
<212> TYPE: DNA
<213> ORGANISM: Artificial Sequence
<220> FEATURE:
<223> OTHER INFORMATION: PCR primer

<400> SEQUENCE: 399
ggacggtttc gaacttctag c                              21

<210> SEQ ID NO 400
<211> LENGTH: 39
<212> TYPE: DNA
<213> ORGANISM: Artificial Sequence
<220> FEATURE:
<223> OTHER INFORMATION: PCR primer

<400> SEQUENCE: 400
tgtaaaacga cggccagtcg aggcatcttc atcttcaac           39

<210> SEQ ID NO 401
<211> LENGTH: 21
<212> TYPE: DNA
<213> ORGANISM: Artificial Sequence
<220> FEATURE:
<223> OTHER INFORMATION: PCR primer

<400> SEQUENCE: 401
gataaagctc ccacagttcc c                              21

<210> SEQ ID NO 402
<211> LENGTH: 41
<212> TYPE: DNA
<213> ORGANISM: Artificial Sequence
<220> FEATURE:
<223> OTHER INFORMATION: PCR primer

<400> SEQUENCE: 402
tgtaaaacga cggccagtct cttttctctt caattttcaa t        41

<210> SEQ ID NO 403
<211> LENGTH: 21
<212> TYPE: DNA
<213> ORGANISM: Artificial Sequence
<220> FEATURE:
<223> OTHER INFORMATION: PCR primer

<400> SEQUENCE: 403
tacagttgcc catacaggag g                              21

<210> SEQ ID NO 404
<211> LENGTH: 39
<212> TYPE: DNA
<213> ORGANISM: Artificial Sequence
<220> FEATURE:
<223> OTHER INFORMATION: PCR primer

<400> SEQUENCE: 404
```
tgtaaaacga cggccagtca aacaggtgac gaggtgaat                                39

<210> SEQ ID NO 405
<211> LENGTH: 21
<212> TYPE: DNA
<213> ORGANISM: Artificial Sequence
<220> FEATURE:
<223> OTHER INFORMATION: PCR primer

<400> SEQUENCE: 405
atcaagatcg actgaaccac g                                                  21

<210> SEQ ID NO 406
<211> LENGTH: 39
<212> TYPE: DNA
<213> ORGANISM: Artificial Sequence
<220> FEATURE:
<223> OTHER INFORMATION: PCR primer

<400> SEQUENCE: 406
tgtaaaacga cggccagttt ggctttgatt gcttcaact                               39

<210> SEQ ID NO 407
<211> LENGTH: 21
<212> TYPE: DNA
<213> ORGANISM: Artificial Sequence
<220> FEATURE:
<223> OTHER INFORMATION: PCR primer

<400> SEQUENCE: 407
tgaggcttaa ccttaggagg c                                                  21

<210> SEQ ID NO 408
<211> LENGTH: 39
<212> TYPE: DNA
<213> ORGANISM: Artificial Sequence
<220> FEATURE:
<223> OTHER INFORMATION: PCR primer

<400> SEQUENCE: 408
tgtaaaacga cggccagttt tcaaatccaa gtggtggag                               39

<210> SEQ ID NO 409
<211> LENGTH: 21
<212> TYPE: DNA
<213> ORGANISM: Artificial Sequence
<220> FEATURE:
<223> OTHER INFORMATION: PCR primer

<400> SEQUENCE: 409
gggaaaccat ttcgtaccct a                                                  21

<210> SEQ ID NO 410
<211> LENGTH: 39
<212> TYPE: DNA
<213> ORGANISM: Artificial Sequence
<220> FEATURE:
<223> OTHER INFORMATION: PCR primer

<400> SEQUENCE: 410
tgtaaaacga cggccagtaa ttcccaattc tcattcgtg                               39

<210> SEQ ID NO 411
<211> LENGTH: 21
<212> TYPE: DNA

```
<213> ORGANISM: Artificial Sequence
<220> FEATURE:
<223> OTHER INFORMATION: PCR primer

<400> SEQUENCE: 411
ttgccatcgt agaaaatggt c                                              21

<210> SEQ ID NO 412
<211> LENGTH: 39
<212> TYPE: DNA
<213> ORGANISM: Artificial Sequence
<220> FEATURE:
<223> OTHER INFORMATION: PCR primer

<400> SEQUENCE: 412
tgtaaaacga cggccagtcc ttaacacatt tttgcttca                            39

<210> SEQ ID NO 413
<211> LENGTH: 21
<212> TYPE: DNA
<213> ORGANISM: Artificial Sequence
<220> FEATURE:
<223> OTHER INFORMATION: PCR primer

<400> SEQUENCE: 413
tgtcgtcttt tgaccatttc c                                              21

<210> SEQ ID NO 414
<211> LENGTH: 39
<212> TYPE: DNA
<213> ORGANISM: Artificial Sequence
<220> FEATURE:
<223> OTHER INFORMATION: PCR primer

<400> SEQUENCE: 414
tgtaaaacga cggccagttt atcatgtgca gacaatacc                            39

<210> SEQ ID NO 415
<211> LENGTH: 24
<212> TYPE: DNA
<213> ORGANISM: Artificial Sequence
<220> FEATURE:
<223> OTHER INFORMATION: PCR primer

<400> SEQUENCE: 415
gattaaacat acatgcaaca ttga                                           24

<210> SEQ ID NO 416
<211> LENGTH: 39
<212> TYPE: DNA
<213> ORGANISM: Artificial Sequence
<220> FEATURE:
<223> OTHER INFORMATION: PCR primer

<400> SEQUENCE: 416
tgtaaaacga cggccagtgg ttgaaatcga catgagagg                            39

<210> SEQ ID NO 417
<211> LENGTH: 21
<212> TYPE: DNA
<213> ORGANISM: Artificial Sequence
<220> FEATURE:
<223> OTHER INFORMATION: PCR primer

<400> SEQUENCE: 417
ccaacacttt aagcctccaa a                                              21
```

<210> SEQ ID NO 418
<211> LENGTH: 41
<212> TYPE: DNA
<213> ORGANISM: Artificial Sequence
<220> FEATURE:
<223> OTHER INFORMATION: PCR primer

<400> SEQUENCE: 418
tgtaaaacga cggccagttg ttctcctctc ttcgtctctt g        41

<210> SEQ ID NO 419
<211> LENGTH: 21
<212> TYPE: DNA
<213> ORGANISM: Artificial Sequence
<220> FEATURE:
<223> OTHER INFORMATION: PCR primer

<400> SEQUENCE: 419
ccggttctgt ttggtagtga a        21

<210> SEQ ID NO 420
<211> LENGTH: 39
<212> TYPE: DNA
<213> ORGANISM: Artificial Sequence
<220> FEATURE:
<223> OTHER INFORMATION: PCR primer

<400> SEQUENCE: 420
tgtaaaacga cggccagtaa ccagagaaaa atccaacca        39

<210> SEQ ID NO 421
<211> LENGTH: 21
<212> TYPE: DNA
<213> ORGANISM: Artificial Sequence
<220> FEATURE:
<223> OTHER INFORMATION: PCR primer

<400> SEQUENCE: 421
ccttaggcac attgaaaacc a        21

<210> SEQ ID NO 422
<211> LENGTH: 39
<212> TYPE: DNA
<213> ORGANISM: Artificial Sequence
<220> FEATURE:
<223> OTHER INFORMATION: PCR primer

<400> SEQUENCE: 422
tgtaaaacga cggccagtta agggttcatg ctcaccatc        39

<210> SEQ ID NO 423
<211> LENGTH: 23
<212> TYPE: DNA
<213> ORGANISM: Artificial Sequence
<220> FEATURE:
<223> OTHER INFORMATION: PCR primer

<400> SEQUENCE: 423
aacatgcaca attaagcatt caa        23

<210> SEQ ID NO 424
<211> LENGTH: 39
<212> TYPE: DNA
<213> ORGANISM: Artificial Sequence
<220> FEATURE:

<223> OTHER INFORMATION: PCR primer

<400> SEQUENCE: 424
tgtaaaacga cggccagtac ctgaaaggcc acaaaagat                                    39

<210> SEQ ID NO 425
<211> LENGTH: 21
<212> TYPE: DNA
<213> ORGANISM: Artificial Sequence
<220> FEATURE:
<223> OTHER INFORMATION: PCR primer

<400> SEQUENCE: 425
aattcgggtg gaataacaag c                                                      21

<210> SEQ ID NO 426
<211> LENGTH: 40
<212> TYPE: DNA
<213> ORGANISM: Artificial Sequence
<220> FEATURE:
<223> OTHER INFORMATION: PCR primer

<400> SEQUENCE: 426
tgtaaaacga cggccagttt gcctcggatt attacttgtg                                   40

<210> SEQ ID NO 427
<211> LENGTH: 21
<212> TYPE: DNA
<213> ORGANISM: Artificial Sequence
<220> FEATURE:
<223> OTHER INFORMATION: PCR primer

<400> SEQUENCE: 427
gcaatcacct tagcattttg g                                                      21

<210> SEQ ID NO 428
<211> LENGTH: 39
<212> TYPE: DNA
<213> ORGANISM: Artificial Sequence
<220> FEATURE:
<223> OTHER INFORMATION: PCR primer

<400> SEQUENCE: 428
tgtaaaacga cggccagtgc cagttttggg caatttat                                    39

<210> SEQ ID NO 429
<211> LENGTH: 21
<212> TYPE: DNA
<213> ORGANISM: Artificial Sequence
<220> FEATURE:
<223> OTHER INFORMATION: PCR primer

<400> SEQUENCE: 429
gttcaagcat ggaaagtttg g                                                      21

<210> SEQ ID NO 430
<211> LENGTH: 42
<212> TYPE: DNA
<213> ORGANISM: Artificial Sequence
<220> FEATURE:
<223> OTHER INFORMATION: PCR primer

<400> SEQUENCE: 430
tgtaaaacga cggccagtgg gacctaatat gatgaactta ca                                42

```
<210> SEQ ID NO 431
<211> LENGTH: 21
<212> TYPE: DNA
<213> ORGANISM: Artificial Sequence
<220> FEATURE:
<223> OTHER INFORMATION: PCR primer

<400> SEQUENCE: 431
tgacagtttc cacaatcctc c                                              21

<210> SEQ ID NO 432
<211> LENGTH: 42
<212> TYPE: DNA
<213> ORGANISM: Artificial Sequence
<220> FEATURE:
<223> OTHER INFORMATION: PCR primer

<400> SEQUENCE: 432
tgtaaaacga cggccagtga cgaactcttt tcttttctga ca                       42

<210> SEQ ID NO 433
<211> LENGTH: 21
<212> TYPE: DNA
<213> ORGANISM: Artificial Sequence
<220> FEATURE:
<223> OTHER INFORMATION: PCR primer

<400> SEQUENCE: 433
acaagaagaa gattgcgacg a                                              21

<210> SEQ ID NO 434
<211> LENGTH: 40
<212> TYPE: DNA
<213> ORGANISM: Artificial Sequence
<220> FEATURE:
<223> OTHER INFORMATION: PCR primer

<400> SEQUENCE: 434
tgtaaaacga cggccagttg aaggaagaag gaagaaggaa                          40

<210> SEQ ID NO 435
<211> LENGTH: 21
<212> TYPE: DNA
<213> ORGANISM: Artificial Sequence
<220> FEATURE:
<223> OTHER INFORMATION: PCR primer

<400> SEQUENCE: 435
aatttggact ttgattgtgc g                                              21

<210> SEQ ID NO 436
<211> LENGTH: 41
<212> TYPE: DNA
<213> ORGANISM: Artificial Sequence
<220> FEATURE:
<223> OTHER INFORMATION: PCR primer

<400> SEQUENCE: 436
tgtaaaacga cggccagtca agaaccagat catcaacaac a                        41

<210> SEQ ID NO 437
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 437
aaatttcttt ccattggctc c                                              21

<210> SEQ ID NO 438
<211> LENGTH: 42
<212> TYPE: DNA
<213> ORGANISM: Artificial Sequence
<220> FEATURE:
<223> OTHER INFORMATION: PCR primer

<400> SEQUENCE: 438
tgtaaaacga cggccagttt catgaatttg cttctattgc at                       42

<210> SEQ ID NO 439
<211> LENGTH: 21
<212> TYPE: DNA
<213> ORGANISM: Artificial Sequence
<220> FEATURE:
<223> OTHER INFORMATION: PCR primer

<400> SEQUENCE: 439 agcttttca acgagttcag c                                               21

<210> SEQ ID NO 440
<211> LENGTH: 39
<212> TYPE: DNA
<213> ORGANISM: Artificial Sequence
<220> FEATURE:
<223> OTHER INFORMATION: PCR primer

<400> SEQUENCE: 440
tgtaaaacga cggccagttt tcatcaacat caaacaccg                           39

<210> SEQ ID NO 441
<211> LENGTH: 21
<212> TYPE: DNA
<213> ORGANISM: Artificial Sequence
<220> FEATURE:
<223> OTHER INFORMATION: PCR primer

<400> SEQUENCE: 441
ttcttggctt cgacttcttc a                                              21

<210> SEQ ID NO 442
<211> LENGTH: 37
<212> TYPE: DNA
<213> ORGANISM: Artificial Sequence
<220> FEATURE:
<223> OTHER INFORMATION: PCR primer

<400> SEQUENCE: 442
tgtaaaacga cggccagtcc gattggactc ggaactt                             37

<210> SEQ ID NO 443
<211> LENGTH: 21
<212> TYPE: DNA
<213> ORGANISM: Artificial Sequence
<220> FEATURE:
<223> OTHER INFORMATION: PCR primer

<400> SEQUENCE: 443
ggatttcgtt tgggttcatt t                                              21

<210> SEQ ID NO 444
<211> LENGTH: 39
```

-continued

<212> TYPE: DNA
<213> ORGANISM: Artificial Sequence
<220> FEATURE:
<223> OTHER INFORMATION: PCR primer

<400> SEQUENCE: 444
tgtaaaacga cggccagttc tgtaacacag gcagagtcg                    39

<210> SEQ ID NO 445
<211> LENGTH: 21
<212> TYPE: DNA
<213> ORGANISM: Artificial Sequence
<220> FEATURE:
<223> OTHER INFORMATION: PCR primer

<400> SEQUENCE: 445
cacacatcaa agcccctaaa a                                       21

<210> SEQ ID NO 446
<211> LENGTH: 39
<212> TYPE: DNA
<213> ORGANISM: Artificial Sequence
<220> FEATURE:
<223> OTHER INFORMATION: PCR primer

<400> SEQUENCE: 446
tgtaaaacga cggccagtac tccatcaact ggttcaccg                    39

<210> SEQ ID NO 447
<211> LENGTH: 21
<212> TYPE: DNA
<213> ORGANISM: Artificial Sequence
<220> FEATURE:
<223> OTHER INFORMATION: PCR primer

<400> SEQUENCE: 447
cagttgatgc atagaaacgc a                                       21

<210> SEQ ID NO 448
<211> LENGTH: 40
<212> TYPE: DNA
<213> ORGANISM: Artificial Sequence
<220> FEATURE:
<223> OTHER INFORMATION: PCR primer

<400> SEQUENCE: 448
tgtaaaacga cggccagtaa gcgatttcat tagtagttgt                   40

<210> SEQ ID NO 449
<211> LENGTH: 21
<212> TYPE: DNA
<213> ORGANISM: Artificial Sequence
<220> FEATURE:
<223> OTHER INFORMATION: PCR primer

<400> SEQUENCE: 449
tcaccagcac atgaatcaaa a                                       21

<210> SEQ ID NO 450
<211> LENGTH: 40
<212> TYPE: DNA
<213> ORGANISM: Artificial Sequence
<220> FEATURE:
<223> OTHER INFORMATION: PCR primer

<400> SEQUENCE: 450

-continued

```
tgtaaaacga cggccagtaa caacctagat tttctcgacc                40

<210> SEQ ID NO 451
<211> LENGTH: 21
<212> TYPE: DNA
<213> ORGANISM: Artificial Sequence
<220> FEATURE:
<223> OTHER INFORMATION: PCR primer

<400> SEQUENCE: 451
agggttgatg cagatgttac g                                    21

<210> SEQ ID NO 452
<211> LENGTH: 39
<212> TYPE: DNA
<213> ORGANISM: Artificial Sequence
<220> FEATURE:
<223> OTHER INFORMATION: PCR primer

<400> SEQUENCE: 452
tgtaaaacga cggccagtat tgcaatcatc ttctcccct                 39

<210> SEQ ID NO 453
<211> LENGTH: 22
<212> TYPE: DNA
<213> ORGANISM: Artificial Sequence
<220> FEATURE:
<223> OTHER INFORMATION: PCR primer

<400> SEQUENCE: 453
aacaatatga tctggcatgt cg                                   22

<210> SEQ ID NO 454
<211> LENGTH: 39
<212> TYPE: DNA
<213> ORGANISM: Artificial Sequence
<220> FEATURE:
<223> OTHER INFORMATION: PCR primer

<400> SEQUENCE: 454
tgtaaaacga cggccagtgg aagatcacca ttttgtcca                 39

<210> SEQ ID NO 455
<211> LENGTH: 21
<212> TYPE: DNA
<213> ORGANISM: Artificial Sequence
<220> FEATURE:
<223> OTHER INFORMATION: PCR primer

<400> SEQUENCE: 455
aggtacaagc catgatgtcc a                                    21

<210> SEQ ID NO 456
<211> LENGTH: 40
<212> TYPE: DNA
<213> ORGANISM: Artificial Sequence
<220> FEATURE:
<223> OTHER INFORMATION: PCR primer

<400> SEQUENCE: 456
tgtaaaacga cggccagttt tccaaacttt ccttctttg                 40

<210> SEQ ID NO 457
<211> LENGTH: 21
<212> TYPE: DNA
<213> ORGANISM: Artificial Sequence
```

```
<220> FEATURE:
<223> OTHER INFORMATION: PCR primer

<400> SEQUENCE: 457
acaagaagaa gattgcgacg a                                              21

<210> SEQ ID NO 458
<211> LENGTH: 40
<212> TYPE: DNA
<213> ORGANISM: Artificial Sequence
<220> FEATURE:
<223> OTHER INFORMATION: PCR primer

<400> SEQUENCE: 458
tgtaaaacga cggccagttg aaggaagaag gaagaaggaa                          40

<210> SEQ ID NO 459
<211> LENGTH: 21
<212> TYPE: DNA
<213> ORGANISM: Artificial Sequence
<220> FEATURE:
<223> OTHER INFORMATION: PCR primer

<400> SEQUENCE: 459
cgcagcacat gtaacttgaa a                                              21

<210> SEQ ID NO 460
<211> LENGTH: 38
<212> TYPE: DNA
<213> ORGANISM: Artificial Sequence
<220> FEATURE:
<223> OTHER INFORMATION: PCR primer

<400> SEQUENCE: 460
tgtaaaacga cggccagtca cattctcttc gtgccctc                            38

<210> SEQ ID NO 461
<211> LENGTH: 21
<212> TYPE: DNA
<213> ORGANISM: Artificial Sequence
<220> FEATURE:
<223> OTHER INFORMATION: PCR primer

<400> SEQUENCE: 461
tccgaaaaag gtgacagatt g                                              21

<210> SEQ ID NO 462
<211> LENGTH: 39
<212> TYPE: DNA
<213> ORGANISM: Artificial Sequence
<220> FEATURE:
<223> OTHER INFORMATION: PCR primer

<400> SEQUENCE: 462
tgtaaaacga cggccagtgg ctcacaacaa caacaaaat                           39

<210> SEQ ID NO 463
<211> LENGTH: 22
<212> TYPE: DNA
<213> ORGANISM: Artificial Sequence
<220> FEATURE:
<223> OTHER INFORMATION: PCR primer

<400> SEQUENCE: 463
ccaaacagat ctaaagttcc ca                                             22
```

```
<210> SEQ ID NO 464
<211> LENGTH: 39
<212> TYPE: DNA
<213> ORGANISM: Artificial Sequence
<220> FEATURE:
<223> OTHER INFORMATION: PCR primer

<400> SEQUENCE: 464
tgtaaaacga cggccagttg cttgattatt gctaatcgg                              39

<210> SEQ ID NO 465
<211> LENGTH: 21
<212> TYPE: DNA
<213> ORGANISM: Artificial Sequence
<220> FEATURE:
<223> OTHER INFORMATION: PCR primer

<400> SEQUENCE: 465
taaatgcaag gtaggtggtg g                                                  21

<210> SEQ ID NO 466
<211> LENGTH: 38
<212> TYPE: DNA
<213> ORGANISM: Artificial Sequence
<220> FEATURE:
<223> OTHER INFORMATION: PCR primer

<400> SEQUENCE: 466
tgtaaaacga cggccagtcg aggacgagtt ctggtcaa                                38

<210> SEQ ID NO 467
<211> LENGTH: 21
<212> TYPE: DNA
<213> ORGANISM: Artificial Sequence
<220> FEATURE:
<223> OTHER INFORMATION: PCR primer

<400> SEQUENCE: 467
aagaccaaga ggaatcaccg t                                                  21

<210> SEQ ID NO 468
<211> LENGTH: 39
<212> TYPE: DNA
<213> ORGANISM: Artificial Sequence
<220> FEATURE:
<223> OTHER INFORMATION: PCR primer

<400> SEQUENCE: 468
tgtaaaacga cggccagtta atttcattcg cgatcacac                              39

<210> SEQ ID NO 469
<211> LENGTH: 21
<212> TYPE: DNA
<213> ORGANISM: Artificial Sequence
<220> FEATURE:
<223> OTHER INFORMATION: PCR primer

<400> SEQUENCE: 469
tgaatgtgag gaagtgggtt t                                                  21

<210> SEQ ID NO 470
<211> LENGTH: 42
<212> TYPE: DNA
<213> ORGANISM: Artificial Sequence
<220> FEATURE:
<223> OTHER INFORMATION: PCR primer
```

```
<400> SEQUENCE: 470
tgtaaaacga cggccagtcc gcctcaaata gttataaact tc                    42

<210> SEQ ID NO 471
<211> LENGTH: 21
<212> TYPE: DNA
<213> ORGANISM: Artificial Sequence
<220> FEATURE:
<223> OTHER INFORMATION: PCR primer

<400> SEQUENCE: 471
agtactattg caatggcgtg g                                           21

<210> SEQ ID NO 472
<211> LENGTH: 39
<212> TYPE: DNA
<213> ORGANISM: Artificial Sequence
<220> FEATURE:
<223> OTHER INFORMATION: PCR primer

<400> SEQUENCE: 472
tgtaaaacga cggccagtgg tttcgcttgg aattctgat                        39

<210> SEQ ID NO 473
<211> LENGTH: 21
<212> TYPE: DNA
<213> ORGANISM: Artificial Sequence
<220> FEATURE:
<223> OTHER INFORMATION: PCR primer

<400> SEQUENCE: 473
atttttccac ttctggtggg a                                           21

<210> SEQ ID NO 474
<211> LENGTH: 39
<212> TYPE: DNA
<213> ORGANISM: Artificial Sequence
<220> FEATURE:
<223> OTHER INFORMATION: PCR primer

<400> SEQUENCE: 474
tgtaaaacga cggccagtca acacaatcat tttgggagc                        39

<210> SEQ ID NO 475
<211> LENGTH: 23
<212> TYPE: DNA
<213> ORGANISM: Artificial Sequence
<220> FEATURE:
<223> OTHER INFORMATION: PCR primer

<400> SEQUENCE: 475
tcttgttgat ataatctacg gaa                                         23

<210> SEQ ID NO 476
<211> LENGTH: 39
<212> TYPE: DNA
<213> ORGANISM: Artificial Sequence
<220> FEATURE:
<223> OTHER INFORMATION: PCR primer

<400> SEQUENCE: 476
tgtaaaacga cggccagtcc tgatggtcat cactaagcc                        39

<210> SEQ ID NO 477
```

```
<211> LENGTH: 21
<212> TYPE: DNA
<213> ORGANISM: Artificial Sequence
<220> FEATURE:
<223> OTHER INFORMATION: PCR primer

<400> SEQUENCE: 477
gggacccaat aaccgaaaat a                                              21

<210> SEQ ID NO 478
<211> LENGTH: 40
<212> TYPE: DNA
<213> ORGANISM: Artificial Sequence
<220> FEATURE:
<223> OTHER INFORMATION: PCR primer

<400> SEQUENCE: 478
tgtaaaacga cggccagttt tgataaacca atctcccaca                          40

<210> SEQ ID NO 479
<211> LENGTH: 20
<212> TYPE: DNA
<213> ORGANISM: Artificial Sequence
<220> FEATURE:
<223> OTHER INFORMATION: PCR primer

<400> SEQUENCE: 479
gaaggttttg ggtggtgatg                                                20

<210> SEQ ID NO 480
<211> LENGTH: 38
<212> TYPE: DNA
<213> ORGANISM: Artificial Sequence
<220> FEATURE:
<223> OTHER INFORMATION: PCR primer

<400> SEQUENCE: 480
tgtaaaacga cggccagtcc atggctcttt cctaccaa                            38

<210> SEQ ID NO 481
<211> LENGTH: 21
<212> TYPE: DNA
<213> ORGANISM: Artificial Sequence
<220> FEATURE:
<223> OTHER INFORMATION: PCR primer

<400> SEQUENCE: 481
tggttgatca atgttcctcc t                                              21

<210> SEQ ID NO 482
<211> LENGTH: 38
<212> TYPE: DNA
<213> ORGANISM: Artificial Sequence
<220> FEATURE:
<223> OTHER INFORMATION: PCR primer

<400> SEQUENCE: 482
tgtaaaacga cggccagtaa agagattggg tcggtgaa                            38

<210> SEQ ID NO 483
<211> LENGTH: 23
<212> TYPE: DNA
<213> ORGANISM: Artificial Sequence
<220> FEATURE:
<223> OTHER INFORMATION: PCR primer

<400> SEQUENCE: 483
```

```
aataaacaca gattccaaat cca                                           23

<210> SEQ ID NO 484
<211> LENGTH: 42
<212> TYPE: DNA
<213> ORGANISM: Artificial Sequence
<220> FEATURE:
<223> OTHER INFORMATION: PCR primer

<400> SEQUENCE: 484
tgtaaaacga cggccagttc ttcatcgctt tcttctattt ca                      42

<210> SEQ ID NO 485
<211> LENGTH: 20
<212> TYPE: DNA
<213> ORGANISM: Artificial Sequence
<220> FEATURE:
<223> OTHER INFORMATION: PCR primer

<400> SEQUENCE: 485
tcaggacaaa ctgccatttc                                               20

<210> SEQ ID NO 486
<211> LENGTH: 39
<212> TYPE: DNA
<213> ORGANISM: Artificial Sequence
<220> FEATURE:
<223> OTHER INFORMATION: PCR primer

<400> SEQUENCE: 486
tgtaaaacga cggccagttg cattgaagca aattaacga                          39

<210> SEQ ID NO 487
<211> LENGTH: 20
<212> TYPE: DNA
<213> ORGANISM: Artificial Sequence
<220> FEATURE:
<223> OTHER INFORMATION: PCR primer

<400> SEQUENCE: 487
tacgtagccc cttgctcatt                                               20

<210> SEQ ID NO 488
<211> LENGTH: 39
<212> TYPE: DNA
<213> ORGANISM: Artificial Sequence
<220> FEATURE:
<223> OTHER INFORMATION: PCR primer

<400> SEQUENCE: 488
tgtaaaacga cggccagtca aaccatttcc tccattgtg                          39

<210> SEQ ID NO 489
<211> LENGTH: 21
<212> TYPE: DNA
<213> ORGANISM: Artificial Sequence
<220> FEATURE:
<223> OTHER INFORMATION: PCR primer

<400> SEQUENCE: 489
ttgggttgtc aataatgctc a                                             21

<210> SEQ ID NO 490
<211> LENGTH: 40
<212> TYPE: DNA
```

```
<213> ORGANISM: Artificial Sequence
<220> FEATURE:
<223> OTHER INFORMATION: PCR primer

<400> SEQUENCE: 490
tgtaaaacga cggccagttt gtcacgagtg ttggaatttt                              40

<210> SEQ ID NO 491
<211> LENGTH: 20
<212> TYPE: DNA
<213> ORGANISM: Artificial Sequence
<220> FEATURE:
<223> OTHER INFORMATION: PCR primer

<400> SEQUENCE: 491
gcgtgctagg tttgagagga                                                    20

<210> SEQ ID NO 492
<211> LENGTH: 41
<212> TYPE: DNA
<213> ORGANISM: Artificial Sequence
<220> FEATURE:
<223> OTHER INFORMATION: PCR primer

<400> SEQUENCE: 492
tgtaaaacga cggccagttc aaaaccctaa aacctttct c                             41

<210> SEQ ID NO 493
<211> LENGTH: 20
<212> TYPE: DNA
<213> ORGANISM: Artificial Sequence
<220> FEATURE:
<223> OTHER INFORMATION: PCR primer

<400> SEQUENCE: 493
ttctcttcaa gtgggaggta                                                    20

<210> SEQ ID NO 494
<211> LENGTH: 38
<212> TYPE: DNA
<213> ORGANISM: Artificial Sequence
<220> FEATURE:
<223> OTHER INFORMATION: PCR primer

<400> SEQUENCE: 494
tgtaaaacga cggccagtaa atggaagaaa gtgtcacg                                38

<210> SEQ ID NO 495
<211> LENGTH: 21
<212> TYPE: DNA
<213> ORGANISM: Artificial Sequence
<220> FEATURE:
<223> OTHER INFORMATION: PCR primer

<400> SEQUENCE: 495
tgcaacagaa gaagcaaaac a                                                  21

<210> SEQ ID NO 496
<211> LENGTH: 42
<212> TYPE: DNA
<213> ORGANISM: Artificial Sequence
<220> FEATURE:
<223> OTHER INFORMATION: PCR primer

<400> SEQUENCE: 496
tgtaaaacga cggccagttc tagaaaaagc aatgatgtga ga                           42
```

```
<210> SEQ ID NO 497
<211> LENGTH: 20
<212> TYPE: DNA
<213> ORGANISM: Artificial Sequence
<220> FEATURE:
<223> OTHER INFORMATION: PCR primer

<400> SEQUENCE: 497
aaggaacaat cccagttttt                                             20

<210> SEQ ID NO 498
<211> LENGTH: 38
<212> TYPE: DNA
<213> ORGANISM: Artificial Sequence
<220> FEATURE:
<223> OTHER INFORMATION: PCR primer

<400> SEQUENCE: 498
tgtaaaacga cggccagtgc gtaacgtaac aacattca                         38

<210> SEQ ID NO 499
<211> LENGTH: 20
<212> TYPE: DNA
<213> ORGANISM: Artificial Sequence
<220> FEATURE:
<223> OTHER INFORMATION: PCR primer

<400> SEQUENCE: 499
ccttagccaa gcaagtaaaa                                             20

<210> SEQ ID NO 500
<211> LENGTH: 40
<212> TYPE: DNA
<213> ORGANISM: Artificial Sequence
<220> FEATURE:
<223> OTHER INFORMATION: PCR primer

<400> SEQUENCE: 500
tgtaaaacga cggccagttt cttcttctag gaatttggag                       40

<210> SEQ ID NO 501
<211> LENGTH: 20
<212> TYPE: DNA
<213> ORGANISM: Artificial Sequence
<220> FEATURE:
<223> OTHER INFORMATION: PCR primer

<400> SEQUENCE: 501
tgagagcatt gatttttgtg                                             20

<210> SEQ ID NO 502
<211> LENGTH: 38
<212> TYPE: DNA
<213> ORGANISM: Artificial Sequence
<220> FEATURE:
<223> OTHER INFORMATION: PCR primer

<400> SEQUENCE: 502
tgtaaaacga cggccagttt cgcagaacct aaattcat                         38

<210> SEQ ID NO 503
<211> LENGTH: 20
<212> TYPE: DNA
<213> ORGANISM: Artificial Sequence
<220> FEATURE:
```

<223> OTHER INFORMATION: PCR primer

<400> SEQUENCE: 503
ggattgtgat gaagaaatgg                                          20

<210> SEQ ID NO 504
<211> LENGTH: 38
<212> TYPE: DNA
<213> ORGANISM: Artificial Sequence
<220> FEATURE:
<223> OTHER INFORMATION: PCR primer

<400> SEQUENCE: 504
tgtaaaacga cggccagtta tctcccttct ccttctcc                      38

<210> SEQ ID NO 505
<211> LENGTH: 20
<212> TYPE: DNA
<213> ORGANISM: Artificial Sequence
<220> FEATURE:
<223> OTHER INFORMATION: PCR primer

<400> SEQUENCE: 505
gtgggtgagg atgtgtgtat                                          20

<210> SEQ ID NO 506
<211> LENGTH: 38
<212> TYPE: DNA
<213> ORGANISM: Artificial Sequence
<220> FEATURE:
<223> OTHER INFORMATION: PCR primer

<400> SEQUENCE: 506
tgtaaaacga cggccagtta ggtcatggct attgcttc                      38

<210> SEQ ID NO 507
<211> LENGTH: 20
<212> TYPE: DNA
<213> ORGANISM: Artificial Sequence
<220> FEATURE:
<223> OTHER INFORMATION: PCR primer

<400> SEQUENCE: 507
cgttgatgat gttcttgatg                                          20

<210> SEQ ID NO 508
<211> LENGTH: 38
<212> TYPE: DNA
<213> ORGANISM: Artificial Sequence
<220> FEATURE:
<223> OTHER INFORMATION: PCR primer

<400> SEQUENCE: 508
tgtaaaacga cggccagtgc ctgaactatt gtgaatgg                      38

<210> SEQ ID NO 509
<211> LENGTH: 20
<212> TYPE: DNA
<213> ORGANISM: Artificial Sequence
<220> FEATURE:
<223> OTHER INFORMATION: PCR primer

<400> SEQUENCE: 509
tgaaattcac atcaactgga                                          20

```
<210> SEQ ID NO 510
<211> LENGTH: 38
<212> TYPE: DNA
<213> ORGANISM: Artificial Sequence
<220> FEATURE:
<223> OTHER INFORMATION: PCR primer

<400> SEQUENCE: 510
tgtaaaacga cggccagtca ccaccttcac ctaagaaa                          38

<210> SEQ ID NO 511
<211> LENGTH: 21
<212> TYPE: DNA
<213> ORGANISM: Artificial Sequence
<220> FEATURE:
<223> OTHER INFORMATION: PCR primer

<400> SEQUENCE: 511
agcgtaaagt aaaacccttt c                                           21

<210> SEQ ID NO 512
<211> LENGTH: 38
<212> TYPE: DNA
<213> ORGANISM: Artificial Sequence
<220> FEATURE:
<223> OTHER INFORMATION: PCR primer

<400> SEQUENCE: 512
tgtaaaacga cggccagttt gggcttaatt tgactgat                          38

<210> SEQ ID NO 513
<211> LENGTH: 20
<212> TYPE: DNA
<213> ORGANISM: Artificial Sequence
<220> FEATURE:
<223> OTHER INFORMATION: PCR primer

<400> SEQUENCE: 513
ggtcatacga gctcctccat                                             20

<210> SEQ ID NO 514
<211> LENGTH: 37
<212> TYPE: DNA
<213> ORGANISM: Artificial Sequence
<220> FEATURE:
<223> OTHER INFORMATION: PCR primer

<400> SEQUENCE: 514
tgtaaaacga cggccagtcc ctgggttttt gatccag                           37

<210> SEQ ID NO 515
<211> LENGTH: 20
<212> TYPE: DNA
<213> ORGANISM: Artificial Sequence
<220> FEATURE:
<223> OTHER INFORMATION: PCR primer

<400> SEQUENCE: 515
cattggtgga cgaggtctct                                             20

<210> SEQ ID NO 516
<211> LENGTH: 41
<212> TYPE: DNA
<213> ORGANISM: Artificial Sequence
<220> FEATURE:
<223> OTHER INFORMATION: PCR primer
```

<400> SEQUENCE: 516
tgtaaaacga cggccagttc cccttaagct tcactctttt c          41

<210> SEQ ID NO 517
<211> LENGTH: 19
<212> TYPE: DNA
<213> ORGANISM: Artificial Sequence
<220> FEATURE:
<223> OTHER INFORMATION: PCR primer

<400> SEQUENCE: 517
ccattgcggt ggctactct          19

<210> SEQ ID NO 518
<211> LENGTH: 38
<212> TYPE: DNA
<213> ORGANISM: Artificial Sequence
<220> FEATURE:
<223> OTHER INFORMATION: PCR primer

<400> SEQUENCE: 518
tgtaaaacga cggccagttc cgatcttgcg tcctaact          38

<210> SEQ ID NO 519
<211> LENGTH: 20
<212> TYPE: DNA
<213> ORGANISM: Artificial Sequence
<220> FEATURE:
<223> OTHER INFORMATION: PCR primer

<400> SEQUENCE: 519
ggcaggaaca gatccttgaa          20

<210> SEQ ID NO 520
<211> LENGTH: 45
<212> TYPE: DNA
<213> ORGANISM: Artificial Sequence
<220> FEATURE:
<223> OTHER INFORMATION: PCR primer

<400> SEQUENCE: 520
tgtaaaacga cggccagtga agaagaaaaa gagatagatc tgtgg          45

<210> SEQ ID NO 521
<211> LENGTH: 20
<212> TYPE: DNA
<213> ORGANISM: Artificial Sequence
<220> FEATURE:
<223> OTHER INFORMATION: PCR primer

<400> SEQUENCE: 521
aacctacgct agggttgcag          20

<210> SEQ ID NO 522
<211> LENGTH: 39
<212> TYPE: DNA
<213> ORGANISM: Artificial Sequence
<220> FEATURE:
<223> OTHER INFORMATION: PCR primer

<400> SEQUENCE: 522
tgtaaaacga cggccagtaa gtgccaaaga acagggttt          39

<210> SEQ ID NO 523
<211> LENGTH: 20

```
<212> TYPE: DNA
<213> ORGANISM: Artificial Sequence
<220> FEATURE:
<223> OTHER INFORMATION: PCR primer

<400> SEQUENCE: 523
tcacaaaaac tgcataaagc                                              20

<210> SEQ ID NO 524
<211> LENGTH: 38
<212> TYPE: DNA
<213> ORGANISM: Artificial Sequence
<220> FEATURE:
<223> OTHER INFORMATION: PCR primer

<400> SEQUENCE: 524
tgtaaaacga cggccagtct agtgccaaca caaaaaca                          38

<210> SEQ ID NO 525
<211> LENGTH: 20
<212> TYPE: DNA
<213> ORGANISM: Artificial Sequence
<220> FEATURE:
<223> OTHER INFORMATION: PCR primer

<400> SEQUENCE: 525
cccttcacag aatgattgat                                              20

<210> SEQ ID NO 526
<211> LENGTH: 38
<212> TYPE: DNA
<213> ORGANISM: Artificial Sequence
<220> FEATURE:
<223> OTHER INFORMATION: PCR primer

<400> SEQUENCE: 526
tgtaaaacga cggccagtgg ttcgtgtatt tgttcgat                          38

<210> SEQ ID NO 527
<211> LENGTH: 20
<212> TYPE: DNA
<213> ORGANISM: Artificial Sequence
<220> FEATURE:
<223> OTHER INFORMATION: PCR primer

<400> SEQUENCE: 527
acaaaaactc tcccggcttt                                              20

<210> SEQ ID NO 528
<211> LENGTH: 45
<212> TYPE: DNA
<213> ORGANISM: Artificial Sequence
<220> FEATURE:
<223> OTHER INFORMATION: PCR primer

<400> SEQUENCE: 528
tgtaaaacga cggccagtag tatagtgatg aagtggtagt gaaca                  45

<210> SEQ ID NO 529
<211> LENGTH: 20
<212> TYPE: DNA
<213> ORGANISM: Artificial Sequence
<220> FEATURE:
<223> OTHER INFORMATION: PCR primer

<400> SEQUENCE: 529
```

```
gggaaaaggt gtagccattg                                              20
```

<210> SEQ ID NO 530
<211> LENGTH: 43
<212> TYPE: DNA
<213> ORGANISM: Artificial Sequence
<220> FEATURE:
<223> OTHER INFORMATION: PCR primer

<400> SEQUENCE: 530

```
tgtaaaacga cggccagttc tgagagagag acaaacaaaa caa                    43
```

<210> SEQ ID NO 531
<211> LENGTH: 20
<212> TYPE: DNA
<213> ORGANISM: Artificial Sequence
<220> FEATURE:
<223> OTHER INFORMATION: PCR primer

<400> SEQUENCE: 531

```
cagggtcaga gcaacaatca                                              20
```

<210> SEQ ID NO 532
<211> LENGTH: 38
<212> TYPE: DNA
<213> ORGANISM: Artificial Sequence
<220> FEATURE:
<223> OTHER INFORMATION: PCR primer

<400> SEQUENCE: 532

```
tgtaaaacga cggccagtgc tacaacagcg ctacatcg                          38
```

<210> SEQ ID NO 533
<211> LENGTH: 20
<212> TYPE: DNA
<213> ORGANISM: Artificial Sequence
<220> FEATURE:
<223> OTHER INFORMATION: PCR primer

<400> SEQUENCE: 533

```
aggaaggaga gggacgaaag                                              20
```

<210> SEQ ID NO 534
<211> LENGTH: 38
<212> TYPE: DNA
<213> ORGANISM: Artificial Sequence
<220> FEATURE:
<223> OTHER INFORMATION: PCR primer

<400> SEQUENCE: 534

```
tgtaaaacga cggccagtaa aggtgttggg ttttgtgg                          38
```

<210> SEQ ID NO 535
<211> LENGTH: 20
<212> TYPE: DNA
<213> ORGANISM: Artificial Sequence
<220> FEATURE:
<223> OTHER INFORMATION: PCR primer

<400> SEQUENCE: 535

```
ctgctttggt ttggaagaaa                                              20
```

<210> SEQ ID NO 536
<211> LENGTH: 42
<212> TYPE: DNA
<213> ORGANISM: Artificial Sequence

```
<220> FEATURE:
<223> OTHER INFORMATION: PCR primer

<400> SEQUENCE: 536
tgtaaaacga cggccagtgg aaagaatatg caatttctcg at                42

<210> SEQ ID NO 537
<211> LENGTH: 21
<212> TYPE: DNA
<213> ORGANISM: Artificial Sequence
<220> FEATURE:
<223> OTHER INFORMATION: PCR primer

<400> SEQUENCE: 537
tgaactttga agccacattg a                                       21

<210> SEQ ID NO 538
<211> LENGTH: 39
<212> TYPE: DNA
<213> ORGANISM: Artificial Sequence
<220> FEATURE:
<223> OTHER INFORMATION: PCR primer

<400> SEQUENCE: 538
tgtaaaacga cggccagtaa aatccagaag cacgagtga                    39

<210> SEQ ID NO 539
<211> LENGTH: 21
<212> TYPE: DNA
<213> ORGANISM: Artificial Sequence
<220> FEATURE:
<223> OTHER INFORMATION: PCR primer

<400> SEQUENCE: 539
gccctaaaag ttgaaagagc a                                       21

<210> SEQ ID NO 540
<211> LENGTH: 38
<212> TYPE: DNA
<213> ORGANISM: Artificial Sequence
<220> FEATURE:
<223> OTHER INFORMATION: PCR primer

<400> SEQUENCE: 540
tgtaaaacga cggccagtca cgagggaaca cttcatca                     38

<210> SEQ ID NO 541
<211> LENGTH: 20
<212> TYPE: DNA
<213> ORGANISM: Artificial Sequence
<220> FEATURE:
<223> OTHER INFORMATION: PCR primer

<400> SEQUENCE: 541
ccaatgcaat tcggtaatcc                                         20

<210> SEQ ID NO 542
<211> LENGTH: 38
<212> TYPE: DNA
<213> ORGANISM: Artificial Sequence
<220> FEATURE:
<223> OTHER INFORMATION: PCR primer

<400> SEQUENCE: 542
tgtaaaacga cggccagtcg ttatttatcc ctccgggt                     38
```

<210> SEQ ID NO 543
<211> LENGTH: 20
<212> TYPE: DNA
<213> ORGANISM: Artificial Sequence
<220> FEATURE:
<223> OTHER INFORMATION: PCR primer

<400> SEQUENCE: 543
tcacaatggg cacctaatca                                              20

<210> SEQ ID NO 544
<211> LENGTH: 38
<212> TYPE: DNA
<213> ORGANISM: Artificial Sequence
<220> FEATURE:
<223> OTHER INFORMATION: PCR primer

<400> SEQUENCE: 544
tgtaaaacga cggccagtca attttcgctg actgacca                          38

<210> SEQ ID NO 545
<211> LENGTH: 20
<212> TYPE: DNA
<213> ORGANISM: Artificial Sequence
<220> FEATURE:
<223> OTHER INFORMATION: PCR primer

<400> SEQUENCE: 545
gccatttgct tcaaccttgt                                              20

<210> SEQ ID NO 546
<211> LENGTH: 38
<212> TYPE: DNA
<213> ORGANISM: Artificial Sequence
<220> FEATURE:
<223> OTHER INFORMATION: PCR primer

<400> SEQUENCE: 546
tgtaaaacga cggccagtgc cattgctgga atcgtaat                          38

<210> SEQ ID NO 547
<211> LENGTH: 20
<212> TYPE: DNA
<213> ORGANISM: Artificial Sequence
<220> FEATURE:
<223> OTHER INFORMATION: PCR primer

<400> SEQUENCE: 547
gggcaaaaca ggaaatgaaa                                              20

<210> SEQ ID NO 548
<211> LENGTH: 38
<212> TYPE: DNA
<213> ORGANISM: Artificial Sequence
<220> FEATURE:
<223> OTHER INFORMATION: PCR primer

<400> SEQUENCE: 548
tgtaaaacga cggccagtat tcgataagga tggcgatg                          38

<210> SEQ ID NO 549
<211> LENGTH: 20
<212> TYPE: DNA
<213> ORGANISM: Artificial Sequence
<220> FEATURE:
<223> OTHER INFORMATION: PCR primer

<400> SEQUENCE: 549
tgtcgtcgta tcatttccga                                         20

<210> SEQ ID NO 550
<211> LENGTH: 38
<212> TYPE: DNA
<213> ORGANISM: Artificial Sequence
<220> FEATURE:
<223> OTHER INFORMATION: PCR primer

<400> SEQUENCE: 550
tgtaaaacga cggccagtgg agatatgctc attcccca                     38

<210> SEQ ID NO 551
<211> LENGTH: 21
<212> TYPE: DNA
<213> ORGANISM: Artificial Sequence
<220> FEATURE:
<223> OTHER INFORMATION: PCR primer

<400> SEQUENCE: 551
ttgaaagcac aaggtttcag c                                       21

<210> SEQ ID NO 552
<211> LENGTH: 20
<212> TYPE: DNA
<213> ORGANISM: Artificial Sequence
<220> FEATURE:
<223> OTHER INFORMATION: PCR primer

<400> SEQUENCE: 552
gtgactttga tgccggagtt                                         20

<210> SEQ ID NO 553
<211> LENGTH: 20
<212> TYPE: DNA
<213> ORGANISM: Artificial Sequence
<220> FEATURE:
<223> OTHER INFORMATION: PCR primer

<400> SEQUENCE: 553
agataggaat ttgggtcggg                                         20

<210> SEQ ID NO 554
<211> LENGTH: 38
<212> TYPE: DNA
<213> ORGANISM: Artificial Sequence
<220> FEATURE:
<223> OTHER INFORMATION: PCR primer

<400> SEQUENCE: 554
tgtaaaacga cggccagtac aaccatgatg tgggaatg                     38

<210> SEQ ID NO 555
<211> LENGTH: 20
<212> TYPE: DNA
<213> ORGANISM: Artificial Sequence
<220> FEATURE:
<223> OTHER INFORMATION: PCR primer

<400> SEQUENCE: 555
gcagggctga gactccagta                                         20

<210> SEQ ID NO 556

```
<211> LENGTH: 38
<212> TYPE: DNA
<213> ORGANISM: Artificial Sequence
<220> FEATURE:
<223> OTHER INFORMATION: PCR primer

<400> SEQUENCE: 556
tgtaaaacga cggccagtag ccctgctttt tctcctct                              38

<210> SEQ ID NO 557
<211> LENGTH: 20
<212> TYPE: DNA
<213> ORGANISM: Artificial Sequence
<220> FEATURE:
<223> OTHER INFORMATION: PCR primer

<400> SEQUENCE: 557
aaagtgacat gatccacagg                                                  20

<210> SEQ ID NO 558
<211> LENGTH: 42
<212> TYPE: DNA
<213> ORGANISM: Artificial Sequence
<220> FEATURE:
<223> OTHER INFORMATION: PCR primer

<400> SEQUENCE: 558
tgtaaaacga cggccagtgc taagaaagca tggggttgtt gg                         42

<210> SEQ ID NO 559
<211> LENGTH: 20
<212> TYPE: DNA
<213> ORGANISM: Artificial Sequence
<220> FEATURE:
<223> OTHER INFORMATION: PCR primer

<400> SEQUENCE: 559
gtggcgtttc aaatccttgt                                                  20

<210> SEQ ID NO 560
<211> LENGTH: 38
<212> TYPE: DNA
<213> ORGANISM: Artificial Sequence
<220> FEATURE:
<223> OTHER INFORMATION: PCR primer

<400> SEQUENCE: 560
tgtaaaacga cggccagttt gactcaaaca caccccaa                              38

<210> SEQ ID NO 561
<211> LENGTH: 20
<212> TYPE: DNA
<213> ORGANISM: Artificial sequence
<220> FEATURE:
<223> OTHER INFORMATION: Forward primer

<400> SEQUENCE: 561
aactcaaacc cgaacaatgc                                                  20

<210> SEQ ID NO 562
<211> LENGTH: 22
<212> TYPE: DNA
<213> ORGANISM: Artificial sequence
<220> FEATURE:
<223> OTHER INFORMATION: Reverse primer

<400> SEQUENCE: 562
```

```
atgaagctgt tgttgttgca gt                                              22

<210> SEQ ID NO 563
<211> LENGTH: 21
<212> TYPE: DNA
<213> ORGANISM: Artificial sequence
<220> FEATURE:
<223> OTHER INFORMATION: Forward primer

<400> SEQUENCE: 563
ccacctcatc actccgtaaa a                                               21

<210> SEQ ID NO 564
<211> LENGTH: 22
<212> TYPE: DNA
<213> ORGANISM: Artificial sequence
<220> FEATURE:
<223> OTHER INFORMATION: Reverse primer

<400> SEQUENCE: 564
aatagggttt gattgaggag ca                                              22

<210> SEQ ID NO 565
<211> LENGTH: 23
<212> TYPE: DNA
<213> ORGANISM: Artificial sequence
<220> FEATURE:
<223> OTHER INFORMATION: Forward primer

<400> SEQUENCE: 565
cgacgaacag aagctaagag atg                                             23

<210> SEQ ID NO 566
<211> LENGTH: 22
<212> TYPE: DNA
<213> ORGANISM: Artificial sequence
<220> FEATURE:
<223> OTHER INFORMATION: Reverse primer

<400> SEQUENCE: 566
cagagcaata agaacaccag ga                                              22

<210> SEQ ID NO 567
<211> LENGTH: 21
<212> TYPE: DNA
<213> ORGANISM: Artificial sequence
<220> FEATURE:
<223> OTHER INFORMATION: Forward primer

<400> SEQUENCE: 567
actcttcctc gccacttcaa c                                               21

<210> SEQ ID NO 568
<211> LENGTH: 24
<212> TYPE: DNA
<213> ORGANISM: Artificial sequence
<220> FEATURE:
<223> OTHER INFORMATION: Reverse primer

<400> SEQUENCE: 568
tgcatgtaat atctatcttt ggaa                                            24

<210> SEQ ID NO 569
<211> LENGTH: 22
<212> TYPE: DNA
```

```
-continued

<213> ORGANISM: Artificial sequence
<220> FEATURE:
<223> OTHER INFORMATION: Forward primer

<400> SEQUENCE: 569 ccaaaccota ggagtctgag gt                                              22

<210> SEQ ID NO 570
<211> LENGTH: 19
<212> TYPE: DNA
<213> ORGANISM: Artificial sequence
<220> FEATURE:
<223> OTHER INFORMATION: Reverse primer

<400> SEQUENCE: 570
gagaggattt cggtgatgt                                                  19

<210> SEQ ID NO 571
<211> LENGTH: 20
<212> TYPE: DNA
<213> ORGANISM: Artificial sequence
<220> FEATURE:
<223> OTHER INFORMATION: Forward primer

<400> SEQUENCE: 571
cactttccac actcaaacca                                                 20
```